US012774291B2

(12) United States Patent
Quibell et al.

(10) Patent No.: US 12,774,291 B2
(45) Date of Patent: Oct. 27, 2026

(54) COMPOUNDS AS MODULATORS OF ENDOPLASMIC RETICULUM AMINOPEPTIDASE 1 (ERAP1)

(71) Applicant: GREY WOLF THERAPEUTICS LIMITED, Abingdon (GB)

(72) Inventors: Martin Quibell, Oxford (GB); Jason John Shiers, Oxford (GB); Michael Sparenberg, Oxford (GB); Eleanor Ivens, Oxford (GB)

(73) Assignee: Grey Wolf Therapeutics Limited, Abingdon (GB)

( * ) Notice: Subject to any disclaimer, the term of this patent is extended or adjusted under 35 U.S.C. 154(b) by 664 days.

(21) Appl. No.: 18/004,386

(22) PCT Filed: Sep. 21, 2021

(86) PCT No.: PCT/GB2021/052453
§ 371 (c)(1),
(2) Date: Jan. 5, 2023

(87) PCT Pub. No.: WO2022/064187
PCT Pub. Date: Mar. 31, 2022

(65) Prior Publication Data

US 2024/0300976 A1 Sep. 12, 2024

(30) Foreign Application Priority Data

Sep. 22, 2020 (GB) ...................................... 2014944

(51) Int. Cl.
*C07D 515/04* (2006.01)
*A61K 31/4365* (2006.01)
*A61K 45/06* (2006.01)

(52) U.S. Cl.
CPC ........ *C07D 515/04* (2013.01); *A61K 31/4365* (2013.01); *A61K 45/06* (2013.01)

(58) Field of Classification Search
CPC ... A61K 31/4365; A61K 45/06; C07D 515/04
See application file for complete search history.

(56) References Cited

FOREIGN PATENT DOCUMENTS

GR 1008348 B 11/2014
WO WO 2020/104822 A1 5/2020
(Continued)

OTHER PUBLICATIONS

Wagner et al., "Down-regulation of ERAP1 mRNA expression in non-small cell lung cancer," BMC Cancer. Apr. 26, 2023;23(1):383. (Year: 2023).*

Reeves et al., The role of polymorphic ERAP1 in autoinflammatory disease, Bioscience Reports (2018) 38. (Year: 2018).*

Georgiadis et al., "Inhibitors of ER Aminopeptidase 1 and 2: From Design to Clinical Application", *Current Medicinal Chemistry* 26(15):2715-2729 (2019).

International Search Report and Written Opinion for International Application No. PCT/GB2021/052453, mailed Nov. 19, 2021, 10 pages.

Maben et al., "Discovery of Selective Inhibitors of Endoplasmic Reticulum Aminopeptidase 1", *Journal of Medicinal Chemistry* 63:103-121 (2020).

Advanced Organic Chemistry, Reactions, Mechanisms, and Structure, 3rd Edition, editor J. Mar. 1985.

(Continued)

*Primary Examiner* — Jared Barsky
(74) *Attorney, Agent, or Firm* — Lathrop GPM LLP; Brian C. Trinque

(57) ABSTRACT

A compound of formula (I-1), or a pharmaceutically accept able salt or hydrate thereof, formula (I-1) wherein: ring A is a monocyclic 5, 6, or 7-membered heterocycloalkyl ring optionally substituted by one or more substituents selected from alkyl, CN, cycloalkyl, OH, alkoxy, halo, haloalkyl and heteroaryl, wherein said heteroaryl group is in turn optionally further substituted with one or more groups selected from halo and alkyl, and wherein one or two carbons in the 5, 6, or 7-membered heterocycloalkyl ring are optionally replaced by a group selected from O, NH, S and CO; L is a linker group which is a 2 to 7-membered saturated or unsaturated aliphatic group, wherein one or two carbon atoms in said group, other than the carbon atom directly bonded to ring A, are optionally replaced by a heteroatom-containing group selected from O, NH and S, and wherein when two carbon atoms are replaced, the heteroatom-containing groups are separated by at least two carbon atoms and the linker group is at least a 5-membered group; the group X—Y is —$NR_{23}SO_2$— or —$SO_2NR_{23}$—; $R_1$ is H, CN or alkyl; $R_2$ is selected from COOH, tetrazolyl and $C(O)NHSO_2R_{24}$; $R_3$ is selected from H, halo and alkyl; $R_4$ is selected from H and halo; $R_6$ is H; $R_7$ is selected from H, CN, haloalkyl, halo, $SO_2$-alkyl, $SO_2NR_{18}R_{19}$, $CONR_{20}R_{21}$, heteroaryl and alkyl, wherein said heteroaryl group is optionally substituted by one or more substituents select ed from alkyl, halo, alkoxy, CN, haloalkyl and OH; $R_8$ is selected from H, alkyl, haloalkyl and halo; $R_9$ is H, alkyl or halo; $R_{18}$-$R_{21}$ and $R_{23}$ are each independently selected from H and alkyl; $R_{24}$ is selected from alkyl and cyclopropyl. Further aspects of the invention relate to such compounds for use in the field of immuno-oncology and related applications.

(I-1)

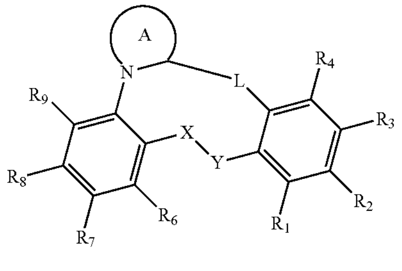

34 Claims, No Drawings

(56) References Cited

FOREIGN PATENT DOCUMENTS

WO WO 2020/225569 A1 11/2020
WO WO 2021/094763 A1 5/2021

OTHER PUBLICATIONS

Anderson et al., "The Process of Structure-Based Drug Design", *Chemistry & Biology* 10(9):787-797 (2003).
Berge et al., "Pharmaceutical Salts", *Journal of Pharmaceutical Sciences*, 66(1):1-19 (1977).
CAS Registry No. 161265-03-8, retrieved Sep. 16, 2025.
CAS Registry No. 246047-72-3, retrieved Sep. 16, 2025.
CAS Registry No. 301224-40-8, retrieved Sep. 16, 2025.
Chen et al., "Silencing or inhibition of endoplasmic reticulum aminopeptidase 1 (ERAP1) suppresses free heavy chain expression and Th17 responses in ankylosing spondylitis", *Annals of the Rheumatic Diseases* 75:916-923 (2016).
Cifaldi et al., "ERAP1 Regulates Natural Killer Cell Function by Controlling the Engagement of Inhibitory Receptors", *Cancer Research* 75(5):824-834 (2015).
Conde-Jaldon et al., "Epistatic Interaction of ERAP1 and HLA-B in Behçet Disease: A Replication Study in the Spanish Population", *PLoS One* 9(7):e102100 (2014).
Evans et al., "Interaction between ERAP1 and HLA-B27 in ankylosing spondylitis implicates peptide handling in the mechanism for HLA-B27 in disease susceptibility", *Nature Genetics* 43(8):761-767 (2011).
Fingl et al., "The Pharmacological Basis of Therapeutics", Chapter 1—General Principles, pp. 1-46 (1975).
Fletcher, "The Mitsunobu reaction in the 21$^{st}$ century", *Organic Chemistry Frontiers* 2:739-752 (2015).
Grubbs et al., "Ring-Closing Metathesis and Related Processes in Organic Synthesis", *Accounts of Chemical Research* 28(11):446-452 (1995).
Handbook of Pharmaceutical Excipients, 2nd Edition, edited by A. Wade and P. Weller (1994).
James et al., "Induction of Protective Antitumor Immunity through Attenuation of ERAAP Function", *The Journal of Immunology* 190(11):5839-5846 (2013).
Karttunen et al., "Detection of rare antigen-presenting cells by the lacZ T-cell activation assay suggests an expression cloning strategy for T-cell antigens", *PNAS USA* 89:6020-6024 (1992).
Kim et al., "Human cytomegalovirus microRNA miR-US4-1 inhibits CD8+T cell responses by targeting the aminopeptidase ERAP1", *Nature Immunology* 12(10):984-991 (2011).
Kuiper et al., "Intraocular Interleukin-17 and Proinflammatory Cytokines in HLA-A29-Associated Birdshot Chorioretinopathy", *American Journal of Ophthalmology* 152(2):177-182 (2011).
Kuiper et al., "Interleukin-17 production and T helper 17 cells in peripheral blood mononuclear cells in response to ocular lysate in patients with birdshot chorioretinopathy", *Molecular Vision* 19:2606-2614 (2013).
Kuiper et al., "A genome-wide association study identifies a functional ERAP2 haplotype associated with birdshot chorioretinopathy", *Human Molecular Genetics* 23(22):6081-6087 (2014).
Kuiper et al., "Functionally distinct ERAP1 and ERAP2 are a hallmark of HLA-A29-(Birdshot) Uveitis", *Human Molecular Genetics* 27(24):4333-4343 (2018).
Nagarajan et al., "ERAAP shapes the peptidome associated with classical and non-classical MHC class I molecules"; *Journal of Immunology* 197(4):1035-1043 (2016).
Nicolaou et al., "Calicheamicin θ: A Rationally Designed Molecule with Extremely Potent and Selective DNA Cleaving Properties and Apoptosis Inducing Activity", *Angewandte Chemie Intl. Ed. Engl.*, 33(2):183-186 (1994).
Pepelyayeva et al., "ERAP1 deficient mice have reduced Type 1 regulatory T cells and develop skeletal and intestinal features of Ankylosing Spondylitis", *Scientific Reports* 8:12464 (2018).
Purcell et al., "Mass spectrometry-based identification of MHC-bound peptides for immunopeptidomics", *Nature Protocols* 14:1687-1707 (2019).
Reeves et al., "Functionally distinct ERAP1 allotype combinations distinguish individuals with Ankylosing Spondylitis", *PNAS USA* 111(49):17594-17599 (2014).
Reeves et al., "The role of polymorphic ERAP1 in autoinflammatory disease", *Bioscience Reports* 38 (2018).
Remington's Pharmaceutical Sciences, 17$^{th}$ Edition, Mack Publishing Co. (A. R. Gennaro editor) (1985).
Rizvi et al., "Mutational landscape determines sensitivity to PD-1 blockade in non-small cell lung cancer", *Science* 348(6230):124-128 (2015).
Serwold et al., "ERAAP customizes peptides for MHC class I molecules in the endoplasmic reticulum", *Nature* 419:480-483 (2002).
Sheehan, "The ramifications of HLA-B27", *Journal of the Royal Society of Medicine* 97(1):10-14 (Jan. 2004).
Smith, "Update on Ankylosing Spondylitis: Current Concepts in Pathogenesis", *Current Allergy and Asthma Reports* 15(1):489 (Jan. 2015).
Snyder et al., "Genetic Basis for Clinical Response to CTLA-4 Blockade in Melanoma", *The New England Journal of Medicine* 371(23):2189-2199 (2014).
Steinbach et al., "ERAP1 overexpression in HPV-induced malignancies: A possible novel immune evasion mechanism", *Oncoimmunology* 6(7):e1336594 (2017).
Strange et al., "Genome-wide association study identifies new psoriasis susceptibility loci and an interaction between HLA-C and ERAP1", *Nature Genetics* 42(11):985-990 (2010).
Swamy et al., "Mitsunobu and Related Reactions: Advances and Applications", *Chemical Reviews* 109(6):2551-2651 (2009).
Swamy et al., "Mitsunobu and Related Reactions: Advances and Applications", *Chemical Reviews* S1-S67—Supporting Information (2009).
Tenzer et al., "Antigen processing influences HIV-specific cytotoxic T lymphocyte immunodominance", *Nature Immunology* 10(6):636-646 (2009).
Thiel, "Structure-aided drug design's next generation", *Nature Biotechnology* 22(5):513-519 (2004).
Tsuchiya et al., "Practical and Scalable Synthesis of a Glucokinase Activator via One-Pot Difluorination and Julia Olefination", *Organic Process Research & Development* 24(7):1294-1303 (2020).
Uniprot Q9NZ08, Jun. 2, 2021.
Van Allen et al., "Genomic correlates of response to CTLA-4 blockade in metastatic melanoma", *Science* 350(6257):207-211 (2015).

* cited by examiner

COMPOUNDS AS MODULATORS OF ENDOPLASMIC RETICULUM AMINOPEPTIDASE 1 (ERAP1)

The present invention relates to compounds that are capable of modulating ERAP1. The compounds have potential therapeutic applications in the treatment of a variety of disorders, including proliferative, viral, immune and inflammatory disorders.

BACKGROUND TO THE INVENTION

ERAP1 (Endoplasmic Reticulum Aminopeptidase 1; also referred to as APPILS or ARTS1) is an aminopeptidase important in the generation of a proportion of antigens and neoantigens as part of the antigen presentation pathway[1]. The antigen presentation pathway starts with the breakdown of proteins by the proteasome into peptides. These peptides are transported into the endoplasmic reticulum where a proportion are processed by ERAP1 before binding to the Major Histocompatibility Complex Class I (MHC Class 1)[1]. Antigens bound to MHC Class I are then transported to the surface of a cell and presented to $CD8^+$ T-cells and recognised as either self or non-self. Neoantigens are antigens that are specific to cancer and can be recognised as foreign by the immune system leading to destruction of cancer cells. Neoantigens are created either as a direct result of somatic mutations in the DNA of cancer cells, leading to the generation of mutated proteins, or through the indirect consequences of somatic mutations on protein processing and expression. Those cancers with higher rates of mutation and correspondingly higher levels of neoantigens have much greater response rates to the checkpoint inhibitor immunotherapies anti-PD-1 (e.g. pembrolizumab, nivolumab), anti-PD-L1 (e.g. atezolizumab, avelumab, durvalumab) and anti-CTLA4 antibodies (e.g. ipilimumab, tremelimuab) compared with cancers harbouring lower numbers of neoantigens[2, 3].

The role of ERAP1 in the antigen presentation pathway is to trim a proportion of peptides, via its aminopeptidase activity, to create antigens and neoantigens of the optimal length for binding to MHC Class I. ERAP1 also over-trims some neoantigens, preventing their binding to MHC Class I and presentation at the cell surface[4]. Ablation of ERAP1 activity has been shown to change the antigen and neoantigen repertoire, leading to an increase in presentation of certain antigens/neoantigens and the presentation of entirely novel antigens/neoantigens[5]. In addition, ERAP1 ablation causes $CD8^+$ T cell dependent tumour rejection in mouse cancer models[4].

Accordingly, modulators of ERAP1 activity may be useful for cancer treatment, either used alone or in combination with current cancer immunotherapy agents, including checkpoint inhibitors, because they change the antigens and neoantigens presented on the surface of cancer cells and make them more visible to the immune system, leading to tumour attack and destruction.

Knockdown of ERAP1 is also shown to reduce the levels of regulatory-like T cells and enhance the killing of cancer cells by natural killer cells[6, 7] This suggests that modulators of ERAP1 activity might be effective cancer treatments by both modulating cancer cell visibility and creating a more anti-tumourogenic immune response. ERAP1's peptide processing role in antigen presentation is also applicable in infectious viral disease.

Maben et al (*J. Med. Chem.* 2020; 63, 103-121) disclose compounds that selectively inhibit ERAP1 over its paralogues ERAP2 and IRAP. WO 2020/104822 (Grey Wolf Therapeutics Limited) discloses a series of aryl sulfonamide compounds that are capable of modulating ERAP1.

The present invention seeks to provide further compounds that are capable of modulating ERAP1. Such compounds have potential therapeutic applications in the treatment of a variety of disorders, including proliferative disorders, immune disorders and inflammatory disorders.

STATEMENT OF INVENTION

A first aspect of the invention relates to a compound of formula (I-1), or a pharmaceutically acceptable salt or hydrate thereof, (I-1)

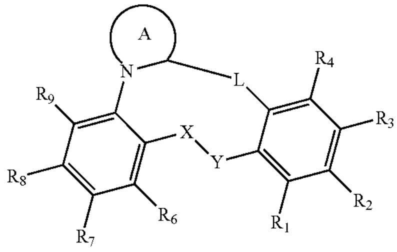

wherein:

ring A is a monocyclic 5, 6, or 7-membered heterocycloalkyl ring optionally substituted by one or more substituents selected from alkyl, CN, cycloalkyl, OH, alkoxy, halo, haloalkyl and heteroaryl, wherein said heteroaryl group is in turn optionally further substituted with one or more groups selected from halo and alkyl, and wherein one or two carbons in the 5, 6, or 7-membered heterocycloalkyl ring are optionally replaced by a group selected from O, NH, S and CO;

L is a linker group which is a 2 to 7-membered saturated or unsaturated aliphatic group, wherein one or two carbon atoms in said group, other than the carbon atom directly bonded to ring A, are optionally replaced by a heteroatom-containing group selected from 0, NH and S, and wherein when two carbon atoms are replaced, the heteroatom-containing groups are separated by at least two carbon atoms and the linker group is at least a 5-membered group;

the group X—Y is $—NR_{23}SO_2—$ or $—SO_2NR_{23}—$;

$R_1$ is selected from H, CN and alkyl;

$R_2$ is selected from COOH, tetrazolyl and $C(O)NHSO_2R_{24}$;

$R_3$ is selected from H, halo and alkyl;

$R_4$ is selected from H and halo;

$R_6$ is H;

$R_7$ is selected from H, CN, haloalkyl, halo, $SO_2$-alkyl, $SO_2NR_{18}R_{19}$, $CONR_{20}R_{21}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

$R_{18}$-$R_{21}$ and $R_{23}$ are each independently selected from H and alkyl; and $R_{24}$ is selected from alkyl and cyclopropyl.

The invention also encompasses enantiomers of compounds of formula (I), and mixtures of enantiomers, including racemic mixtures.

Advantageously, the presently claimed compounds are capable of modulating ERAP 1, thereby rendering the compounds of therapeutic interest in the treatment of various disorders, for example, in the field of oncology and immuno-oncology.

Another aspect of the invention relates to a pharmaceutical composition comprising at least one compound as described herein and a pharmaceutically acceptable carrier, diluent or excipient.

Another aspect of the invention relates to a compound as described herein for use in medicine.

Another aspect of the invention relates to the use of a compound as described herein in the preparation of a medicament for treating or preventing a disorder selected from a proliferative disorder, an immune disorder, a viral disorder and an inflammatory disorder.

Another aspect of the invention relates to a compound as described herein for use in the prevention or treatment of a disorder caused by, associated with or accompanied by any abnormal ERAP1 activity.

Another aspect of the invention relates to the use of a compound as described herein in the preparation of a medicament for the prevention or treatment of a disorder caused by, associated with or accompanied by abnormal ERAP1 activity.

Another aspect of the invention relates to a method of treating a mammal having a disease state alleviated by modulation of ERAP1, wherein the method comprises administering to a mammal a therapeutically effective amount of a compound as described herein.

Another aspect of the invention relates to a compound as described herein for use in treating or preventing a disease state alleviated by modulation of ERAP1.

Another aspect of the invention relates to the use of a compound as described herein in the preparation of a medicament for treating or preventing a disease state alleviated by modulation of ERAP1.

Another aspect of the invention relates to a method of treating or preventing a disorder selected from a proliferative disorder, an immune disorder, a viral disorder and an inflammatory disorder in a subject, wherein the method comprises administering to the subject a therapeutically effective amount of a compound as described herein.

DETAILED DESCRIPTION

The present invention relates to bis-aryl sulfonamide compounds that are capable of modulating ERAP1. One aspect of the invention relates to compounds of formula (I-1) as described above.

The group L is a linker group which is a 2 to 7-membered saturated or unsaturated aliphatic group, wherein one or two carbons in said group, other than the carbon directly bonded to ring A, are optionally replaced by a heteroatom-containing group selected from O, NH and S, and wherein when two carbons are replaced, the heteroatom-containing groups are separated by at least two carbons and the linker group is at least a 5-membered group. Thus, the carbon of the L group directly attached to ring A cannot be optionally replaced by a heteroatom-containing group. Furthermore, where there are two carbons in the linker group replaced by a heteroatom-containing group, the group must be at least a 5-membered linker, and the heteroatom-containing groups must be separated by at least two carbons, i.e. they cannot be adjacent to one another, or separated by a single carbon. For shorter 2- to 4-membered linker groups, only one carbon can be optionally replaced by a heteroatom-containing group.

Preferably, L is an acyclic aliphatic group.

In one preferred embodiment, L is a 2 to 5-membered saturated or unsaturated aliphatic group, wherein one or two carbons in said group, other than the carbon directly bonded to ring A, are optionally replaced by a heteroatom-containing group selected from O, NH and S, and wherein when two carbons are replaced, the heteroatom-containing groups are separated by at least two carbons and the linker group is a 5-membered group.

In one preferred embodiment, L is a 3 to 5-membered saturated or unsaturated aliphatic group, more preferably a 4- or 5-membered saturated or unsaturated aliphatic group, wherein one or two carbons in group, other than the carbon directly bonded to ring A, are optionally replaced by a heteroatom-containing group selected from O, NH and S, and wherein when two carbons are replaced, the heteroatom-containing groups are separated by at least two carbons and the linker group is a 5-membered group.

In one preferred embodiment, L is a 3 to 5-membered saturated aliphatic group, more preferably a 4- or 5-membered saturated aliphatic group, wherein one or two carbons in said group, other than the carbon directly bonded to ring A, are optionally replaced by a heteroatom-containing group selected from O and NH, and wherein when two carbons are replaced, the heteroatom-containing groups are separated by at least two carbons and the linker group is a 5-membered group.

In one preferred embodiment, L is a 3 to 5-membered unsaturated aliphatic group, more preferably a 4- or 5-membered unsaturated aliphatic group, wherein one or two carbons in said group, other than the carbon directly bonded to ring A, are optionally replaced by a heteroatom-containing group selected from O and NH, and wherein when two carbons are replaced, the heteroatom-containing groups are separated by at least two carbons and the linker group is a 5-membered group.

In one preferred embodiment, L is a 3 to 5-membered unsaturated aliphatic group, more preferably a 4- or 5-membered unsaturated aliphatic group, wherein one carbon atom in said group, other than the carbon atom directly bonded to ring A, is optionally replaced by a heteroatom-containing group selected from O and NH In one preferred embodiment, L is a 5-membered saturated aliphatic group wherein one carbon is replaced by a heteroatom-containing group selected from O and NH, more preferably O.

In one preferred embodiment, L is a 5-membered saturated aliphatic group wherein two carbons are replaced by a heteroatom-containing group selected from O and NH, more preferably O.

In one preferred embodiment, L is a 5-membered unsaturated aliphatic group wherein one carbon is replaced by a heteroatom-containing group selected from O and NH, more preferably O.

In one preferred embodiment, L is a 4-membered saturated aliphatic group wherein one carbon is replaced by a heteroatom-containing group selected from O and NH, more preferably O.

In one preferred embodiment, L is a 4-membered unsaturated aliphatic group wherein one carbon is replaced by a heteroatom-containing group selected from O and NH, preferably O.

In one preferred embodiment, L is a 5-membered linker group which is an alkylene group wherein one or two carbons are optionally replaced with a heteroatom-containing group selected from O, NH and S, with the proviso that (i) where two carbons are replaced, the two heteroatom-containing groups are separated by two carbons, and (ii) the replacement is not at the carbon attached to ring A.

In one preferred embodiment, L is a 5-membered linker group which is an alkylene group wherein one carbon is optionally replaced with a heteroatom-containing group selected from O, NH and S, more preferably O and NH, with the proviso that the replacement is not at the carbon attached to ring A.

In one preferred embodiment, L is a 5-membered linker group which is an alkylene group wherein two carbons are optionally replaced with a heteroatom-containing group selected from O, NH and S, more preferably O and NH, with the proviso that (i) where two carbons are replaced, the two heteroatom-containing groups are separated by two carbons, and (ii) the replacement is not at the carbon attached to ring A.

In one preferred embodiment, L is 5-membered linker group which is an alkenylene group wherein one carbon is optionally replaced with a heteroatom-containing group selected from O, NH and S, more preferably O and NH, with the proviso that the replacement is not at the carbon attached to ring A.

In one preferred embodiment, L is 4-membered linker group which is an alkylene group wherein one carbon is optionally replaced with a heteroatom-containing group selected from O, NH and S, more preferably O and NH, with the proviso that the replacement is not at the carbon attached to ring A.

In one preferred embodiment, L is 4-membered linker group which is an alkenylene group wherein one carbon is optionally replaced with a heteroatom-containing group selected from O, NH and S, more preferably O and NH, with the proviso that the replacement is not at the carbon attached to ring A.

The compounds of formula (I-1) contain a chiral centre, denoted * in the structure below:

(I-1)

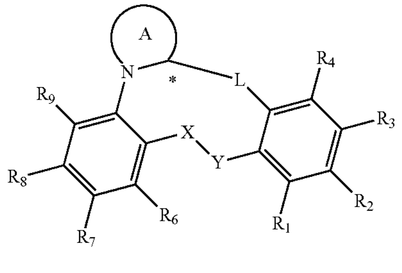

Thus, the compounds of formula (I-1) can exist as two different enantiomers, S-(I-1) and R-(I-1):

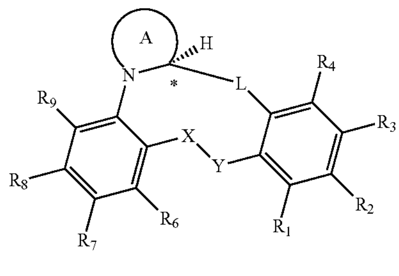

-continued

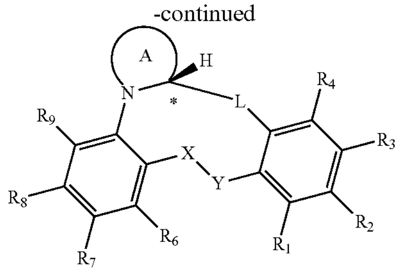

For the avoidance of doubt, the invention encompasses the compounds in either of the above configurations, as well as mixtures thereof, including racemic mixtures. In one preferred embodiment, the compound is in the form of a mixture comprising a compound of formula S-(I-1) and its corresponding enantiomer of formula R-(I-1). In one preferred embodiment, the mixture is a racemic mixture, i.e. a 50:50 mixture of a compound of formula S-(I-1) and its corresponding enantiomer of formula R-(I-1).

Racemic mixtures can be used to prepare enantiomerically pure compounds of formula S-(I-1) or R-(I-1) by separating the compounds of formula S-(I-1) or R-(I-1) by standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of compounds of formula S-(I-1) or R-(I-1). Mixtures enriched with either a compound of formula S-(I-1) or R-(I-1) can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one particularly preferred embodiment, the compound is in the form of a mixture comprising a compound of formula S-(I-1) and its corresponding enantiomer of formula R-(I-1), wherein the weight:weight ratio of said compound of formula S-(I-1) to said compound of formula R-(I-1) is greater than 1.05:1, more preferably, greater than 2:1, even more preferably greater than 5:1, even more preferably greater than 10:1.

In one particularly preferred embodiment, the compound is in the form of a mixture comprising a compound of formula S-(I-1) and its corresponding enantiomer of formula R-(I-1), which is substantially enriched with said compound of formula S-(I-1).

In one embodiment, the compound is in the form of a mixture comprising a compound of formula S-(I-1) and its corresponding enantiomer of formula R-(I-1), wherein the weight:weight ratio of said compound of formula R-(I-1) to said compound of formula S-(I-1) is greater than 1.05:1, more preferably, greater than 2:1, even more preferably greater than 5:1, even more preferably greater than 10:1.

In one embodiment, the compound is in the form of a mixture comprising a compound of formula S-(I-1) and its corresponding enantiomer of formula R-(I-1), which is substantially enriched with said compound of formula R-(I-1).

"Alkyl" is defined herein as a straight-chain or branched alkyl radical, preferably $C_{1-20}$ alkyl, more preferably $C_{1-12}$ alkyl, even more preferably $C_{1-10}$ alkyl or $C_{1-6}$ alkyl, for example, methyl, ethyl, propyl, isopropyl, butyl, isobutyl, tert-butyl, pentyl, hexyl. More preferably, the alkyl is a $C_{1-3}$ alkyl. The term "alkyl"/"alk" in "haloalky" or "alkoxy" is construed accordingly.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, tetrazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc. Particularly preferred heteroaryl groups include 1H-imidazol-5-yl, 1H-imidazol-4-yl, 1H-imidazol-2-yl, 1H-pyrrol-1-yl, 1H-pyrrol-2-yl, 1H-pyrrol-3-yl, 1H-pyrrol-4-yl, 1H-pyrrol-5-yl, 1H-pyrazol-1-yl, 1H-pyrazol-5-yl, 1H-pyrazol-3-yl, 1H-pyrazol-4-yl, oxazol-2-yl, oxazol-4-yl, oxazol-5-yl, 1H-1,2,4-triazol-3-yl, 1H-1,2,4-triazol-5-yl, 1H-1,2,4-triazol-1-yl, 1H-1,2,3-triazol-4-yl, 1H-1,2,3-triazol-5-yl, 1H-1,2,3-triazol-1-yl, thiazol-5-yl, thiazol-2-yl, thiazol-4-yl, 1H-1,2,3,4-tetrazol-4-yl, 2H-1,2,3,4-tetrazol-5-yl, oxazol-5-yl, oxazol-4-yl, oxazol-2-yl, isoxazol-3-yl, isoxazol-4-yl, isoxazol-5-yl, isothiazol-3-yl, isothiazol-4-yl, isothiazol-5-yl, pyradizin-3-yl, pyradizin-4-yl, pyrazinyl, 1,3,4-oxadizol-2-yl, 1,3,4-oxadizol-5-yl, 1,2,5-oxadiazol-3-yl, 1,2,5-oxadiazol-4-yl, 1,2,3-oxadiazol-4-yl, 1,2,3-oxadiazol-5-yl, 1,2,4-oxadiazol-3-yl, 1,2,4-oxadiazol-5-yl, isoxazol-5-yl, isoxazol-4-yl and isoxazol-3-yl.

"Heterocycloalkyl" refers to a cyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is monocyclic or bicyclic. Preferably, the heterocycloalkyl group is a $C_{3-7}$-heterocycloalkyl, more preferably a $C_{3-6}$-heterocycloalkyl. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

In a preferred embodiment, the invention relates to a compound of formula (I), or a pharmaceutically acceptable salt or hydrate thereof, (I)

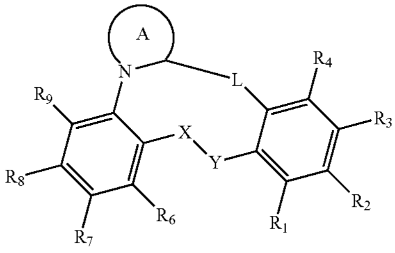

wherein:

ring A is a monocyclic 5, 6, or 7-membered heterocycloalkyl ring optionally substituted by one or more substituents selected from alkyl, CN, cycloalkyl, OH, alkoxy, halo, haloalkyl and heteroaryl, wherein said heteroaryl group is in turn optionally further substituted with one or more groups selected from halo and alkyl, and wherein one or two carbons in the 5, 6, or 7-membered heterocycloalkyl ring are optionally replaced by a group selected from O, NH, S and CO;

L is a group selected from:
$-(CR_{10}R_{11})_r-(CR_{12}R_{13})-O-$;
$-(CR_{10}R_{11})_nC(R_{16})=C(R_{17})-(CR_{12}R_{13})_m-O-$;
$-(CR_{14}R_{15})\text{-}Q\text{-}(CR_{12}R_{13})_s-O-$;
$-(CR_{10}R_{11})_u-(CR_{12}R_{13})-$;
$-(CR_{10}R_{11})_t-C(R_{16})=C(R_{17})-$;
$-(CR_{14}R_{15})\text{-}Q\text{-}(CR_{12}R_{13})_m-C(R_{16})=C(R_{17})-$; and
$-(CR_{14}R_{15})\text{-}Q\text{-}(CR_{12}R_{13})_t$;

Q is O, S or $NR_{22}$;

the group X—Y is $-NR_{23}SO_2-$ or $-SO_2NR_{23}-$;

$R_1$ is selected from H, CN and alkyl;

$R_2$ is selected from COOH, tetrazolyl and $C(O)NHSO_2R_{24}$;

$R_3$ is selected from H, halo and alkyl;

$R_4$ is selected from H and halo;

$R_6$ is H;

$R_7$ is selected from H, CN, haloalkyl, halo, $SO_2$-alkyl, $SO_2NR_{18}R_{19}$, $CONR_{20}R_{21}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

each $R_{10}$ is H;

each $R_{11}$ is independently selected from H, F, alkyl and OH;

$R_{12}$-$R_{23}$ are each independently selected from H and alkyl;

$R_{24}$ is selected from alkyl and cyclopropyl;

m is 1 or 2;

n is 0, 1 or 2;

r is 0, 1, 2, 3, 4 or 5;

s is 2;

t is 1, 2 or 3; and u is 1, 2, 3, 4, 5 or 6.

In one preferred embodiment, the compound of the invention is of formula (I) as defined above, wherein L is a group selected from:
$-(CR_{10}R_{11})_r-(CR_{12}R_{13})-O-$;
$-(CR_{10}R_{11})_nC(R_{16})=C(R_{17})-(CR_{12}R_{13})_m-O-$; and
$-(CR_{14}R_{15})\text{-}Q\text{-}(CR_{12}R_{13})_s-O-$.

In one preferred embodiment, L is $-(CR_{10}R_{11})_r-(CR_{12}R_{13})-O-$, where r is 0, 1, 2, 3, 4 or 5. Preferably, r is 0, 1, 2, 3 or 4, more preferably, 0, 1, 2 or 3. In one particularly preferred embodiment, r is 0. In another particularly preferred embodiment, r is 1. In another particularly preferred embodiment, r is 2. In another particularly preferred embodiment, r is 3.

In one preferred embodiment, $R_{12}$-$R_{23}$ are each independently selected from H and $C_{1-6}$-alkyl, more preferably, H and $C_{1-3}$-alkyl.

In one preferred embodiment, $R_{22}$ and $R_{23}$ are each independently selected from H and $C_{1-3}$-alkyl. More preferably, $R_{22}$ and $R_{23}$ are both H.

In one preferred embodiment, L is $—(CR_{10}R_{11})_r—(CR_{12}R_{13})—O—$, where r is 0, 1, 2, 3, 4 or 5, each $R_{11}$ is H, and $R_{12}$ and $R_{13}$ are as defined above. More preferably, $R_{12}$ and $R_{13}$ are both H.

In another preferred embodiment, L is $—(CR_{10}R_{11})_r—(CR_{12}R_{13})—O—$, where r is 0, 1, 2, 3, 4 or 5, each $R_{11}$ is independently F or OH, and $R_{12}$ and $R_{13}$ are as defined above. More preferably, $R_{12}$ and $R_{13}$ are both H.

In one particularly preferred embodiment, L is selected from:

$—CH_2—O—$;
$—CH_2—CH_2—O—$;
$—CH_2—CH_2—CH_2—O—$;
$—CH_2—CH_2—CH_2—CH_2—O—$;
$—CH(OH)—CH(OH)—CH_2—O—$;
$—CH(OH)—CH_2—CH_2—O—$;
$—CH_2—CH(OH)—CH_2—O—$;
$—CH(F)—CH(F)—CH_2—O—$;
$—CH(F)—CH_2—CH_2—O—$;
$—CH_2—CH(F)—CH_2—O—$;
$—CH(F)—CH(OH)—CH_2—O—$;
$—CH(OH)—CH(F)—CH_2—O—$;
$—CH_2—CH(OH)—CH(OH)—CH_2—O—$;
$—CH_2—CH(OH)—CH_2—CH_2—O—$;
$—CH_2—CH_2—CH(OH)—CH_2—O—$;
$—CH_2—CH(F)—CH(F)—CH_2—O—$;
$—CH_2—CH(F)—CH_2—CH_2—O—$;
$—CH_2—CH_2—CH(F)—CH_2—O—$;
$—CH_2—CH(F)—CH(OH)—CH_2—O—$; and
$—CH_2—CH(OH)—CH(F)—CH_2—O—$.

In another preferred embodiment, L is $—(CR_{10}R_{11})_nC(R_{16})═C(R_{17})—(CR_{12}R_{13})_m—O—$, where m is 1 or 2 and n is 0, 1 or 2.

In one preferred embodiment, m is 1.
In one preferred embodiment, m is 2.
In one preferred embodiment, n is 0.
In one preferred embodiment, n is 1.
In one preferred embodiment, n is 2.
In one preferred embodiment, m is 1 and n is 0.
In one preferred embodiment, m is 1 and n is 1.
In one preferred embodiment, m is 1 and n is 2.
In one preferred embodiment, m is 2 and n is 0.
In one preferred embodiment, m is 2 and n is 1.
In one preferred embodiment, m is 2 and n is 2.

In highly preferred embodiment, the sum of m+n is ≤2. Thus, in one particularly preferred embodiment, m is 1 and n is 0, or m is 1 and n is 1, or m is 2 and n is 0.

In one particularly preferred embodiment, L is selected from:

$CH_2—CH═CH—CH_2—O—$; and
$—CH═CH—CH_2—O—$.

In another preferred embodiment, L is $—(CR_{14}R_{15})$-Q-$(CR_{12}R_{13})_s—O—$ where Q is O, S or NH or NMe, and s is 2. In one preferred embodiment, Q is S. In one preferred embodiment, Q is NH. In one particularly preferred embodiment, Q is O.

In one particularly preferred embodiment, L is selected from:

$—CH_2—O—CH_2—CH_2—O—$;
$—CH_2—NH—CH_2—CH_2—O—$; and
$—CH_2—S—CH_2—CH_2—O—$.

In another preferred embodiment, L is $—(CR_{10}R_{11})_u—(CR_{12}R_{13})—$, wherein u is 1, 2, 3, 4, or 6. More preferably for this embodiment, u is 1, 2, 3 or 4. In one particularly preferred embodiment, u is 4. More preferably, L is $—CH_2—CH_2—CH_2—CH_2—CH_2—$.

In another preferred embodiment, L is $—(CR_{10}R_{11})_t—C(R_{16})═C(R_{17})—$ where t is 1, 2 or 3. Preferably for this embodiment, t is 2 or 3, more preferably 3. More preferably, L is $—CH_2CH_2CH_2CH═CH—$.

In another preferred embodiment, L is $—(CR_{14}R_{15})$-Q-$(CR_{12}R_{13})_m—C(R_{16})═C(R_{17})—$ where Q is O, S, NH or NMe, and m is 1 or 2. Preferably for this embodiment, Q is O. Preferably for this embodiment, m is 1. Even more preferably, L is $—CH_2—O—CH_2—CH═CH—$.

In another preferred embodiment, L is $—(CR_{14}R_{15})$-Q-$(CR_{12}R_{13})_t$, where Q is O, S or NH or NMe and t is 1, 2 or 3. Preferably for this embodiment, t is 2 or 3, more preferably 3. More preferably, L is $—CH_2—O—CH_2—CH_2—CH_2—$.

In one preferred embodiment, X—Y is NH—$SO_2$ or NMe-$SO_2$, more preferably NH—$SO_2$.

In one preferred embodiment, ring A is a monocyclic 5-membered heterocycloalkyl ring optionally substituted by one or more substituents selected from alkyl, CN, cycloalkyl, OH, alkoxy, halo, haloalkyl and heteroaryl, wherein said heteroaryl group is in turn optionally further substituted with one or more groups selected from halo and alkyl, and wherein one or two carbons in the 5, 6, or 7-membered heterocycloalkyl ring are optionally replaced by a group selected from O, NH, S and CO. In one preferred embodiment, ring A is a pyrrolidinyl group.

In one preferred embodiment, ring A is a monocyclic 6-membered heterocycloalkyl ring optionally substituted by one or more substituents selected from alkyl, CN, cycloalkyl, OH, alkoxy, halo, haloalkyl and heteroaryl, wherein said heteroaryl group is in turn optionally further substituted with one or more groups selected from halo and alkyl, and wherein one or two carbons in the 5, 6, or 7-membered heterocycloalkyl ring are optionally replaced by a group selected from O, NH, S and CO. In one preferred embodiment, ring A is a piperidinyl group.

In one preferred embodiment, the compound of the invention is of formula (Ia), or a pharmaceutically acceptable salt or hydrate thereof:

(Ia)

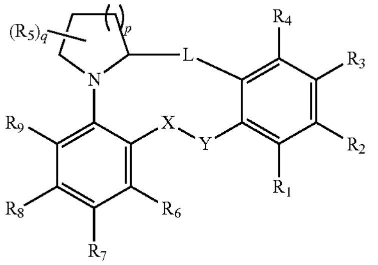

wherein:

p is 1, 2, or 3;

$R^5$ is selected from alkyl, CN, cycloalkyl, OH, alkoxy, halo, haloalkyl and heteroaryl, wherein said heteroaryl group is in turn optionally further substituted with one or more groups selected from halo and alkyl;

q is 0, 1, 2, 3 or 4; and $R_{1-4}$, $R_{6-9}$, X, Y and L are as defined above.

In one preferred embodiment, p is 2.

In one preferred embodiment, the compound of the invention is of formula (Ib), or a pharmaceutically acceptable salt or hydrate thereof:

(Ib)

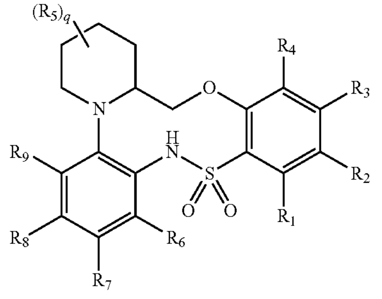

where q and $R_{1-9}$ are as defined above.

In one preferred embodiment, the compound of the invention is of formula (Ic), or a pharmaceutically acceptable salt or hydrate thereof:

(Ic)

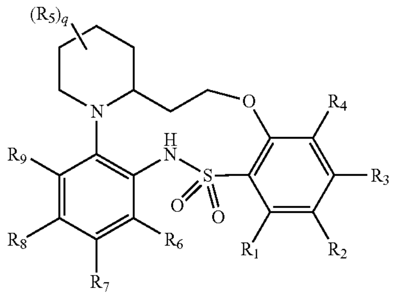

where q and $R_{1-9}$ are as defined above.

In one preferred embodiment, the compound of the invention is of formula (Id), or a pharmaceutically acceptable salt or hydrate thereof:

(Id)

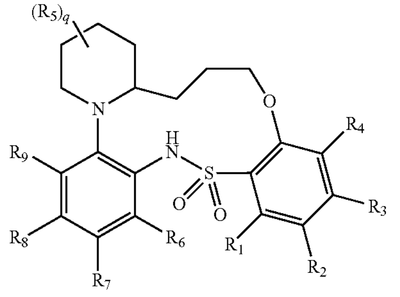

where q and $R_{1-9}$ are as defined above.

In one preferred embodiment, the compound of the invention is of formula (Ie), or a pharmaceutically acceptable salt or hydrate thereof:

(Ie)

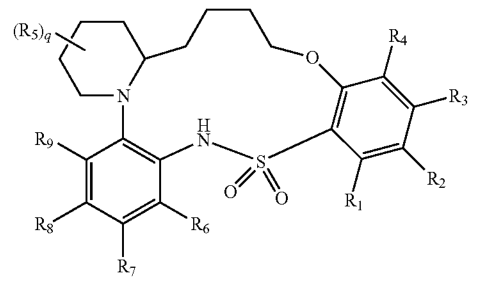

where q and $R_{1-9}$ are as defined above.

In one particularly preferred embodiment, the compound of the invention is of formula S-(Ie), or a pharmaceutically acceptable salt or hydrate thereof:

S-(Ie)

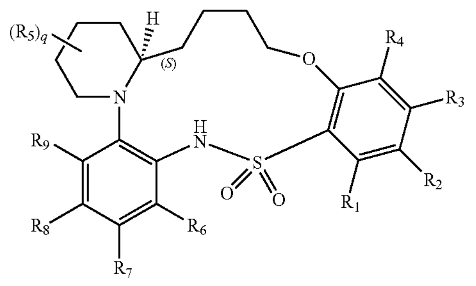

where q and $R_{1-9}$ are as defined above. In one preferred embodiment, the compound is in enantiomerically pure form.

In another preferred embodiment, the compound of the invention is of formula R-(Ie), or a pharmaceutically acceptable salt or hydrate thereof:

R-(Ie)

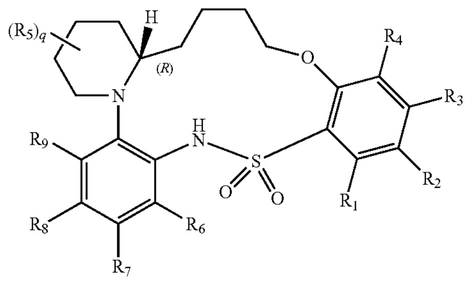

where q and $R_{1-9}$ are as defined above. In one preferred embodiment, the compound is in enantiomerically pure form.

In one preferred embodiment, the compound is in the form of a mixture comprising a compound of formula S-(Ie) and its corresponding enantiomer of formula R-(Ie). In one preferred embodiment, the mixture is a racemic mixture, i.e. a 50:50 mixture of a compound of formula S-(Ie) and its corresponding enantiomer of formula R-(Ie).

Racemic mixtures can be used to prepare enantiomerically pure compounds of formula S-(Ie) or R-(Ie) by separating the compounds of formula S-(Ie) or R-(Ie) by standard methods, for example by chemical resolution using optically active acid or by the use of column chromatography or reverse-phase column chromatography using a substantially optically active (or "chiral") stationary phase as known to those skilled in the art. Racemic mixtures can also be used to prepare enantiomerically enriched mixtures of compounds of formula S-(Ie) or R-(Ie). Mixtures enriched with either a compound of formula S-(Ie) or R-(Ie) can also be obtained from the appropriate enantiomerically enriched precursors.

In one preferred embodiment of the invention, the compound is in the form of a mixture comprising enantiomers wherein the weight:weight ratio is at least approximately 2:1 or greater, preferably at least approximately 5:1 or greater, most preferably at least approximately 10:1 or greater in favour of the enantiomer that displays significant in vitro and/or in vivo activity (the eutomer).

In one particularly preferred embodiment, the compound is in the form of a mixture comprising a compound of formula S-(Ie) and its corresponding enantiomer of formula R-(le), wherein the weight:weight ratio of said compound of formula S-(Ie) to said compound of formula R-(Ie) is greater than 1.05:1, more preferably, greater than 2:1, even more preferably greater than 5:1, even more preferably greater than 10:1.

In one particularly preferred embodiment, the compound is in the form of a mixture comprising a compound of formula S-(Ie) and its corresponding enantiomer of formula R-(le), which is substantially enriched with said compound of formula S-(Ie).

In one embodiment, the compound is in the form of a mixture comprising a compound of formula S-(Ie) and its corresponding enantiomer of formula R-(Ie), wherein the weight:weight ratio of said compound of formula R-(Ie) to said compound of formula S-(Ie) is greater than 1.05:1, more preferably, greater than 2:1, even more preferably greater than 5:1, even more preferably greater than 10:1.

In one embodiment, the compound is in the form of a mixture comprising a compound of formula S-(Ie) and its corresponding enantiomer of formula R-(Ie), which is substantially enriched with said compound of formula R-(Ie).

In one preferred embodiment, the compound of the invention is of formula (If), or a pharmaceutically acceptable salt or hydrate thereof:

(If)

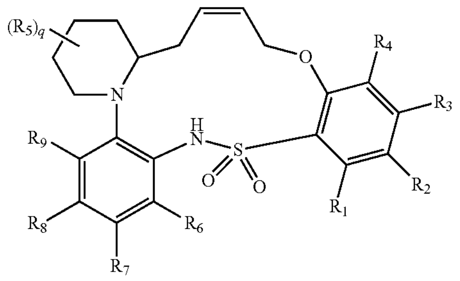

where q and $R_{1-9}$ are as defined above.

In another preferred embodiment, the compound of the invention is of formula (Ij), or a pharmaceutically acceptable salt or hydrate thereof:

(Ij)

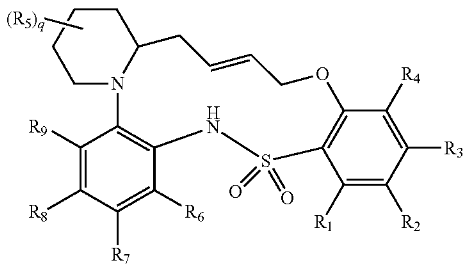

where q and $R_{1-9}$ are as defined above.

In formula (If) the double bond in the linker group is in the Z-configuration, whereas in formula (Ij) it is in the E-configuration. The E-configuration, i.e. Formula (Ij), is particularly preferred.

In one preferred embodiment, the compound of the invention is of formula (Ig), or a pharmaceutically acceptable salt or hydrate thereof:

(Ig)

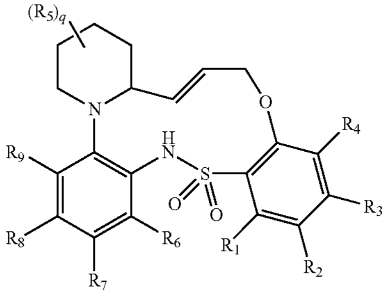

where q and $R_{1-9}$ are as defined above.

In one preferred embodiment, the compound of the invention is of formula (Im), or a pharmaceutically acceptable salt or hydrate thereof:

(Im)

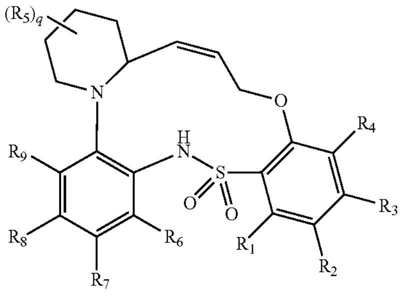

where q and $R_{1-9}$ are as defined above.

In one preferred embodiment, the compound of the invention is of formula (In), or a pharmaceutically acceptable salt or hydrate thereof:

(In)

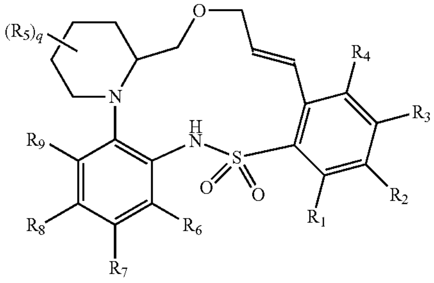

where q and $R_{1-9}$ are as defined above.

In one preferred embodiment, the compound of the invention is of formula (Ip), or a pharmaceutically acceptable salt or hydrate thereof:

(Ip)

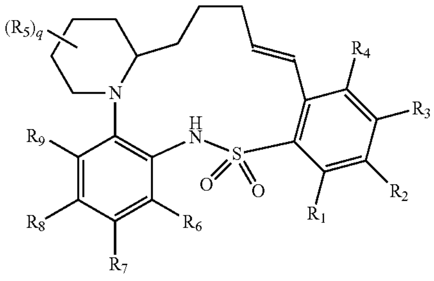

where q and $R_{1-9}$ are as defined above.

In one preferred embodiment, the compound of the invention is of formula (Iq), or a pharmaceutically acceptable salt or hydrate thereof:

(Iq)

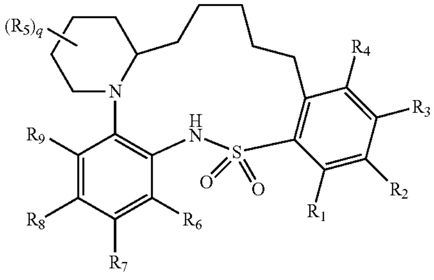

where q and $R_{1-9}$ are as defined above.

In one preferred embodiment, the compound of the invention is of formula (Ir), or a pharmaceutically acceptable salt or hydrate thereof:

(Ir)

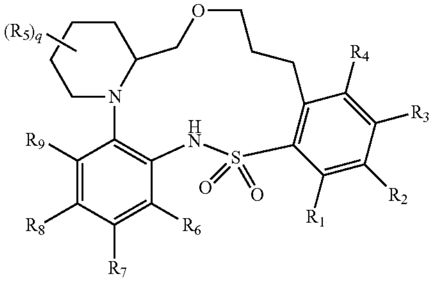

where q and $R_{1-9}$ are as defined above.

In the above preferred embodiments, q is preferably 0.

Advantageously, compounds of formula (I) with a 4-atom linker, L, e.g. compounds of formulae (Id) or (Ig) or (Im), or a 5-atom linker, L, e.g. compounds of formulae (Ie) or (If) or (Ij) or (In) or (Ip) or (Iq) or (Ir), display high potency (as measured using an in vitro assay) and good permeability. Compounds of formula (I) with a 5-atom saturated linker, L, e.g. compounds of formula (Ie) or (Iq) or (Ir), or a 4- or 5-atom unsaturated linker, L, e.g. compounds of formula (If) or (Ig) or (Ij) or (Im) or (In) or (Ip) display particularly good potency as measured using an in vitro assay. Further details of these properties are described in the accompanying examples.

In one preferred embodiment, $R_2$ is selected from COOH, tetrazolyl and $C(O)NHSO_2R_{24}$, where $R_{24}$ is $C_{1-3}$-alkyl or cyclopropyl, more preferably Me, isopropyl or cyclopropyl. Preferably, $R_2$ is selected from COOH, tetrazolyl and $C(O)NHSO_2Me$, $C(O)NHSO_2iPr$ and $C(O)NHSO_2$-cyclopropyl. More preferably, $R_2$ is COOH.

In one preferred embodiment, $R_3$ is selected from H, Cl and alkyl.

In one preferred embodiment, $R_7$ is selected from CN, haloalkyl, $SO_2$-alkyl, $SO_2NR_{18}R_{19}$ and tetrazolyl.

In one preferred embodiment, $R_7$ is selected from $CF_3$, CN and $SO_2Me$.

In one preferred embodiment, $R_8$ is selected from H, Cl, F and Me, more preferably H, Cl and F.

In one preferred embodiment, $R_1$, $R_3$ and $R_4$ are all H.

In one preferred embodiment, $R_6$ and $R_9$ are H.

In one preferred embodiment, $R_9$ is H, $C_{1-6}$-alkyl or chloro, more preferably, H or $C_{1-6}$-alkyl, even more preferably H.

In one preferred embodiment, $R_{11}$ is H or $C_{1-6}$-alkyl, more preferably, H or Me, even more preferably H.

In one preferred embodiment, $R_{12-21}$ are each independently H or $C_{1-6}$-alkyl, more preferably, H or Me, even more preferably H.

In one preferred embodiment, the compound is selected from the following:

(1)

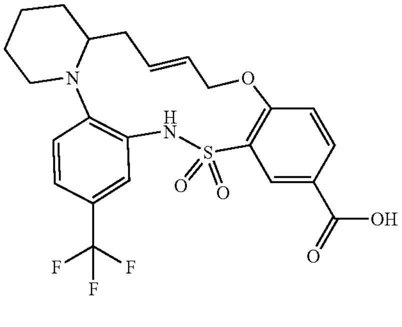

-continued
(2)
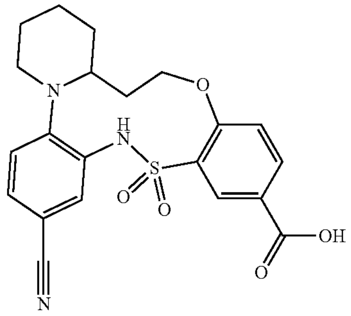
(6) E1
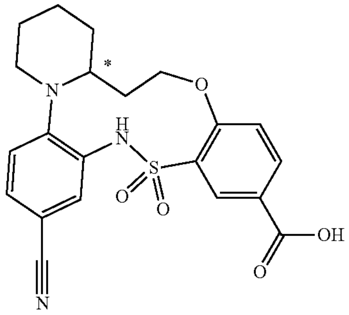
(7) E2
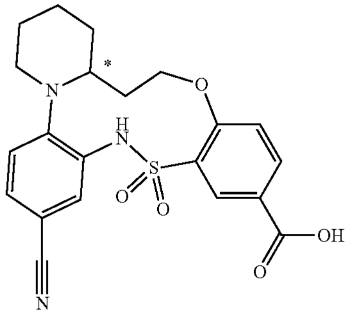
(3)
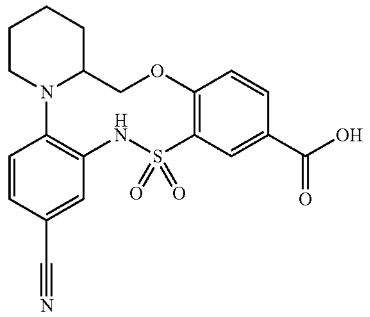
(10) E1
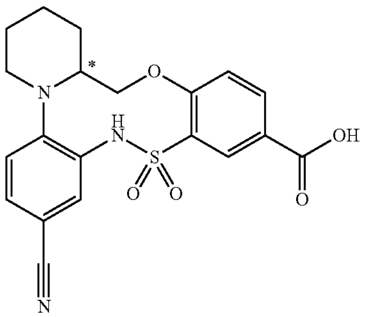
-continued
(11) E2
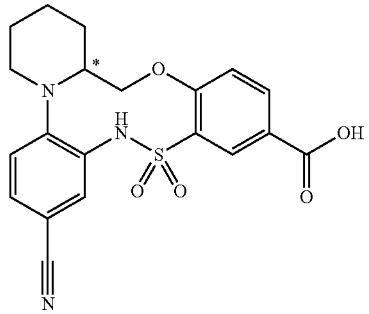
(4)
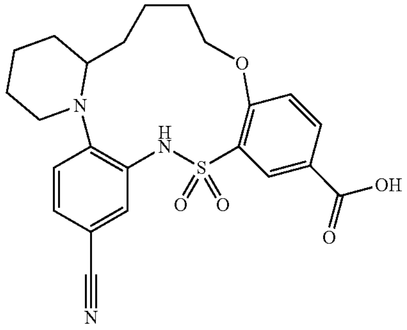
(12) E1
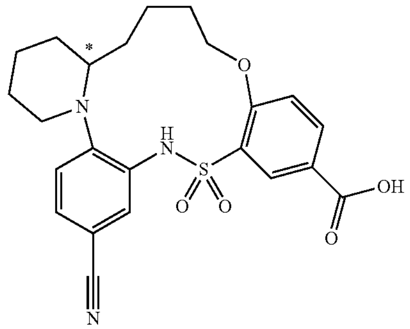
(13) E2
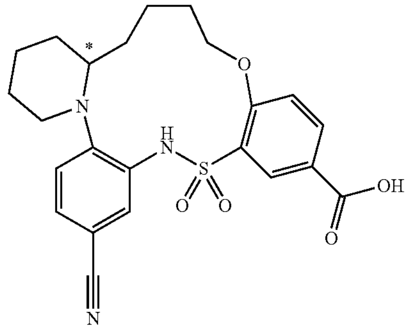
(5)
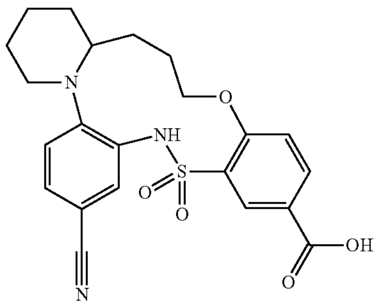

-continued
(8) E1
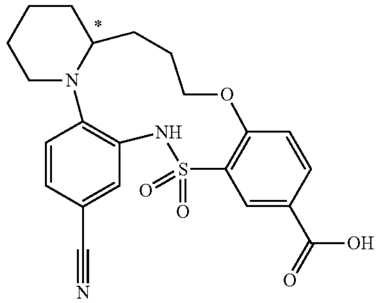
(9) E2
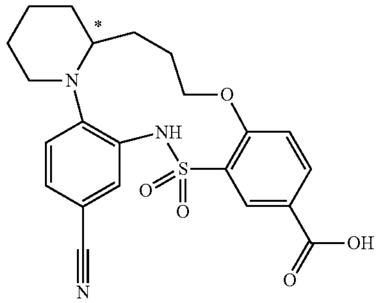
(14)
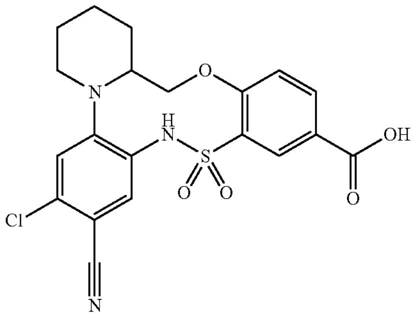
(16) E1
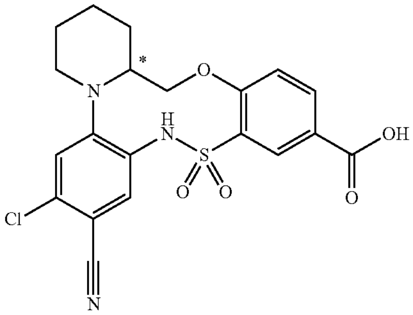
(17) E2
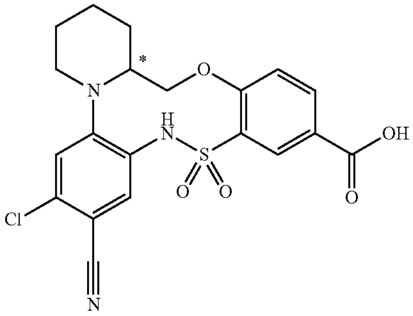
-continued
(15)
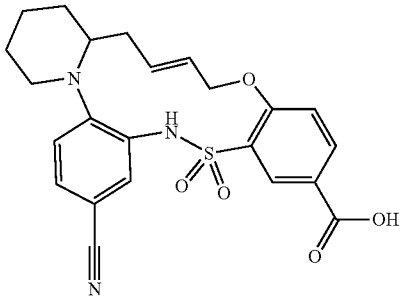
(32) E1
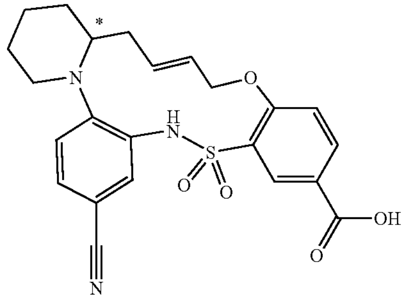
(33) E2
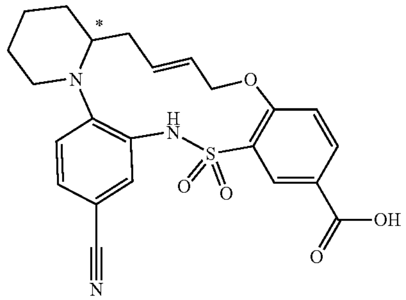
(18)
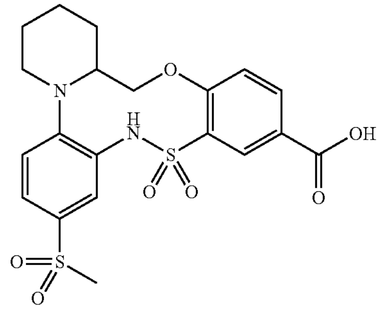
(19) E1
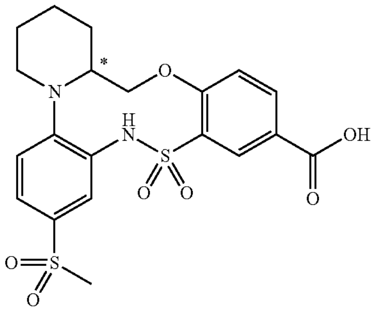

-continued
(20) E2
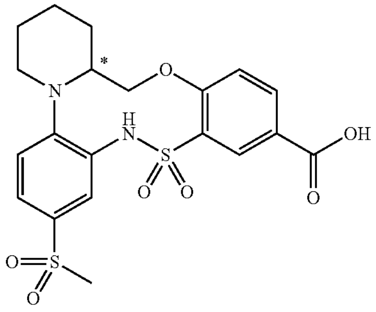
(21)
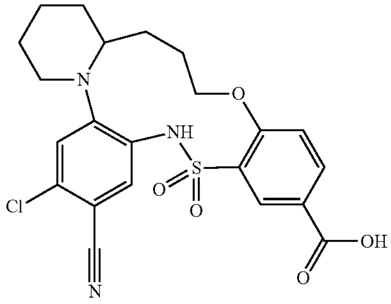
(22)
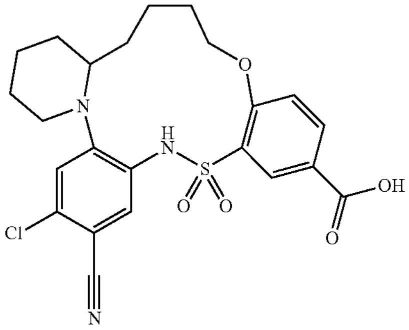
(26) E1
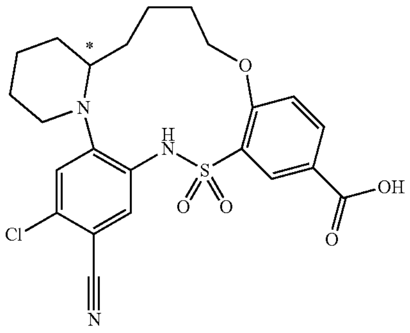
(27) E2
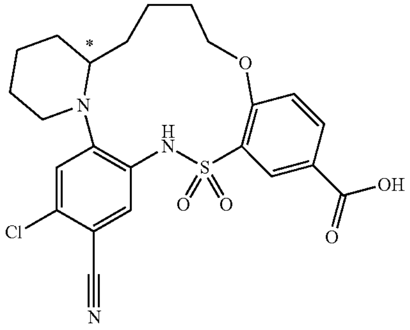
-continued
(52) or (26R)
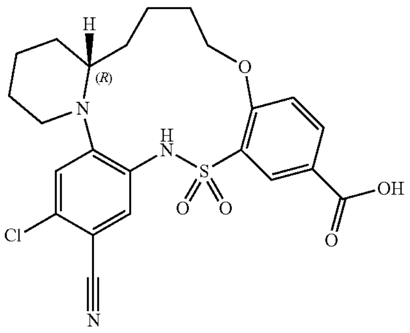
(53) or (27S)
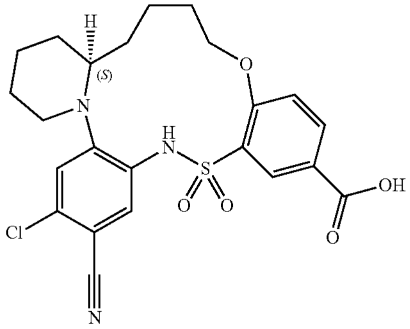
(23)
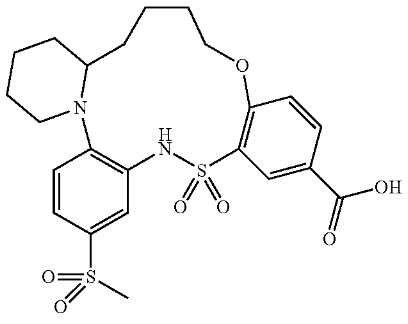
(24)
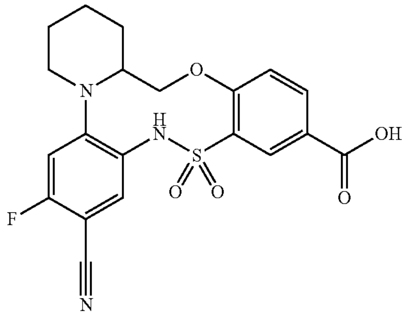

-continued
(37) E1
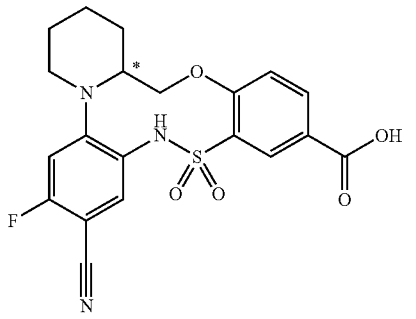
(38) E2
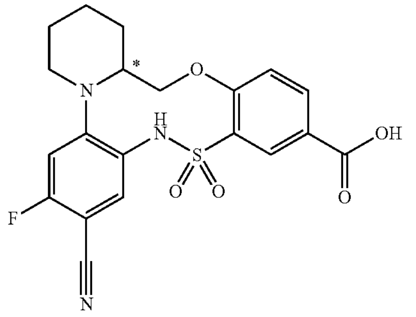
(25)
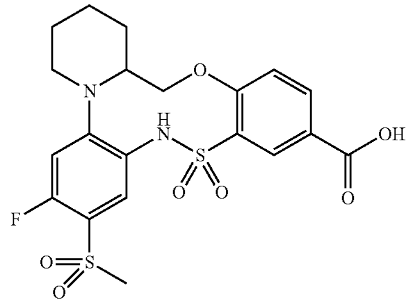
(39) E1
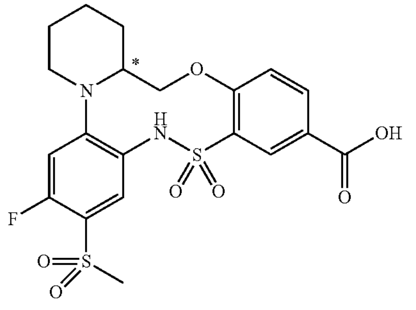
(40) E2
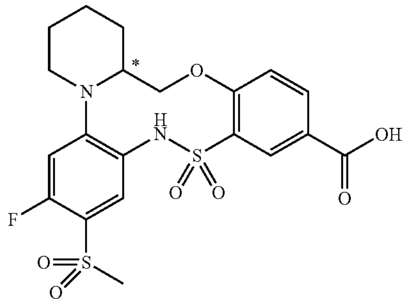
-continued
(28)
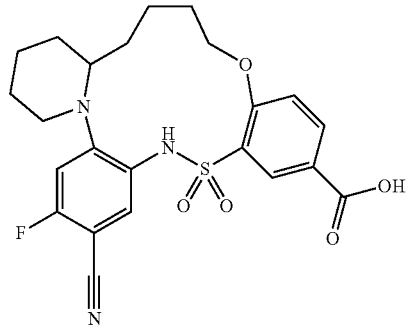
(55) E1
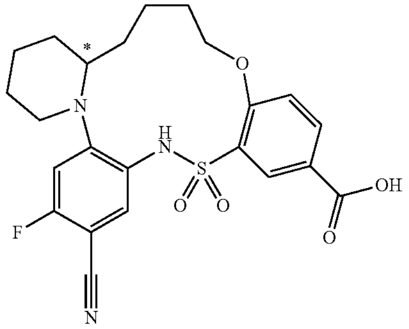
(56) E2
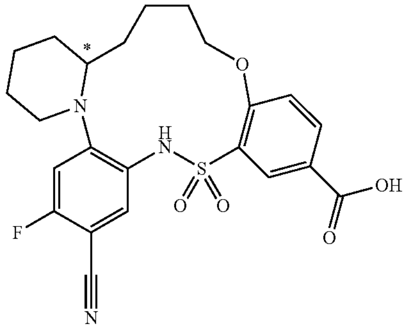
(29)
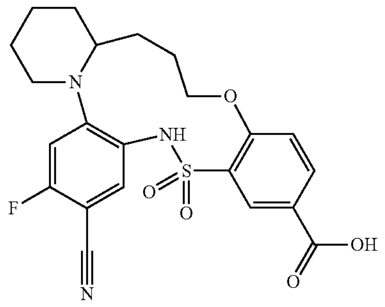
(41) E1
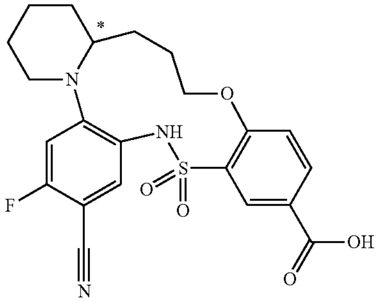

-continued
(42) E2
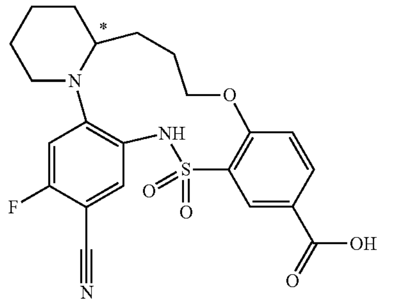
(30)
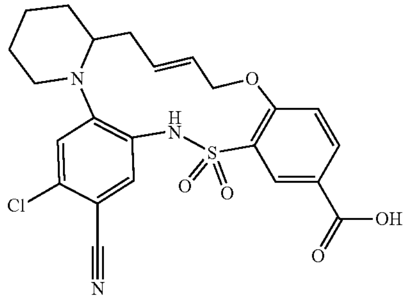
(45) E1
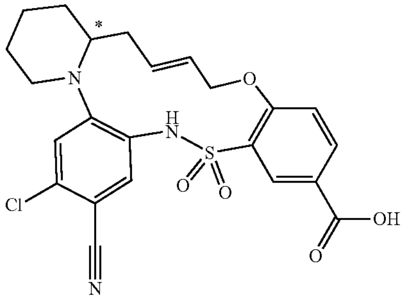
(46) E2
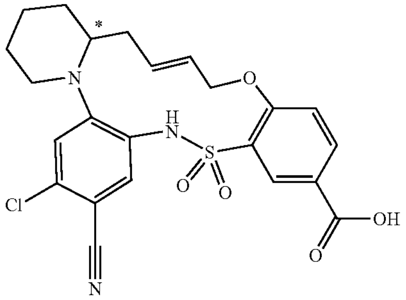
(31)
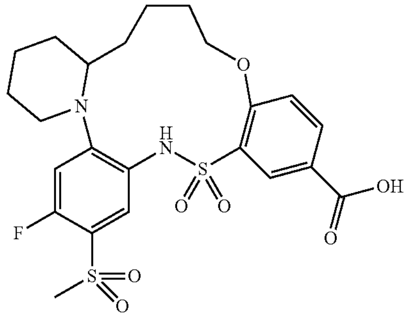
-continued
(43) E1
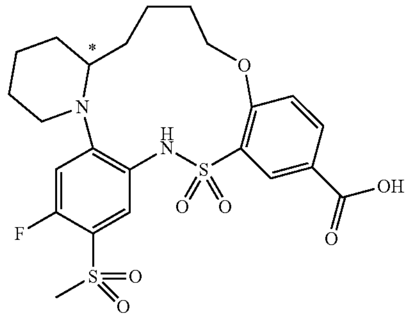
(44) E2
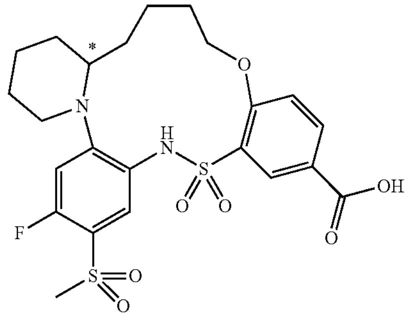
(34)
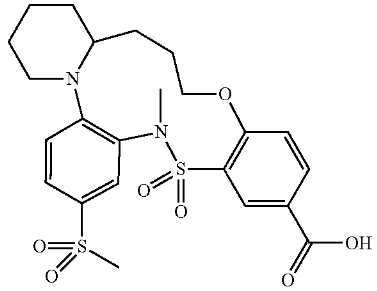
(35)
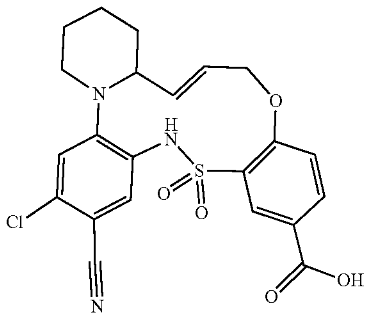
(47) E1
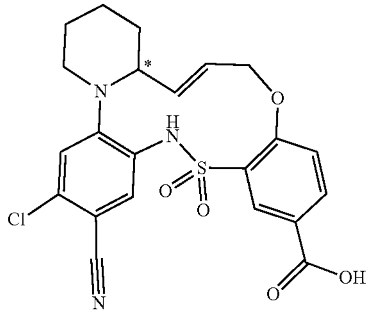

-continued
(48) E2
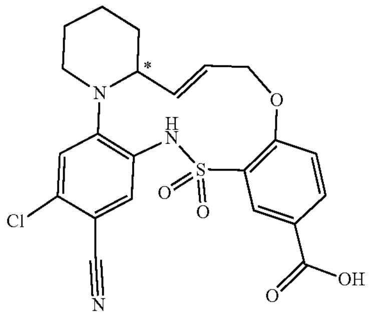
(36)
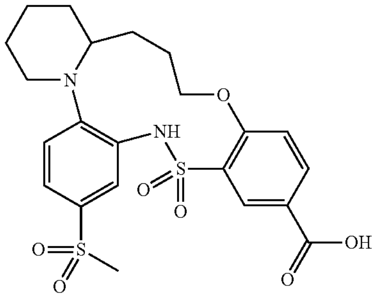
(49) E1
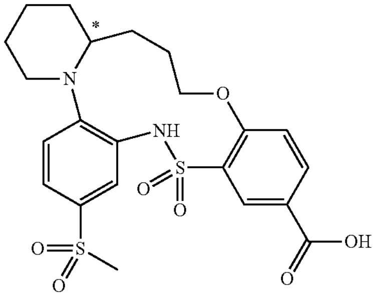
(50) E2
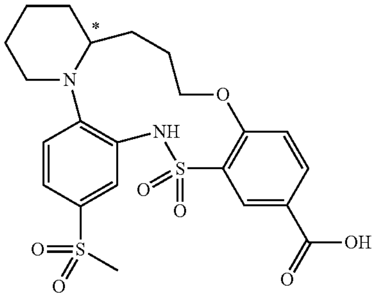
(51)
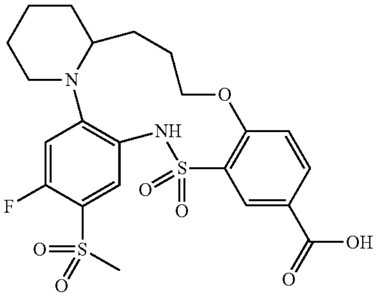
-continued
(54)
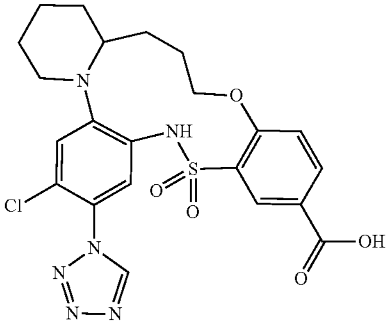
(57)
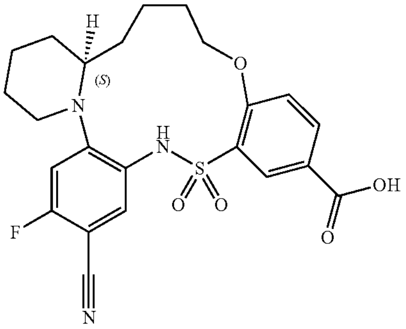
(58) from (48) E2
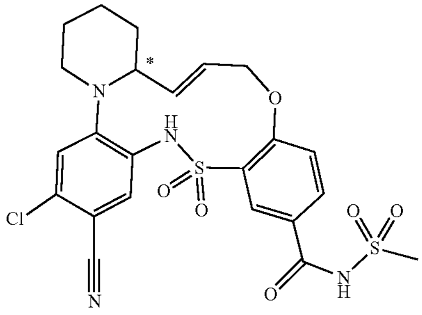
(59)
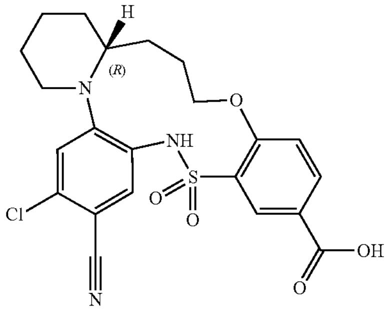
(60)
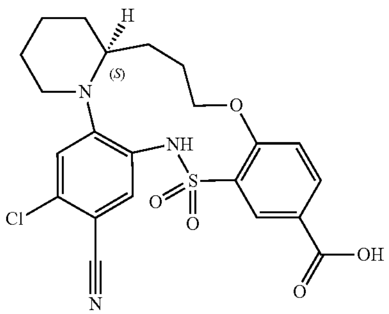

-continued
(61)
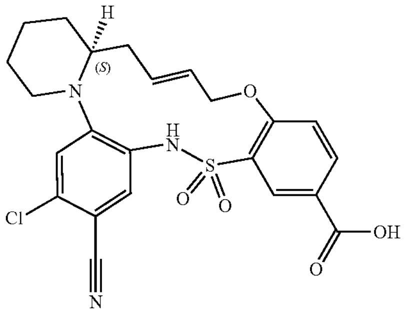
(62)
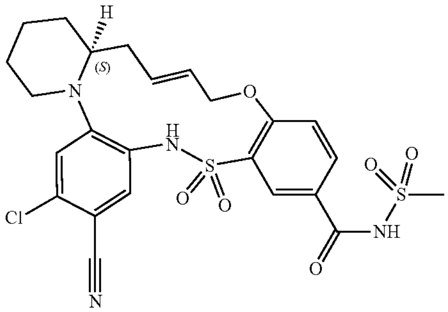
(63)
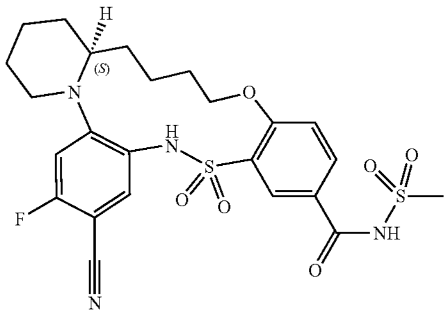
(64)
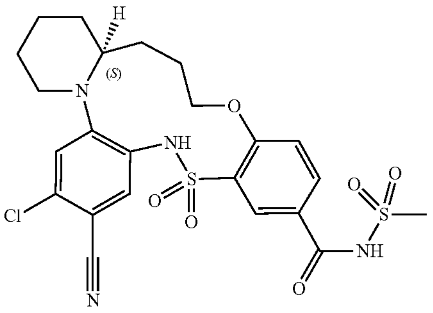
(65)
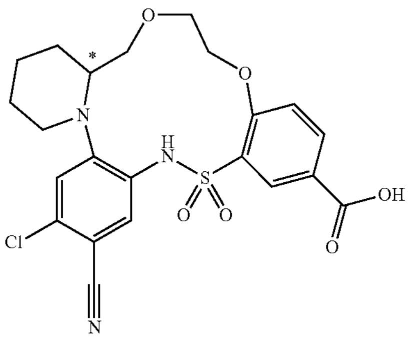
-continued
(67) E1
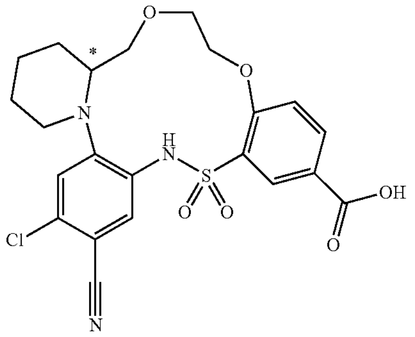
(68) E2
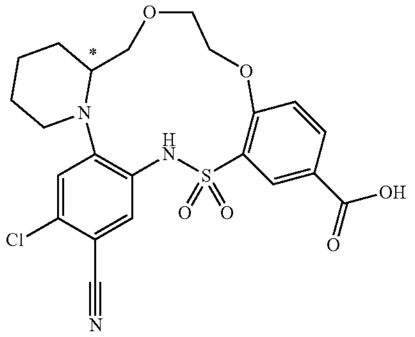
(69)
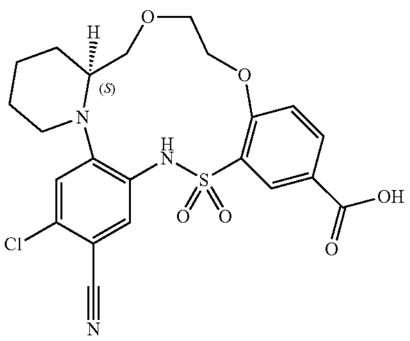
(66)
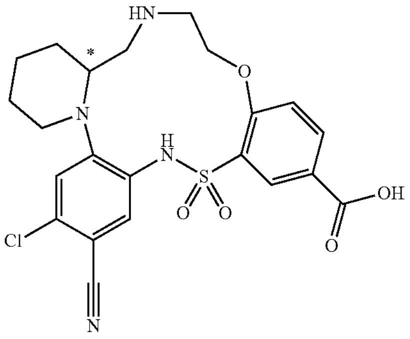

-continued (70)

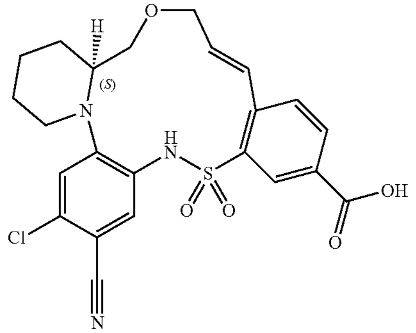

(71)

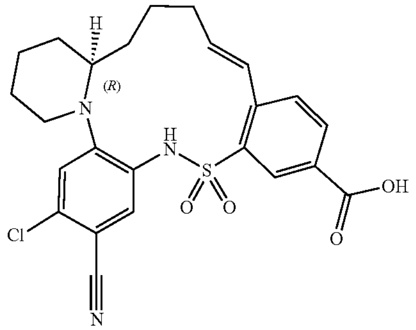

(72)

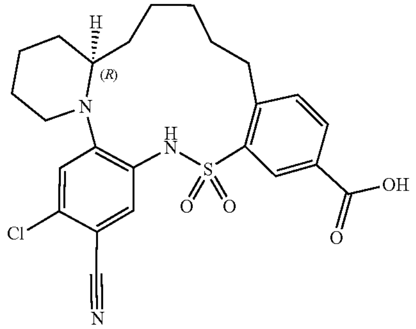

(73)

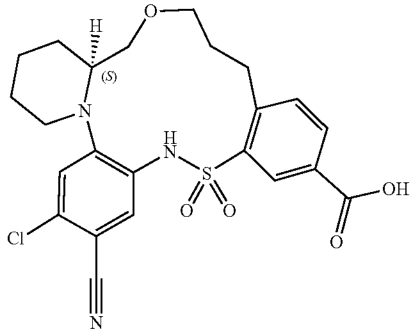

and pharmaceutically acceptable salts and hydrates thereof. Examples are racemic at the single chiral centre, otherwise, E1 and E2 refer to separated enantiomers 1 and 2 of undefined absolute configuration.

In one preferred embodiment, the compound of the invention exhibits an 1050 against Decapeptide WRVYEKC (Dnp)ALK-acid (where Dnp is Dinitrophenyl maleimide) (10-mer) of 250 nM to 1000 nM, more preferably, <250 nM. Further details of this assay are detailed in the accompanying examples.

In one preferred embodiment, the compound of the invention is selected from the following compounds: (1), (3)-(5), (8)-(15), (17)-(19), (21)-(32), (34)-(36), (38), (39) and (41)-(57), (59), (60), (61), (65), (67)-(73).

In an even more preferred embodiment, the compound of the invention is selected from the following compounds: (1), (3)-(5), (8)-(10), (13)-(15), (17), (19), (21), (22), (24)-(32), (34)-(36), (38), (39), (41)-(43), (45), (46), (48), (49) and (52)-(57), (59), (60), (61), (65), (67)-(70), (72) and (73).

Therapeutic Applications

One aspect of the invention relates to compounds as described herein for use in medicine. The compounds have particular use in the field of oncology and immuno-oncology, as described in more detail below.

Yet another aspect of the invention relates to compounds as described herein for use in treating or preventing a disorder selected from a proliferative disorder, an immune disorder, an inflammatory disorder and a viral disorder.

In a preferred embodiment, the compound of the invention modulates ERAP1.

In one embodiment the compound inhibits the activity of ERAP1.

In an alternative embodiment the compound increases the activity of ERAP1.

In one embodiment the compound of the invention may change the repertoire of presented antigens.

One aspect of the invention relates to a compound as described herein for use in treating a proliferative disorder. Preferably, the proliferative disorder is a cancer or leukemia.

A cancer may be selected from: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

Without wishing to be bound by theory, it is understood that ERAP1 modulators are capable of changing at least 10% of the antigen and neoantigen repertoire of cancer cells, as measured using immunopeptidomics and mass spectrometry analysis. Approximately 50% of this change is an upregulation in the presentation of certain antigens and neoantigens, whilst the other 50% is the presentation of entirely novel antigens and neoantigens. Both changes lead to an increase in the visibility of the tumour to the immune system, leading to measurable changes in the $CD8^+$ T cell repertoire and $CD8^+$ T cell activation status. This change in $CD8^+$ T cell response leads to immune-mediated tumour clearance and can be potentially enhanced by combining with cancer therapeutics such as antibody checkpoint inhibitors (e.g. anti-PD-1).

Without wishing to be bound by theory, it is understood that modulators of ERAP1 cause killing of cancer cells by natural killer (NK) cells due to disruption of the interaction between killer cell Ig-like receptors (KIR) or lectin-like receptor CD94-NKG2A on NK cells with classical or non-classical MHC-I-peptide (pMHC-I) complexes on cancer cells.

In one preferred embodiment, the disorder is cancer, and the compound increases the visibility of cancer cells to the immune system by altering the repertoire of antigens and neoantigens presented to the immune system.

A further aspect of the invention relates to a method of increasing the visibility of cancer cells to the immune system in a subject by altering the repertoire of antigens and neoantigens presented to the immune system, said method comprising administering to the subject a compound as described herein.

In one preferred embodiment, the compound increases the CD8+ T cell response to the cancer cell.

In one preferred embodiment, the compound of the invention is for use in the treatment of a disease of uncontrolled cell growth, proliferation and/or survival, an inappropriate cellular immune response, or an inappropriate cellular inflammatory response, particularly in which the uncontrolled cell growth, proliferation and/or survival, inappropriate cellular immune response, or inappropriate cellular inflammatory response is modulated by the ERAP1 pathway.

In one preferred embodiment, the disease of uncontrolled cell growth, proliferation and/or survival, inappropriate cellular immune response, or inappropriate cellular inflammatory response is selected from a haematological tumour, a solid tumour and/or metastases thereof.

More preferably, the compound is for use in treating a disorder selected from leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The compound may kill cancer cells, reduce the number of proliferating cells in the cancer and/or reduce the volume or size of a tumour comprising the cancer cells. The compound may reduce the number of metastasising cancer cells.

In one embodiment the compound may be used in treating cancer in a subject who has previously had cancer. The compound may be used to reduce the likelihood of the cancer recurring, or the likelihood of further cancer developing. The compound may induce a neoantigen in the recurring or further cancer to which the subject already possesses an existing immune response. As such, the compound may increase or boost an immune response against the cancer.

In one embodiment the compound is for use in preventing cancer. The compound may be used for prophylaxis against the development of cancer. That is to say, the compound may stimulate an immune response, such as a vaccine response, against a future cancer. The compound may stimulate in a subject an immune response directed to a neoantigen. Once a cancer develops in the subject, they may be treated again with the compound (or a different compound) to stimulate development of the same neoantigen, thereby eliciting the subject's pre-existing immune response to said neoantigen to treat or prevent the cancer.

The same or a different compound may be used before and after the cancer develops in a subject.

In one embodiment the compound may be used for the prevention of cancer.

In one embodiment the subject may previously have had cancer, may have a familial history of cancer, may have a high risk for developing cancer, may have a genetic predisposition to developing cancer, or may have been exposed to a carcinogenic agent. In one embodiment the subject may be in remission from cancer.

One embodiment provides ex vivo generated antigen-presenting cells, such as dendritic cells (DCs). The antigen-presenting cells may be produced ex vivo to present neoantigens, such as those generated by a compound according to the present invention. The compound may be used in a method for producing ex vivo an antigen-presenting cell which presents a neo-antigen, and wherein the cell may be used as a vaccine against cancer.

The antigen presenting cell such as a dendritic cell may be pulsed or loaded with the neo-antigen or genetically modified (via DNA or RNA transfer) to express one, two or more neo-antigens. Methods of preparing dendritic cell vaccines are known in the art.

The neo-antigen may be generated from the subject's normal tissue in which ERAP1 is modulated with a compound according to the invention. Sources of normal tissue may be fibroblasts or B cells, for example, that can be readily expanded in vitro. Alternatively, RNA from the cancer, total or mRNA enriched poly A+ RNA may be used. Poly A+ RNA can be also amplified to generate sufficient antigen for DC loading and thereby limit the ex vivo culture step.

In one embodiment a dendritic cell which has been treated with the compound as described above may be used to treat a subject. The dendritic cell may be contacted with the compound ex vivo, and then the dendritic cell may be administered to the subject. The compound may therefore be used in vitro or in vivo, for example either for in situ treatment or for ex vivo treatment followed by the administration of the treated cells to the subject.

Another aspect of the invention relates to a compound as described above for use in treating an immune disorder. In one preferred embodiment, the immune disorder is an autoimmune disorder.

Examples of the autoimmune disorders include, but are not limited to: rheumatoid arthritis (RA), myasthenia gravis (MG), multiple sclerosis (MS), systemic lupus erythematosus (SLE), autoimmune thyroiditis (Hashimoto's thyroiditis), Graves' disease, inflammatory bowel disease, autoimmune uveoretinitis, polymyositis and certain types of diabetes, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia, psoriasis, Behçet's disease, birdshot chorioretinopathy and autoimmune polyendocrinopathies.

Polymorphisms in the ERAP1 gene that impact ERAP1 enzymatic activity are strongly associated with an increased risk of autoimmunity, including the diseases ankylosing spondylitis, psoriasis, Behçet's disease and birdshot chorioretinopathy[11]. Variants of ERAP1 that reduce ERAP1 enzymatic activity are protective against disease, whilst those that reportedly elevate activity are associated with increased disease risk[12]. This suggests that modulation of ERAP1 activity could be an effective treatment for autoimmune diseases.

Thus, in one preferred embodiment, the immune disorder is selected from ankylosing spondylitis, psoriasis, Behçet's disease and birdshot chorioretinopathy.

In one preferred embodiment, the immune disorder is ankylosing spondylitis. Ankylosing spondylitis (AS) is a type of arthritis in which there is long term inflammation of the joints of the spine. Typically the joints where the spine joins the pelvis are also affected. Occasionally other joints such as the shoulders or hips are involved. Between 0.1% and 1.8% of people are affected and onset is typically in young adults. Although the cause of ankylosing spondylitis is unknown, it involves a combination of genetic and environmental factors. More than 90% of those affected have a specific human leukocyte antigen known as the HLA-B27 antigen.[13] In addition, certain variants of ERAP1, in conjunction with HLA-B27, are clearly associated with either an elevated or reduced risk of disease, providing evidence of a clear role for modulated antigen presentation in disease.[18] There is no cure for ankylosing spondylitis and current treatments serve only to improve symptoms and prevent worsening. Medications used to date include NSAIDs, steroids, DMARDs such as sulfasalazine, and biologic agents such as infliximab.

In one preferred embodiment, the immune disorder is Behçet's disease (BD). Behçet's disease (BD) is a type of inflammatory disorder which affects multiple parts of the body. The most common symptoms include painful mouth sores, genital sores, inflammation of parts of the eye, and arthritis. The cause is not well-defined, and whilst environmental factors play a role, genetic studies have shown an increased risk of disease in patients carrying HLA-B51 in conjunction with specific variants of ERAP1.[19] The disease is primarily characterized by auto-inflammation of the blood vessels, hence it is sometimes characterised as an auto-inflammatory disease. There is currently no cure for Behçet's disease, but the symptoms can be controlled with medicines that reduce inflammation in the affected parts of the body, for example, with corticosteroids, immunosuppressants or biological therapies that target the biological processes involved in the process of inflammation.

In one preferred embodiment, the immune disorder is birdshot chorioretinopathy. Birdshot chorioretinopathy, also known as Birdshot Uveitis or HLA-A29 Uveitis, is a rare form of bilateral posterior uveitis affecting the eye. It causes severe, progressive inflammation of both the choroid and retina. Symptoms include floaters, blurred vision, photopsia (flashing lights in eyes), loss of color vision and nyctalopia. Birdshot chorioretinopathy is thought to be an autoimmune disease. The disease has strong association with the Human leukocyte antigen haplotype (HLA)-A29. This indicates a role for T-lymphocytes in the pathogenesis. Birdshot chorioretinopathy is associated with IL-17, a hallmark cytokine of TH17 cells that play an important role in autoimmunity.[15, 16] A genome-wide association study has ascertained HLA-A29:02 as the primary risk factor and identified that both ERAP1 and ERAP2 are associated with birdshot chorioretinopathy.[17, 20] Genetic variants within the ERAP1 and ERAP2 loci modulate enzyme activity and also mRNA and protein expression. ERAP2 is an aminopeptidase that, together with ERAP1, trims peptides in the endoplasmic reticulum and loads these peptides on HLA molecules for presentation to T cells of the immune system.

In one preferred embodiment, the immune disorder is psoriasis. Psoriasis is a chronic skin disease in which skin cells rapidly build up on the surface of the skin forming scales and red patches that are itchy and sometimes painful. The cause is not well-defined but includes both environmental and genetic factors. HLA-006 strongly associates with risk of disease and variants in ERAP1, possibly in conjunction with HLA-006, are also strongly associated with disease.[21] There is no cure for psoriasis and current treatments serve only to improve symptoms and prevent worsening. Medications used in therapy include steroids, methotrexate, sulfasalazine, and biologic agents such as etanercept.

Another aspect of the invention relates to a compound as described above for use in treating or preventing a viral disorder. Modulators of ERAP1 such as the compounds described herein are capable of changing the antigen repertoire of multiple viruses, which leads to the recognition and destruction of viral infected cells. Accordingly, ERAP1 modulators have potential therapeutic applications in the treatment of viral infection and diseases. ERAP1 modulates certain viral antigens, including those from human papilloma virus (HPV), human cytomegalovirus (CMV) hepatitis C (HCV) and human immunodeficiency virus (HIV)[8, 9, 10]. In addition, knockdown of ERAP1 in HPV infected cells changes the repertoire of presented HPV antigens leading to greater recognition by $CD8^+$ T cells[6].

In one preferred embodiment, the viral disorder is a viral disease or viral infection selected from HIV, HPV, CMV and HCV.

In one preferred embodiment, the viral disorder is HIV.

In one preferred embodiment, the viral disorder is HPV.

In one preferred embodiment, the viral disorder is CMV.

In one preferred embodiment, the viral disorder is HCV.

Another aspect relates to a compound as described herein for use in the prevention or treatment of a disorder caused by, associated with or accompanied by abnormal activity against ERAP1.

Another aspect relates to a compound as described herein for use in the prevention or treatment of an ERAP1-associated disease or disorder.

Yet another aspect relates to the use of a compound as described herein in the preparation of a medicament for the prevention or treatment of a disorder caused by, associated with or accompanied by any abnormal activity against ERAP1.

As used herein the phrase "preparation of a medicament" includes the use of the components of the invention directly as the medicament in addition to their use in any stage of the preparation of such a medicament.

Another aspect relates to the use of a compound as described above in the preparation of a medicament for treating or preventing a disorder selected from a proliferative disorder, an immune disorder, a viral disorder and an inflammatory disorder.

Yet another aspect relates to the use of a compound as described herein in the preparation of a medicament for the prevention or treatment of an ERAP1-associated disease or disorder.

Another aspect of the invention relates to a method of treating an ERAP1-associated disease or disorder in a subject. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Another aspect relates to a method of treating a disorder selected from a proliferative disorder, an immune disorder, a viral disorder and an inflammatory disorder in a subject, said method comprising administering to the subject a compound as described herein.

Yet another aspect of the invention relates to a method of treating a subject having a disease state alleviated by modulation of ERAP1 wherein the method comprises administering to the subject a therapeutically effective amount of a compound according to the invention.

Another aspect relates to a method of treating a disease state alleviated by modulation of ERAP1, wherein the method comprises administering to a subject a therapeutically effective amount of a compound according to the invention.

Preferably, the subject is a mammal, more preferably a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "ERAP1-related disease or disorder" refers to a disease or disorder characterized by inappropriate ERAP1 activity. Inappropriate activity refers to either an increase or decrease in ERAP1 activity relative to wildtype ERAP1 (Uniprot ID Q9NZ08), caused by variation in the ERAP1 protein sequence, as measured by enzyme or cellular assays. Inappropriate activity could also be due to overexpression of ERAP1 in diseased tissue compared with healthy adjacent tissue.

Preferred diseases or disorders that the compounds described herein may be useful in preventing include proliferative disorders, viral disorders, immune disorders and inflammatory disorders as described hereinbefore.

Thus, the present invention further provides use of compounds as defined herein for the preparation or manufacture of medicaments for the treatment of diseases where it is desirable to modulate ERAP1. Such diseases include proliferative disorders, viral disorders, immune disorders and inflammatory disorders as described hereinbefore.

In one preferred embodiment, the compound activates ERAP1's conversion of (L)-leucine-7-amido-4-methylcoumarin (L-AMC) to (L)-leucine and the fluorescent molecule 7-amino-4-methylcoumarin. While the same assay can also identify inhibitors of ERAP1's cleavage of the amide bond in L-AMC, for the purposes of this application this assay is referred to as the "L-AMC activator assay". The potency of any activator is calculated and expressed as the concentration of the activator required to increase the enzyme activity of ERAP1 by 50% over its baseline level (i.e. an $EC_{50}$).

In one preferred embodiment, the compound exhibits an $EC_{50}$ value in an L-AMC activator assay of less than about 25 μM. More preferably, the compound exhibits an $EC_{50}$ value in the L-AMC activator assay of less than about 10 μM, more preferably, less than about 5 μM, even more preferably, less than about 1 μM, even more preferably, less than about 0.1 μM, even more preferably, less than about 0.01 μM.

In one preferred embodiment, the compound inhibits ERAP1's ability to hydrolyse the decapeptide substrate WRVYEKCdnpALK. This peptide has minimal fluorescence as the N-terminal tryptophan residue's fluorescence is quenched by the dinitrophenol (DNP) residue within the peptide. However, as ERAP1 hydrolyses the N-terminal amide bond and tryptophan is released this internal quenching is lost and the reaction is monitored by the increase in tryptophan fluorescence over the course of the assay. For the purposes of this application this assay is referred to as the "1 Omer inhibition assay" and compound potencies are calculated and expressed as 1050 as would be familiar to a person skilled in the art.

In one preferred embodiment, the compound exhibits an $IC_{50}$ value in the 10mer assay of less than about 25 μM. More preferably, the compound exhibits an $IC_{50}$ value in the 10mer assay of less than about 10 μM, more preferably, less than about 5 μM, even more preferably, less than about 1 μM, even more preferably, less than about 0.1 μM, even more preferably, less than about 0.01 μM.

Pharmaceutical Compostions

The invention also relates to pharmaceutical compositions comprising a compound as described herein in admixed with a pharmaceutically acceptable diluent, excipient or carrier. For use according to the present invention, the compounds or physiologically acceptable salts, esters or other physiologically functional derivatives thereof, described herein, may be presented as a pharmaceutical formulation, comprising the compounds or physiologically acceptable salt, ester or other physiologically functional derivative thereof, together with one or more pharmaceutically acceptable carriers therefor and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and PJ Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant (s), suspending agent(s), coating agent(s), solubilising agent (s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound as described herein into conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3$^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

The present invention also includes all suitable isotopic variations of the compound or a pharmaceutically acceptable salt thereof. An isotopic variation of a compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}O$, $^{14}O$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Atropisomers

Some of the compounds of the invention may exist as atropisomers. Atropisomers are stereoisomers arising because of hindered rotation about a single bond, where energy differences due to steric strain or other contributors create a barrier to rotation that is high enough to allow for isolation of individual conformers. The invention encompasses all such atropisomers.

Prodrugs

The invention further includes the compounds of the present invention in prodrug form, i.e. covalently bonded compounds which release the active parent drug in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms. Preferably, the solvate is a hydrate.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The dosages disclosed herein are exemplary of the average case. There can of course be individual instances where higher or lower dosage ranges are merited, and such are within the scope of this invention.

The dosage amount will further be modified according to the mode of administration of the compound. For example, to achieve an "effective amount" for acute therapy, parenteral administration of a compound is typically preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to modulate ERAP1. The compounds may be administered one to four times daily at a level to achieve a total daily dose of about 0.4 to about 400 mg/kg/day. The precise amount of a compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

A further aspect of the invention relates to a combination comprising a compound as described herein and one or more additional active agents. In a particularly preferred embodiment, the one or more compounds of the invention are administered in combination with one or more additional active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

In one preferred embodiment, the additional active agent is an immunotherapy agent, more preferably a cancer immunotherapy agent. An "immunotherapy agent" refers to a treatment that uses the subject's own immune system to fight diseases such as cancer.

In one preferred embodiment the compound of the invention inhibits the activity of ERAP1, and the compound is administered in combination with an immunotherapy. The compound may increase the sensitivity of cancer cells to an immunotherapy. The immunotherapy may be mediated by T cells. In one embodiment the compound may increase the number of CD8+ T cells in a tumour.

In one embodiment the compound may be used to treat cancers which are weakly responsive or not responsive to immunotherapies.

In one preferred embodiment, the additional active agent is a molecule capable of immune checkpoint intervention, a co-stimulatory antibody, a chemotherapy agent, a radiotherapy agent, a targeted therapy agent or an antibody, particularly a monoclonal antibody.

In one preferred embodiment the additional active agent is a molecule capable of immune checkpoint intervention.

Immune checkpoint molecules include CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRP, CD47, CD48, 2B4, B7.1, B7.2, ILT-2, ILT-4, TIGIT, HHLA2, IDO, CD39, CD73, A2aR and butyrophilins.

Immune checkpoint molecules include both inhibitory and activatory molecules, and interventions may apply to either or both types of molecule.

Immune checkpoint inhibitors include, but are not limited to, PD-1 inhibitors, PD-L1 inhibitors, LAG-3 inhibitors, TIM-3 inhibitors, TIGIT inhibitors, BTLA inhibitors and CTLA-4 inhibitors, for example. Co-stimulatory antibodies deliver positive signals through immune-regulatory receptors including but not limited to ICOS, CD137, CD27 OX-40 and GITR.

In one highly preferred embodiment, the additional active agent is an antibody checkpoint inhibitor. Suitable examples of antibody checkpoint inhibitors, include, but are not limited to, anti-PD-1 antibodies, anti-PD-L1 antibodies and anti-CTLA4 antibodies. In one preferred embodiment, the antibody checkpoint inhibitor is an anti-PD-1 antibody, more preferably selected from pembrolizumab, cemiplimab and nivolumab.

In one preferred embodiment, the antibody checkpoint inhibitor is an anti-PD-L1 antibody, more preferably selected from atezolizumab, avelumab and durvalumab.

In one preferred embodiment, the antibody checkpoint inhibitor is an anti-CTLA4 antibody, more preferably selected from ipilimumab and tremelimumab.

In one preferred embodiment the immunotherapy is an anti-cancer vaccine or virus, such as an oncolytic virus.

In one preferred embodiment the immunotherapy is a cell-based therapy. In one embodiment the cell-based therapy may be a T cell therapy, such as adoptive T cell therapy, or therapy with CAR-T cells.

Adoptive cell-based immunotherapy may include the following: Irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, for example expressing cytokines such as GM-CSF, and/or to express tumor-associated antigen (TAA) antigens, such as Mage-1, gp-100, patient-specific neoantigen vaccines, and the like.

In a further embodiment, the immunotherapy may comprise non-cell-based immunotherapies. In one embodiment, compositions comprising antigens with or without vaccine-enhancing adjuvants may be used. Such compositions exist in many well-known forms, such as peptide compositions, oncolytic viruses, and recombinant antigen comprising fusion proteins.

In an alternative embodiment, immunomodulatory interleukins, such as IL-2, IL-6, IL-7, IL-12, IL-17, IL-23, as well as modulators thereof (e.g., blocking antibodies or more potent or longer lasting forms) may be used. Immunomodulatory cytokines, such as interferons, G-CSF, imiquimod, T F alpha, and the like, as well as modulators thereof (e.g., blocking antibodies or more potent or longer lasting forms) may also be used. In another embodiment, immunomodulatory chemokines, such as CCL3, CCL26, and CXCL7, and the like, as well as modulators thereof (e.g., blocking antibodies or more potent or longer lasting forms) may be used. In a further embodiment, immunomodulatory molecules targeting immunosuppression, such as STAT3 signaling modulators, FkappaB signaling modulators, and immune checkpoint modulators, may be used.

In another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (Cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an EVIPDH inhibitor, mycophenolic acid, myriocin, fingolimod, an NF-xB inhibitor, raloxifene, drotrecogin alfa, denosumab, an F-xB signaling cascade inhibitor, disulfiram, olmesartan, dithiocarbamate, a proteasome inhibitor, bortezomib, MG132, Prol, PI-0052, curcumin, genistein, resveratrol, parthenolide, thalidomide, lenalidomide, flavopiridol, non-steroidal anti-inflammatory drugs (NSAIDs), arsenic tri oxide, dehydroxymethylepoxyquinomycin (DHMEQ), I3C(indole-3-carbinol)/DIM(di-indolmethane) (13C/DIM), Bay 1 1-7082, luteolin, cell permeable peptide SN-50, IKBa-super repressor overexpression, FKB decoy oligodeoxynucleotide (ODN), or a derivative or analog of any thereto, may be used.

In yet another embodiment, immunomodulatory antibodies or protein may be used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CDII a antibody, efalizumab, an anti-CD 18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-S antibody, mepolizumab, an IgE inhibitor, omalizumab, talizumab, an IL12 inhibitor, an IL23 inhibitor, ustekinumab.

In one embodiment, the subject may be undergoing or have previously undergone treatment with a chemotherapeutic agent. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM 1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-a, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

Process

Compounds of formula (I) containing an alkenyl linker can be prepared by ring closing metathesis.

Thus, in one embodiment the invention relates to a process for preparing a compound of formula (Ih) or (Ik) (wherein L is $-(CR_{10}R_{11})_nC(R_{16})=C(R_{17})-(CR_{12}R_{13})_m-O-$ and $R_{10}$, $R_{11}$, $R_{12}$, $R_{13}$, $R_{16}$ and $R_{17}$ are H):

(Ih)

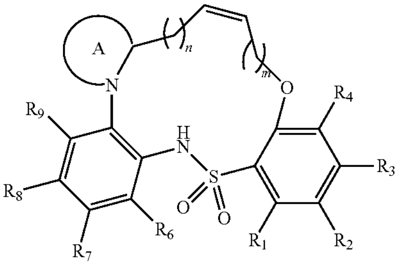

-continued (Ik)

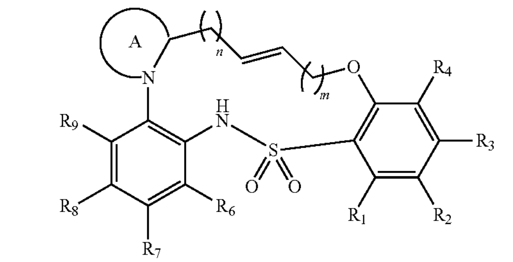

wherein:

A, n, m, $R_1$, $R_3$, $R_4$ and $R_6$-$R_9$ are as defined above for formula (I);

$R_2$ is COOH;

said process comprising the steps of:

(i) subjecting a compound of formula (IIh), where $R_{2'}$ is $CO_2$-alkyl, to ring closing metathesis; and (ii) hydrolysing the product formed in step (i) to convert the $R_2$ group to COOH:

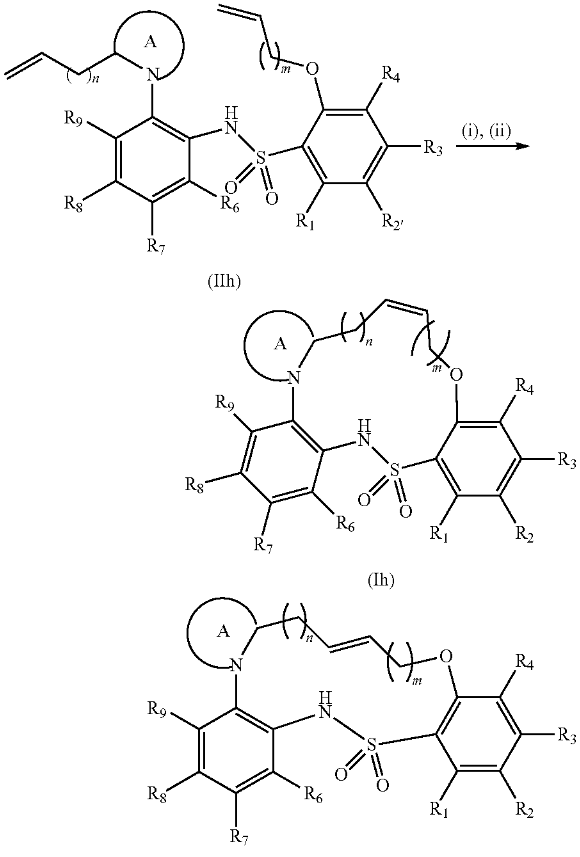

(IIh)

(Ih)

(Ik)

The skilled person would be familiar with suitable reagents and reaction conditions for ring closing metathesis. Suitable reagents are described, for example, in Grubbs, H. et al (*Acc. Chem. Res.* 1995, 28, 11, 446-452). Derivatives in which $R_2$ is $C(O)NHSO_2R_{24}$ can be prepared by treating the corresponding acid with $NH_2SO_2R_{24}$. The skilled person would understand that the ring closing metathesis step can lead to compounds in which the double bond in the linker group is in the E-configuration (Ik) or the Z configuration (Ih). The E- and Z-isomers can be separated by routine purification techniques (such as chromatography) with which the skilled person would be familiar.

Compounds in which L is $-(CR_{10}R_{11})_nC(R_{16})=C(R_{17})-(CR_{12}R_{13})_m-O-$ can be converted using conventional chemistry into the corresponding saturated mono- or di-hydroxylated or mono- or di-fluorinated or mixed fluorinated/hydroxylated derivatives by reacting the alkene functionality with the appropriate reagent. It may be necessary or desirable to carry out a specific reaction using either the final carboxylic acid, or its methyl ester precursor followed by hydrolysis (for example, with LiOH(aq)/THF). For example, dihydroxylation of the alkene functionality using osmium tetroxide, potassium osmate, or Os EnCat™ 40, provides the corresponding vicinal diol. Alternatively, hydroboration of the alkene functionality using E diborane, 9-BBN, or a borane complex, followed by oxidative work-up with hydrogen peroxide, affords the corresponding mono-alcohol. This in turn can be converted to the mono-fluoro derivative using standard deoxyfluorination conditions (for example, by treatment with bis(2-methoxyethyl) aminosulfur trifluoride (Deoxoflur). Epoxidation of the alkene functionality (for example, by treatment with $H_2O_2$/sodium tungstate dihydrate) provides an intermediate that can be ring-opened with a source of fluoride (for example, $Et_3N{\cdot}3HF$) to provide the corresponding fluorohydrin, which in turn can be subjected to deoxyfluorination using standard conditions (for example, by treatment with pertluorobutanesulfonyl fluoride) to afford the 1,2-difluoroalkane. Such transformations have been described, for example, in Org. Process Res. Dev. 2020, 24, 7, 1294-1303.

In one preferred embodiment, the process comprises preparing said compound of formula (IIh) from a compound of formula (IIIh) and a compound of formula (IVh):

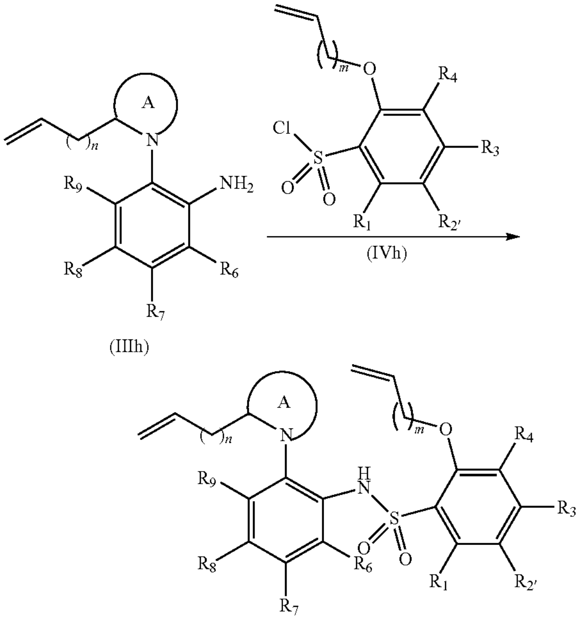

(IVh)

(IIIh)

(IIh)

Preferably, the reaction is carried out in DCM/pyridine.

In one preferred embodiment, $R_1$, $R_3$, $R_4$, $R_6$ and $R_9$ are H.

Compounds of formula (I) containing an alkyl linker can be prepared by a Mitsunobu reaction.

Thus, another embodiment of the invention relates to a process for preparing a compound of formula (Ii) (where L is —$(CR_{10}R_{11})_r(CR_{12}R_{13})$—O— and $R_{10}$, $R_{11}$, $R_{12}$ and $R_{13}$ are H):

(Ii)

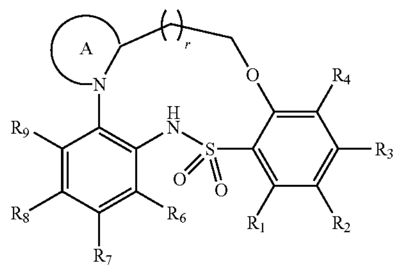

wherein:

A, r, $R_1$, $R_3$, $R_4$ and $R_6$-$R_9$ are as defined above;

$R_2$ is $CO_2H$;

said process comprising the steps of:

(i) subjecting a compound of formula (IIi), where $R_2$ is $CO_2$-alkyl, to Mitsunobu ring closure; and (ii) hydrolysing the product formed in step (i) to convert the $R_2$ group to COOH:

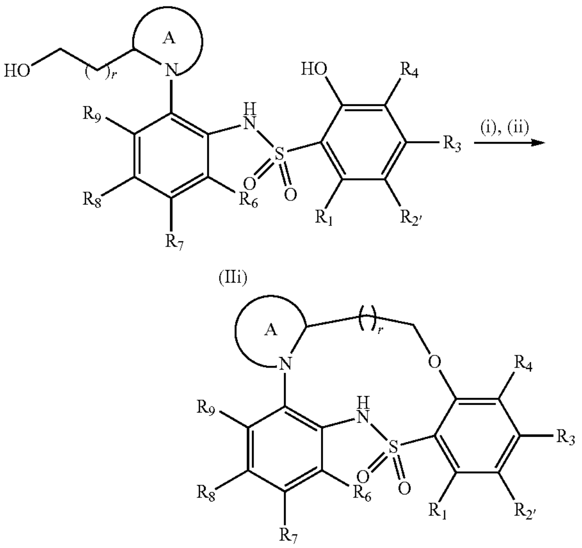

(IIi)

(Ii)

The skilled person would be familiar with suitable reagents and reaction conditions for Mitsunobu ring closure. The Mitsunobu reaction involves the dehydrative coupling of a primary to a pronucleophile (NuH), which is mediated by the reaction between a dialkyl azodicarboxylate and a trialkyl- or triarylphosphine. Suitable reagents are described, for example, in Fletcher, S. (*Org. Chem. Front.*, 2015, 2, 739-752) and K. C. Kumara Swamy et al (*Chem. Rev.* 2009, 109, 6, 2551-2651). Typical Mitsunobu reagents include diethyl azodicarboxylate (DEAD) or diisopropyl azodicarboxylate (DIAD) and triphenylphosphine ($PPh_3$). The Mitsunobu reaction proceeds under mild, essentially neutral conditions, and typically at 0° C. to room temperature.

Standard solvents for the reaction include THF, diethyl ether, dichloromethane and toluene, although more polar solvents, including ethyl acetate, acetonitrile and DMF, may also be used.

In one preferred embodiment, the process comprises preparing said compound of formula (IIi) from a compound of formula (IIIi) and a compound of formula (IVi):

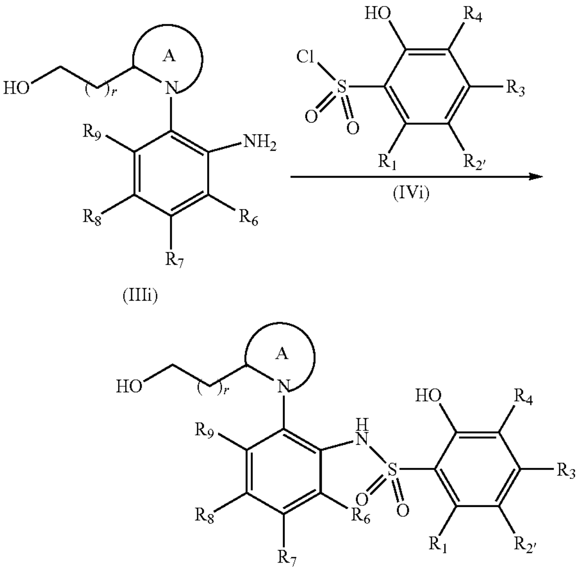

(IIIi)

(IIi)

In one highly preferred embodiment, $R_1$, $R_3$, $R_4$, $R_6$ and $R_9$ are H.

Preferably, the reaction is carried out in DCM/pyridine.

Compounds in which L is —$(CR_{14}R_{15})$-Q-$(CR_{12}R_{13})_s$—O— where Q is O can be prepared, for example, by treating a hydroxyalkyl-substituted N-protected precursor of ring A with a hydroxyl-protected bromoalcohol, followed by removal of the hydroxyl protecting group. An illustrative example is shown below:

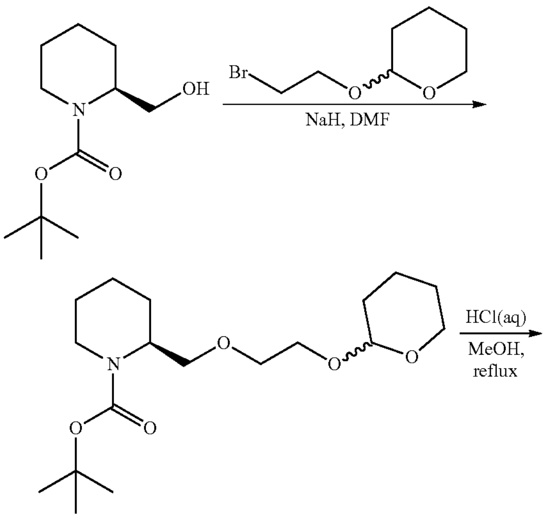

-continued

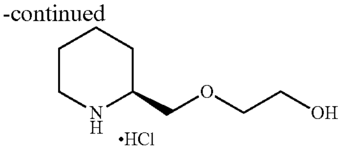

The skilled person would understand that other protecting groups and reagents could also be used.

Alternatively, compounds in which L is —$(CR_{14}R_{15})$-Q-$(CR_{12}R_{13})_s$—O— where Q is O can be prepared, for example, by using SEM protection of the primary alcohol as shown below:

-continued

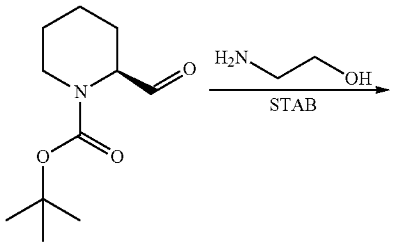

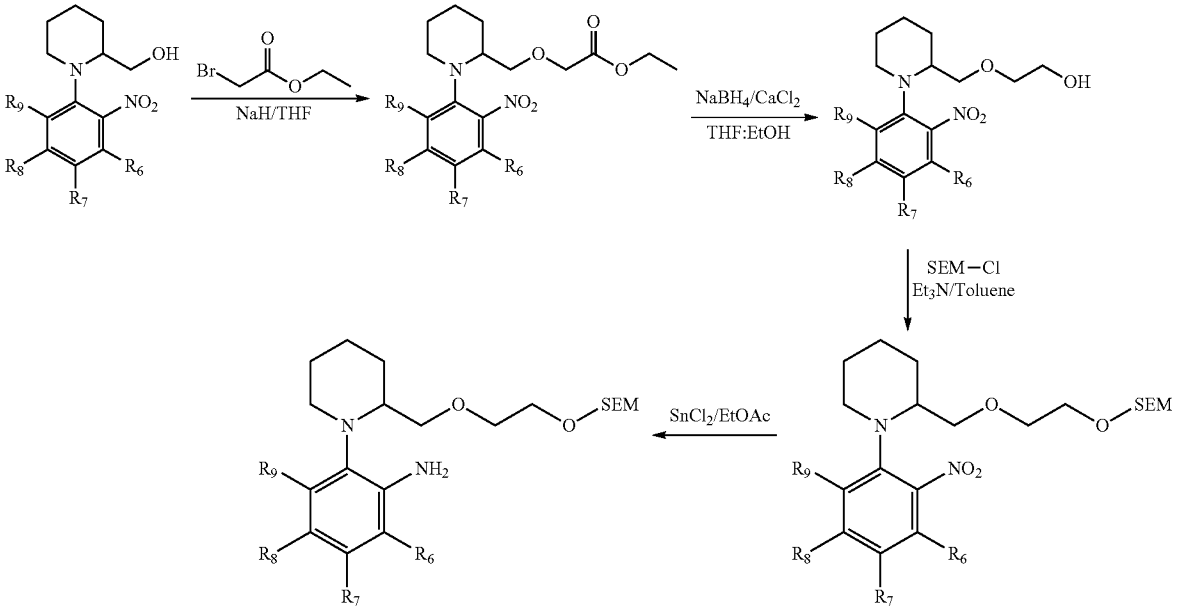

The SEM-protected intermediate so formed is then coupled with an aryl sulfonamide, followed by removal of the SEM protection group and cyclisation via a Mitsunobu reaction in the presence of DIAD and an appropriate trialkyl phosphine. See Examples 65 and 69 described in the accompanying examples section.

Compounds in which L is —$(CR_{14}R_{15})$-Q-$(CR_{12}R_{13})_s$—O— where Q is NH can be prepared, for example, by oxidising a hydroxyalkyl-substituted N-protected precursor of ring A to the corresponding aldehyde, reacting with an aminoalcohol and then protecting the secondary NH group so formed, before removing the N-protecting group from the A-ring. An illustrative example is shown below:

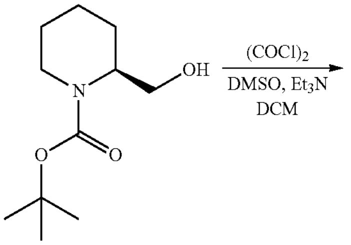

-continued

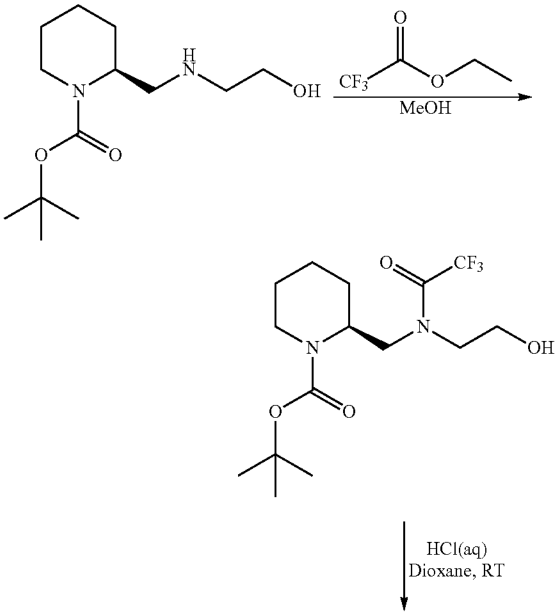

-continued

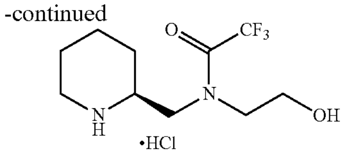

The skilled person would understand that other protecting groups and reagents could also be used.

Alternatively, compounds in which L is —$(CR_{14}R_{15})$-Q-$(CR_{12}R_{13})_s$—O— where Q is NH can be prepared, for example, by using SEM protection of the primary alcohol as shown below:

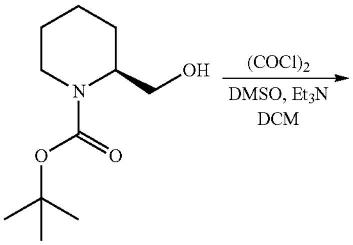

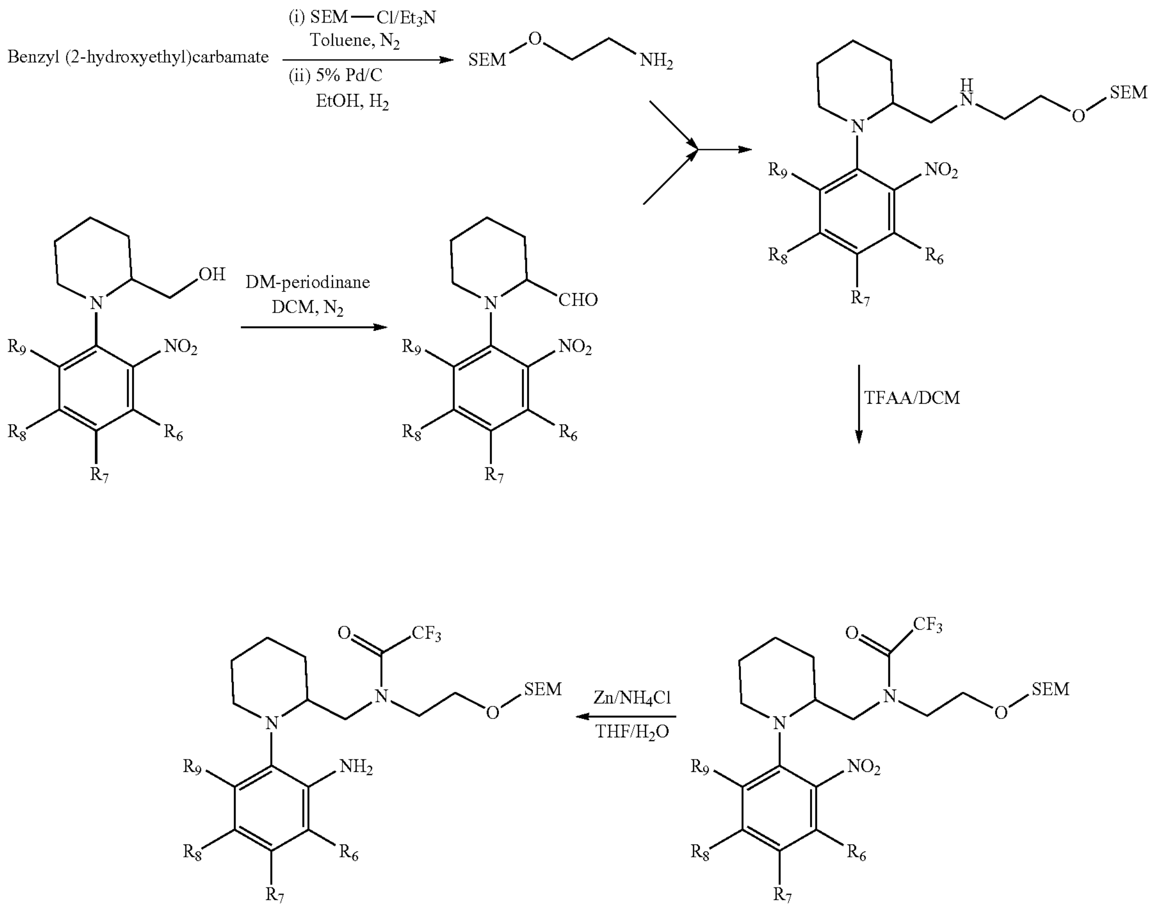

The SEM-protected intermediate so formed is then coupled with an aryl sulfonamide, followed by removal of the SEM protection group and cyclisation in the presence of trialkyl phosphine/imidazole/$I_2$. Finally, the $CF_3CO$ group is removed. See Example 66 described in the accompanying examples section.

Compounds in which L is —$(CR_{14}R_{15})$-Q-$(CR_{12}R_{13})_s$—O— where Q is N-alkyl can be prepared, for example, by oxidising a hydroxyalkyl-substituted N-protected precursor of ring A to the corresponding aldehyde, reacting with an alkyl aminoalcohol, and then removing the N-protecting group from the A-ring. An illustrative example is shown below:

-continued

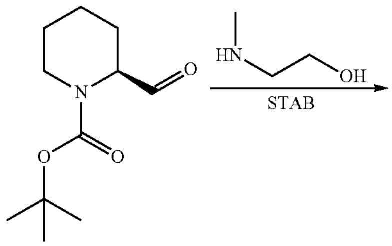

-continued

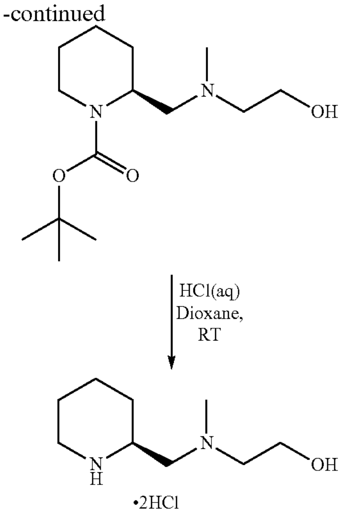

Again, the skilled person would understand that other protecting groups and reagents could also be used.

Another preferred embodiment of the invention relates to a process for preparing a compound of formula (Iv), (i.e. where L is —$(CR_{14}R_{15})$-Q-$(CR_{12}R_{13})_m$—$C(R_{16})$═C$(R_{17})$—, where $R_{12}$-$R_{17}$ are all H and Q is O):

(Iv)

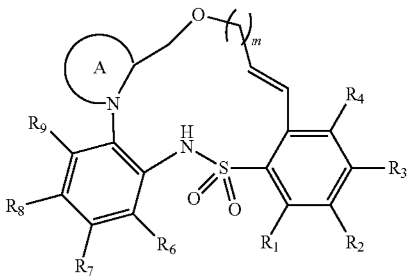

wherein:

A, m, $R_1$, $R_3$, $R_4$ and $R_6$-$R_9$ are as defined above;

$R_2$ is COOH;

said process comprising the steps of:

(i) subjecting a compound of formula (Iv.1), where $R_2$ is $CO_2$-alkyl, to ring closing metathesis; and (ii) hydrolysing the product formed in step (i) to convert the $R_2$ group to COOH:

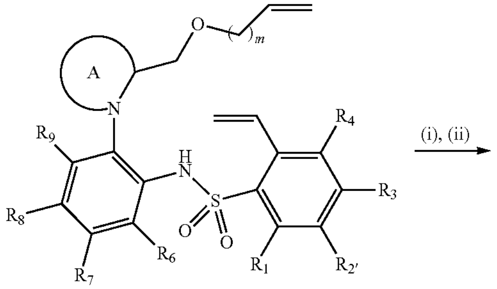

(Iv.1)

-continued

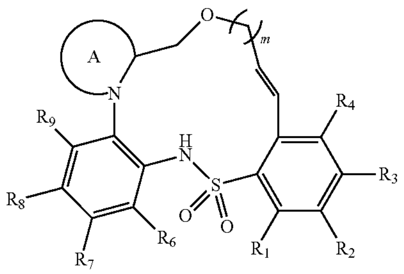

(Iv)

Compounds wherein L is —$(CR_{14}R_{15})$-Q-$(CR_{12}R_{13})_t$ can be prepared by hydrogenating the corresponding unsaturated derivatives, for example, where L is —$(CR_{14}R_{15})$-Q-$(CR_{12}R_{13})_m$—$C(R_{16})$═$C(R_{17})$.

Another preferred embodiment of the invention relates to a process for preparing a compound of formula (Iw) (i.e. where L is —$(CR_{10}R_{11})_t$—$C(R_{16})$═$C(R_{17})$— and $R_{10}$, $R_{11}$, $R_{16}$ and $R_{17}$ are all H):

(Iw)

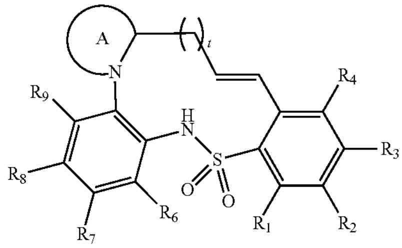

wherein:

A, t, $R_1$, $R_3$, $R_4$ and $R_6$-$R_9$ are as defined above;

$R_2$ is COOH;

said process comprising the steps of:

(iii) subjecting a compound of formula (Iw.1), where $R_{2'}$ is $CO_2$-alkyl, to ring closing metathesis; and (iv) hydrolysing the product formed in step (i) to convert the $R_2$ group to COOH:

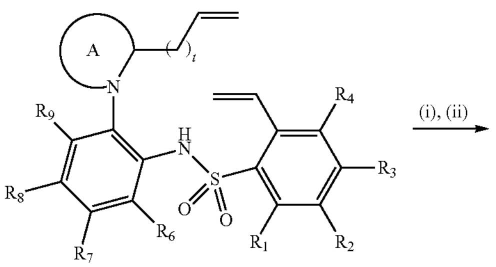

(Iw.1)

-continued

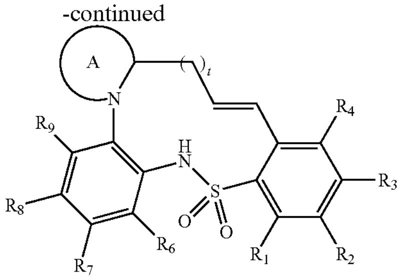

(Iw)

Compounds wherein L is —$(CR_{10}R_{11})_u$—$(CR_{12}R_{13})$— can be prepared by hydrogenating the corresponding unsaturated derivatives, for example, where L is —$(CR_{10}R_{11})_t$—$C(R_{16})$=$C(R_{17})$—.

The present invention is further described by way of the following non-limiting examples.

EXAMPLES

Where the preparation of starting materials is not described, these are commercially available, known in the literature, or readily obtainable by those skilled in the art using standard procedures. Where it is indicated that compounds were prepared analogously to earlier examples or intermediates, it will be appreciated by the skilled person that the reaction time, number of equivalents of reagents, solvent, concentration and temperature can be modified for each specific reaction and that it may be necessary or desirable to employ different work-up or purification techniques.

Abbreviations

AcOH: acetic acid; aq: aqueous; br: broad; ca.: circa; d: doublet; dba: dibenzylideneacetone; DCM: dichloromethane; dioxane: 1,4-dioxane; DIAD: Diisopropyl azodicarboxylate; DIPEA: N,N-diisopropylethylamine; EtOAc: ethyl acetate; $Et_3N$: triethylamine; Grubbs-Hoveyda 2nd Gen: (1,3-Bis-(2,4,6-trimethylphenyl)-2-imidazolidinylidene)dichloro(o-isopropoxyphenylmethylene)ruthenium (CAS: 301224-40-8); h: hours; HPLC: high performance liquid chromatography; IPA, isopropanol; LC: liquid chromatography; m: multiplet; M: molar, molecular ion; MeCN: acetonitrile; MeOH: methanol; min: minutes; MS: mass spectrometry; NMR: nuclear magnetic resonance; PDA: photodiode array; q: quartet; RT: room temperature (ca. 20° C.); s: singlet, solid; t: triplet; TBME: tert-butyl methyl ether; TFA: trifluoroacetic acid; THF: tetrahydrofuran; $t_R$: retention time; UPLC: ultra performance liquid chromatography; UV: ultraviolet; Xantphos: 4,5-Bis(diphenylphosphino)-9,9-dimethylxanthene (CAS: 161265-03-8). DAD: diode array detection; DOE: 1,2-dichloroethane; DMP: Dess-Martin periodinane; DMSO: dimethylsulfoxide; dppf: 1,1'-Bis(diphenylphosphino)ferrocene; EtOH: ethanol; Grubbs 2nd Gen: Benzylidene[1,3-bis(2,4,6-trimethylphenyl)-2-imidazolidinylidene]dichloro(tricyclohexylphosphine)ruthenium (CAS: 246047-72-3); $R_f$: retention factor; SEM-CI: 2-(chloromethoxy)ethyl-trimethylsilane; SFC: super-critical fluid chromatography; TLC: thin-layer chromatography Other abbreviations are intended to convey their generally accepted meaning.

Separation of Enantiomers by Chiral Chromatography

It will be appreciated that the enantiomers of the compounds described above can be isolated using techniques well known in the art, including, but not limited to, chiral chromatography.

Scheme 1

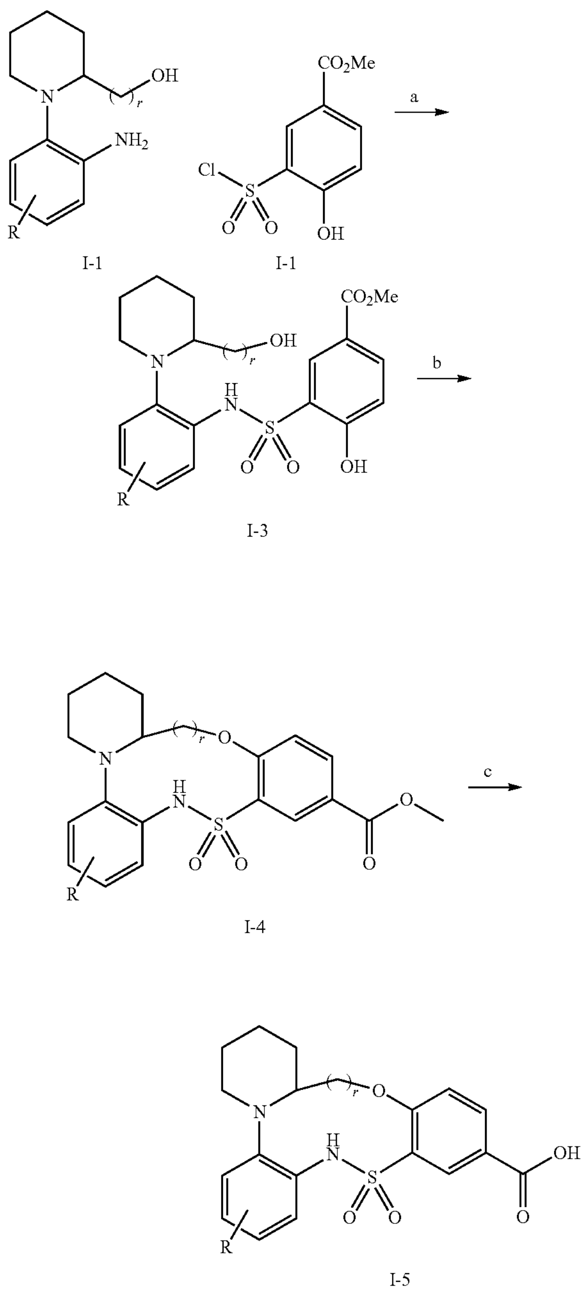

I-1 I-1

I-3

I-4

I-5

Reagents: (a) Pyridine, DCM; (b) DIAD, $R_3P$, DCM; (c) LiOH, $H_2O$, THF, MeOH

Sulfonamide coupling of aniline I-1 and sulfonyl chloride 1-2 provided sulfonamide 1-3. The macrocycle was ring-closed using a Mitsunobu reaction in the presence of DIAD and an appropriate trialkyl phosphine to afford ester intermediate 1-4, which was hydrolysed to the corresponding carboxylic acid 1-5. In the structure 1-5, the group '—$(CH_2)_r$—O—' then corresponds to 'L' in general formula I.

Scheme 2

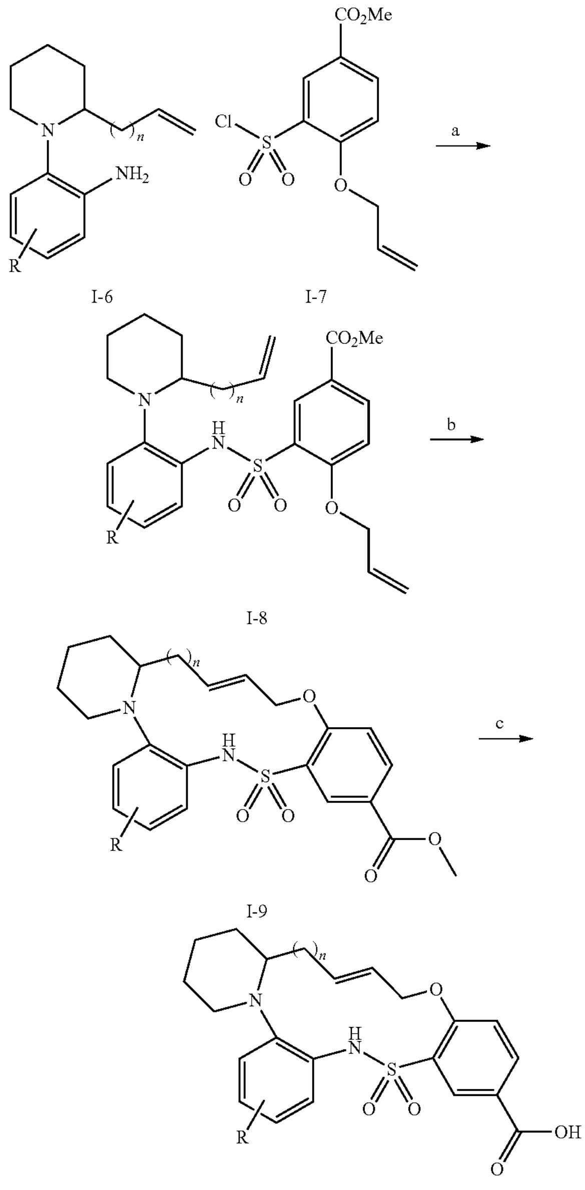

I-6 I-7 I-8 I-9 I-10

Reagents: (a) Pyridine, DCM; (b) Grubbs-Hoveyda 2nd Gen, DCM; (c) LiOH, $H_2O$, THF, MeOH Sulfonamide coupling of aniline I-6 and sulfonyl chloride I-7 provided sulfonamide I-8. The macrocycle was ring-closed using a ring-closing metathesis reaction in the presence of Grubbs-Hoveyda 2nd Gen catalyst to afford ester intermediate I-9, which was hydrolysed to the corresponding carboxylic acid I-10. In the structure I-10, the group '$-(CH_2)_n-CH=CH-CH_2-O-$' then corresponds to 'L' in general formula I.

Scheme 3

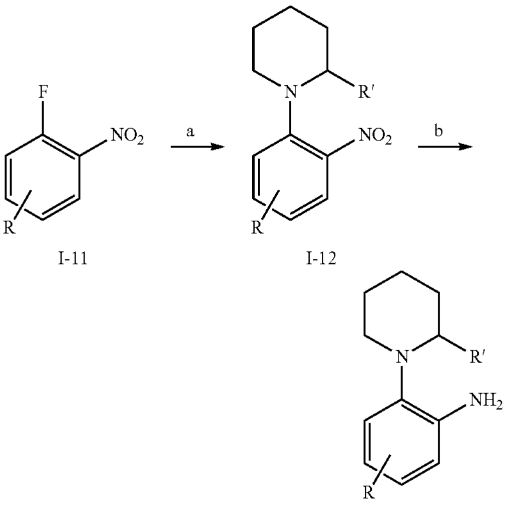

I-11 I-12

I-1: R' = $-(CH_2)_r-OH$

I-6: R' = $-(CH_2)_n-CH=CH_2$

Reagents: (a) Amine, $Et_3N$, DCM; (b) Zn, $NH_4Cl$.

Nucleophilic aromatic substitution of aryl fluoride (I-11) with the appropriate substituted piperidine, followed by reduction of the resultant nitro-compound I-12 provided anilines I-1 and I-6.

General Experimental Conditions

All starting materials and solvents were obtained either from commercial sources or prepared according to the literature citation. Reaction mixtures were magnetically stirred and reactions performed at room temperature (ca. 20° C.) unless otherwise indicated. Column chromatography was performed on an automated flash chromatography system, such as a CombiFlash Rf system, using pre-packed silica (40 μm) cartridges, unless otherwise indicated.

$^1$H NMR spectra were recorded using a Bruker Avance III HD spectrometer at 500 MHz, equipped with a Bruker 5 mm SmartProbe™. Chemical shifts are expressed in parts per million using either the central peaks of the residual protic solvent or an internal standard of tetramethylsilane as references. The spectra were recorded at 298 K unless otherwise indicated.

Analytical UPLC-MS experiments to determine retention times and associated mass ions were performed using a Waters ACQUITY UPLC® H-Class system, equipped with ACQUITY PDA Detector and ACQUITY QDa Mass Detector, running one of the analytical methods described below.

Analytical LC-MS experiments to determine retention times and associated mass ions were performed using an Agilent 1200 series HPLC system coupled to an Agilent 1956, 6100 or 6120 series single quadrupole mass spectrometer running one of the analytical methods described below.

Preparative HPLC purifications were performed either using a Waters X-Select CSH C18, 5 μm, 19×50 mm column using a gradient of MeCN and water, both modified with 0.1% v/v formic acid, or on a Waters X-Bridge BEH 018, 5 μm, 19×50 mm column using a gradient of MeCN and 10 mM ammonium bicarbonate(aq). Fractions were collected following detection by UV at a single wavelength measured by a variable wavelength detector.

Nomenclature of structures was generated using 'Structure to Name' conversion from ChemDraw® Professional 17 (PerkinElmer).

Analytical Methods

Method 1—Acidic 3 Min Method

Column: Waters ACQUITY UPLC® CSH C18, 1.7 μm, 2.1×30 mm at 40° C.
Detection: UV at 254 nm unless otherwise indicated, MS by electrospray ionisation
Solvents: A: 0.1% v/v Formic acid in water, B: 0.1% v/v Formic acid in MeCN

| Gradient: | | | |
| --- | --- | --- | --- |
| Time | % A | % B | Flow rate (ml/min) |
| 0.00 | 95 | 5 | 0.77 |
| 0.11 | 95 | 5 | 0.77 |
| 2.15 | 5 | 95 | 0.77 |
| 2.56 | 5 | 95 | 0.77 |
| 2.83 | 95 | 5 | 0.77 |
| 3.00 | 95 | 5 | 0.77 |

Method 2—Basic 3 Min Method

Column: Waters ACQUITY UPLC® BEH C18, 1.7 μm, 2.1×30 mm at 40° C.
Solvents: A: 10 mM ammonium bicarbonate(aq), B: MeCN
(other parameters the same as Method 1)

Method 3—Acidic 4 Min Method

Column: Waters X-Select CSH C18, 2.5 μm, 4.6×30 mm at 40° C.
Detection: UV at 254 nm unless otherwise indicated, MS by electrospray ionisation
Solvents: A: 0.1% v/v Formic acid in water, B: 0.1% v/v Formic acid in MeCN

| Gradient: | | | |
| --- | --- | --- | --- |
| Time | % A | % B | Flow rate (ml/min) |
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 4—Basic 4 Min Method

Column: Waters X-Bridge BEH C18, 2.5 μm, 4.6×30 mm at 40° C.
Solvents: A: 10 mM ammonium bicarbonate(aq), B: MeCN
(other parameters the same as Method 3)

Method 5—Acidic 3 Min Method

Column: Waters ACQUITY UPLC® CSH C18, 1.7 μm, 2.1×30 mm at 40° C.

Detection: UV at 254 nm unless otherwise indicated, MS by electrospray ionisation
Solvents: A: 0.1% v/v Formic acid in water, B: MeCN
Gradient: $t_0$=2% B, $t_{2.5\ min}$=100% B, $t_{3.0\ min}$=100% B Method 6—Basic 3 Min Method Column: Waters ACQUITY UPLC® BEH C18, 1.7 μm, 2.1×30 mm at 40° C.
Solvents: A: 0.1% w/v ammonia(aq), B: MeCN
Other parameters as Method 5

Method 7—Acidic 3 Min Method

Column: Waters Cortecs C18, 2.7 μm, 30×2.1 mm at 40° C.
Detection: UV at 254 nm unless otherwise indicated, MS by electrospray ionisation
Solvents: A: 0.1% v/v Formic acid in water, B: MeCN
Gradient: $t_0$=5% B, $t_{2.5\ min}$=100% B, $t_{3.0\ min}$=100% B

EXAMPLES

In the following section, the Examples are racemic at the single chiral centre, otherwise, E1 and E2 refer to separated enantiomers 1 and 2 of undefined absolute configuration.

Example 1: (E)-2-(trifluoromethyl)-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide

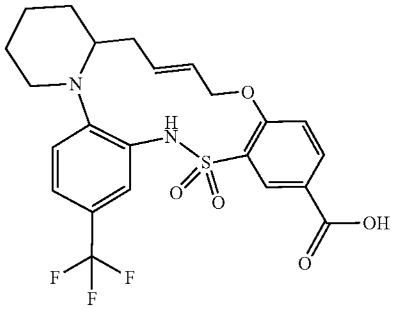 [SMILES: O=C(O)c1ccc2c(c1)S(=O)(=O)Nc1cc(C(F)(F)F)ccc1N1CCCCC1C/C=C/CO2]

Step 1: methyl 3-bromo-4-((tert-butyldimethylsilyl)oxy)benzoate: A solution of methyl 3-bromo-4-hydroxybenzoate (2 g, 8.66 mmol) and imidazole (710 mg, 10.4 mmol) in DCM (40 mL) at 0° C. was treated with added tert-butyldimethylsilyl chloride (1.44 g, 9.55 mmol). The mixture was warmed to RT and stirred overnight. The mixture was washed with 1 M HCl(aq) (30 mL) and passed through a phase separator, then concentrated onto silica and purified by chromatography on silica gel (40 g cartridge, 0-50% EtOAc/isohexane) to afford the title compound (1.37 g, 3.89 mmol, 45% yield, 98% purity) as a clear colourless oil. UPLC-MS (Method 1): m/z 229.2 $(M-TBS)^-$ at 2.21 min.

Step 2: methyl 3-(benzylthio)-4-((tert-butyldimethylsilyl)oxy)benzoate: A solution of the product from Step 1 above (1.37 g, 3.89 mmol, 98% purity) in dioxane (15 mL) was treated with added $Pd_2(dba)_3$ (356 mg, 0.389 mmol), Xantphos (337 mg, 583 μmol), DIPEA (1.4 mL, 8.02 mmol) and then benzyl mercaptan (0.48 mL, 4.06 mmol). The mixture was heated to 100° C. and stirred overnight. The mixture was concentrated onto silica and purified by chromatography on silica gel (40 g cartridge, 0-100% DCM/isohexane) to afford the title compound (435 mg, 1.09 mmol, 28% yield, 97% purity) as a dark orange oil. UPLC-MS (Method 1):), m/z 387.1 $(M-H)^-$ at 2.26 min.

Step 3: methyl 4-((tert-butyldimethylsilyl)oxy)-3-(chlorosulfonyl)benzoate: A mixture of the product from Step 2 above (435 mg, 1.09 mmol, 97% purity), AcOH (70 µl, 1.22 mmol) and water (140 µl, 7.77 mmol) in MeCN (5.5 mL) at −10° C. was treated with 1,3-dichloro-5,5-dimethylimidazolidine-2,4-dione (321 mg, 1.63 mmol). The mixture was stirred at −10° C. for 2 h. The mixture was concentrated in vacuo to ~0.5 mL, diluted with water (20 mL) and extracted with DCM (2×30 mL). The combined organic extracts were passed through a phase separator and the solvent was removed in vacuo. The residue was loaded onto silica and partially purified by chromatography on silica gel (24 g cartridge, 0-50% EtOAc/isohexane) to afford the title compound (274 mg) as a pale-yellow oil.

Step 4: methyl 3-bromo-4-((2-(trimethylsilyl)ethoxy)methoxy)benzoate: A solution of methyl 3-bromo-4-hydroxybenzoate (2 g, 8.66 mmol) and DIPEA (4.5 mL, 25.8 mmol) in DCM (25 mL) at 0° C. was treated with 2-(trimethylsilyl)ethoxymethyl chloride (1.8 mL, 10.2 mmol) slowly. The mixture was warmed to RT and stirred overnight. The mixture was concentrated onto silica and purified by chromatography on silica gel (40 g cartridge, 0-100% DCM/isohexane) to afford the title compound (2.15 g, 5.77 mmol, 67% yield, 97% purity) as a clear colourless oil. UPLC-MS (Method 1): m/z 229.5 $(M-SEM)^-$ at 2.03 min. $^1H$ NMR (500 MHz, DMSO-$d_6$) δ 8.10 (d, J=2.2 Hz, 1H), 7.93 (dd, J=8.7, 2.2 Hz, 1H), 7.32 (d, J=8.7 Hz, 1H), 5.43 (s, 2H), 3.83 (s, 3H), 3.75 (t, J=8.2 Hz, 2H), 0.88 (t, J=8.2 Hz, 2H), −0.05 (s, 9H).

Step 5: methyl 3-(benzylthio)-4-((2-(trimethylsilyl)ethoxy)methoxy)benzoate: A mixture of the product from Step 4 above (2.15 g, 5.77 mmol, 97% purity), DIPEA (2.1 mL, 12.0 mmol), $Pd_2(dba)_3$ (529 mg, 577 µmol) and Xantphos (501 mg, 866 µmol) in dioxane (25 mL) was treated with benzyl mercaptan (750 µl, 6.34 mmol) and the mixture was heated to 100° C. and stirred overnight. The mixture was filtered through Celite®, washing with EtOAc, and the filtrate was concentrated in vacuo. The residue was loaded onto silica and purified by chromatography on silica gel (40 g cartridge, 0-100% DCM/isohexane) to afford the title compound (2.45 g, 3.27 mmol, 57% yield, 54% purity) as a yellow oil. UPLC-MS (Method 2): m/z 403.5 $(M-H)^-$ at 2.13 min.

Step 6: methyl 3-(chlorosulfonyl)-4-((2-(trimethylsilyl)ethoxy)methoxy)benzoate: A solution of the product from Step 5 above (2.45 g, 3.27 mmol), AcOH (210 µl, 3.67 mmol) and water (410 µl, 22.8 mmol) in MeCN (16 mL) at −10° C. was treated with 1,3-dichloro-5,5-dimethylimidazolidine-2,4-dione (966 mg, 4.90 mmol) in 4 portions. The mixture was stirred at −10° C. for 2 h 15 min. The mixture was concentrated in vacuo to −2 mL, diluted with water (20 mL) and extracted with DCM (2×30 mL). The organic extracts were combined and passed through a phase separator and the solvent was removed in vacuo. The residue was loaded onto silica and purified by chromatography on silica gel (40 g cartridge, 0-100% DCM/isohexane) to afford the title compound (1.13 g, 2.67 mmol, 82% yield, 90% purity) as a clear colourless oil. $^1H$ NMR (500 MHz, DMSO-$d_6$) δ 8.33 (d, J=2.4 Hz, 1H), 7.87 (dd, J=8.6, 2.4 Hz, 1H), 7.16 (d, J=8.6 Hz, 1H), 5.31 (s, 2H), 3.82 (s, 3H), 3.79-3.72 (m, 2H), 0.90-0.83 (m, 2H), −0.04 (s, 9H).

Step 7: 2-allyl-1-(2-nitro-4-(trifluoromethyl)phenyl)piperidine: A mixture of 1-fluoro-2-nitro-4-(trifluoromethyl)benzene (1.1 mL, 7.86 mmol), 2-allylpiperidine hydrochloride (1.3 g, 8.04 mmol) and $Et_3N$ (4.5 mL, 32.3 mmol) in DCM (30 mL) was stirred at RT overnight. The mixture was concentrated onto silica and purified by chromatography on silica gel (40 g cartridge, 0-50% DCM/isohexane) to afford the title compound (2.05 g, 5.02 mmol, 64% yield, 77% purity) as a yellow oil. UPLC-MS (Method 1): m/z 315.3 $(M+H)^+$ at 1.98 min. $^1H$ NMR (500 MHz, DMSO-$d_6$) δ 8.09 (d, J=2.3 Hz, 1H), 7.79 (dd, J=8.8, 2.3 Hz, 1H), 7.49 (d, J=8.8 Hz, 1H), 5.61 (ddt, J=17.2, 10.1, 7.1 Hz, 1H), 5.01 (dd, J=17.1, 2.0 Hz, 1H), 4.92 (dd, J=10.1, 2.0 Hz, 1H), 3.62-3.54 (m, 1H), 3.31-3.19 (m, 1H), 2.91-2.83 (m, 1H), 2.33-2.26 (m, 2H), 1.78-1.46 (m, 6H).

Step 8: 2-(2-ally/piperidin-1-yl)-5-(trifluoromethyl)aniline: A mixture of the product from Step 7 above (2.05 g, 5.02 mmol, 77% purity), iron (1.8 g, 32.2 mmol) and ammonium chloride (420 mg, 7.85 mmol) in IPA/water (2:1, 45 mL) was heated to 90° C. and stirred overnight. The mixture was filtered through Celite®, washing with EtOAc and the filtrate concentrated in vacuo. The residue was extracted with DCM (2×40 mL), the combined organic extracts were washed with brine (20 mL), passed through a phase separator and the solvent was removed in vacuo. The residue was loaded onto silica and purified by chromatography on silica gel (40 g cartridge, 0-50% EtOAc/isohexane) to afford the title compound (617 mg, 1.93 mmol, 39% yield, 89% purity) as a yellow oil. UPLC-MS (Method 1): m/z 285.4 $(M+H)^+$ at 1.97 min. $^1H$ NMR (500 MHz, DMSO-$d_6$) δ 7.13 (d, J=8.2 Hz, 1H), 6.97 (d, J=2.2 Hz, 1H), 6.82 (dd, J=8.2, 2.2 Hz, 1H), 5.69-5.54 (m, 1H), 5.23 (s, 2H), 4.95-4.90 (m, 1H), 4.90-4.83 (m, 1H), 3.10-3.00 (m, 1H), 2.98-2.87 (m, 1H), 2.46-2.38 (m, 1H), 2.09-1.90 (m, 2H), 1.83-1.69 (m, 2H), 1.67-1.55 (m, 2H), 1.46-1.31 (m, 2H).

Step 9: methyl 3-(N-(2-(2-ally/piperidin-1-yl)-5-(trifluoromethyl)phenyl)sulfamoyl)-4-hydroxybenzoate (from OTBS protected sulfonyl chloride): A mixture of the product from Step 8 above (207 mg, 648 µmol, 89% purity), the product from Step 3 above (274 mg) and pyridine (160 µl, 1.98 mmol) in DCM (3 mL) was stirred at 35° C. over the weekend. The mixture was loaded onto silica and purified by chromatography on silica gel (24 g cartridge, 0-50% EtOAc/isohexane) to afford the title compound (113 mg, 195 µmol, 30% yield, 86% purity) as a purple solid. UPLC-MS (Method 1): m/z 499.4 $(M+H)^+$, 497.3 $(M-H)^-$, at 1.88 min.

Step 10: methyl 3-(N-(2-(2-ally/piperidin-1-yl)-5-(trifluoromethyl)phenyl)sulfamoyl)-4-hydroxybenzoate (from OSEM protected sulfonyl chloride): A mixture of the product from Step 8 above (200 mg, 626 µmol, 89% purity), the product from Step 6 above (291 mg, 689 µmol, 90% purity) and pyridine (160 µl, 1.98 mmol) in DCM (3 mL) was stirred at 35° C. over the weekend. The mixture was concentrated onto silica and purified by chromatography on silica gel (24 g cartridge, 0-100% EtOAc/isohexane) to afford the title compound (154 mg, 198 µmol, 32% yield, 64% purity) as a brown solid. UPLC-MS (Method 1): m/z 499.4 $(M+H)^+$, 497.4 $(M-H)^-$, at 1.87 min.

Step 11: methyl 3-(N-(2-(2-ally/piperidin-1-yl)-5-(trifluoromethyl)phenyl)-N-(tert-butoxycarbonyl)sulfamoyl)-4-hydroxybenzoate: The combined product from Steps 9 and 10 above (267 mg) and DMAP (48 mg, 393 µmol) in THE (5 mL) was treated with di-tert-butyl dicarbonate (0.28 mL, 1.21 mmol) and the mixture was stirred at RT for 4 h. The mixture was concentrated onto silica and purified by chromatography on silica gel (24 g cartridge, 0-100% DCM/isohexane) to afford the title compound (146 mg, 178 µmol, 45% yield, 73% purity) as a clear colourless oil. The product was contaminated with ~20% methyl 3-(N-(2-(2-allylpiperidin-1-yl)-5-(trifluoromethyl)phenyl)-N-(tert-butoxycarbonyl)sulfamoyl)-4-((tert-butoxycarbonyl)oxy)benzoate (48 μmol, 12% yield). UPLC-MS (Method 1): m/z 599.5 $(M+H)^+$, 597.4 $(M-H)^-$, at 2.09 min.

Step 12: methyl 4-(allyloxy)-3-(N-(2-(2-ally/piperidin-1-yl)-5-(trifluoromethyl)phenyl)-N-(tert-butoxycarbonyl)sulfamoyl)benzoate: A solution of the product from Step 11 above (146 mg, 178 μmol, 73% purity) containing 3-(N-(2-(2-allylpiperidin-1-yl)-5-(trifluoromethyl)phenyl)-N-(tert-butoxycarbonyl)sulfamoyl)-4-((tert-butoxycarbonyl)oxy) benzoate (48 μmol) in DCM (1.2 mL) was treated with piperidine (10 μl, 101 μmol) and the mixture was stirred at RT for 1 h. allyl bromide (40 μl, 462 μmol) and DIPEA (0.13 mL, 744 μmol) were added and the mixture was stirred at RT for 5 days. The mixture was concentrated onto silica and purified by chromatography on silica gel (12 g cartridge, 0-100% DCM/isohexane) to afford the title compound (118 mg, 172 μmol, 76% yield, 93% purity) as a clear colourless oil. UPLC-MS (Method 1): m/z 639.5 $(M+H)^+$ at 2.22 min.

Step 13: (E)-20-tert-butyl 17-methyl 2-(trifluoromethyl)-6,7,8,9,9a,10-hexahydrodibenzo[b,f]pyrido[1,2-h][1,4,5,8]oxathiadiazacyclotridecine-17,20(13H)-dicarboxylate 19,19-dioxide: A solution of the product from Step 12 above (108 mg, 169 μmol) in DCM (4 mL) was sparged with $N_2$ for 5 min, and then Grubbs-Hoveyda 2nd Gen (30 mg, 0.033 mmol) was added. The mixture was stirred at RT for 6 h and then at 35° C. overnight. Additional Grubbs-Hoveyda 2nd Gen (30 mg, 0.048 mmol) was added and stirring at 35° C. was continued overnight. The mixture was concentrated onto silica and purified by chromatography on silica gel (12 g cartridge, 0-50% EtOAc/isohexane) to afford the title compound (46 mg, 0.056 mmol, 33% yield, 74% purity) as a pale brown oil. The product was contaminated with ~36% (E)-methyl 2-(trifluoromethyl)-6,7,8,9,9a,10,13,20-octahydrodibenzo[b,f]pyrido[1,2-h][1,4,5,8]oxathiadiazacyclotridecine-17-carboxylate 19,19-dioxide (0.032 mmol, 19% yield). UPLC-MS (Method 1): m/z 633.4 $(M+Na)^+$ at 2.04 min.

Step 14: (E)-methyl 2-(trifluoromethyl)-6,7,8,9,9a,10,13,20-octahydrodibenzo[b,f]pyrido[1,2-h][1,4,5,8]oxathiadiazacyclotridecine-17-carboxylate 19,19-dioxide: A mixture of the product from Step 13 above (46 mg, 0.056 mmol, 74% purity) containing (E)-methyl 2-(trifluoromethyl)-6,7,8,9,9a,10,13,20-octahydrodibenzo[b,f]pyrido[1,2-h][1,4,5,8]oxathiadiazacyclotridecine-17-carboxylate 19,19-dioxide (0.032 mmol), and 4 M HCl in dioxane) (80 μl, 0.320 mmol) in dioxane (2 mL) and water (1 mL) was heated to 60° C. and stirred overnight. The mixture was diluted with water (5 mL) and extracted with EtOAc (3×10 mL). The organic extracts were combined and washed with brine (10 mL), passed through a phase separator and concentrated in vacuo to afford the title compound (37.8 mg, 0.062 mmol, 71% yield, 84% purity) as a brown oil, which was used without further purification. UPLC-MS (Method 1): m/z 511.4 $(M+H)^+$, 509.3 $(M-H)^-$, at 1.90 min.

Step 15: (E)-2-(trifluoromethyl)-6,7,8,9,9a,10,13,20-octahydrodibenzo[b,f]pyrido[1,2-h][1,4,5,8]oxathiadiazacyclotridecine-17-carboxylic acid 19,19-dioxide: A mixture of the product from Step 14 above (37.8 mg, 0.062 mmol, 84% purity) and $LiOH \cdot H_2O$ (10 mg, 0.238 mmol) in THE/MeOH/water (4:1:1, 1.08 mL) was stirred at 40° C. for 2 h. The mixture was diluted with water (10 mL), acidified to ~pH 4 with 1 M HCl(aq) and extracted with EtOAc (3×20 mL). The organic extracts were combined and washed with brine (10 mL), passed through a phase separator and the solvent was removed in vacuo. The residue was loaded onto silica and purified by chromatography on silica gel (12 g cartridge, 0-100% EtOAc/isohexane) to afford the title compound (11.6 mg, 0.023 mmol, 39% yield, 99% purity) as a white solid. UPLC-MS (Method 1): m/z 497.4 $(M+H)^+$, 495.4 $(M-H)^-$, at 1.75 min. $^1H$ NMR (500 MHz, Methanol-$d_4$) δ 8.73 (dd, J=12.6, 2.2 Hz, 1H), 8.21 (ddd, J=10.7, 8.7, 2.2 Hz, 1H), 7.52-7.38 (m, 1.5H), 7.30-7.28 (m, 0.5H), 7.26-7.14 (m, 1.5H), 7.02-6.97 (m, 0.5H), 6.02-5.88 (m, 1H), 5.82-5.73 (m, 0.5H), 5.20-5.11 (m, 0.5H), 4.98-4.89 (m, 0.5H), 4.68-4.58 (m, 1H), 4.04 (t, J=9.8 Hz, 0.5H), 3.51-3.42 (m, 0.5H), 3.04-2.90 (m, 1H), 2.55-2.45 (m, 0.5H), 2.44-2.30 (m, 1H), 2.27-2.18 (m, 0.5H), 2.17-2.08 (m, 0.5H), 2.02-1.86 (m, 2H), 1.84-1.58 (m, 3H), 1.58-1.43 (m, 1H), 1.34-1.26 (m, 1H). Two exchangeable protons not observed.

Example 2: 2-cyano-7,8,9,9a,10,11-hexahydro-6H,18H-dibenzo[b,f]pyrido[1,2-h][1]oxa[4]thia[5,8]diazacycloundecine-15-carboxylic acid 17,17-dioxide

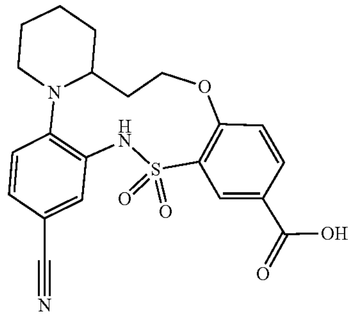 [SMILES: N#Cc1ccc2c(c1)NS(=O)(=O)c1cc(C(=O)O)ccc1OCCC1CCCCN21]

Step 1: methyl 3-bromo-4-((2-(trimethylsilyl)ethoxy)methoxy)benzoate: A solution of methyl 3-bromo-4-hydroxybenzoate (17.8 g, 77.1 mmol) and DIPEA (40.0 mL, 230 mmol) in DCM (250 mL) at 0° C. was treated with (2-(chloromethoxy)ethyl)trimethylsilane (16.0 mL, 90.2 mmol). The mixture was warmed to RT and stirred overnight. The mixture was concentrated onto silica and purified by chromatography on silica gel (330 g cartridge, 0-100% DCM/isohexane) to afford the title compound (26.3 g, 72.1 mmol, 93% yield, 99% purity) as a clear colourless oil. $^1H$ NMR (500 MHz, DMSO-$d_6$) δ 8.09 (d, J=2.1 Hz, 1H), 7.93 (dd, J=8.7, 2.1 Hz, 1H), 7.32 (d, J=8.7 Hz, 1H), 5.43 (s, 2H), 3.83 (s, 3H), 3.78-3.71 (m, 2H), 0.92-0.83 (m, 2H), −0.05 (s, 9H).

Step 2: methyl 3-(benzylthio)-4-((2-(trimethylsilyl)ethoxy)methoxy)benzoate: A solution of the product from Step 1 above (26.3 g, 72.1 mmol, 99% purity) and DIPEA (26.0 mL, 149 mmol) in dioxane (320 mL) was sparged with $N_2$ for 10 min. $Pd_2(dba)_3$ (1.70 g, 1.86 mmol) and Xantphos (2.10 g, 3.63 mmol) were added and the mixture was sparged with $N_2$ for 5 min. Benzyl mercaptan (8.80 mL, 74.4 mmol) was added and the mixture was heated to 100° C. and stirred overnight. The mixture was filtered through Celite®, the filter cake was washed with EtOAc, and the filtrate was concentrated in vacuo. The residue was loaded onto silica and purified by chromatography on silica gel (330 g cartridge, 0-100% DCM/isohexane) to afford the title compound (30.1 g, 70.8 mmol, 98% yield, 95% purity) as an orange oil. $^1H$ NMR (500 MHz, DMSO-$d_6$) δ 7.81 (d, J=2.1 Hz, 1H), 7.75 (dd, J=8.6, 2.1 Hz, 1H), 7.38-7.35 (m, 2H), 7.32-7.28 (m, 2H), 7.26-7.21 (m, 1H), 7.18 (d, J=8.6 Hz, 1H), 5.39 (s, 2H), 4.22 (s, 2H), 3.80 (s, 3H), 3.78-3.71 (m, 2H), 0.92-0.85 (m, 2H), −0.05 (s, 9H).

Step 3: methyl 3-(chlorosulfonyl)-4-hydroxybenzoate: A solution of the product from Step 2 above (30.1 g, 70.8 mmol, 95% purity) in AcOH (2.50 mL), water (2.50 mL) and MeCN (235 mL) at −10° C. was treated with 1,3-dichloro-5,5-dimethylimidazolidine-2,4-dione (20.9 g, 106 mmol) in 5 portions and the mixture was held at −10° C. for 4 h. The mixture was concentrated to −60 mL and extracted with DCM (2×250 mL). The combined organic extracts were passed through a phase separator and the solvent was removed in vacuo.

The residue was loaded onto silica and purified by chromatography on silica gel (330 g cartridge, 0-50% EtOAc/isohexane) to afford the title compound (15.4 g, 57.1 mmol, 81% yield, 93% purity) as a white solid. $^1$H NMR (500 MHz, DMSO-$d_6$) δ 8.10 (d, J=2.2 Hz, 1H), 7.82 (dd, J=8.6, 2.2 Hz, 1H), 6.90 (d, J=8.6 Hz, 1H), 3.82 (s, 3H). One exchangeable proton not observed.

Step 4: 4-(2-(2-hydroxyethyl)piperidin-1-yl)-3-nitrobenzonitrile: A mixture of 4-fluoro-3-nitrobenzonitrile (2.00 g, 12.0 mmol), 2-(piperidin-2-yl)ethan-1-ol (1.63 g, 12.6 mmol) and $Et_3N$ (3.40 mL, 24.4 mmol) in DCM (60 mL) was stirred at 35° C. for 5 h. The mixture was washed with 1 M HCl(aq) (30 mL) and the organic layer was concentrated in vacuo to afford the title compound (3.61 g, 11.8 mmol, 98% yield, 90% purity) as an orange oil. UPLC-MS (Method 1): m/z 276.3 $(M+H)^+$ at 1.26 min. $^1$H NMR (500 MHz, DMSO-$d_6$) δ 8.24 (d, J=2.1 Hz, 1H), 7.80 (dd, J=9.0, 2.1 Hz, 1H), 7.40 (d, J=9.0 Hz, 1H), 4.39 (t, J=4.8 Hz, 1H), 4.00-3.91 (m, 1H), 3.37-3.26 (m, 2H), 3.24-3.15 (m, 1H), 2.87-2.77 (m, 1H), 1.87-1.54 (m, 7H), 1.54-1.40 (m, 1H).

Step 5: 3-amino-4-(2-(2-hydroxyethyl)piperidin-1-yl) benzonitrile: A solution of the product from Step 4 above (3.31 g, 10.8 mmol, 90% purity) in THE (40 mL) and water (13 mL) was treated with zinc (4.24 g, 64.9 mmol) and ammonium chloride (3.47 g, 64.9 mmol) and the resultant mixture was stirred at RT overnight. Additional zinc (4.24 g, 64.9 mmol) and ammonium chloride (3.47 g, 64.9 mmol) were added and stirring was continued for 3 days. The mixture was filtered through Celite® and the filter cake was washed with EtOAc. The filtrate was diluted with water (20 mL) and extracted with EtOAc (3×50 mL). The organic extracts were combined and washed with brine (30 mL), passed through a phase separator, and the solvent was removed in vacuo. The mixture was loaded onto silica and purified by chromatography on silica gel (80 g cartridge, 0-100% EtOAc/isohexane) to afford the title compound (2.48 g, 8.39 mmol, 78% yield, 83% purity) as a clear red oil. UPLC-MS (Method 1): m/z 246.4 $(M+H)^+$ at 1.09 min. $^1$H NMR (500 MHz, DMSO-$d_6$) δ 7.04 (d, J=8.0 Hz, 1H), 6.97 (d, J=2.0 Hz, 1H), 6.93 (dd, J=8.0, 2.0 Hz, 1H), 5.21 (s, 2H), 4.26 (t, J=5.1 Hz, 1H), 3.29-3.22 (m, 2H), 3.17-3.10 (m, 1H), 2.99-2.91 (m, 1H), 2.43 (ddd, J=11.7, 8.4, 3.5 Hz, 1H), 1.89-1.81 (m, 1H), 1.73-1.54 (m, 3H), 1.46-1.35 (m, 4H).

Step 6: methyl 3-(N-(5-cyano-2-(2-(2-hydroxyethyl)piperidin-1-yl)phenyl)sulfamoyl)-4-hydroxybenzoate: A mixture of the product from Step 5 above (1.00 g, 3.38 mmol, 83% purity), pyridine (820 μL, 10.2 mmol) and the product from Step 3 above (1.09 g, 4.06 mmol, 93% purity) in DCM (15 mL) was heated to 35° C. and stirred for 4 days. The mixture was concentrated onto silica and partially purified by chromatography on silica gel (40 g cartridge, 0-100% EtOAc/isohexane) and then by chromatography on silica gel (24 g cartridge, 0-10% MeOH/DCM) to afford the title compound (421 mg, 770 μmol, 23% yield, 84% purity) as a tan solid. UPLC-MS (Method 1): m/z 460.4 $(M+H)^+$, 458.3 $(M-H)^-$, at 1.32 min.

Step 7: methyl 2-cyano-7,8,9,9a,10,11-hexahydro-6H, 18H-dibenzo[b,f]pyrido[1,2-h][1]oxa[4]thia[5,8]diazacycloundecine-15-carboxylate 17,17-dioxide: A solution of the product from Step 6 above (421 mg, 770 μmol, 84% purity) and tri-n-butylphosphine (660 μl, 2.67 mmol) in DCM (140 mL) was treated with DIAD (520 μL, 2.67 mmol) and the mixture was stirred at RT for 4 h. The mixture was concentrated onto silica and purified by chromatography on silica gel (24 g cartridge, 0-100% EtOAc/isohexane) to afford the title compound (383 mg, 520 μmol, 68% yield, 60% purity) as a pale yellow oil. UPLC-MS (Method 1): m/z 442.4 $(M+H)^+$, 440.3 $(M-H)^-$, at 1.54 min.

Step 8: 2-cyano-7,8,9,9a,10,11-hexahydro-6H, 18H-dibenzo[b,f]pyrido[1,2-h][1]oxa[4]thia[5,8]diazacycloundecine-15-carboxylic acid 17,17-dioxide: A mixture of the product from Step 7 above (370 mg, 503 μmol, 60% purity) and $LiOH \cdot H_2O$ (85.0 mg, 2.03 mmol) in THF/MeOH/water (4:1:1, 3 mL) was stirred at 40° C. overnight. The mixture was diluted with water (15 mL), acidified to ~pH 4 with 1 M HCl(aq) and extracted with EtOAc (3×30 mL). The organic extracts were combined and washed with brine (15 mL), passed through a phase separator and the solvent was removed in vacuo. The residue was loaded onto silica and partially purified by chromatography on silica gel (24 g cartridge, 0-100% EtOAc/isohexane) and then purified by preparative HPLC (Waters, Acidic (0.1% Formic acid), Acidic, Waters X-Select Prep-C18, 5 μm, 19×50 mm column, 35-65% (0.1% Formic acid in MeCN)/(0.1% Formic Acid in Water)) to afford the title compound (44.7 mg, 102 μmol, 20% yield, 98% purity) as a white solid. UPLC-MS (Method 1): m/z 428.5 $(M+H)^+$, 426.3 $(M-H)^-$, at 1.34 min. $^1$H NMR (500 MHz, DMSO-$d_6$) δ 12.80 (s, 1H), 11.39 (s, 1H), 7.99 (s, 1H), 7.94 (dd, J=8.5, 2.2 Hz, 1H), 7.64 (d, J=8.5 Hz, 1H), 7.50 (s, 1H), 7.12-6.89 (m, 2H), 3.93-3.39 (m, 2H), 2.89-2.66 (m, 2H), 1.78-1.55 (m, 3H), 1.51-0.83 (m, 6H).

Example 3: 8-cyano-12,13,14,15,15a,16-hexahydro-6H-dibenzo[b,f]pyrido[1,2 h][1,4,5,8]oxathiadiazecine-3-carboxylic acid 5,5-dioxide

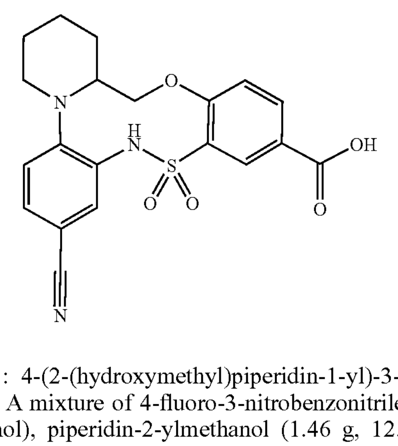

Step 1: 4-(2-(hydroxymethyl)piperidin-1-yl)-3-nitrobenzonitrile: A mixture of 4-fluoro-3-nitrobenzonitrile (2.00 g, 12.0 mmol), piperidin-2-ylmethanol (1.46 g, 12.6 mmol) and $Et_3N$ (3.40 mL, 24.4 mmol) in DCM (60 mL) was stirred at 35° C. for 4 h. The mixture was washed with 1 M HCl(aq) (30 mL) and the organic layer was concentrated in vacuo to afford the title compound (3.58 g, 11.6 mmol, 97% yield, 85% purity) as an orange oil. UPLC-MS (Method 1): m/z 262.3 $(M+H)^+$, at 1.22 min. $^1H$ NMR (500 MHz, DMSO-$d_6$) δ 8.23 (d, J=2.1 Hz, 1H), 7.80 (dd, J=8.9, 2.1 Hz, 1H), 7.37 (d, J=8.9 Hz, 1H), 4.63 (t, J=5.2 Hz, 1H), 3.63-3.46 (m, 3H), 3.26-3.17 (m, 1H), 3.03-2.95 (m, 1H), 1.76-1.62 (m, 3H), 1.60-1.47 (m, 3H).

Step 2: 3-amino-4-(2-(hydroxymethyl)piperidin-1-yl) benzonitrile: A mixture of the product from Step 1 above (3.58 g, 11.6 mmol, 85% purity), iron (3.25 g, 58.2 mmol) and ammonium chloride (3.11 g, 58.2 mmol) in IPA (60 mL) and water (30 mL) was heated to 90° C. and stirred over the weekend. The mixture was filtered through Celite® and the filter cake was washed with EtOAc. The filtrate was concentrated in vacuo to −40 mL and extracted with EtOAc (3×100 mL). The combined organic extracts were washed with brine (40 mL), passed through a phase separator and the solvent was removed in vacuo. The residue was loaded onto silica and purified by chromatography on silica gel (80 g cartridge, 0-100% EtOAc/isohexane) to afford the title compound (1.12 g, 4.60 mmol, 40% yield, 95% purity) as an orange oil. UPLC-MS (Method 1): m/z 232.2 $(M+H)^+$ at 1.03 min. $^1H$ NMR (500 MHz, DMSO-$d_6$) δ 7.10 (d, J=8.0 Hz, 1H), 6.97-6.90 (m, 2H), 5.26 (s, 2H), 4.40 (t, J=5.4 Hz, 1H), 3.32-3.25 (m, 1H), 3.23-3.15 (m, 1H), 3.11-3.03 (m, 1H), 3.02-2.94 (m, 1H), 2.59-2.51 (m, 1H), 1.92-1.84 (m, 1H), 1.73-1.67 (m, 1H), 1.64-1.56 (m, 2H), 1.53-1.37 (m, 2H).

Step 3: methyl 3-(N-(5-cyano-2-(2-(hydroxymethyl)piperidin-1-yl)phenyl)sulfamoyl)-4-hydroxybenzoate: A mixture of the product from Step 2 above (1.12 g, 4.60 mmol, 95% purity), the product from Example 2 Step 3 (2.32 g, 8.60 mmol, 93% purity) and pyridine (1.20 mL, 14.9 mmol) in DCM (20 mL) was stirred at 35° C. for 4 days. The mixture was concentrated onto silica and purified by chromatography on silica gel (80 g cartridge, 0-100% EtOAc/isohexane), followed by trituration with TBME, to afford the title compound (1.18 g, 2.44 mmol, 53% yield, 92% purity) as a white solid. UPLC-MS (Method 1): m/z 446.4 $(M+H)^+$, 444.3 $(M-H)^-$, at 1.32 min.

Step 4: methyl 8-cyano-12,13,14,15,15a,16-hexahydro-6H-dibenzo[b,f]pyrido[1,2-h][1,4,5,8]oxathiadiazecine-3-carboxylate 5,5-dioxide: A solution of the product from Step 3 above (1.17 g, 2.42 mmol, 92% purity) and triphenylphosphine (1.90 g, 7.25 mmol) in DCM (50 mL) was treated with DIAD (1.40 mL, 7.20 mmol) and the mixture was stirred at RT overnight. The mixture was concentrated onto silica and purified by chromatography on silica gel (40 g cartridge, 0-100% EtOAc/isohexane) to afford the title compound (535 mg, 939 μmol, 39% yield, 75% purity) as a pale green foam. UPLC-MS (Method 1): m/z 450.4 $(M+Na)^+$, 426.3 $(M-H)^-$, at 1.51 min. $^1H$ NMR (500 MHz, DMSO-$d_6$) δ 11.97 (s, 1H), 8.33 (d, J=2.2 Hz, 1H), 8.08 (dd, J=8.6, 2.2 Hz, 1H), 7.44 (d, J=2.0 Hz, 1H), 7.37 (dd, J=8.8, 2.0 Hz, 1H), 7.08 (d, J=8.6 Hz, 1H), 7.06 (d, J=8.8 Hz, 1H), 4.12-4.01 (m, 1H), 3.95 (dd, J=14.1, 3.8 Hz, 1H), 3.85 (s, 3H), 3.31-3.27 (m, 1H), 2.95-2.87 (m, 1H), 2.67-2.57 (m, 1H), 1.79-1.61 (m, 3H), 1.43-1.25 (m, 2H), 1.17-1.04 (m, 1H).

Step 5: 8-cyano-12,13,14,15,15a,16-hexahydro-6H-dibenzo[b,f]pyrido[1,2-h][1,4,5,8]oxathiadiazecine-3-carboxylic acid 5,5-dioxide: A mixture of the product from Step 4 above (535 mg, 939 μmol, 75% purity) and $LiOH·H_2O$ (158 mg, 3.75 mmol) in THE/MeOH/water (4:1:1, 4.5 mL) was stirred at 40° C. for 2 days. The mixture was diluted with water (20 mL), acidified to ~pH 4 with 1 M HCl(aq) and extracted with EtOAc (3×40 mL). The organic extracts were combined and washed with brine (20 mL), passed through a phase separator and the solvent was removed in vacuo. The crude product was purified by preparative HPLC (Waters, Acidic (0.1% Formic acid), Acidic, Waters X-Select Prep-C18, 5 μm, 19×50 mm column, 35-65% (0.1% Formic acid in MeCN)/(0.1% Formic Acid in Water)) to afford the title compound (45.1 mg, 107 μmol, 11% yield, 98% purity) as a light-grey solid. UPLC-MS (Method 1): m/z 414.4 $(M+H)^+$, 412.3 $(M-H)^-$, at 1.33 min. $^1H$ NMR (500 MHz, DMSO-$d_6$) δ 12.99 (s, 1H), 11.86 (s, 1H), 8.31 (d, J=2.2 Hz, 1H), 8.04 (dd, J=8.6, 2.2 Hz, 1H), 7.42 (d, J=2.1 Hz, 1H), 7.35 (dd, J=8.8, 2.1 Hz, 1H), 7.06 (d, J=2.7 Hz, 1H), 7.04 (d, J=3.0 Hz, 1H), 4.06 (d, J=12.9 Hz, 1H), 3.95 (dd, J=14.1, 3.8 Hz, 1H), 3.31-3.27 (m, 1H), 2.96-2.88 (m, 1H), 2.61 (td, J=12.8, 2.7 Hz, 1H), 1.75 (d, J=11.9 Hz, 1H), 1.71-1.63 (m, 2H), 1.45-1.27 (m, 2H), 1.18-1.07 (m, 1H).

Example 4: 2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide

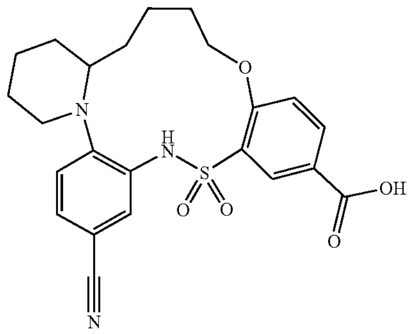 [SMILES: N#Cc1ccc2c(c1)NS(=O)(=O)c1cc(C(=O)O)ccc1OCCCCC1CCCCN21]

Step 1: 4-(2-(4-hydroxybutyl)piperidin-1-yl)-3-nitrobenzonitrile: A mixture of 4-fluoro-3-nitrobenzonitrile (1.00 g, 6.02 mmol), 4-(piperidin-2-yl)butan-1-ol (1.00 g, 6.36 mmol) and $Et_3N$ (1.70 mL, 12.2 mmol) in DCM (25 mL) was stirred at 35° C. overnight. The mixture was washed with 1 M HCl(aq) (30 mL) and the organic layer was concentrated in vacuo to afford the title compound (2.26 g, 5.96 mmol, 99% yield, 80% purity) as an orange oil. UPLC-MS (Method 1): m/z 304.4 $(M+H)^+$ at 1.40 min. $^1H$ NMR (500 MHz, DMSO-$d_6$) δ 8.25 (d, J=2.1 Hz, 1H), 7.80 (dd, J=9.0, 2.1 Hz, 1H), 7.40 (d, J=9.0 Hz, 1H), 4.31 (t, J=5.1 Hz, 1H), 3.70 (d, J=4.9 Hz, 1H), 3.31-3.26 (m, 2H), 3.25-3.17 (m, 1H), 2.86-2.79 (m, 1H), 1.80-1.38 (m, 8H), 1.38-1.05 (m, 4H).

Step 2: 3-amino-4-(2-(4-hydroxybutyl)piperidin-1-yl) benzonitrile: A mixture of the product from Step 1 above (2.26 g, 5.96 mmol, 80% purity), ammonium chloride (1.59 g, 29.8 mmol) and iron (1.66 g, 29.8 mmol) in IPA (20 mL) and water (10 mL) was heated to 90° C. and stirred overnight. The mixture was filtered through Celite®, washing with EtOAc, and the filtrate was extracted with EtOAc (3×40 mL). The organic extracts were combined and washed with brine (40 mL), passed through a phase separator, and the solvent was removed in vacuo. The residue was loaded onto silica and purified by chromatography on silica gel (40 g cartridge, 0-100% EtOAc/isohexane) to afford the title compound (788 mg, 2.80 mmol, 47% yield, 97% purity) as a yellow oil. UPLC-MS (Method 1): m/z 274.4 $(M+H)^+$ at 1.27 min. $^1H$ NMR (500 MHz, DMSO-$d_6$) δ 7.04 (d, J=8.0 Hz, 1H), 6.97 (d, J=2.0 Hz, 1H), 6.93 (dd, J=8.0, 2.0 Hz, 1H), 5.20 (s, 2H), 4.24 (t, J=5.1 Hz, 1H), 3.28-3.19 (m, 2H), 3.04-2.97 (m, 1H), 2.96-2.90 (m, 1H), 2.47-2.38 (m, 1H), 1.88-1.80 (m, 1H), 1.74-1.68 (m, 1H), 1.65-1.54 (m, 2H), 1.44-1.35 (m, 2H), 1.26-1.05 (m, 6H).

Step 3: methyl 3-(N-(5-cyano-2-(2-(4-hydroxybutyl)piperidin-1-yl)phenyl)sulfamoyl)-4-hydroxybenzoate: A mixture of the product from Step 2 above (788 mg, 2.80 mmol, 97% purity), the product from Example 2 Step 3 (1.51 g, 5.62 mmol, 93% purity) and pyridine (0.7 mL, 8.69 mmol) in DCM (12 mL) was stirred at 35° C. for 4 days. The mixture was concentrated onto silica and purified by chromatography on silica gel (40 g cartridge, 0-100% EtOAc/isohexane), followed by trituration with TBME, to afford the title compound (389 mg, 678 μmol, 24% yield, 85% purity) as a white solid. UPLC-MS (Method 1): m/z 488.5 $(M+H)^+$, 486.3 $(M-H)^-$, at 1.43 min.

Step 4: methyl 2-cyano-7,8,9,9a,10,11,12,13-octahydro-6H, 20H-dibenzo[b,f]pyrido[1,2-h][1]oxa[4]thia[5,8]diazacyclotridecine-17-carboxylate 19,19-dioxide: A solution of the product from Step 3 above (389 mg, 678 μmol, 85% purity) and triphenylphosphine (534 mg, 2.03 mmol) in DCM (10 mL) was treated with DIAD (400 μL, 2.06 mmol) and the mixture was stirred at RT for 2 h. The mixture was concentrated onto silica and purified by chromatography on silica gel (24 g cartridge, 0-100% EtOAc/isohexane) to afford the title compound (125 mg, 232 μmol, 34% yield, 87% purity) as a white solid. U PLC-MS (Method 1): m/z 470.4 $(M+H)^+$, 468.3 $(M-H)^-$, at 1.81 min.

Step 5: 2-cyano-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide: A mixture of the product from Step 4 above (125 mg, 232 μmol, 87% purity) and $LiOH{\cdot}H_2O$ (39.0 mg, 929 μmol) in THE/MeOH/water (4:1:1, 1.05 mL) was stirred at 40° C. overnight. The mixture was diluted with water (10 mL), acidified to ~pH 4 with 1 M HCl(aq) and extracted with EtOAc (3×20 mL). The organic extracts were combined and washed with brine (10 mL), passed through a phase separator and the solvent was removed in vacuo. The crude product was purified by preparative HPLC (Waters, Acidic (0.1% Formic acid), Acidic, Waters X-Select Prep-C18, 5 μm, 19×50 mm column, 35-65% (0.1% Formic acid in MeCN)/(0.1% Formic Acid in Water)) to afford the title compound (27.8 mg, 60.4 μmol, 26% yield, 99% purity) as a white solid. UPLC-MS (Method 1): m/z 456.4 $(M+H)^+$, 454.3 $(M-H)^-$, at 1.64 min. $^1H$ NMR (500 MHz, DMSO-$d_6$) δ 13.27 (s, 1H), 8.64 (s, 1H), 8.57 (d, J=2.2 Hz, 1H), 8.16 (dd, J=8.8, 2.2 Hz, 1H), 7.53 (d, J=8.3 Hz, 1H), 7.41 (d, J=8.3 Hz, 1H), 7.35 (d, J=8.8 Hz, 1H), 7.17 (s, 1H), 4.33-4.24 (m, 1H), 4.15-4.08 (m, 1H), 2.92-2.84 (m, 1H), 2.65-2.55 (m, 1H), 1.88-1.76 (m, 2H), 1.73-1.62 (m, 2H), 1.61-1.51 (m, 2H), 1.50-1.13 (m, 7H).

Example 5: 2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

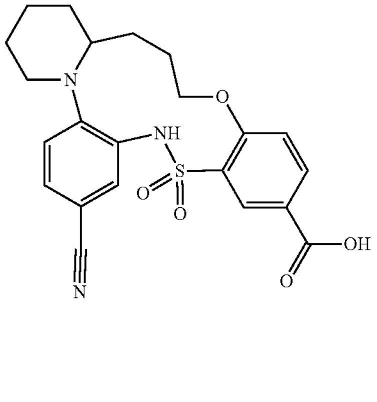

Step 1: 4-(2-(3-hydroxypropyl)piperidin-1-yl)-3-nitrobenzonitrile: A mixture of 4-fluoro-3-nitrobenzonitrile (1.10 g, 6.62 mmol), 3-(piperidin-2-yl)propan-1-ol (1.00 g, 6.98 mmol) and $Et_3N$ (2.00 mL, 14.3 mmol) in DCM (30 mL) was stirred at 35° C. overnight. The mixture was washed with 1 M HCl(aq) (30 mL) and the organic layer was concentrated in vacuo to afford the title compound (2.00 g, 4.77 mmol, 72% yield, 69% purity) as an orange oil. UPLC-MS (Method 1): m/z 290.3 $(M+H)^+$ at 1.33 min.

Step 2: 3-amino-4-(2-(3-hydroxypropyl)piperidin-1-yl) benzonitrile: A mixture of the product from Step 1 above (2.00 g, 4.77 mmol, 69% purity), ammonium chloride (1.53 g, 28.6 mmol) and zinc (1.87 g, 28.6 mmol) in THE (20 mL) and water (6.7 mL) was stirred at RT overnight. The mixture was filtered through Celite®, the filter cake was washed with EtOAc, and the filtrate was extracted with EtOAc (3×40 mL). The organic extracts were combined and washed with brine (20 mL), passed through a phase separator and the solvent was removed in vacuo. The mixture was loaded onto silica and purified by chromatography on silica gel (40 g cartridge, 0-100% EtOAc/isohexane) to afford the title compound (928 mg, 3.40 mmol, 71% yield, 95% purity) as a red oil. UPLC-MS (Method 1): m/z 260.4 $(M+H)^+$, at 1.20 min.

Step 3: methyl 3-(N-(5-cyano-2-(2-(3-hydroxypropyl)piperidin-1-yl)phenyl)sulfamoyl)-4-hydroxybenzoate: A mixture of the product from Step 2 above (928 mg, 3.40 mmol, 95% purity), the product from Example 2 Step 3 (1.71 g, 6.35 mmol, 93% purity) and pyridine (0.8 mL, 9.93 mmol) in DCM (15 mL) was stirred at 35° C. for 2 days. The mixture was concentrated onto silica and purified by chromatography on silica gel (40 g cartridge, 0-100% EtOAc/isohexane) to afford the title compound (467 mg, 809 μmol, 24% yield, 82% purity) as a orange solid. UPLC-MS (Method 1): m/z 474.5 $(M+H)^+$, 472.3 $(M-H)^-$, at 1.39 min.

Step 4: methyl 2-cyano-6,7,8,9,9a,10,11,12-octahydro-19H-dibenzo[b,f]pyrido[1,2-h][1]oxa[4]thia[5,8]diazacyclododecine-16-carboxylate 18,18-dioxide: A solution of the product from Step 3 above (467 mg, 809 μmol, 82% purity) and triphenylphosphine (744 mg, 2.84 mmol) in DCM (15 mL) was added DIAD (560 μL, 2.88 mmol) and the mixture was stirred at RT for 2 h. The mixture was concentrated onto silica and purified by chromatography on silica gel (24 g cartridge, 0-100% EtOAc/isohexane) to afford the title compound (165 mg, 217 μmol, 27% yield, 60% purity) as an orange oil. UPLC-MS (Method 1): m/z 456.4 $(M+H)^+$, 454.3 $(M-H)^-$, at 1.75 min.

Step 5: 2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide: A mixture of the product from Step 4 above (165 mg, 217 μmol, 60% purity) and $LiOH{\cdot}H_2O$ (37 mg, 882 μmol) in THE/MeOH/water (4:1:1, 1.05 mL) was stirred at 40° C. overnight. The mixture was diluted with water (10 mL), acidified to ~pH 4 with 1 M HCl(aq) and extracted with EtOAc (3×20 mL). The combined organic extracts were washed with brine (10 mL), passed through a phase separator, and the solvent was removed in vacuo. The crude product was purified by preparative HPLC (Waters, Acidic (0.1% Formic acid), Acidic, Waters X-Select Prep-C 18, 5 μm, 19×50 mm column, 35-65% (0.1% Formic acid in MeCN)/(0.1% Formic Acid in Water)) to afford the title compound (16.4 mg, 35.3 μmol, 16% yield, 95% purity) as a pale yellow solid. UPLC-MS (Method 1): m/z 442.4 $(M+H)^+$, 440.3 $(M-H)^-$, at 1.58 min. $^1H$ NMR (500 MHz, DMSO-$d_6$) δ 13.26 (s, 1H), 8.90 (s, 1H), 8.51 (d, J=2.2 Hz, 1H), 8.13 (d, J=8.6 Hz, 1H), 7.57 (d, J=8.6 Hz, 1H), 7.47 (d, J=8.2 Hz, 1H), 7.33 (s, 1H), 7.17 (d, J=8.7 Hz, 1H), 4.20-4.11 (m, 1H), 3.99-3.91 (m, 1H), 3.43-3.33 (m, 1H), 2.89-2.83 (m, 1H), 2.46-2.40 (m, 1H), 1.97-1.85 (m, 1H), 1.85-1.73 (m, 2H), 1.72-1.52 (m, 5H), 1.47-1.37 (m, 1H), 1.18-1.05 (m, 1H).

Example 6: 2-cyano-7,8,9,9a,10,11-hexahydro-6H, 18H-dibenzo[b,f]pyrido[1,2-h][1]oxa[4]thia[5,8] diazacycloundecine-15-carboxylic acid 17,17-dioxide Enantiomer 1

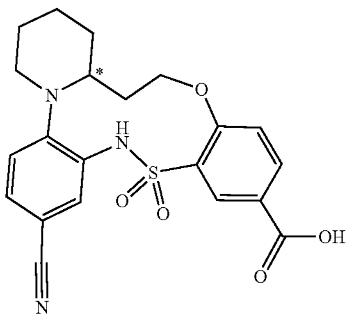 [SMILES: N#Cc1ccc2c(c1)NS(=O)(=O)c1cc(C(=O)O)ccc1OCCC1CCCCN21]

Example 2 was dissolved at 30 mg/ml in 1:1 DCM:MeOH with heating and sonication. The resultant mixture was filtered and then separated by chiral SFC (Waters prep 15 with UV detection by DAD at 210-400 nm, 40° C., 120 bar on a ChiralPAK IC 10×250 mm, 5 μm column, flow rate 15 mL/min, eluting with 15% (0.1% ammonia in 1:1 MeCN/MeOH)/$CO_2$). The clean fractions were pooled, rinsed with MeOH, and concentrated in vacuo. The residue was dissolved in EtOAc (5 mL) and washed with brine (2×5 mL). The organic layer was passed through a phase separator and the solvent was removed in vacuo to afford the title compound (13.0 mg, 29.8 μmol, 33% yield, 98% purity) as a pale tan solid. SFC (Waters UPC$^2$, ChiralPAK IC 4.6×250 mm, 5 μm column, flow rate 4 mL/min, eluting with 30% (0.1% ammonia in 1:1 MeCN/MeOH)/$CO_2$) $t_R$ 2.69 min. Other analytical data consistent with Example 2.

Example 7: 2-cyano-7,8,9,9a,10,11-hexahydro-6H, 18H-dibenzo[b,f]pyrido[1,2-h][1]oxa[4]thia[5,8] diazacycloundecine-15-carboxylic acid 17,17-dioxide Enantiomer 2

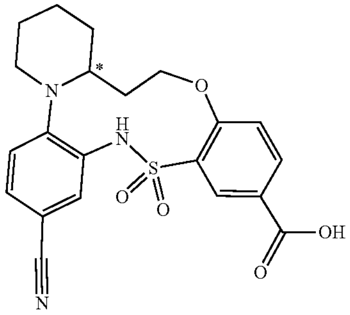 [SMILES: N#Cc1ccc2c(c1)NS(=O)(=O)c1cc(C(=O)O)ccc1OCCC1CCCCN21]

The title compound (13.4 mg, 30.1 μmol, 33% yield, 96% purity) was obtained as a pale tan solid from the chiral separation performed in Example 6. SFC (Waters UPC$^2$, ChiralPAK IC 4.6×250 mm, 5 μm column, flow rate 4 mL/min, eluting with 30% (0.1% ammonia in 1:1 MeCN/MeOH)/$CO_2$) $t_R$ 3.00 min. Other analytical data consistent with Example 2.

Example 8: 2-cyano-6,7,8,9,9a,10,11,12-octahydro-19H-dibenzo[b,f]pyrido[1,2-h][1]oxa[4]thia[5,8] diazacyclododecine-16-carboxylic acid 18,18-dioxide Enantiomer 1

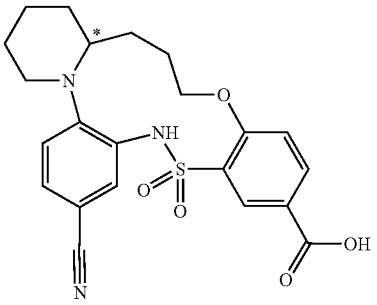

Example 5 was dissolved at 25 mg/ml in 1:1 DCM:MeOH with heating and sonication. The resultant mixture was filtered and then separated by chiral SFC (Waters prep 15 with UV detection by DAD at 210-400 nm, 40° C., 120 bar on a ChiralPAK IC 10×250 mm, 5 μm column, flow rate 15 mL/min, eluting with 15% MeOH/$CO_2$). The clean fractions were pooled, rinsed with MeOH and concentrated in vacuo to afford the title compound (2.2 mg, 4.9 μmol, 2% yield, 98% purity) as a white solid. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 2.81 min. Other analytical data consistent with Example 5.

Example 9: 2-cyano-6,7,8,9,9a,10,11,12-octahydro-19H-dibenzo[b,f]pyrido[1,2-h][1]oxa[4]thia[5,8] diazacyclododecine-16-carboxylic acid 18,18-dioxide Enantiomer 2

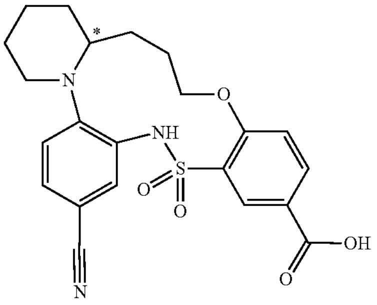

The title compound (2.1 mg, 4.7 μmol, 2% yield, 98% purity) was obtained as a white solid from the chiral separation performed in Example 8. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 3.39 min. Other analytical data consistent with Example 5.

Example 10: 8-cyano-12,13,14,15,15a,16-hexahydro-6H-dibenzo[b,f]pyrido[1,2-h][1,4,5,8]oxathiadiazecine-3-carboxylic acid 5,5-dioxide Enantiomer 1

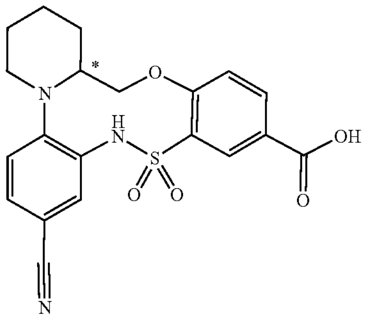 [SMILES: N#Cc1ccc2c(c1)NS(=O)(=O)c1cc(C(=O)O)ccc1OCC1CCCCN21]

Example 3 was dissolved to 25 mg/ml in 1:1 DCM:MeOH with heating and sonication. The resultant mixture was then filtered and separated by chiral SFC (Waters prep 15 with UV detection by DAD at 210-400 nm, 40° C., 120 bar on a ChiralPAK IC 10×250 mm, 5 μm column, flow rate 15 mL/min, eluting with 20% MeOH)/$CO_2$). The clean fractions were pooled, rinsed with MeOH and concentrated in vacuo to afford the title compound (8.3 mg, 19.1 μmol, 2% yield, 95% purity) as a green solid. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 5.67 min. Other analytical data consistent with Example 3.

Example 11: 8-cyano-12,13,14,15,15a,16-hexahydro-6H-dibenzo[b,f]pyrido[1,2-h][1,4,5,8]oxathiadiazecine-3-carboxylic acid 5,5-dioxide Enantiomer 2

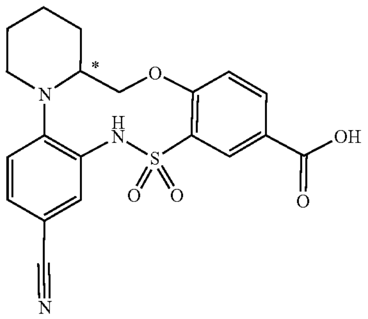 [SMILES: N#Cc1ccc2c(c1)NS(=O)(=O)c1cc(C(=O)O)ccc1OCC1CCCCN21]

The title compound (8.4 mg, 19.5 μmol, 2% yield, 96% purity) and was obtained as a green solid from the chiral separation performed in Example 10. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 6.16 min. Other analytical sata consistent with Example 3.

Example 12: 2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide Enantiomer 1

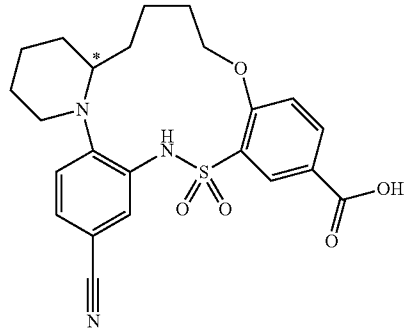 [SMILES: N#Cc1ccc2c(c1)NS(=O)(=O)c1cc(C(=O)O)ccc1OCCCCC1CCCCN21]

Example 4 was dissolved to 25 mg/ml in 1:1 DCM:MeOH with heating and sonication. The resultant mixture was filtered and then separated by chiral SFC (Waters prep 15 with UV detection by DAD at 210-400 nm, 40° C., 120 bar on a ChiralPAK IC 10×250 mm, 5 μm column, flow rate 15 mL/min, eluting with 35% MeOH/$CO_2$). The clean fractions were pooled, rinsed with MeOH and concentrated in vacuo to afford the title compound (6.4 mg, 13.8 μmol, 6% yield, 98% purity) as a light tan solid. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 3.09 min. Other analytical data consistent with Example 4.

Example 13: 2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide Enantiomer 2

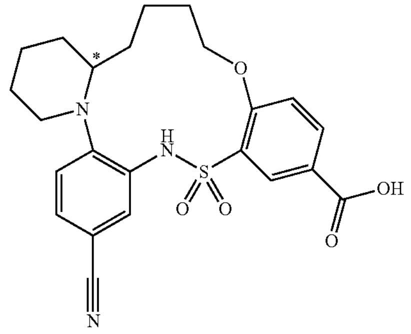 [SMILES: N#Cc1ccc2c(c1)NS(=O)(=O)c1cc(C(=O)O)ccc1OCCCCC1CCCCN21]

The title compound (6.8 mg, 14.6 μmol, 6% yield, 98% purity) was obtained as a light tan solid from the chiral separation performed in Example 12. SFC (Waters UPC$^2$, ChiralPAK IC 4.6×250 mm, 5 μm column, flow rate 4 mL/min, eluting with 35% (0.1% ammonia in MeOH)/$CO_2$) $t_R$ 3.42 min. Other analytical data consistent with Example 4.

Example 14: 9-chloro-8-cyano-12,13,14,15,15a,16-hexahydro-6H-dibenzo[b,f]pyrido[1,2-h][1,4,5,8]oxathiadiazecine-3-carboxylic acid 5,5-dioxide

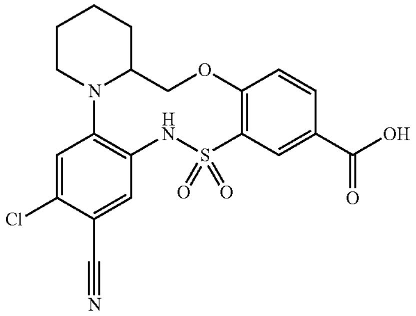 [SMILES: N#Cc1cc2c(cc1Cl)N1CCCCC1COc1ccc(C(=O)O)cc1S(=O)(=O)N2]

Step 1: 2-chloro-4-fluoro-5-nitrobenzonitrile: A 2 L three-neck flask equipped with thermometer, dropping funnel and bubbler was charged with 2-chloro-4-fluorobenzonitrile (50.0 g, 321 mmol) and sulfuric acid (344 mL) and cooled to 0° C. Nitric acid (320 mL, 90% w/w) was added over 90 min via dropping funnel at a rate that the inner temperature stayed below 20° C. Upon complete addition the mixture was warmed to RT and stirred for 2 h. The mixture was poured onto ice and left standing until all ice melted. The precipitate was collected by filtration, washing with water, and then dried in vacuo to afford the title compound (55.8 g, 276 mmol, 86% yield) as a pale yellow solid. $^1$H NMR (500 MHz, DMSO-$d_6$) δ 8.96 (d, J=7.7 Hz, 1H), 8.30 (d, J=10.9 Hz, 1H).

Step 2: 2-chloro-4-(2-(hydroxymethyl)piperidin-1-yl)-5-nitrobenzonitrile: A mixture of the product from Step 1 above (2.00 g, 9.97 mmol), piperidin-2-ylmethanol (1.22 g, 10.5 mmol) and $Et_3N$ (3.40 mL, 24.4 mmol) in DCM (50 mL) was stirred at 35° C. overnight. The mixture was washed with 1 M HCl(aq) (30 mL) and the organic layer was concentrated in vacuo to afford the title compound (3.06 g, 9.93 mmol, 100% yield, 96% purity) as an orange oil. UPLC-MS (Method 1): m/z 296.3 $(M+H)^+$, 294.2 $(M-H)^-$, at 1.35 min. $^1$H NMR (500 MHz, DMSO-$d_6$) δ 8.37 (s, 1H), 7.53 (s, 1H), 4.69 (t, J=5.4 Hz, 1H), 3.72-3.64 (m, 1H), 3.62-3.56 (m, 1H), 3.47 (dt, J=11.2, 5.8 Hz, 1H), 3.27-3.18 (m, 1H), 3.07-3.01 (m, 1H), 1.73-1.63 (m, 3H), 1.58-1.45 (m, 3H).

Step 3: 5-amino-2-chloro-4-(2-(hydroxymethyl)piperidin-1-yl)benzonitrile: A mixture of the product from Step 2 above (3.06 g, 9.93 mmol, 96% purity), ammonium chloride (1.59 g, 29.8 mmol) and zinc (1.95 g, 29.8 mmol) in THE (40 mL) and water (13 mL) was stirred at RT for 3 days. The mixture was filtered through Celite®, the filter cake was washed with EtOAc, and the filtrate was extracted with EtOAc (3×50 mL). The organic extracts were combined and washed with brine (20 mL), then passed through a phase separator. The solvent was removed in vacuo to afford the title compound (2.12 g, 7.82 mmol, 79% yield, 98% purity) as a pale red solid. UPLC-MS (Method 1): m/z 266.4 $(M+H)^+$ at 1.29 min. $^1$H NMR (500 MHz, DMSO-$d_6$) δ 7.15 (s, 1H), 7.02 (s, 1H), 5.33 (s, 2H), 4.48 (t, J=5.4 Hz, 1H), 3.39-3.33 (m, 1H), 3.28-3.21 (m, 1H), 3.21-3.15 (m, 1H), 3.06-2.99 (m, 1H), 2.67-2.59 (m, 1H), 1.90-1.81 (m, 1H), 1.70-1.63 (m, 1H), 1.63-1.56 (m, 2H), 1.54-1.41 (m, 2H).

9-chloro-8-cyano-12,13,14,15,15a,16-hexahydro-6H-dibenzo[b,f]pyrido[1,2-h][1,4,5,8]oxathiadiazecine-3-carboxylic acid 5,5-dioxide (436 mg, 965 μmol, 99% purity) was prepared as a white solid from the product from Step 3 above following the general method outlined in Example 3 Steps 3-5. UPLC-MS (Method 1): m/z 448.6 $(M+H)^+$, 446.4 $(M-H)^-$, at 1.41 min. $^1$H NMR (500 MHz, DMSO-$d_6$) δ 13.02 (s, 1H), 11.83 (s, 1H), 8.31 (d, J=2.2 Hz, 1H), 8.05 (dd, J=8.6, 2.2 Hz, 1H), 7.49 (s, 1H), 7.22 (s, 1H), 7.04 (d, J=8.6 Hz, 1H), 4.10 (d, J=13.2 Hz, 1H), 3.92 (dd, J=14.4, 4.1 Hz, 1H), 3.27 (dd, J=14.4, 9.1 Hz, 1H), 2.88-2.80 (m, 1H), 2.60 (td, J=12.9, 2.8 Hz, 1H), 1.73 (d, J=12.2 Hz, 1H), 1.69-1.61 (m, 2H), 1.44-1.33 (m, 1H), 1.33-1.22 (m, 1H), 1.14-1.02 (m, 1H).

Example 15: (E)-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide

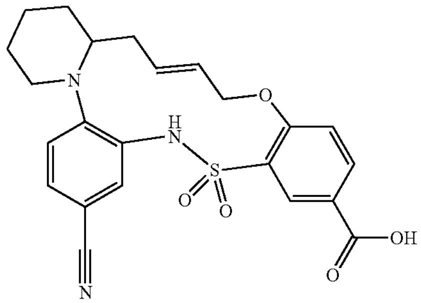 [SMILES: N#Cc1ccc2c(c1)NS(=O)(=O)c1cc(C(=O)O)ccc1OC/C=C/CC1CCCCN21]

Step 1: methyl 3-(benzylthio)-4-hydroxybenzoate: Two reactions were carried out on a 5 g, g and 20 reactions were carried out on a 1 g scale according to the following procedure and combined for work-up and purification. A solution of methyl 3-bromo-4-hydroxybenzoate (5 g, 21.6 mmol) and benzyl mercaptan (2.95 g, 23.8 mmol) in dioxane (50 mL) was treated with Xantphos (1.22 g, 3.24 mmol), $Pd_2(dba)_3$ (1.98 g, 2.16 mmol) and DIPEA (136 mL, 740 mmol) at RT. The reaction mixture was purged with $N_2$ for 20 min. The mixture was heated to 110° C. and stirred for 16 h. The three reactions mixtures were allowed to cooled to RT and were combined, filtered through Celite®, washing with EtOAc (100 mL). The filtrate was concentrated in vacuo and the residue partitioned between EtOAc (1 L) and water (700 mL). The layers were separated, and the aqueous layer extracted with EtOAc (1 L). The organic layers were combined and dried over $Na_2SO_4$, then concentrated under in vacuo. The residue was purified by chromatography on silica gel (2.5% EtOAc in hexane) to afford the title compound (19 g, 69.3 mmol, 53% yield) as an orange semi-solid. $^1$H NMR (400 MHz, DMSO-$d_6$) δ 10.91 (s, 1H), 7.74 (d, J=2.0 Hz, 1H), 7.66 (dd, J=8.4, 2.4 Hz, 1H), 7.34-7.22 (m, 5H), 6.90 (d, J=8.4 Hz, 1H), 4.17 (s, 2H), 3.77 (s, 3H).

Step 2: methyl 4-(allyloxy)-3-(benzylthio)benzoate: A solution of the product from Step 1 above (19 g, 69.3 mmol) in DMSO (30 mL) was treated with $K_2CO_3$ (19.1 g, 138 mmol) at RT. 3-bromoprop-1-ene (8.81 g, 72.7 mmol) was added dropwise and the resultant mixture was stirred at RT for 2 h. The mixture was diluted with ice-cold water (600 mL) and extracted with ethyl acetate (2×1 L). The organic layers were combined and washed with ice-cold water (2×500 mL), dried over $Na_2SO_4$ and concentrated in vacuo. The residue was purified by chromatography on silica gel (4% EtOAc in hexane) to afford the title compound (17 g, 54.1 mmol, 78% yield, 82% purity) as yellow semi-solid. $^1$H NMR (400 MHz, DMSO-$d_6$) δ 7.83-7.75 (m, 2H), 7.41-7.35 (m, 2H), 7.32-7.28 (m, 2H), 7.25-7.21 (m, 1H), 7.08 (d, J=8.4 Hz, 1H), 6.01-6.10 (m, 1H), 5.45 (dd, J=17.2, 1.6 Hz, 1H), 5.29 (dd, J=10.4, 1.2 Hz, 1H), 4.70 (d, J=4.8 Hz, 2H), 4.21 (s, 2H), 3.80 (s, 3H).

Step 3: methyl 4-(allyloxy)-3-(chlorosulfonyl)benzoate: A solution of the product from Step 2 above (17 g, 54.1 mmol, 82% purity) in AcOH (340 mL) and water (34 mL) at was cooled to −10° C. NCS (21.7 g, 162 mmol) was added portionwise maintaining the temperature below 0° C. The resultant mixture was stirred at between −10° C. to 10° C. for 3 h. The mixture was diluted with ice-cold water (700 mL) and extracted with DCM (3×500 mL). The organic layers were combined and washed with ice-cold water (2×1 L), dried over $Na_2SO_4$ and concentrated in vacuo. The residue was partially purified by chromatography on silica gel (8-10% EtOAc in hexane). The obtained material (4.5 g) was stirred in n-hexane (50 mL) for 30 min, filtered and dried in vacuo to afford the title compound (4.3 g, 14.8 mmol, 27% yield, 99% purity) as a white solid. $^1$H NMR (400 MHz, DMSO-$d_6$) δ 14.59 (s, 1H), 8.32 (d, J=2.4 Hz, 1H), 7.88 (dd, J=8.4, 2.0 Hz, 1H), 7.06 (d, J=8.8 Hz, 1H), 6.00-5.94 (m, 1H), 5.59 (dd, J=17.2, 2.0H, 1H), 5.22 (dd, J=10.4, 1.6 Hz, 1H), 4.68-4.67 (m, 2H), 3.81 (s, 3H).

Step 4: 4-(2-ally/piperidin-1-yl)-3-nitrobenzonitrile: A mixture of 4-fluoro-3-nitrobenzonitrile (1.00 g, 6.02 mmol), 2-allylpiperidine hydrochloride (1.00 g, 6.19 mmol) and $Et_3N$ (3.50 mL, 25.1 mmol) in DCM (25 mL) was stirred at 35° C. for 3 days. The mixture was washed with saturated $NH_4Cl$(aq) (30 mL), passed through a phase separator and the solvent was removed in vacuo to afford the title compound (1.72 g, 6.02 mmol, 100% yield, 95% purity) as an orange solid. UPLC-MS (Method 1): m/z 272.3 $(M+H)^+$ at 1.71 min. $^1$H NMR (500 MHz, DMSO-$d_6$) δ 8.26 (d, J=2.1 Hz, 1H), 7.81 (dd, J=8.9, 2.1 Hz, 1H), 7.39 (d, J=8.9 Hz, 1H), 5.62 (ddt, J=17.1, 10.1, 7.1 Hz, 1H), 5.08-5.00 (m, 1H), 4.96-4.90 (m, 1H), 3.73-3.67 (m, 1H), 3.30-3.22 (m, 1H), 2.93-2.87 (m, 1H), 2.43-2.29 (m, 2H), 1.75-1.44 (m, 6H).

Step 5: 4-(2-ally/piperidin-1-yl)-3-aminobenzonitrile: A mixture of the product from Step 4 above (1.72 g, 6.02 mmol, 95% purity), ammonium chloride (1.93 g, 36.1 mmol) and zinc (2.36 g, 36.1 mmol) in THE (20 mL) and water (6.7 mL) was stirred at RT overnight. Additional zinc (2.36 g, 36.1 mmol) and ammonium chloride (1.93 g, 36.1 mmol) were added and stirring at RT was continued overnight. The mixture was filtered through Celite®, washing with EtOAc, and the filtrate was extracted with EtOAc (3×40 mL). The organic extracts were combined, washed with brine (40 mL), passed through a phase separator, and the solvent was removed in vacuo. The mixture was loaded onto silica and purified by chromatography on (40 g cartridge, 0-50% EtOAc/isohexane) to afford the title compound (1.13 g, 4.64 mmol, 77% yield, 99% purity) as a pale pink oil. UPLC-MS (Method 1): m/z 242.4 $(M+H)^+$ at 1.72 min. $^1$H NMR (500 MHz, DMSO-$d_6$) δ 7.09 (d, J=8.0 Hz, 1H), 6.98 (d, J=2.0 Hz, 1H), 6.94 (dd, J=8.0, 2.0 Hz, 1H), 5.60 (ddt, J=17.2, 10.2, 7.1 Hz, 1H), 5.23 (s, 2H), 4.94-4.89 (m, 1H), 4.89-4.83 (m, 1H), 3.13-3.07 (m, 1H), 2.99-2.91 (m, 1H), 2.43 (ddd, J=12.1, 8.6, 3.8 Hz, 1H), 2.10-2.01 (m, 1H), 2.01-1.90 (m, 1H), 1.82-1.75 (m, 1H), 1.74-1.67 (m, 1H), 1.65-1.55 (m, 2H), 1.45-1.34 (m, 2H).

Step 6: methyl 4-(allyloxy)-3-(N-(2-(2-ally/piperidin-1-yl)-5-cyanophenyl)sulfamoyl)benzoate: A mixture of the product from Step 5 above (1.08 g, 4.43 mmol, 99% purity), the product from Step 3 above (1.55 g, 5.32 mmol) and pyridine (1.10 mL, 13.7 mmol) in DCM (20 mL) was heated to 35° C. and stirred overnight. The mixture was concentrated onto silica and purified by chromatography on silica gel (40 g cartridge, 0-50% EtOAc/isohexane) to afford the title compound (1.67 g, 3.30 mmol, 75% yield, 98% purity) as a pale-yellow solid. UPLC-MS (Method 1): m/z 496.4 $(M+H)^+$, 494.2 $(M-H)^-$, at 1.91 min. $^1$H NMR (500 MHz, DMSO-$d_6$) b 8.83 (s, 1H), 8.38 (d, J=2.3 Hz, 1H), 8.19 (dd, J=8.7, 2.3 Hz, 1H), 7.63 (d, J=1.9 Hz, 1H), 7.52 (dd, J=8.2, 1.9 Hz, 1H), 7.45-7.38 (m, 2H), 6.03-5.92 (m, 1H), 5.54-5.43 (m, 2H), 5.32 (dd, J=10.7, 1.7 Hz, 1H), 4.88-4.72 (m, 4H), 3.86 (s, 3H), 3.11-3.04 (m, 1H), 2.71-2.66 (m, 1H), 2.55-2.51 (m, 1H), 1.80-1.66 (m, 4H), 1.59-1.48 (m, 2H), 1.41-1.27 (m, 2H).

Step 7: methyl (E)-2-cyano-7,8,9,9a,10,13-hexahydro-6H, 20H-dibenzo[b,f]pyrido[1,2-h][1]oxa[4]thia[5,8]diazacyclotridecine-17-carboxylate 19,19-dioxide: A solution of the product from Step 6 above (1.52 g, 3.01 mmol, 98% purity) and Grubbs-Hoveyda 2nd Gen (95.0 mg, 151 μmol) in DCM (60 mL) was stirred at RT overnight. The mixture was concentrated onto silica and purified by chromatography on silica gel (40 g cartridge, 0-100% EtOAc/isohexane) and then triturated with DCM/heptane to afford the title compound (947 mg, 1.98 mmol, 66% yield, 98% purity) as a light brown solid. UPLC-MS (Method 1): m/z 467.3 $(M+H)^+$, 466.5 $(M-H)^-$, at 1.70 min. $^1$H NMR (500 MHz, DMSO-$d_6$) δ 8.57 (d, J=2.2 Hz, 1H), 8.23-8.18 (m, 2H), 7.63 (d, J=8.9 Hz, 1H), 7.51 (d, J=8.3 Hz, 1H), 7.46 (dd, J=8.1, 1.9 Hz, 1H), 7.13 (d, J=1.7 Hz, 1H), 6.00-5.86 (m, 1H), 5.16-5.10 (m, 1H), 4.92-4.86 (m, 1H), 4.70 (dd, J=12.3, 9.5 Hz, 1H), 3.91 (s, 3H), 3.38-3.32 (m, 1H), 2.83 (d, J=11.9 Hz, 1H), 2.36-2.30 (m, 1H), 2.10-2.01 (m, 1H), 2.01-1.95 (m, 1H), 1.86-1.73 (m, 3H), 1.69-1.62 (m, 1H), 1.62-1.54 (m, 1H), 1.48-1.36 (m, 1H).

Step 8: (E)-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide: A mixture of the product from Step 7 above (200 mg, 419 μmol, 98% purity) and LiOH·$H_2O$ (70 mg, 1.67 mmol) in THE/MeOH/water (4:1:1, 2.1 mL) was stirred at 40° C. overnight. The mixture was diluted with water (30 mL), acidified to ~pH 4 with 1 M HCl(aq) and extracted with EtOAc (3×50 mL). The organic extracts were combined and washed with brine (50 mL), passed through a phase separator and the solvent was removed in vacuo. The residue was triturated with TBME to afford the title compound (142 mg, 310 μmol, 74% yield, 99% purity) as a light-grey solid. UPLC-MS (Method 1): m/z 454.4 $(M+H)^+$, 452.4 $(M-H)^-$, at 1.54 min. $^1$H NMR (500 MHz, DMSO-$d_6$) δ 13.31 (s, 1H), 8.56 (d, J=2.2 Hz, 1H), 8.22-8.14 (m, 2H), 7.60 (d, J=8.9 Hz, 1H), 7.50 (d, J=8.3 Hz, 1H), 7.45 (dd, J=8.2, 1.9 Hz, 1H), 7.13 (d, J=1.8 Hz, 1H), 5.99-5.88 (m, 1H), 5.19-5.08 (m, 1H), 4.93-4.84 (m, 1H), 4.75-4.63 (m, 1H), 3.36-3.33 (m, 1H), 2.88-2.79 (m, 1H), 2.38-2.33 (m, 1H), 2.10-1.93 (m, 2H), 1.87-1.72 (m, 3H), 1.72-1.62 (m, 1H), 1.62-1.50 (m, 1H), 1.48-1.33 (m, 1H).

Example 16: 9-chloro-8-cyano-12,13,14,15,15a,16-hexahydro-6H-dibenzo[b,f]pyrido[1,2-h][1,4,5,8]oxathiadiazecine-3-carboxylic acid 5,5-dioxide Enantiomer 1

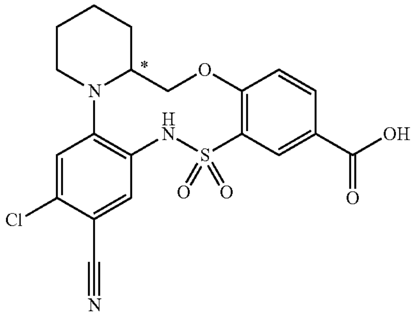 [SMILES: N#Cc1cc2c(cc1Cl)N1CCCCC1COc1ccc(C(=O)O)cc1S(=O)(=O)N2]

Example 14 was dissolved to 50 mg/mL in MeOH/DCM with sonication and heating, then filtered and separated by chiral SFC (Waters prep 15 with UV detection by DAD at 210-400 nm, 40° C., 120 bar on a ChiralPak IG 10×250 mm, 5 μm column, flow rate 15 mL/min, eluting with 25% $MeOH/CO_2$). The clean fractions were pooled, rinsed with MeOH and concentrated in vacuo to afford the title compound (86.2 mg, 191 μmol, 43% yield, 99% purity) as a light-yellow solid. SFC (Waters $UPC^2$, ChiralPak IG 4.6×250, 5 μm column, flow rate 4 mL/min, eluting with 25% (0.1% $NH_3$/MeOH)/$CO_2$): $t_R$ 3.06 min. Other analytical data consistent with Example 14.

Example 17: 9-chloro-8-cyano-12,13,14,15,15a,16-hexahydro-6H-dibenzo[b,f]pyrido[1,2-h][1,4,5,8]oxathiadiazecine-3-carboxylic acid 5,5-dioxide Enantiomer 2

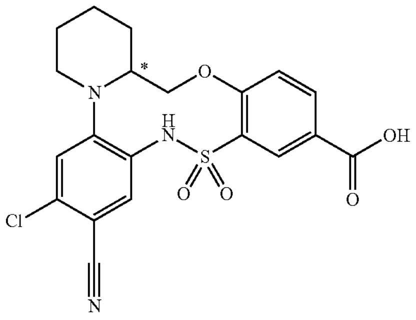 [SMILES: N#Cc1cc2c(cc1Cl)N1CCCCC1COc1ccc(C(=O)O)cc1S(=O)(=O)N2]

The title compound (80.8 mg, 179 μmol, 41%, 99% purity) was obtained as a light-yellow solid from the chiral separation performed in Example 16. SFC (Waters $UPC^2$, ChiralPak IG 4.6×250, 5 μm column, flow rate 4 mL/min, eluting with 25% (0.1% $NH_3$/MeOH)/$CO_2$): $t_R$ 4.13 min. Other analytical data consistent with Example 14.

Example 18: 8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide

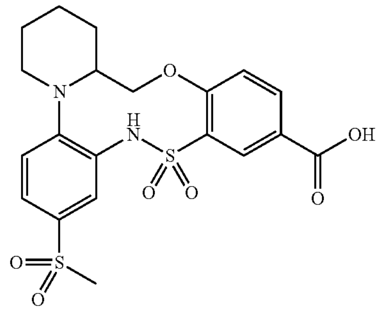 [SMILES: CS(=O)(=O)c1ccc2c(c1)NS(=O)(=O)c1cc(C(=O)O)ccc1OCC1CCCCN21]

Step 1: (1-(4-(methylsulfonyl)-2-nitrophenyl)piperidin-2-yl)methanol: A mixture of 1-fluoro-4-(methylsulfonyl)-2-nitrobenzene (1.00 g, 4.56 mmol), piperidin-2-ylmethanol (552 mg, 4.79 mmol) and $Et_3N$ (1.30 mL, 9.33 mmol) in DCM (20 mL) was stirred at 35° C. overnight. The mixture was washed with 1 M HCl(aq) (2×10 mL), passed through a phase separator and the solvent was removed in vacuo to afford the title compound (1.46 g, 4.41 mmol, 97% yield, 95% purity) as an orange oil. UPLC-MS (Method 1): m/z 315.3 $(M+H)^+$, 313.3 $(M-H)^-$, at 1.06 min. $^1H$ NMR (500 MHz, DMSO-$d_6$) δ 8.18 (d, J=2.4 Hz, 1H), 7.88 (dd, J=9.0, 2.4 Hz, 1H), 7.46 (d, J=9.0 Hz, 1H), 4.63 (t, J=5.3 Hz, 1H), 3.63-3.50 (m, 3H), 3.24-3.19 (m, 4H), 3.02-2.96 (m, 1H), 1.77-1.63 (m, 3H), 1.60-1.49 (m, 3H).

Step 2: (1-(2-amino-4-(methylsulfonyl)phenyl)piperidin-2-yl)methanol: A mixture of the product from Step 1 above (1.46 g, 4.41 mmol, 95% purity), ammonium chloride (708 mg, 13.2 mmol) and zinc (865 mg, 13.2 mmol) in THF (15 mL) and water (5 mL) was stirred at RT for 5 h. The mixture was filtered through Celite®, the filter cake was washed with EtOAc, and the filtrate was extracted with EtOAc (3×30 mL). The organic extracts were combined and washed with brine (15 mL), passed through a phase separator, and the solvent was removed in vacuo to afford the title compound (687 mg, 2.15 mmol, 49% yield, 89% purity) as a dark brown oil. UPLC-MS (Method 1): m/z 285.4 $(M+H)^+$ at 0.83 min. 8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide (175 mg, 360 μmol, 96% purity) was prepared as a beige solid from the product from Step 3 above following the general method outlined in Example 3 Steps 3-5. UPLC-MS (Method 1): m/z 467.3 $(M+H)^+$, 465.3 $(M-H)^-$, at 1.17 min. $^1H$ NMR (500 MHz, DMSO-$d_6$) δ 12.95 (s, 1H), 11.86 (s, 1H), 8.32 (d, J=2.2 Hz, 1H), 8.02 (dd, J=8.6, 2.3 Hz, 1H), 7.66 (d, J=2.2 Hz, 1H), 7.41 (dd, J=9.0, 2.3 Hz, 1H), 7.09 (d, J=9.0 Hz, 1H), 7.04 (d, J=8.6 Hz, 1H), 4.09-4.04 (m, 1H), 4.02 (dd, J=14.0, 3.8 Hz, 1H), 3.37 (dd, J=14.0, 8.8 Hz, 1H), 3.02-2.98 (m, 1H), 2.96 (s, 3H), 2.68-2.59 (m, 1H), 1.80-1.74 (m, 1H), 1.73-1.67 (m, 2H), 1.45-1.33 (m, 2H), 1.19-1.11 (m, 1H).

Example 19: 8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide Enantiomer 1

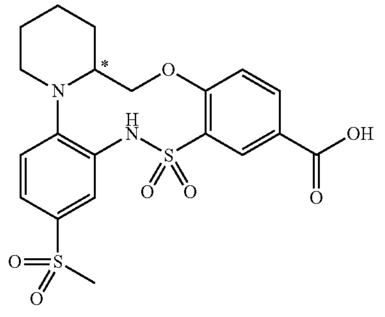 [SMILES: CS(=O)(=O)c1ccc2c(c1)NS(=O)(=O)c1cc(C(=O)O)ccc1OCC1CCCCN21]

Example 18 was dissolved at 50 mg/ml in MeOH/DCM (1:1) with sonication. The mixture was filtered and then separated by chiral SFC (Waters prep 15 with UV detection by DAD at 210-400 nm, 40° C., 120 bar on a ChiralPAK IC 10×250 mm, 5 μm column, flow rate 15 mL/min, eluting with 35% (0.1% TFA/MeOH)/$CO_2$). The clean fractions were pooled, rinsed with MeOH, and concentrated in vacuo. The residue was dissolved in EtOAc (10 mL), washed with 1:1 brine/water (5 mL), passed through a phase separator and the solvent was removed in vacuo to afford the title compound (65.6 mg, 136 μmol, 38% yield, 97% purity) as a light-green solid. SFC (Waters UPC$^2$, ChiralPAK IC 4.6×250, 5 μm column, flow rate 4 mL/min, eluting with 35% (0.1% $NH_3$/MeOH)/$CO_2$): $t_R$ 2.54 min. Other analytical data consistent with Example 18.

Example 20: 8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide Enantiomer 1

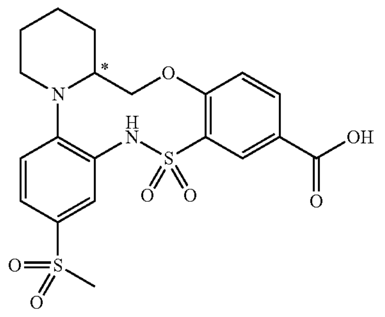 [SMILES: CS(=O)(=O)c1ccc2c(c1)NS(=O)(=O)c1cc(C(=O)O)ccc1OCC1CCCCN21]

The title compound (67.0 mg, 141 μmol, 39% yield, 98% purity) was obtained as a light-green solid from the chiral separation performed in Example 19. SFC (Waters UPC$^2$, ChiralPAK IC 4.6×250, 5 μm column, flow rate 4 mL/min, eluting with 35% (0.1% $NH_3$/MeOH)/$CO_2$) $t_R$ 3.17 min. Other analytical data consistent with Example 18.

Example 21: 3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

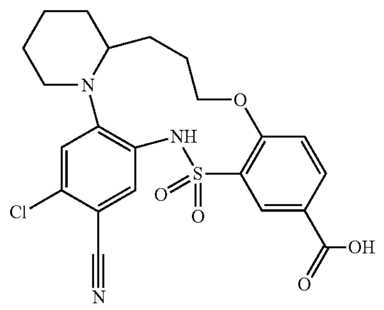 [SMILES: N#Cc1cc2c(cc1Cl)N1CCCCC1CCCOc1ccc(C(=O)O)cc1S(=O)(=O)N2]

Step 1: 2-chloro-4-(2-(3-hydroxypropyl)piperidin-1-yl)-5-nitrobenzonitrile: A mixture of the product from Example 14 Step 1 (650 mg, 3.24 mmol), 3-(piperidin-2-yl)propan-1-ol (491 mg, 3.43 mmol) and $Et_3N$ (900 μl, 6.46 mmol) in DCM (15 mL) was stirred at 35° C. for 5 days. The mixture was concentrated onto silica and purified by chromatography on silica gel (24 g cartridge, 0-100% EtOAc/isohexane) to afford the title compound (302 mg, 914 μmol, 28% yield, 98% purity) as an orange oil. UPLC-MS (Method 1): m/z 324.7 $(M+H)^+$ at 1.42 min. $^1H$ NMR (500 MHz, DMSO-$d_6$) δ 8.39 (s, 1H), 7.60 (s, 1H), 4.38 (s, 1H), 3.86-3.81 (m, 1H), 3.36-3.30 (m, 2H), 3.22 (td, J=12.9, 2.9 Hz, 1H), 2.86-2.80 (m, 1H), 1.81-1.70 (m, 2H), 1.67-1.51 (m, 5H), 1.50-1.39 (m, 1H), 1.39-1.20 (m, 2H).

Step 2: 5-amino-2-chloro-4-(2-(3-hydroxypropyl)piperidin-1-yl) benzonitrile: A mixture of the product from Step 1 above (302 mg, 914 μmol, 98% purity), ammonium chloride (293 mg, 5.48 mmol) and zinc (359 mg, 5.48 mmol) in THE (3 mL) and water (1 mL) was stirred for 6 h. The mixture was filtered through Celite®, the filter cake was washed with EtOAc, and the filtrate was extracted with EtOAc (3×10 mL). The organic extracts were combined and washed with brine (10 mL), passed through a phase separator, and the solvent was removed in vacuo to afford the title compound (272 mg, 907 μmol, 99% yield, 98% purity) as a brown oil. UPLC-MS (Method 1): m/z 294.2 $(M+H)^+$ at 1.40 min.

3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide (11.1 mg, 22.2 μmol, 95% purity) was prepared as a white solid from the product from Step 2 above following the general method outlined in Example 5 Steps 3-5. UPLC-MS (Method 1): m/z 476.3 $(M+H)^+$, 474.4 $(M-H)^-$, at 1.66 min. $^1H$ NMR (500 MHz, DMSO-$d_6$) δ 13.25 (s, 1H), 9.05 (s, 1H), 8.51 (d, J=2.2 Hz, 1H), 8.15 (dd, J=8.8, 2.2 Hz, 1H), 7.64 (s, 1H), 7.45 (s, 1H), 7.22 (d, J=8.8 Hz, 1H), 4.19-4.05 (m, 2H), 3.56-3.49 (m, 1H), 2.94-2.87 (m, 1H), 2.61-2.53 (m, 1H), 1.89-1.36 (m, 8H), 1.34-1.23 (m, 1H), 1.20-1.13 (m, 1H).

Example 22: 3-chloro-2-cyano-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

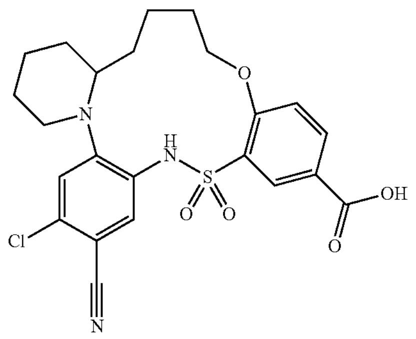 [SMILES: N#Cc1cc2c(cc1Cl)N1CCCCC1CCCCOc1ccc(C(=O)O)cc1S(=O)(=O)N2]

Step 1: 2-chloro-4-(2-(4-hydroxybutyl)piperidin-1-yl)-5-nitrobenzonitrile: A mixture of the product from Example 14 Step 1 (600 mg, 2.99 mmol), 4-(piperidin-2-yl)butan-1-ol (500 mg, 3.18 mmol) and $Et_3N$ (900 µl, 6.46 mmol) in DCM (15 mL) was stirred at 35° C. for 2 days. The mixture was concentrated onto silica and purified by chromatography on silica gel (24 g cartridge, 0-100% EtOAc/isohexane) to afford the title compound (919 mg, 2.5 mmol, 85% yield, 93% purity) as an orange oil. UPLC-MS (Method 1): m/z 338.3 $(M+H)^+$ at 1.49 min. $^1H$ NMR (500 MHz, DMSO-$d_6$) δ 8.38 (s, 1H), 7.59 (s, 1H), 4.30 (t, J=5.1 Hz, 1H), 3.84-3.79 (m, 1H), 3.31-3.27 (m, 2H), 3.22 (td, J=12.9, 2.9 Hz, 1H), 2.86-2.80 (m, 1H), 1.80-1.68 (m, 2H), 1.68-1.58 (m, 3H), 1.58-1.42 (m, 3H), 1.42-1.27 (m, 2H), 1.26-1.07 (m, 2H).

Step 2: 5-amino-2-chloro-4-(2-(4-hydroxybutyl)piperidin-1-yl)benzonitrile: A mixture of the product from Step 1 above (919 mg, 2.53 mmol, 93% purity), ammonium chloride (812 mg, 15.2 mmol) and zinc (993 mg, 15.2 mmol) in THE (9 mL) and water (3 mL) was stirred at RT for 6 h. The mixture was filtered through Celite®, the filter cake was washed with EtOAc, and the filtrate was extracted with EtOAc (3×40 mL). The organic extracts were combined, washed with brine (20 mL), passed through a phase separator, and the solvent removed in vacuo to afford the title compound (748 mg, 2.38 mmol, 94% yield, 98% purity) as a dark brown oil. UPLC-MS (Method 1): m/z 308.3 $(M+H)^+$ at 1.49 min. 3-chloro-2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide (41.7 mg, 82.6 µmol, 97% purity) was obtained as a pale yellow solid from the product from Step 2 above following the general method outlined in Example 4 Steps 3-5. UPLC-MS (Method 1): m/z 490.3 $(M+H)^+$, 488.3 $(M-H)^-$, at 1.72 min. $^1H$ NMR (500 MHz, DMSO-$d_6$) δ 13.27 (s, 1H), 8.72 (s, 1H), 8.56 (d, J=2.2 Hz, 1H), 8.17 (dd, J=8.8, 2.2 Hz, 1H), 7.67 (s, 1H), 7.36 (d, J=8.8 Hz, 1H), 7.27 (s, 1H), 4.33-4.25 (m, 1H), 4.18-4.11 (m, 1H), 3.39-3.33 (m, 1H), 2.93-2.87 (m, 1H), 2.68-2.63 (m, 1H), 1.86-1.19 (m, 12H).

Example 23: 2-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

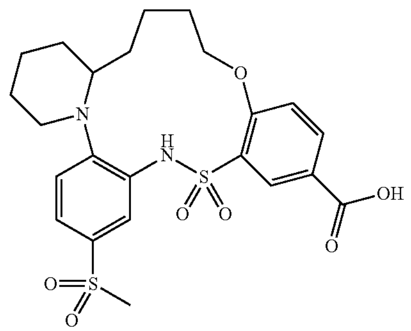 [SMILES: CS(=O)(=O)c1ccc2c(c1)NS(=O)(=O)c1cc(C(=O)O)ccc1OCCCCC1CCCCN21]

Step 1: 4-(1-(4-(methylsulfonyl)-2-nitrophenyl)piperidin-2-yl)butan-1-ol: A mixture of 1-fluoro-4-(methylsulfonyl)-2-nitrobenzene (650 mg, 2.97 mmol), 4-(piperidin-2-yl)butan-1-ol (500 mg, 3.18 mmol) and $Et_3N$ (900 µl, 6.46 mmol) in DCM (15 mL) was stirred at 35° C. for 2 days. The mixture was concentrated onto silica and purified by chromatography on silica gel (24 g cartridge, 0-100% EtOAc/isohexane) to afford the title compound (1.00 g, 2.69 mmol, 91% yield, 96% purity) as an orange oil. UPLC-MS (Method 1): m/z 357.3 $(M+H)^+$ at 1.23 min. $^1H$ NMR (500 MHz, DMSO-$d_6$) δ 8.19 (d, J=2.4 Hz, 1H), 7.88 (dd, J=9.0, 2.4 Hz, 1H), 7.49 (d, J=9.0 Hz, 1H), 4.29 (t, J=5.1 Hz, 1H), 3.77-3.72 (m, 1H), 3.31-3.25 (m, 2H), 3.25-3.19 (m, 4H), 2.84-2.78 (m, 1H), 1.81-1.73 (m, 1H), 1.73-1.59 (m, 4H), 1.59-1.40 (m, 3H), 1.40-1.26 (m, 2H), 1.26-1.08 (m, 2H).

Step 2: 4-(1-(2-amino-4-(methy/sulfonyl)phenyl)piperidin-2-yl)butan-1-ol: A mixture of the product from Step 1 above (1.00 g, 2.69 mmol, 96% purity), ammonium chloride (864 mg, 16.2 mmol) and zinc (1.06 g, 16.2 mmol) in THE (9 mL) and water (3 mL) was stirred at RT for 6 h. The mixture was filtered through Celite®, the filter cake was washed with EtOAc, and the filtrate was extracted with EtOAc (3×40 mL). The organic extracts were combined and washed with brine (20 mL), passed through a phase separator, and the solvent was removed in vacuo to afford the title compound (306 mg, 591 µmol, 22% yield, 63% purity) as a brown oil. UPLC-MS (Method 1): m/z 327.3 $(M+H)^+$ at 1.08 min.

2-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide (40.6 mg, 77.4 µmol, 97% purity) was obtained as a pale yellow solid from the product from Step 2 above following the general method outlined in Example 4 Steps 3-5. UPLC-MS (Method 1): m/z 509.7 $(M+H)^+$, 507.4 $(M-H)^-$, at 1.46 min. $^1H$ NMR (500 MHz, DMSO-$d_6$) δ 13.19 (s, 1H), 8.66 (s, 1H), 8.58 (d, J=2.2 Hz, 1H), 8.13 (dd, J=8.8, 2.3 Hz, 1H), 7.60 (d, J=8.4 Hz, 1H), 7.46 (dd, J=8.4, 2.2 Hz, 1H), 7.39 (s, 1H), 7.32 (d, J=8.8 Hz, 1H), 4.31-4.25 (m, 1H), 4.10-4.02 (m, 1H), 3.30-3.26 (m, 1H), 2.92 (s, 3H), 2.90-2.84 (m, 1H), 2.58 (s, 1H), 1.89-1.78 (m, 2H), 1.73-1.66 (m, 2H), 1.61-1.54 (m, 2H), 1.49-1.34 (m, 4H), 1.32-1.22 (m, 2H).

Example 24: 8-cyano-9-fluoro-12,13,14,15,15a,16-hexahydro-6H-dibenzo[b,f]pyrido[1,2-h][1,4,5,8]oxathiadiazecine-3-carboxylic acid 5,5-dioxide

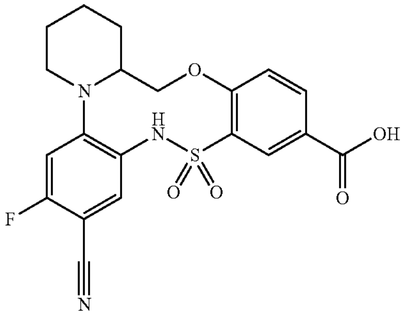 [SMILES: N#Cc1cc2c(cc1F)N1CCCCC1COc1ccc(C(=O)O)cc1S(=O)(=O)N2]

Step 1: 2-fluoro-4-(2-(hydroxymethyl)piperidin-1-yl)-5-nitrobenzonitrile: A mixture of 2,4-difluoro-5-nitrobenzonitrile (1.00 g, 5.43 mmol), piperidin-2-ylmethanol (657 mg, 5.70 mmol) and $Et_3N$ (1.50 mL, 10.8 mmol) in DCM (25 mL) was stirred at 35° C. overnight. The mixture was concentrated onto silica and purified by chromatography on silica gel (40 g cartridge, 0-100% EtOAc/isohexane) to afford the title compound (1.34 g, 4.41 mmol, 81% yield, 92% purity) as an orange solid. UPLC-MS (Method 1): m/z 280.7 $(M+H)^+$, 278.3 $(M-H)^-$, at 1.27 min. $^1H$ NMR (500 MHz, DMSO-$d_6$) δ 8.39 (d, J=7.2 Hz, 1H), 7.32 (d, J=13.2 Hz, 1H), 4.69 (t, J=5.5 Hz, 1H), 3.67 (ddd, J=10.7, 7.5, 5.5 Hz, 1H), 3.58-3.55 (m, 1H), 3.52-3.44 (m, 1H), 3.27-3.18 (m, 1H), 3.06-3.00 (m, 1H), 1.75-1.64 (m, 3H), 1.60-1.46 (m, 3H).

Step 2: 5-amino-2-fluoro-4-(2-(hydroxymethyl)piperidin-1-yl)benzonitrile: A mixture of the product from Step 1 above (1.34 g, 4.41 mmol, 92% purity), ammonium chloride (1.42 g, 26.5 mmol) and zinc (1.73 g, 26.5 mmol) in THE (15 mL) and water (5 mL) was stirred at RT overnight. The mixture was filtered through Celite®, the filter cake was washed with EtOAc, and the filtrate was extracted with EtOAc (3×30 mL). The organic extracts were combined, washed with brine (20 mL), passed through a phase separator, and the solvent was removed in vacuo to afford the title compound (1.26 g, 4.25 mmol, 96% yield, 84% purity) as a brown solid. UPLC-MS (Method 1): m/z 250.4 $(M+H)^+$ at 1.16 min.

8-cyano-9-fluoro-12,13,14,15,15a,16-hexahydro-6H-dibenzo[b,f]pyrido[1,2-h][1,4,5,8]oxathiadiazecine-3-carboxylic acid 5,5-dioxide (112 mg, 252 μmol, 97% purity) was obtained as a light yellow solid from the product from Step 2 above following the general method outlined in Example 3 Steps 3-5. UPLC-MS (Method 1): m/z 432.2 $(M+H)^+$, 430.3 $(M-H)^-$, at 1.34 min. $^1H$ NMR (500 MHz, DMSO-$d_6$) δ 12.99 (s, 1H), 11.79 (s, 1H), 8.29 (d, J=2.2 Hz, 1H), 8.03 (dd, J=8.6, 2.2 Hz, 1H), 7.42 (d, J=7.2 Hz, 1H), 7.08-7.00 (m, 2H), 4.07-4.01 (m, 1H), 3.93 (dd, J=14.4, 4.2 Hz, 1H), 3.25 (dd, J=14.4, 9.3 Hz, 1H), 2.89-2.81 (m, 1H), 2.63-2.54 (m, 1H), 1.76-1.70 (m, 1H), 1.68-1.62 (m, 2H), 1.42-1.32 (m, 1H), 1.31-1.22 (m, 1H), 1.10-1.02 (m, 1H).

Example 25: 9-fluoro-8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide

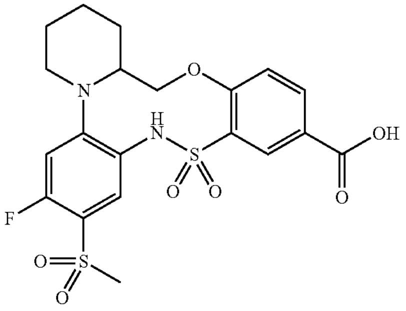 [SMILES: CS(=O)(=O)c1cc2c(cc1F)N1CCCCC1COc1ccc(C(=O)O)cc1S(=O)(=O)N2]

Step 1: (1-(5-fluoro-4-(methylsulfonyl)-2-nitrophenyl)piperidin-2-yl)methanol: A mixture of 1,5-difluoro-2-(methylsulfonyl)-4-nitrobenzene (1.00 g, 1 Eq, 4.22 mmol) [prepared according to the procedure in WO 2020/104822 A1 Example 331 Part A Steps 1-3], piperidin-2-ylmethanol (510 mg, 4.43 mmol) and $Et_3N$ (1.20 mL, 8.61 mmol) in DCM (20 mL) was stirred at 35° C. overnight. The mixture was concentrated onto silica and purified by chromatography on silica gel (40 g cartridge, 0-100% EtOAc/isohexane) to afford the title compound (1.16 g, 3.35 mmol, 80% yield, 96% purity) as an orange solid. UPLC-MS (Method 1): m/z 333.3 $(M+H)^+$, 331.4 $(M-H)^-$, at 1.11 min. $^1H$ NMR (500 MHz, DMSO-$d_6$) δ 8.12 (d, J=7.7 Hz, 1H), 7.35 (d, J=13.7 Hz, 1H), 4.68 (t, J=5.5 Hz, 1H), 3.71-3.64 (m, 1H), 3.64-3.58 (m, 1H), 3.54-3.46 (m, 1H), 3.29 (s, 3H), 3.28-3.20 (m, 1H), 3.06-3.00 (m, 1H), 1.75-1.69 (m, 2H), 1.69-1.65 (m, 1H), 1.60-1.49 (m, 3H).

Step 2: (1-(2-amino-5-fluoro-4-(methylsulfonyl)phenyl)piperidin-2-yl) methanol: A mixture of the product from Step 1 above (1.16 g, 3.35 mmol, 96% purity), ammonium chloride (1.08 g, 20.1 mmol) and zinc (1.31 g, 20.1 mmol) in THE (12 mL) and water (4 mL) was stirred at RT overnight. The mixture was filtered through Celite®, the filter cake was washed with EtOAc, and the filtrate was extracted with EtOAc (3×30 mL). The organic extracts were combined and washed with brine (20 mL), passed through a phase separator and the solvent was removed in vacuo to afford the title compound (1.05 g, 2.99 mmol, 89% yield, 86% purity) as a brown solid. UPLC-MS (Method 1): m/z 303.7 $(M+H)^+$ at 0.95 min. 9-fluoro-8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide (217 mg, 443 μmol, 99% purity) was obtained as a white solid from the product from Step 2 above following the general method outlined in Example 3 Steps 3-5. UPLC-MS (Method 1): m/z 507.2 $(M+Na)^+$, 483.1 $(M-H)^-$, at 1.18 min. $^1H$ NMR (500 MHz, DMSO-$d_6$) δ 12.95 (s, 1H), 11.82 (s, 1H), 8.30 (d, J=2.2 Hz, 1H), 8.03 (dd, J=8.6, 2.2 Hz, 1H), 7.57 (d, J=7.6 Hz, 1H), 7.05 (d, J=8.6 Hz, 1H), 7.02 (d, J=14.2 Hz, 1H), 4.05 (d, J=13.1 Hz, 1H), 3.95 (dd, J=14.2, 4.0 Hz, 1H), 3.36-3.32 (m, 1H), 3.13 (s, 3H), 3.00-2.93 (m, 1H), 2.68-2.59 (m, 1H), 1.78-1.73 (m, 1H), 1.70-1.64 (m, 2H), 1.44-1.28 (m, 2H), 1.18-1.12 (m, 1H).

Example 26: 3-chloro-2-cyano-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide Enantiomer 1

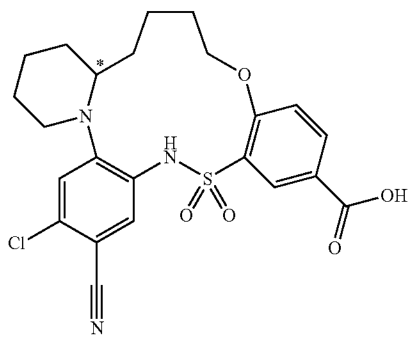 [SMILES: N#Cc1cc2c(cc1Cl)N1CCCCC1CCCCOc1ccc(C(=O)O)cc1S(=O)(=O)N2]

Example 22 was dissolved in DCM/MeOH (1:1, 2 mL) with sonication and heating, and then filtered. The sample was separated by chiral SFC (Waters prep 15 with UV detection by DAD at 210-400 nm, 40° C., 120 bar on a ChiralPak IC 10×250 mm, 5 μm column, flow rate 15 mL/min, eluting with 30% (0.02 M $NH_3$/MeOH)/$CO_2$). The clean fractions were pooled, rinsed with MeOH/DCM and then concentrated in vacuo. The residue was dissolved in EtOAc (1 mL), washed with brine (2×1 mL), dried ($Na_2SO_4$) and concentrated in vacuo to afford the title compound (5.43 mg, 10.6 μmol, 14% yield, 96% purity) as a white solid. SFC (Waters UPC$^2$, ChiralPak IC, 4.6×250 mm column, flow rate 4 mL/min, eluting with 30% (0.02 M $NH_3$/MeOH)/$CO_2$) $t_R$ 4.57 min. Other analytical data consistent with Example 22.

Example 27: 3-chloro-2-cyano-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide Enantiomer 2

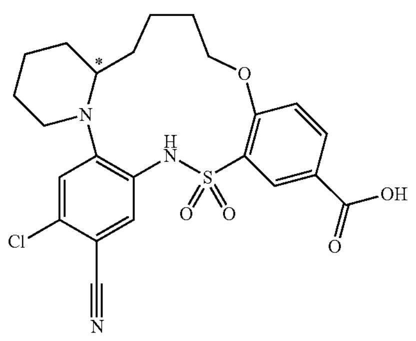 [SMILES: N#Cc1cc2c(cc1Cl)N1CCCCC1CCCCOc1ccc(C(=O)O)cc1S(=O)(=O)N2]

The title compound (4.99 mg, 9.78 μmol, 13% yield, 96% purity) was obtained as a white solid from the chiral separation performed in Example 26. SFC (Waters UPC$^2$, ChiralPak IC, 4.6×250 mm column, flow rate 4 mL/min eluting with 30% (0.02M $NH_3$/MeOH)/$CO_2$) $t_R$ 5.21 min. Other analytical data consistent with Example 22.

Example 28: 2-cyano-3-fluoro-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide

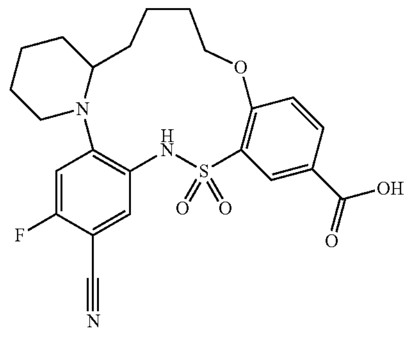 [SMILES: N#Cc1cc2c(cc1F)N1CCCCC1CCCCOc1ccc(C(=O)O)cc1S(=O)(=O)N2]

Step 1: 2-fluoro-4-(2-(4-hydroxybutyl)piperidin-1-yl)-5-nitrobenzonitrile: A mixture of 2,4-difluoro-5-nitrobenzonitrile (300 mg, 1.63 mmol), 4-(piperidin-2-yl)butan-1-ol (302 mg, 1.73 mmol, 90% purity) and $Et_3N$ (450 μl, 3.23 mmol) in DCM (7 mL) was stirred at 35° C. overnight. The mixture was concentrated onto silica and purified by chromatography on silica gel (24 g cartridge, 0-100% EtOAc/isohexane) to afford the title compound (334 mg, 946 μmol, 58% yield, 91% purity) as an orange oil. UPLC-MS (Method 1): m/z 322.7 $(M+H)^+$ at 1.42 min. $^1H$ NMR (500 MHz, DMSO-$d_6$) δ 8.41 (d, J=7.2 Hz, 1H), 7.40 (d, J=13.3 Hz, 1H), 4.31 (t, J=5.1 Hz, 1H), 3.81-3.75 (m, 1H), 3.32-3.27 (m, 2H), 3.22 (td, J=12.9, 2.9 Hz, 1H), 2.88-2.81 (m, 1H), 1.79-1.70 (m, 2H), 1.70-1.59 (m, 3H), 1.59-1.41 (m, 3H), 1.41-1.29 (m, 2H), 1.26-1.08 (m, 2H).

Step 2: 5-amino-2-fluoro-4-(2-(4-hydroxybutyl)piperidin-1-yl)benzonitrile: A mixture of the product from Step 1 above (334 mg, 946 μmol, 91% purity), ammonium chloride (304 mg, 5.67 mmol) and zinc (371 mg, 5.67 mmol) in THE (5 mL) and water (2 mL) was stirred at RT for 2 days. The mixture was filtered through Celite®, the filter cake was washed with EtOAc, and the filtrate was extracted with EtOAc (3×10 mL). The organic extracts were combined and washed with brine (10 mL), passed through a phase separator, and the solvent was removed in vacuo to afford the title compound (281 mg, 829 μmol, 88% yield, 86% purity) as a brown oil. UPLC-MS (Method 1): m/z 292.3 $(M+H)^+$ at 1.39 min. $^1H$ NMR (500 MHz, DMSO-$d_6$) δ 6.99 (d, J=11.1 Hz, 1H), 6.93 (d, J=6.7 Hz, 1H), 4.99 (s, 2H), 4.25 (t, J=5.1 Hz, 1H), 3.30-3.20 (m, 2H), 3.20-3.14 (m, 1H), 3.05-2.97 (m, 1H), 1.87-1.80 (m, 1H), 1.69-1.56 (m, 3H), 1.48-1.39 (m, 2H), 1.39-1.01 (m, 7H). 2-cyano-3-fluoro-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide (6.82 mg, 13.5 μmol, 6% yield, 94% purity) was obtained as a light brown solid from the product from Step 2 above following the general method outlined in Example 4 Steps 3-5. UPLC-MS (Method 1): m/z 474.3 $(M+H)^+$, 472.2 $(M-H)^-$, at 1.63 min. $^1H$ NMR (500 MHz, DMSO-$d_6$) δ 13.25 (s, 1H), 8.55 (d, J=2.3 Hz, 2H), 8.16 (d, J=8.7 Hz, 1H), 7.52 (d, J=10.4 Hz, 1H), 7.35 (d, J=8.7 Hz, 1H), 7.27-7.17 (m, 1H), 4.33-4.23 (m, 1H), 4.21-4.09 (m, 1H), 3.42-3.34 (m, 1H), 3.00-2.90 (m, 1H), 2.72-2.65 (m, 1H), 1.87-1.40 (m, 6H), 1.39-1.07 (m, 6H).

Example 29: 2-cyano-3-fluoro-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

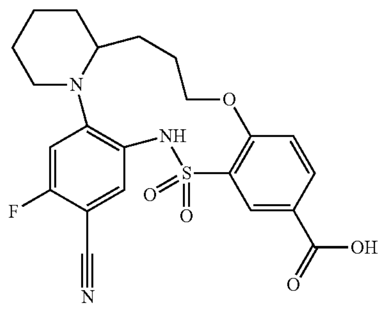 [SMILES: N#Cc1cc2c(cc1F)N1CCCCC1CCCOc1ccc(C(=O)O)cc1S(=O)(=O)N2]

Step 1: 2-fluoro-4-(2-(3-hydroxypropyl)piperidin-1-yl)-5-nitrobenzonitrile: A mixture of 2,4-difluoro-5-nitrobenzonitrile (600 mg, 3.26 mmol), 3-(piperidin-2-yl)propan-1-ol (500 mg, 3.49 mmol) and $Et_3N$ (910 μL, 6.53 mmol) in DCM (15 mL) was stirred at 35° C. for 4 days. The mixture was concentrated onto silica and purified by chromatography on silica gel (40 g cartridge, 0-100% EtOAc/isohexane) to afford the title compound (561 mg, 1.66 mmol, 51% yield, 91% purity) as an orange oil. UPLC-MS (Method 1): m/z 308.3 $(M+H)^+$ at 1.33 min. $^1H$ NMR (500 MHz, DMSO-$d_6$) δ 8.41 (d, J=7.3 Hz, 1H), 7.40 (d, J=13.3 Hz, 1H), 4.38 (t, J=5.1 Hz, 1H), 3.82-3.76 (m, 1H), 3.36-3.31 (m, 2H), 3.26-3.17 (m, 1H), 2.87-2.81 (m, 1H), 1.81-1.71 (m, 2H), 1.68-1.51 (m, 5H), 1.50-1.40 (m, 1H), 1.38-1.13 (m, 2H).

Step 2: 5-amino-2-fluoro-4-(2-(3-hydroxypropyl)piperidin-1-yl)benzonitrile: A mixture of the product from Step 1 above (561 mg, 1.66 mmol, 91% purity), ammonium chloride (533 mg, 9.97 mmol) and zinc (652 mg, 9.97 mmol) in THE (6 mL) and water (2 mL) was stirred at RT overnight. The mixture was filtered through Celite®, the filter cake was washed with EtOAc, and the filtrate was extracted with EtOAc (3×20 mL). The organic extracts were combined, washed with brine (15 mL), dried ($Na_2SO_4$) and the solvent was removed in vacuo to afford the title compound (480 mg, 1.59 mmol, 96% yield, 92% purity) as a brown oil. UPLC-MS (Method 1): m/z 278.5 $(M+H)^+$ at 1.28 min. $^1H$ NMR (500 MHz, DMSO-$d_6$) δ 7.00 (d, J=11.2 Hz, 1H), 6.93 (d, J=6.7 Hz, 1H), 5.00 (s, 2H), 4.28 (t, J=5.1 Hz, 1H), 3.26-3.19 (m, 2H), 3.19-3.15 (m, 1H), 3.05-2.97 (m, 1H), 2.48-2.45 (m, 1H), 1.87-1.79 (m, 1H), 1.69-1.55 (m, 3H), 1.48-1.39 (m, 2H), 1.36-1.19 (m, 4H).

2-cyano-3-fluoro-6,7,8,9,9a,10,11,12-octahydro-19H-dibenzo[b,f]pyrido[1,2-h][1]oxa[4]thia[5,8]diazacyclododecine-16-carboxylic acid 18,18-dioxide (23.4 mg, 49.9 μmol, 98% purity) was isolated as a white solid from the product from Step 2 above following the general method outlined in Example 5 Steps 3-5. UPLC-MS (Method 1): m/z 460.3 $(M+H)^+$, 458.4 $(M-H)^-$, at 1.61 min. $^1H$ NMR (500 MHz, DMSO-$d_6$) δ 13.22 (s, 1H), 8.99 (s, 1H), 8.50 (d, J=2.2 Hz, 1H), 8.17-8.12 (m, 1H), 7.46 (d, J=10.9 Hz, 1H), 7.41 (d, J=6.5 Hz, 1H), 7.23 (d, J=8.7 Hz, 1H), 4.17-4.08 (m, 2H), 3.60-3.51 (m, 1H), 2.96-2.89 (m, 1H), 2.62-2.53 (m, 1H), 1.86-1.74 (m, 2H), 1.72-1.53 (m, 5H), 1.52-1.33 (m, 3H).

Example 30: (E)-3-chloro-2-cyano-7,8,9,9a,10,13-hexa hydro-6H, 20H-dibenzo[b,f]pyrido[1,2-h][1]oxa[4]thia[5,8]diazacyclotridecine-17-carboxylic acid 19,19-dioxide

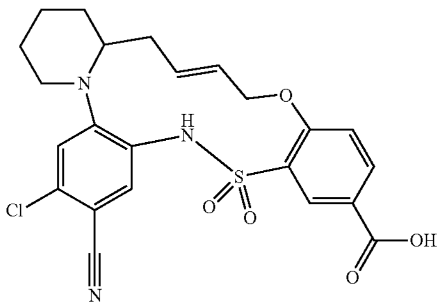 [SMILES: N#Cc1cc2c(cc1Cl)N1CCCCC1C/C=C/COc1ccc(C(=O)O)cc1S(=O)(=O)N2]

Step 1: 4-(2-ally/piperidin-1-yl)-2-chloro-5-nitrobenzonitrile: A mixture of the product from Example 14 Step 1 (600 mg, 2.99 mmol), 2-allylpiperidine hydrochloride (500 mg, 3.09 mmol) and $Et_3N$ (1.70 mL, 12.2 mmol) in DCM (15 mL) was stirred at 35° C. for 2 h. The mixture was sequentially washed with 1 M HCl (2×10 mL) and brine (10 mL), dried ($Na_2SO_4$) and concentrated in vacuo to afford the title compound (920 mg, 2.95 mmol, 99% yield, 98% purity) as an orange solid. UPLC-MS (Method 1): m/z 306.4 $(M+H)^+$ at 1.81 min. $^1H$ NMR (500 MHz, DMSO-$d_6$) δ 8.39 (s, 1H), 7.57 (s, 1H), 5.63 (ddt, J=17.1, 10.1, 7.1 Hz, 1H), 5.08 (dq, J=17.1, 1.6 Hz, 1H), 4.95 (dd, J=10.1, 2.1 Hz, 1H), 3.85-3.77 (m, 1H), 3.27 (td, J=12.8, 3.0 Hz, 1H), 2.95-2.88 (m, 1H), 2.49-2.31 (m, 2H), 1.78-1.69 (m, 1H), 1.69-1.59 (m, 3H), 1.58-1.53 (m, 1H), 1.53-1.44 (m, 1H).

Step 2: 4-(2-allylpiperidin-1-yl)-5-amino-2-chlorobenzonitrile: A mixture of the product from Step 1 above (920 mg, 2.95 mmol, 98% purity), ammonium chloride (946 mg, 17.7 mmol) and zinc (1.16 g, 17.7 mmol) in THE (10 mL) and water (3.3 mL) was stirred at RT overnight. The mixture was filtered through Celite®, the filter cake was washed with EtOAc, and the filtrate was extracted with EtOAc (3×20 mL). The organic extracts were combined, washed with brine (10 mL), dried ($Na_2SO_4$) and the solvent was removed in vacuo to afford the title compound (808 mg, 2.84 mmol, 96% yield, 97% purity) as a dark red oil. UPLC-MS (Method 1): m/z 276.3 $(M+H)^+$ at 1.85 min. $^1H$ NMR (500 MHz, DMSO-$d_6$) δ 7.16 (s, 1H), 7.05 (s, 1H), 5.59 (ddt, J=17.2, 10.2, 7.1 Hz, 1H), 5.32 (s, 2H), 4.95-4.85 (m, 2H), 3.24-3.16 (m, 1H), 3.03-2.95 (m, 1H), 2.49-2.45 (m, 1H), 2.16-2.06 (m, 1H), 1.98-1.90 (m, 1H), 1.83-1.75 (m, 1H), 1.71-1.55 (m, 3H), 1.47-1.37 (m, 2H). (E)-3-chloro-2-cyano-7,8,9,9a,10,13-hexahydro-6H,20H-dibenzo[b,f]pyrido[1,2-h][1]oxa[4]thia[5,8]diazacyclotridecine-17-carboxylic acid 19,19-dioxide (59.3 mg, 119 μmol, 98% purity) was obtained as a tan solid from the product from Step 2 above following the general method outlined in Example 15 Steps 6-8. UPLC-MS (Method 1): m/z 488.2 $(M+H)^+$, 486.3 $(M-H)^-$, at 1.65 min. $^1H$ NMR (500 MHz, DMSO-$d_6$) δ 13.32 (s, 1H), 8.54 (d, J=2.2 Hz, 1H), 8.19 (dd, J=8.8, 2.2 Hz, 1H), 8.17 (s, 1H), 7.67 (s, 1H), 7.61 (d, J=8.9 Hz, 1H), 7.18 (s, 1H), 5.96 (ddd, J=15.0, 9.8, 5.1 Hz, 1H), 5.14-5.08 (m, 1H), 5.05-4.96 (m, 1H), 4.68 (dd, J=12.2, 9.3 Hz, 1H), 3.43-3.35 (m, 1H), 2.88-2.82 (m, 1H), 2.44-2.37 (m, 1H), 2.13-1.97 (m, 2H), 1.86-1.72 (m, 3H), 1.64-1.56 (m, 2H), 1.46-1.38 (m, 1H).

Example 31: 3-fluoro-2-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

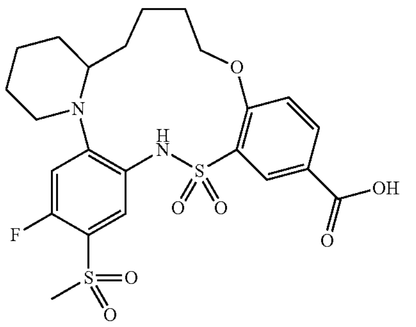 [SMILES: CS(=O)(=O)c1cc2c(cc1F)N1CCCCC1CCCCOc1ccc(C(=O)O)cc1S(=O)(=O)N2]

Step 1: 4-(1-(5-fluoro-4-(methylsulfonyl)-2-nitrophenyl)piperidin-2-yl)butan-1-ol: A mixture of 1,5-difluoro-2-(methylsulfonyl)-4-nitrobenzene (500 mg, 2.11 mmol) [prepared according to the procedure in WO 2020/104822 A1 Example 331 Part A Steps 1-3], 4-(piperidin-2-yl)butan-1-ol (400 mg, 2.29 mmol, 90% purity) and $Et_3N$ (600 μL, 4.30 mmol) in DCM (10 mL) was stirred at 35° C. overnight. The mixture was concentrated onto silica and purified by chromatography on silica gel (24 g cartridge, 0-100% EtOAc/isohexane) to afford the title compound (509 mg, 1.33 mmol, 63% yield, 98% purity) as an orange oil. UPLC-MS (Method 1): m/z 375.6 $(M+H)^+$ at 1.27 min. $^1H$ NMR (500 MHz, DMSO-$d_6$) δ 8.13 (d, J=7.7 Hz, 1H), 7.42 (d, J=13.7 Hz, 1H), 4.31 (t, J=5.1 Hz, 1H), 3.86-3.79 (m, 1H), 3.34-3.32 (m, 1H), 3.30-3.28 (m, 4H), 3.26-3.19 (m, 1H), 2.84-2.78 (m, 1H), 1.81-1.71 (m, 2H), 1.68-1.60 (m, 3H), 1.58-1.50 (m, 2H), 1.49-1.41 (m, 1H), 1.41-1.30 (m, 2H), 1.29-1.20 (m, 1H), 1.18-1.11 (m, 1H).

Step 2: 4-(1-(2-amino-5-fluoro-4-(methylsulfonyl)phenyl)piperidin-2-yl)butan-1-ol: A mixture of the product from Step 1 above (509 mg, 1.33 mmol, 98% purity), ammonium chloride (428 mg, 7.99 mmol) and zinc (523 mg, 7.99 mmol) in THE (5 mL) and water (2 mL) was stirred at RT for 2 days. The mixture was filtered through Celite®, the filter cake was washed with EtOAc, and the filtrate was extracted with EtOAc (3×15 mL). The organic extracts were combined, washed with brine (15 mL), passed through a phase separator, and the solvent was removed in vacuo to afford the title compound (453 mg, 1.26 mmol, 95% yield, 96% purity) as a brown oil. UPLC-MS (Method 1): m/z 345.7 $(M+H)^+$ at 1.20 min. $^1H$ NMR (500 MHz, DMSO-$d_6$) δ 7.12 (d, J=7.3 Hz, 1H), 6.99 (d, J=11.8 Hz, 1H), 5.07 (s, 2H), 4.26 (t, J=5.1 Hz, 1H), 3.29-3.22 (m, 2H), 3.21 (s, 3H), 3.14-3.09 (m, 1H), 3.02-2.96 (m, 1H), 2.48-2.44 (m, 1H), 1.88-1.81 (m, 1H), 1.73-1.53 (m, 3H), 1.45-1.38 (m, 2H), 1.35-1.16 (m, 5H), 1.14-1.04 (m, 1H).

3-fluoro-2-(methylsulfonyl)-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide (27.2 mg, 50.6 μmol, 98% purity) was obtained as a white solid from the product from Step 2 above following the general method outlined in Example 4 Steps 3-5. UPLC-MS (Method 1): m/z 527.2 $(M+H)^+$, 525.0 $(M-H)^-$, at 1.49 min. $^1H$ NMR (500 MHz, DMSO-$d_6$) δ 13.13 (s, 1H), 8.56 (d, J=2.2 Hz, 1H), 8.52 (s, 1H), 8.14 (dd, J=8.8, 2.2 Hz, 1H), 7.53 (d, J=11.2 Hz, 1H), 7.41 (d, J=6.9 Hz, 1H), 7.32 (d, J=8.8 Hz, 1H), 4.31-4.26 (m, 1H), 4.14-4.07 (m, 1H), 3.37-3.31 (m, 1H), 3.13 (s, 3H), 2.94-2.88 (m, 1H), 2.64-2.60 (m, 1H), 1.89-1.74 (m, 2H), 1.73-1.63 (m, 2H), 1.62-1.52 (m, 2H), 1.49-1.37 (m, 4H), 1.35-1.26 (m, 2H).

Example 32: (E)-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide Enantiomer 1

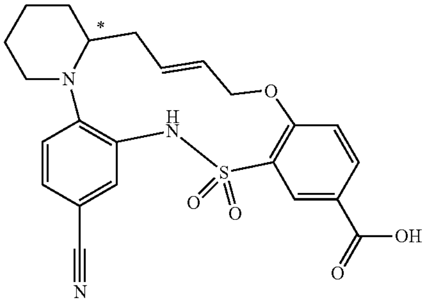 [SMILES: N#Cc1ccc2c(c1)NS(=O)(=O)c1cc(C(=O)O)ccc1OC/C=C/CC1CCCCN21]

Example 15 was dissolved at 4 mg/ml in MeCN and was then separated by chiral SFC (Lux C4 21.2 mm×250 mm, 5 μm column, RT, flow rate 21 mL/min, eluting with 0.1% TFA/MeCN). Enriched fractions were combined, concentrated in vacuo, and the residue further purified under the same conditions. The clean fractions were pooled, rinsed with DCM, and then concentrated in vacuo to afford the title compound (19.4 mg, 42.3 μmol, 24% yield, 99% purity) as a light-yellow solid. SFC (Lux C4 4.6 mm×250 mm, 5 μm column, RT, flow rate 1 mL/min, eluting with 0.1% TFA/MeCN) $t_R$ 4.45 min. Other analytical data consistent with Example 15.

Example 33: (E)-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide Enantiomer 2

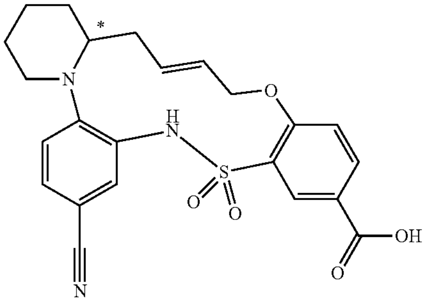 [SMILES: N#Cc1ccc2c(c1)NS(=O)(=O)c1cc(C(=O)O)ccc1OC/C=C/CC1CCCCN21]

The title compound (25.5 mg, 55.7 μmol, 32% yield, 99% purity) was obtained as a light-yellow solid from the chiral separation performed in Example 32. SFC (Lux C4 4.6 mm×250 mm, 5 μm column, RT, flow rate 1 mL/min, eluting with 0.1% TFA/MeCN) $t_R$ 5.04 min. Other analytical data consistent with Example 15.

Example 34: 19-methyl-2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

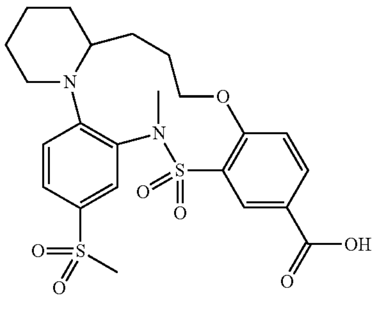 [SMILES: CN1c2cc(S(C)(=O)=O)ccc2N2CCCCC2CCCOc2ccc(C(=O)O)cc2S1(=O)=O]

Step 1: 3-(1-(4-(methylsulfonyl)-2-nitrophenyl)piperidin-2-yl)propan-1-ol: A mixture of 1-fluoro-4-(methylsulfonyl)-2-nitrobenzene (700 mg, 3.19 mmol), 3-(piperidin-2-yl) propan-1-ol (500 mg, 3.49 mmol) and $Et_3N$ (910 µL, 6.53 mmol) in DCM (15 mL) was stirred at 35° C. for 4 days. The mixture was concentrated onto silica and purified by chromatography on silica gel (40 g cartridge, 0-100% EtOAc/isohexane) to afford the title compound (641 mg, 1.67 mmol, 52% yield, 89% purity) as an orange oil. UPLC-MS (Method 1): m/z 343.7 $(M+H)^+$ at 1.14 min. $^1H$ NMR (500 MHz, DMSO-$d_6$) δ 8.19 (d, J=2.3 Hz, 1H), 7.88 (dd, J=9.1, 2.3 Hz, 1H), 7.49 (d, J=9.1 Hz, 1H), 4.36 (t, J=5.1 Hz, 1H), 3.81-3.74 (m, 1H), 3.35-3.31 (m, 2H), 3.27-3.19 (m, 4H), 2.84-2.78 (m, 1H), 1.82-1.52 (m, 7H), 1.52-1.21 (m, 3H).

Step 2: 3-(1-(2-amino-4-(methylsulfonyl)phenyl)piperidin-2-yl)propan-1-ol: A mixture of the product from Step 1 above (641 mg, 1.67 mmol, 89% purity), ammonium chloride (535 mg, 10.0 mmol) and zinc (654 mg, 10.0 mmol) in THE (6 mL) and water (2 mL) was stirred at RT overnight. The mixture was filtered through Celite®, the filter cake was washed with EtOAc, and the filtrate was extracted with EtOAc (3×20 mL). The combined organic extracts were washed with brine (15 mL), dried ($Na_2SO_4$) and the solvent was removed in vacuo to afford the title compound (537 mg, 1.43 mmol, 85% yield, 83% purity) as a brown oil. UPLC-MS (Method 1): m/z 313.3 $(M+H)^+$ at 0.96 min. $^1H$ NMR (500 MHz, DMSO-$d_6$) δ 7.17 (d, J=2.2 Hz, 1H), 7.11 (d, J=8.1 Hz, 1H), 7.03 (dd, J=8.1, 2.2 Hz, 1H), 5.27 (s, 2H), 4.27 (t, J=5.1 Hz, 1H), 3.25-3.17 (m, 2H), 3.09 (s, 3H), 3.03-2.97 (m, 1H), 2.97-2.91 (m, 1H), 2.46-2.37 (m, 1H), 1.87-1.81 (m, 1H), 1.76-1.68 (m, 1H), 1.66-1.56 (m, 2H), 1.46-1.36 (m, 2H), 1.31-1.19 (m, 4H).

Step 3: methyl 4-hydroxy-3-(N-(2-(2-(3-hydroxypropyl) piperidin-1-yl)-5-(methylsulfonyl)phenyl)sulfamoyl)benzoate: A mixture of the product from Step 2 above (537 mg, 1.43 mmol, 83% purity), the product from Example 2 Step 3 (565 mg, 2.14 mmol, 95% purity) and pyridine (350 µL, 4.35 mmol) in DCM (8 mL) was heated to 35° C. and stirred for 3 days. The mixture was concentrated onto silica and partially purified by chromatography on silica gel (40 g cartridge, 0-10% MeOH/DCM) and then purified by chromatography (40 g reverse phase 018 cartridge, 5-40% (0.1% formic acid in MeCN)/(0.1% formic acid(aq))) to afford the title compound (140 mg, 266 µmol, 18% yield) as a clear brown glass. UPLC-MS (Method 1): m/z 527.3 $(M+H)^+$, 525.2 $(M-H)^-$ at 1.23 min.

Step 4: methyl 19-methyl-2-(methy/sulfonyl)-6,7,8,9,9a,10,11,12-octahydro-19H-dibenzo[b,f]pyrido[1,2-h][1]oxa[4]thia[5,8]diazacyclododecine-16-carboxylate 18,18-dioxide: A solution of the product from Step 3 above (140 mg, 266 µmol) and triphenylphosphine (209 mg, 798 µmol) in DCM (5 mL) was treated with DIAD (160 µL, 823 µmol) and the mixture was stirred at RT for 1 h. The mixture was concentrated onto silica and purified by chromatography on silica gel (4 g cartridge, 0-100% EtOAc/isohexane) to afford the title compound (176 mg, 145 µmol, 54% yield, 43% purity) as a light-yellow solid. UPLC-MS (Method 1): m/z 523.3 $(M+H)^+$ at 1.53 min.

Note: methylation of the sulfonamide in this step is postulated to have occurred from contamination of the reaction mixture with methanol.

Step 5: 19-methyl-2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide: A mixture of the product from Step 4 above (176 mg, 145 µmol, 43% purity) and $LiOH·H_2O$ (25.0 mg, 596 µmol) in THF/MeOH/water (4:1:1, 2.1 mL) was stirred at 40° C. overnight. The mixture was diluted with water (5 mL), acidified to ~pH 4 with 1 M HCl(aq) and extracted with EtOAc (3×10 mL). The combined organic extracts were washed with brine (10 mL), dried ($Na_2SO_4$), and the solvent was removed in vacuo. The residue was loaded onto silica and partially purified by chromatography on silica gel (4 g cartridge, 0-100% EtOAc/isohexane) and then purified by preparative HPLC (Waters, Acidic (0.1% Formic acid), Acidic, Waters XSelect CSH column 018, 5 µm, 30×100 mm column, 30-60% (0.1% formic acid in MeCN)/(0.1% formic acid(aq))) to afford the title compound (21.4 mg, 41.2 µmol, 29% yield, 98% purity) as a light-yellow solid. UPLC-MS (Method 1): m/z 509.3 $(M+H)^+$, 507.1 $(M-H)^-$, at 1.39 min. $^1H$ NMR (500 MHz, DMSO-$d_6$) δ 13.25 (s, 1H), 8.51 (d, J=2.3 Hz, 1H), 8.17 (dd, J=8.8, 2.3 Hz, 1H), 7.74 (d, J=2.3 Hz, 1H), 7.67 (dd, J=8.6, 2.3 Hz, 1H), 7.36 (d, J=8.7 Hz, 1H), 7.07 (d, J=8.8 Hz, 1H), 4.61 (d, J=11.7 Hz, 1H), 4.17-4.11 (m, 1H), 4.11-4.03 (m, 1H), 3.17-3.12 (m, 1H), 3.10 (s, 3H), 3.06 (s, 3H), 2.98-2.92 (m, 1H), 2.13-2.03 (m, 1H), 1.77-1.68 (m, 2H), 1.55-1.39 (m, 4H), 1.37-1.30 (m, 2H), 1.18-1.09 (m, 1H).

Example 35: (E)-3-chloro-2-cyano-6,7,8,9,9a,12-hexahydro-19H-dibenzo[b,f]pyrido[1,2-h][1]oxa[4]thia[5,8]diazacyclododecine-16-carboxylic acid 18,18-dioxide

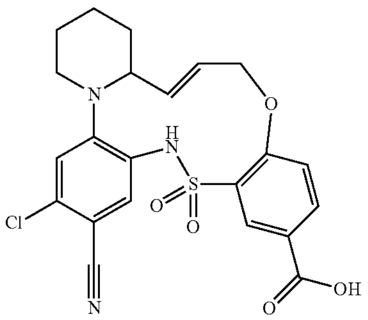 [SMILES: N#Cc1cc2c(cc1Cl)N1CCCCC1/C=C/COc1ccc(C(=O)O)cc1S(=O)(=O)N2]

Step 1: 2-chloro-5-nitro-4-(2-vinylpiperidin-1-yl)benzonitrile: A mixture of the product from Example 14 Step 1 (600 mg, 2.99 mmol), 2-vinylpiperidine hydrochloride (500 mg, 3.39 mmol) and $Et_3N$ (1.70 mL, 12.2 mmol) in DCM (15 mL) was stirred at 35° C. for 4 days. The mixture was sequentially washed with 1 M HCl(aq) (2×20 mL) and brine (20 mL), dried ($Na_2SO_4$) and concentrated in vacuo to afford the title compound (890 mg, 2.99 mmol, 100% yield, 98% purity) as an orange solid. $^1H$ NMR (500 MHz, DMSO-$d_6$) δ 8.43 (s, 1H), 7.54 (s, 1H), 5.87 (ddd, J=17.4, 10.7, 5.1 Hz, 1H), 5.23 (dt, J=10.7, 1.6 Hz, 1H), 5.17 (dt, J=17.4, 1.5 Hz, 1H), 4.37-4.32 (m, 1H), 3.31-3.20 (m, 1H), 2.95-2.88 (m, 1H), 1.84-1.71 (m, 2H), 1.64-1.51 (m, 4H).

Step 2: 5-amino-2-chloro-4-(2-vinylpiperidin-1-yl)benzonitrile: A mixture of the product from Step 1 above (890 mg, 2.99 mmol, 98% purity), ammonium chloride (959 mg, 17.9 mmol) and zinc (1.17 g, 17.9 mmol) in THE (12 mL) and water (4 mL) was stirred at RT overnight. The mixture was filtered through Celite®, the filter cake was washed with EtOAc, and the filtrate was extracted with EtOAc (3×25 mL). The organic extracts were combined and washed with brine (15 mL), dried ($Na_2SO_4$), and the solvent was removed in vacuo to afford the title compound (775 mg, 2.81 mmol, 94% yield, 95% purity) as a light-grey solid. UPLC-MS (Method 1): m/z 262.3 $(M+H)^+$ at 1.75 min. $^1H$ NMR (500 MHz, DMSO-$d_6$) δ 7.07 (s, 1H), 7.02 (s, 1H), 5.55 (ddd, J=17.7, 10.4, 7.6 Hz, 1H), 5.35 (s, 2H), 5.05-4.98 (m, 1H), 4.93 (dd, J=10.4, 1.8 Hz, 1H), 3.69-3.62 (m, 1H), 3.06-2.99 (m, 1H), 2.47-2.38 (m, 1H), 1.80-1.58 (m, 4H), 1.56-1.38 (m, 2H).

Step 3: methyl 4-(allyloxy)-3-(N-(4-chloro-5-cyano-2-(2-vinylpiperidin-1-yl)phenyl)sulfamoyl)benzoate: A mixture of the product from Step 2 above (775 mg, 3.05 mmol, 95% purity), the product from Example 15 Step 3 (976 mg, 3.36 mmol) and pyridine (780 μL, 9.68 mmol) in DCM (16 mL) was heated to 35° C. and stirred for 2 days. The mixture was concentrated onto silica and purified by chromatography on silica gel (40 g cartridge, 0-50% EtOAc/isohexane) to afford the title compound (1.06 g, 1.97 mmol, 65% yield, 96% purity) as a pale yellow solid. UPLC-MS (Method 1): m/z 516.3 $(M+H)^+$, 514.1 $(M-H)^-$, at 1.93 min. $^1H$ NMR (500 MHz, DMSO-$d_6$) δ 9.06 (s, 1H), 8.37 (d, J=2.3 Hz, 1H), 8.19 (dd, J=8.8, 2.3 Hz, 1H), 7.64 (s, 1H), 7.46 (s, 1H), 7.40 (d, J=8.8 Hz, 1H), 5.99-5.88 (m, 1H), 5.49-5.41 (m, 1H), 5.35-5.24 (m, 2H), 4.97-4.89 (m, 1H), 4.87-4.82 (m, 1H), 4.82-4.73 (m, 2H), 3.86 (s, 3H), 3.73-3.66 (m, 1H), 2.80-2.74 (m, 1H), 2.60-2.52 (m, 1H), 1.71-1.62 (m, 2H), 1.55-1.43 (m, 3H), 1.43-1.33 (m, 1H).

Step 4: methyl (E)-3-chloro-2-cyano-6,7,8,9,9a,12-hexahydro-19H-dibenzo[b,f]pyrido[1,2-h][1]oxa[4]thia[5,8]diazacyclododecine-16-carboxylate 18,18-dioxide: A solution of the product from Step 3 above (1.06 g, 1.97 mmol, 96% purity) and Grubbs-Hoveyda 2nd Gen (62.0 mg, 98.6 μmol) in DCM (35 mL) was stirred at RT for 3 days. Additional Grubbs-Hoveyda 2nd Gen (62.0 mg, 98.6 μmol) was added and stirring was continued overnight. The mixture was concentrated onto silica and purified by chromatography on silica gel (40 g cartridge, 0-50% EtOAc/isohexane) to afford the title compound (260 mg, 496 μmol, 25% yield, 93% purity) as a brown solid. UPLC-MS (Method 1): m/z 488.2 $(M+H)^+$, 486.2 $(M-H)^-$, at 1.74 min. $^1H$ NMR (500 MHz, DMSO-$d_6$) δ 9.60 (s, 1H), 8.42 (d, J=2.2 Hz, 1H), 8.11 (d, J=8.7 Hz, 1H), 7.71 (s, 1H), 7.26 (d, J=8.7 Hz, 1H), 7.19 (s, 1H), 5.91 (t, J=11.1 Hz, 1H), 5.62-5.56 (m, 1H), 4.94-4.88 (m, 1H), 4.42-4.30 (m, 1H), 4.17-4.07 (m, 1H), 3.87 (s, 3H), 3.09-3.01 (m, 1H), 2.76-2.68 (m, 1H), 1.83-1.74 (m, 1H), 1.68-1.48 (m, 3H), 1.47-1.38 (m, 1H), 1.13-1.00 (m, 1H).

Step 5: (E)-3-chloro-2-cyano-6,7,8,9,9a,12-hexahydro-19H-dibenzo[b,f]pyrido[1,2-h][1]oxa[4]thia[5,8]diazacyclododecine-16-carboxylic acid 18,18-dioxide: A mixture of the product from Step 4 above (260 mg, 496 μmol, 93% purity) and $LiOH·H_2O$ (83.0 mg, 1.98 mmol) in THF/MeOH/water (4:1:1, 2.25 mL) was stirred at RT overnight. The mixture was diluted with water (10 mL), acidified to ~pH 4 with 1 M HCl(aq) and extracted with EtOAc (3×15 mL). The organic extracts were combined and washed with brine (10 mL), dried ($Na_2SO_4$) and the solvent was removed in vacuo. The residue was loaded onto silica and purified by chromatography on silica gel (12 g cartridge, 0-100% EtOAc/isohexane), then trituration with TBME and isohexane, to afford the title compound (116 mg, 240 μmol, 48% yield, 98% purity) as a beige solid. UPLC-MS (Method 1): m/z 474.1 $(M+H)^+$, 472.5 $(M-H)^-$, at 1.59 min. $^1H$ NMR (500 MHz, DMSO-$d_6$) δ 13.20 (s, 1H), 9.55 (s, 1H), 8.41 (d, J=2.2 Hz, 1H), 8.08 (d, J=8.7 Hz, 1H), 7.71 (s, 1H), 7.26-7.15 (m, 2H), 5.91 (t, J=10.8 Hz, 1H), 5.63-5.57 (m, 1H), 4.89 (dd, J=15.8, 5.0 Hz, 1H), 4.43-4.31 (m, 1H), 4.19-4.11 (m, 1H), 3.09-3.01 (m, 1H), 2.75-2.69 (m, 1H), 1.84-1.74 (m, 1H), 1.67-1.52 (m, 3H), 1.48-1.40 (m, 1H), 1.15-1.03 (m, 1H).

Example 36: 2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

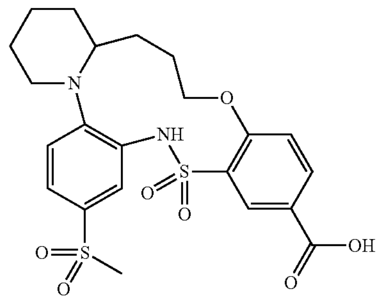 [SMILES: CS(=O)(=O)c1ccc2c(c1)NS(=O)(=O)c1cc(C(=O)O)ccc1OCCCC1CCCCN21]

Step 1: 3-(1-(4-(methylsulfonyl)-2-nitrophenyl)piperidin-2-yl)propan-1-ol: A mixture of 1-fluoro-4-(methylsulfonyl)-2-nitrobenzene (600 mg, 2.74 mmol), 3-(piperidin-2-yl)propan-1-ol hydrochloride (541 mg, 3.01 mmol) and $Et_3N$ (1.60 mL, 11.5 mmol) in DOE (12 mL) was stirred at 70° C. for 5 days. The mixture was concentrated onto silica and purified by chromatography on silica gel (40 g cartridge, 0-10% MeOH/DCM) to afford the title compound (868 mg, 1.14 mmol, 41% yield, 45% purity) as an orange oil. UPLC-MS (Method 1): m/z 343.7 $(M+H)^+$, at 1.17 min.

Step 2: 3-(1-(2-amino-4-(methylsulfonyl)phenyl)piperidin-2-yl)propan-1-ol: A mixture of the product from Step 1 above (868 mg, 1.14 mmol, 45% purity), ammonia chloride (366 mg, 6.84 mmol) and zinc (447 mg, 6.84 mmol) in THE (9 mL) and water (3 mL) was stirred at RT overnight. The mixture was filtered through Celite®, the filter cake was washed with EtOAc and the filtrate was extracted with EtOAc (3×25 mL). The organic extracts were combined and washed with brine (10 mL), dried ($Na_2SO_4$) and the solvent was removed in vacuo. The mixture was loaded onto Celite® and purified by chromatography (80 g reverse phase 018 cartridge, 5-40% (0.1% formic acid in MeCN)/(0.1% formic acid(aq))) to afford the title compound (270 mg, 864 μmol, 75% yield) as a light-orange oil. UPLC-MS (Method 1): m/z 313.4 $(M+H)^+$, at 0.97 min.

2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide (26.8 mg, 52.6 µmol, 97% purity) was obtained as a light-yellow solid from the product from Step 2 above following the general method outlined in Example 5 Steps 3-5. UPLC-MS (Method 1): m/z 495.3 $(M+H)^+$, 493.1 $(M-H)^-$, at 1.43 min. $^1H$ NMR (500 MHz, DMSO-$d_6$) δ 13.20 (s, 1H), 8.89 (s, 1H), 8.51 (d, J=2.2 Hz, 1H), 8.10 (dd, J=8.8, 2.2 Hz, 1H), 7.64 (d, J=8.3 Hz, 1H), 7.55 (d, J=2.1 Hz, 1H), 7.51 (d, J=8.3 Hz, 1H), 7.14 (d, J=8.8 Hz, 1H), 4.19-4.11 (m, 1H), 3.93 (t, J=9.6 Hz, 1H), 3.41-3.33 (m, 1H), 2.92 (s, 3H), 2.90-2.84 (m, 1H), 2.47-2.41 (m, 1H), 1.99-1.88 (m, 1H), 1.87-1.76 (m, 2H), 1.73-1.58 (m, 4H), 1.49-1.36 (m, 1H), 1.22-1.14 (m, 1H), 1.13-1.04 (m, 1H).

Example 37: 8-cyano-9-fluoro-12,13,14,15,15a,16-hexahydro-6H-dibenzo[b,f]pyrido[1,2-h][1,4,5,8]oxathiadiazecine-3-carboxylic acid 5,5-dioxide Enantiomer 1

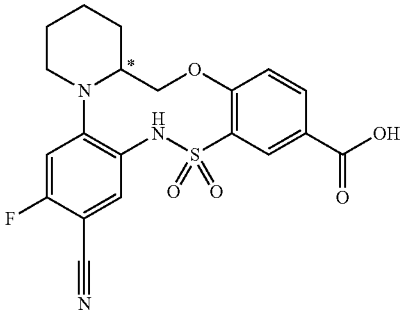 [SMILES: N#Cc1cc2c(cc1F)N1CCCCC1COc1ccc(C(=O)O)cc1S(=O)(=O)N2]

Example 24 was dissolved at 50 mg/ml in MeOH/DCM and was then separated by chiral SFC (Waters prep 15 with UV detection by DAD at 210-400 nm, 40° C., 120 bar on a ChiralPak IC 10×250 mm, 5 µm column, flow rate 15 mL/min, eluting with 25% (0.1% TFA/MeOH)/$CO_2$). The clean fractions were pooled, rinsed with DCM, and then concentrated in vacuo. The residue was dissolved in EtOAc (15 mL) and washed with brine (15 mL), dried ($Na_2SO_4$), and the solvent was removed to afford the title compound (46.1 mg, 104 µmol, 43% yield, 97% purity) as a tan solid. SFC (Waters UPC$^2$, Chiralpak IC, 4.6×250 mm column, flow rate 4 mL/min eluting with 25% (0.1% TFA/MeOH)/$CO_2$) $t_R$ 7.54 min. Other analytical data consistent with Example 24.

Example 38: 8-cyano-9-fluoro-12,13,14,15,15a,16-hexahydro-6H-dibenzo[b,f]pyrido[1,2-h][1,4,5,8]oxathiadiazecine-3-carboxylic acid 5,5-dioxide Enantiomer 2

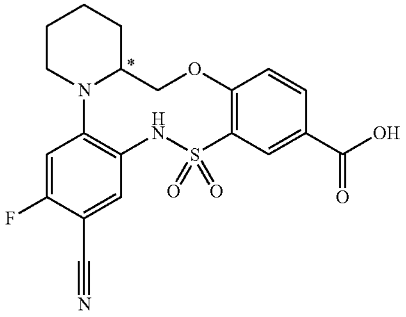 [SMILES: N#Cc1cc2c(cc1F)N1CCCCC1COc1ccc(C(=O)O)cc1S(=O)(=O)N2]

The title compound (48.1 mg, 106 µmol, 44% yield, 95% purity) was obtained as a tan solid from the chiral separation performed in Example 37. SFC (Waters UPC$^2$, Chiralpak IC, 4.6×250 mm column, flow rate 4 mL/min, eluting with 25% (0.1% TFA/MeOH)/$CO_2$) $t_R$ 8.63 min. Other analytical data consistent with Example 24.

Example 39: 9-fluoro-8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide Enantiomer 1

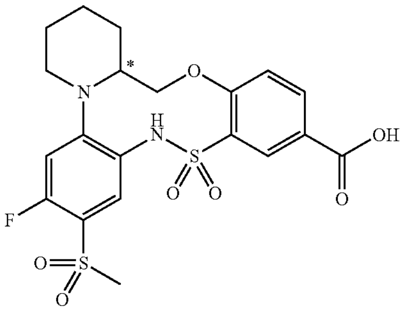 [SMILES: CS(=O)(=O)c1cc2c(cc1F)N1CCCCC1COc1ccc(C(=O)O)cc1S(=O)(=O)N2]

Example 25 was dissolved at 70 mg/ml in MeOH and a few drops of DCM and was then separated by chiral SFC (Waters prep 15 with UV detection by DAD at 210-400 nm, 40° C., 120 bar on a ChiralPak IC 10×250 mm, 5 µm column, flow rate 15 mL/min, eluting with 30% (0.1% $NH_3$/MeOH)/$CO_2$). The clean fractions were pooled, rinsed with DCM, and then concentrated in vacuo. The residue was dissolved in EtOAc (15 mL) and washed with brine (15 mL), dried ($Na_2SO_4$), and the solvent was removed to afford the title compound (59.0 mg, 110 µmol, 25% yield, 90% purity) as a brown solid. SFC (Waters UPC$^2$, Chiralpak IC, 4.6×250 mm column, flow rate 4 mL/min, eluting with 30% (0.1% $NH_3$/MeOH)/$CO_2$) $t_R$ 3.38 min. Other analytical data consistent with Example 25.

Example 40: 9-fluoro-8-(methylsulfonyl)-12,13,14,15,15a,16-hexahydro-6H-dibenzo[b,f]pyrido[1,2-h][1,4,5,8]oxathiadiazecine-3-carboxylic acid 5,5-dioxide Enantiomer 2

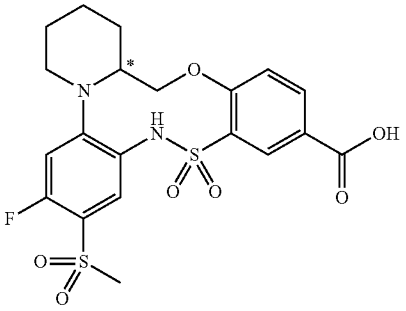 [SMILES: CS(=O)(=O)c1cc2c(cc1F)N1CCCCC1COc1ccc(C(=O)O)cc1S(=O)(=O)N2]

The title compound (55.7 mg, 103 µmol, 24% yield, 90% purity) was obtained as a brown solid from the chiral separation performed in Example 39. SFC (Waters UPC$^2$, Chiralpak IC, 4.6×250 mm column, flow rate 4 mL/min, eluting with 30% (0.1% $NH_3$/MeOH)/$CO_2$) $t_R$ 3.76 min. Other analytical data consistent with Example 25.

Example 41: 2-cyano-3-fluoro-6,7,8,9,9a,10,11,12-octahydro-19H-dibenzo[b,f]pyrido[1,2-h][1]oxa[4]thia[5,8]diazacyclododecine-16-carboxylic acid 18,18-dioxide Enantiomer 1

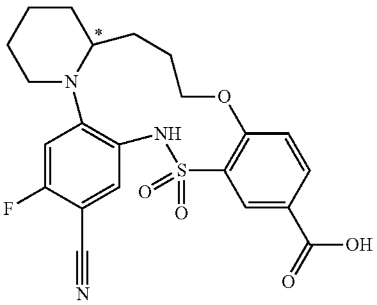 [SMILES: N#Cc1cc2c(cc1F)N1CCCCC1CCCOc1ccc(C(=O)O)cc1S(=O)(=O)N2]

Example 29 was dissolved at 50 mg/ml in MeOH/DCM, sonicated, filtered, and was then separated by chiral SFC (Waters prep 15 with UV detection by DAD at 210-400 nm, 40° C., 120 bar on a ChiralPak IC 10×250 mm, 5 μm column, flow rate 15 mL/min, eluting with 25% (0.1% $NH_3$/MeOH)/$CO_2$). The clean fractions were pooled, rinsed with MeOH, and then concentrated in vacuo. The residue was dissolved in EtOAc (5 mL) and washed with brine (5 mL), dried ($Na_2SO_4$), and the solvent was removed to afford the title compound (5.9 mg, 12.5 μmol, 27% yield, 97% purity) as a white solid. SFC (Waters UPC$^2$, Chiralpak IC, 4.6×250 mm column, flow rate 4 mL/min, eluting with 30% (0.1% $NH_3$/MeOH)/$CO_2$) $t_R$ 3.11 min. Other analytical data consistent with Example 29.

Example 42: 2-cyano-3-fluoro-6,7,8,9,9a,10,11,12-octahydro-19H-dibenzo[b,f]pyrido[1,2-h][1]oxa[4]thia[5,8]diazacyclododecine-16-carboxylic acid 18,18-dioxide Enantiomer 2

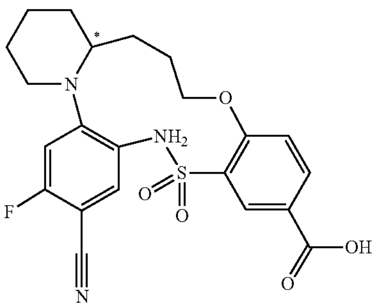

The title compound (5.9 mg, 12.5 μmol, 37% yield, 97% purity) and was obtained as a white solid from the chiral separation performed in Example 41. SFC (Waters UPC$^2$, Chiralpak IC, 4.6×250 mm column, flow rate 4 mL/min, eluting with 30% (0.1% $NH_3$/MeOH)/$CO_2$) $t_R$ 4.08 min. Other analytical data consistent with Example 29.

Example 43: 3-fluoro-2-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide Enantiomer 1

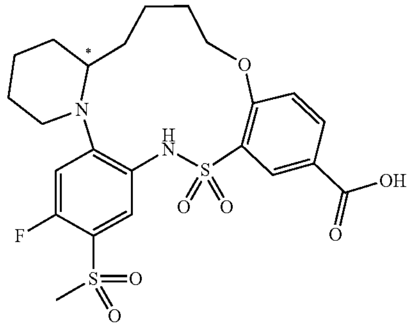 [SMILES: CS(=O)(=O)c1cc2c(cc1F)N1CCCCC1CCCCOc1ccc(C(=O)O)cc1S(=O)(=O)N2]

Example 31 was dissolved at 25 mg/mL in MeOH/DCM with sonication and was then filtered and separated by chiral SFC (Waters prep 15 with UV detection by DAD at 210-400 nm, 40° C., 120 bar on a ChiralPak IC 10×250 mm, 5 μm column, flow rate 15 mL/min, eluting with 30% (0.1% TFA/MeOH)/$CO_2$). The clean fractions were pooled, rinsed with MeOH, and concentrated in vacuo. The residue was dissolved in EtOAc (5 mL) and washed with brine (5 mL), dried ($Na_2SO_4$), and the solvent was removed in vacuo to afford the title compound (9.0 mg, 17 μmol, 47% yield, 97% purity) as a white solid. SFC (Waters UPC$^2$, Chiralpak IC, 4.6×250 mm column, flow rate 4 mL/min, eluting with 35% (0.1% TFA/MeOH)/$CO_2$) $t_R$ 3.82 min. Other analytical data consistent with Example 31.

Example 44: 3-fluoro-2-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide Enantiomer 2

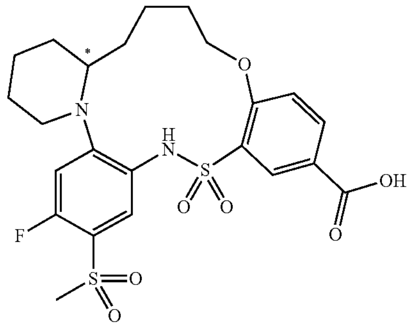 [SMILES: CS(=O)(=O)c1cc2c(cc1F)N1CCCCC1CCCCOc1ccc(C(=O)O)cc1S(=O)(=O)N2]

The title compound (8.4 mg, 15 μmol, 44% yield, 97% purity) was obtained as a white solid from the chiral separation performed in Example 43. SFC (Waters UPC$^2$, Chiralpak IC, 4.6×250 mm column, flow rate 4 mL/min, eluting with 35% (0.1% TFA/MeOH)/$CO_2$) $t_R$ 4.46 min. Other analytical data consistent with Example 31.

Example 45: (E)-3-chloro-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide Enantiomer 1

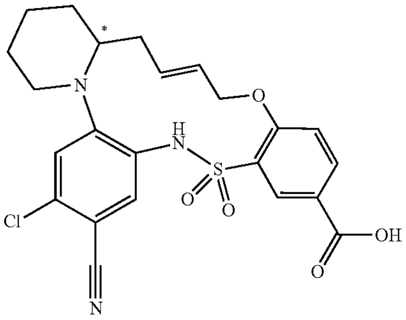 [SMILES: N#Cc1cc2c(cc1Cl)N1CCCCC1C/C=C/COc1ccc(C(=O)O)cc1S(=O)(=O)N2]

Example 30 was dissolved at 5 mg/ml in MeOH/DCM (1:1) and was then separated by chiral SFC (Lux C1 21.2 mm×250 mm, 5 μm column, 40° C., 125 bar, flow rate 50 mL/min, eluting with 35% (0.1% TFA/MeCN)/$CO_2$). The clean fractions were pooled, rinsed with DCM, and then concentrated in vacuo to afford the title compound (12.2 mg, 24.8 μmol, 24% yield, 99% purity) as a white solid. SFC (Lux C1 4.6 mm×250 mm, 5 μm column, 40° C., 125 bar, flow rate 4 mL/min, eluting with 45% (0.1% TFA/MeCN)/$CO_2$) $t_R$ 1.80 min. Other analytical data consistent with Example 30.

Example 46: (E)-3-chloro-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide Enantiomer 2

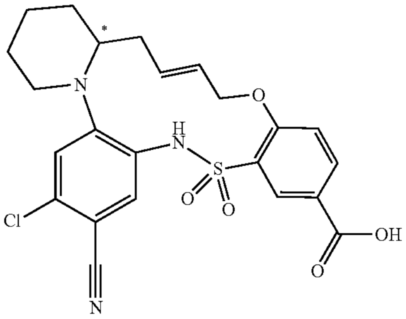 [SMILES: N#Cc1cc2c(cc1Cl)N1CCCCC1C/C=C/COc1ccc(C(=O)O)cc1S(=O)(=O)N2]

The title compound (16.2 mg, 32.9 μmol, 32% yield, 99% purity) was obtained as a white solid from the chiral separation performed in Example 45. SFC (Lux C1 4.6 mm×250 mm, 5 μm column, 40° C., 125 bar, flow rate 4 mL/min, eluting with 45% (0.1% TFA/MeCN)/$CO_2$) $t_R$ 2.36 min. Other analytical data consistent with Example 30.

Example 47: (E)-3-chloro-2-cyano-6,7,8,9,9a,12-hexahydro-19H-dibenzo[b,f]pyrido[1,2-h][1]oxa[4]thia[5,8]diazacyclododecine-16-carboxylic acid 18,18-dioxide Enantiomer 1

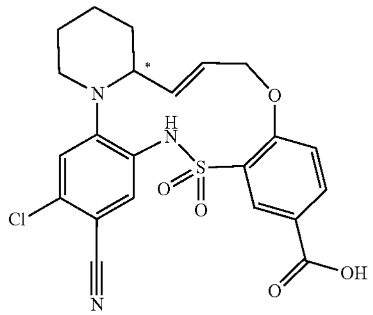 [SMILES: N#Cc1cc2c(cc1Cl)N1CCCCC1/C=C/COc1ccc(C(=O)O)cc1S(=O)(=O)N2]

Example 35 was dissolved at 50 mg/mL in MeOH/DCM with sonication and heating. The mixture was filtered and then separated by chiral SFC (Waters prep 15 with UV detection by DAD at 210-400 nm, 40° C., 120 bar on a Lux C4 10×250 mm, 5 μm column, flow rate 15 mL/min, eluting with 55% (0.1% TFA/MeOH)/$CO_2$). The clean fractions were pooled, rinsed with MeOH concentrated in vacuo. The residue was dissolved in EtOAc (10 mL) and sequentially washed with water (5 mL) and brine (5 mL). The organic layer was dried ($Na_2SO_4$), filtered, and concentrated in vacuo to afford the title compound (41.2 mg, 82.6 μmol, 36% yield, 95% purity) as a brown solid. SFC (Waters $UPC^2$, Lux 04, 4.6×250 mm column, flow rate 4 mL/min, eluting with 60% (0.1% TFA/MeOH)/$CO_2$) $t_R$ 1.98 min. Other analytical data consistent with Example 35.

Example 48: (E)-3-chloro-2-cyano-6,7,8,9,9a,12-hexahydro-19H-dibenzo[b,f]pyrido[1,2-h][1]oxa[4]thia[5,8]diazacyclododecine-16-carboxylic acid 18,18-dioxide Enantiomer 2

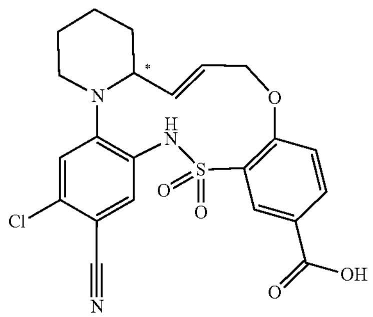 [SMILES: N#Cc1cc2c(cc1Cl)N1CCCCC1/C=C/COc1ccc(C(=O)O)cc1S(=O)(=O)N2]

The title compound (48.7 mg, 101 μmol, 44% yield, 98% purity) and was obtained as a brown solid from the chiral separation performed in Example 47. SFC (Waters $UPC^2$, Lux C4, 4.6×250 mm column, flow rate 4 mL/min, eluting with 60% (0.1% TFA/MeOH)/$CO_2$) $t_R$ 2.26 min. Other analytical data consistent with Example 35.

Example 49: 2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide Enantiomer 1

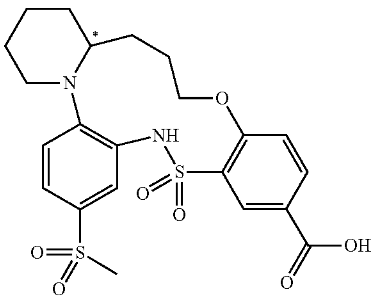

Example 36 was dissolved at 25 mg/mL in MeOH/DCM with sonication and heating. The mixture was filtered and then separated by chiral SFC (Waters prep 15 with UV detection by DAD at 210-400 nm, 40° C., 120 bar on a Chiralpak IC 10×250 mm, 5 μm column, flow rate 15 mL/min, eluting with 30% (0.1% TFA/MeOH)/$CO_2$). The clean fractions were pooled, rinsed with MeOH and concentrated in vacuo. The residue was dissolved in EtOAc (5 mL) and sequentially washed with water (2 mL) and brine (2 mL). The organic layer was dried ($Na_2SO_4$), filtered, and concentrated in vacuo to afford the title compound (7.7 mg, 15.0 μmol, 38% yield, 97% purity) as a pale yellow solid. SFC (Waters UPC$^2$, Chiralpak IC, 4.6×250 mm column, flow rate 4 mL/min, eluting with 35% (0.1% TFA/MeOH)/$CO_2$) $t_R$ 4.01 min. Other analytical data consistent with Example 36.

Example 50: 2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide Enantiomer 2

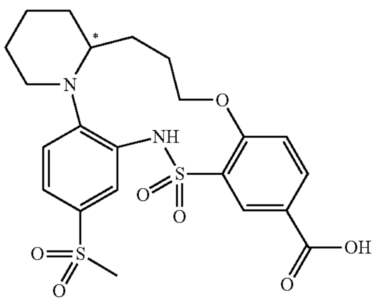

The title compound (7.7 mg, 15.0 μmol, 38% yield, 97% purity) was obtained as a pale-yellow solid from the chiral separation performed in Example 51. SFC (Waters UPC$^2$, Chiralpak IC, 4.6×250 mm column, flow rate 4 mL/min, eluting with 35% (0.1% TFA/MeOH)/$CO_2$) $t_R$ 4.42 min. Other analytical data consistent with Example 36.

Example 51: 3-fluoro-2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

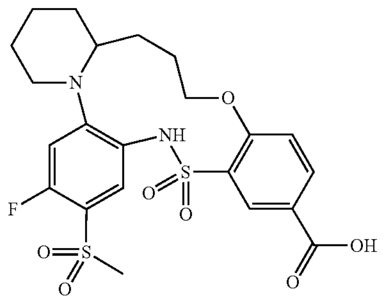

Step 1: 3-(1-(5-fluoro-4-(methylsulfonyl)-2-nitrophenyl)piperidin-2-yl) pro pan-1-ol: A mixture of 1,5-difluoro-2-(methylsulfonyl)-4-nitrobenzene (700 mg, 2.95 mmol) [prepared according to the procedure in WO 2020/104822 A1 Example 331 Part A Steps 1-3], 3-(piperidin-2-yl)propan-1-ol hydrochloride (573 mg, 3.03 mmol, 95% purity) and $Et_3N$ (1.70 mL, 12.2 mmol) in DCM (12 mL) was stirred at 35° C. overnight. The mixture was concentrated onto silica and purified by chromatography on silica gel (24 g cartridge, 0-100% EtOAc/isohexane) to afford the title compound (409 mg, 1.09 mmol, 37% yield, 96% purity) as a yellow solid. UPLC-MS (Method 1): m/z 361.7 $(M+H)^+$ at 1.21 min. $^1H$ NMR (500 MHz, DMSO-$d_6$) δ 8.14 (d, J=7.7 Hz, 1H), 7.43 (d, J=13.8 Hz, 1H), 4.39 (t, J=5.1 Hz, 1H), 3.91-3.78 (m, 1H), 3.37-3.33 (m, 2H), 3.30 (s, 3H), 3.28-3.21 (m, 1H), 2.85-2.79 (m, 1H), 1.84-1.74 (m, 2H), 1.71-1.52 (m, 5H), 1.51-1.32 (m, 2H), 1.32-1.22 (m, 1H).

Step 2: 3-(1-(2-amino-5-fluoro-4-(methylsulfonyl)phenyl)piperidin-2-yl)propan-1-ol: A mixture of the product from Step 1 above (409 mg, 1.09 mmol, 96% purity), ammonium chloride (364 mg, 6.81 mmol) and zinc (445 mg, 6.81 mmol) in THE (4.5 mL) and water (1.5 mL) was stirred at RT overnight. The mixture was filtered through Celite®, the filter cake was washed with EtOAc, and the filtrate was extracted with EtOAc (3×15 mL). The organic extracts were combined and washed with brine (10 mL), dried ($Na_2SO_4$), and the solvent was removed in vacuo to afford the title compound (379 mg, 1.09 mmol, 96% yield, 95% purity) as a light-tan solid. UPLC-MS (Method 1): m/z 331.3 $(M+H)^+$ at 1.12 min. $^1H$ NMR (500 MHz, DMSO-$d_6$) δ 7.13 (d, J=7.3 Hz, 1H), 6.99 (d, J=11.8 Hz, 1H), 5.07 (s, 2H), 4.29 (t, J=5.1 Hz, 1H), 3.26-3.22 (m, 2H), 3.22 (s, 3H), 3.14-3.09 (m, 1H), 3.03-2.95 (m, 1H), 2.49-2.42 (m, 1H), 1.88-1.80 (m, 1H), 1.74-1.53 (m, 3H), 1.44-1.38 (m, 2H), 1.33-1.19 (m, 4H).

3-fluoro-2-(methylsulfonyl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide (26.4 mg, 50.0 μmol, 97% purity) was obtained as a white solid from the product from Step 2 above following the general method outlined in Example 5 Steps 3-5. UPLC-MS (Method 1): m/z 513.1 $(M+H)^+$, 511.0 $(M-H)^-$, at 1.44 min. $^1H$ NMR (500 MHz, DMSO-$d_6$) δ 13.18 (s, 1H), 8.88 (s, 1H), 8.49 (d, J=2.2 Hz, 1H), 8.12 (d, J=8.7 Hz, 1H), 7.61 (d, J=7.1 Hz, 1H), 7.51 (d, J=11.6 Hz, 1H), 7.19 (d, J=8.7 Hz, 1H), 4.18-4.11 (m, 1H), 4.11-4.04 (m, 1H), 3.54-3.47 (m, 1H), 3.15 (s, 3H), 2.94-2.88 (m, 1H), 2.58-2.52 (m, 1H), 1.90-1.68 (m, 3H), 1.67-1.57 (m, 4H), 1.56-1.47 (m, 1H), 1.46-1.36 (m, 1H), 1.34-1.22 (m, 1H).

Example 52: (R)-3-chloro-2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide

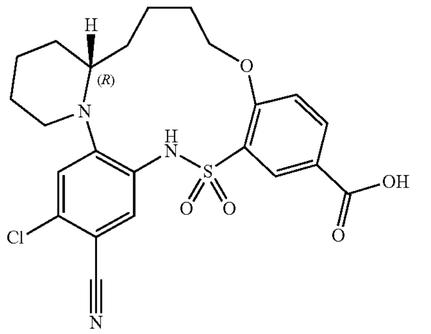

Step 1: tert-butyl (R)-2-(2-oxoethyl)piperidine-1-carboxylate: A stirred solution of DMSO (950 μL, 13.4 mmol) in DCM (27 mL) was treated with oxalyl chloride (550 μL, 6.5 mmol) at −78° C. and the reaction mixture was stirred at −78° C. for 15 min. tert-butyl (R)-2-(2-hydroxyethyl)piperidine-1-carboxylate (1.06 g, 4.62 mmol) in DCM (9 mL) was added dropwise at −78° C. and the solution was stirred at the same temperature for 1 h. $Et_3N$ (3.10 mL, 22.2 mmol) was added and the reaction mixture was allowed to warm to RT. The reaction mixture was diluted with DCM (50 mL) and sequentially washed with water (100 mL) and brine (100 mL), then dried over $MgSO_4$, filtered and concentrated in vacuo to afford the title compound (1.74 g) as a pale yellow oil, which was used in the next step without purification.

Step 2: tert-butyl (R)-2-(4-ethoxy-4-oxobut-2-en-1-yl)piperidine-1-carboxylate: A solution of the product from Step 1 above (1.74 g) in THE (20 mL) at RT was treated with ethyl (triphenylphosphoranylidene)acetate (2.20 g, 6.31 mmol). The resultant mixture was stirred at RT for 4 days. The reaction mixture was concentrated onto silica gel and purified by chromatography on silica gel (24 g cartridge, 0-20% EtOAc/isohexane) to afford the title compound (857 mg, 2.85 mmol, 62% yield over 2 steps, 99% purity) as a colourless oil. $^1H$ NMR (500 MHz, DMSO-$d_6$) δ 6.78 (ddd, J=15.4, 8.5, 6.6 Hz, 1H), 5.88 (dt, J=15.4, 1.4 Hz, 1H), 4.32-4.22 (m, 1H), 4.08 (q, J=7.1 Hz, 2H), 3.89-3.76 (m, 1H), 2.85-2.64 (m, 2H), 2.31-2.21 (m, 1H), 1.62-1.48 (m, 5H), 1.35 (s, 9H), 1.30-1.21 (m, 1H), 1.18 (t, J=7.1 Hz, 3H).

Step 3: tert-butyl (R)-2-(4-ethoxy-4-oxobutyl)piperidine-1-carboxylate: 5% Pd/C (Type 87L, 60% water) (454 mg, 85.3 μmol) was added to a solution of the product from Step 2 above (854 mg, 2.84 mmol, 99% purity) in EtOH (5 mL). The suspension was hydrogenated at RT at 5 bar for 2 h. The reaction mixture was filtered through a glass microfibre frit, washing with EtOH (20 mL), and concentrated in vacuo to afford the title compound (844 mg, 2.73 mmol, 96% yield, 97% purity) as a colourless oil. $^1H$ NMR (500 MHz, DMSO-$d_6$) δ 4.13-4.00 (m, 3H), 3.86-3.76 (m, 1H), 2.77-2.62 (m, 1H), 2.38-2.23 (m, 2H), 1.76-1.65 (m, 1H), 1.57-1.19 (m, 18H), 1.17 (t, J=7.1 Hz, 3H).

Step 4: tert-butyl (R)-2-(4-hydroxybutyl)piperidine-1-carboxylate: $LiAlH_4$ (2 M in THF) (1.50 mL, 3.00 mmol) was added to a solution of the product from Step 3 above (844 mg, 2.73 mmol, 97% purity) in dry THF (17.5 mL) at 0° C. The reaction mixture was stirred at 0° C. for 1 h. The reaction was quenched with sodium sulfate decahydrate (890 mg, 2.76 mmol), stirred for 10 min, then $MgSO_4$ was added and the mixture stirred for 5 min. The mixture was filtered, washed with THF (50 mL) and concentrated in vacuo to afford the title compound (719 mg, 2.65 mmol, 97% yield, 95% purity) as a colourless oil. $^1H$ NMR (500 MHz, DMSO-$d_6$) δ 4.32 (t, J=5.1 Hz, 1H), 4.12-4.02 (m, 1H), 3.86-3.75 (m, 1H), 3.40-3.33 (m, 2H), 2.76-2.63 (m, 1H), 1.67-1.57 (m, 1H), 1.57-1.32 (m, 17H), 1.29-1.11 (m, 3H).

Step 5: (R)-4-(piperidin-2-yl)butan-1-ol hydrochloride: 4 M HCl in dioxane (1.7 mL, 6.80 mmol) was added to solution of the product from Step 4 above (715 mg, 2.64 mmol, 95% purity) in dioxane (10 mL). The reaction mixture was stirred at RT for 23 h. Additional 4 M HCl in dioxane (1.70 mL, 6.80 mmol) was added and the mixture stirred at RT 20 h. The reaction mixture was concentrated in vacuo to afford the title compound (498 mg, 2.49 mmol, 95% yield, 97% purity) as a cream solid. $^1H$ NMR (500 MHz, DMSO-$d_6$) δ 8.87 (br s, 1H), 8.67 (br s, 1H), 3.39 (t, J=6.1 Hz, 2H), 3.22-3.12 (m, 1H), 2.99-2.87 (m, 1H), 2.86-2.74 (m, 1H), 1.88-1.80 (m, 1H), 1.77-1.67 (m, 2H), 1.67-1.53 (m, 2H), 1.53-1.26 (m, 7H).

Step 6: (R)-2-chloro-4-(2-(4-hydroxybutyl)piperidin-1-yl)-5-nitrobenzonitrile: A mixture of the product from Example 14 Step 1 (470 mg, 2.34 mmol), the product from Step 5 above (498 mg, 2.44 mmol, 95% purity) and $Et_3N$ (1.40 mL, 10.0 mmol) in DCM (10 mL) was stirred at 35° C. overnight. The mixture was concentrated onto silica and purified by chromatography on silica gel (24 g cartridge, 0-100% EtOAc/isohexane) to afford the title compound (765 mg, 1.8 mmol, 77% yield, 80% purity) as a dark orange oil. UPLC-MS (Method 1): m/z 338.3 $(M+H)^+$, at 1.51 min. $^1H$ NMR (500 MHz, DMSO-$d_6$) δ 8.38 (s, 1H), 7.59 (s, 1H), 4.30 (t, J=5.1 Hz, 1H), 3.88-3.76 (m, 1H), 3.33-3.28 (m, 2H), 3.26-3.19 (m, 1H), 2.85-2.80 (m, 1H), 1.79-1.68 (m, 2H), 1.66-1.58 (m, 3H), 1.57-1.49 (m, 2H), 1.48-1.40 (m, 1H), 1.39-1.30 (m, 2H), 1.25-1.19 (m, 1H), 1.15-1.11 (m, 1H).

Step 7. (R)-5-amino-2-chloro-4-(2-(4-hydroxybutyl)piperidin-1-yl)benzonitrile: A mixture of the product from Step 6 above (765 mg, 1.81 mmol, 80% purity), $NH_4Cl$ (580 mg, 10.8 mmol) and zinc (710 mg, 10.9 mmol) in THE (12 mL) and Water (4 mL) was stirred at RT for 3 days. Additional $NH_4Cl$ (290 mg, 5.42 mmol) and zinc (360 mg, 5.51 mmol) were added and the reaction was stirred at RT overnight. Additional zinc (360 mg, 5.51 mmol) was added and the reaction was stirred at RT overnight. The mixture was filtered through Celite® and the filter cake was washed with EtOAc (100 mL). The filtrate was washed with brine (100 mL) and the aqueous phase extracted with EtOAc (100 mL). The organic phases were combined, dried ($MgSO_4$) and the solvent was removed in vacuo to afford the title compound (643 mg, 1.6 mmol, 86% yield, 75% purity (inclusive of 22% w/w EtOAc)) as a dark pink oil. UPLC-MS (Method 1): m/z 308.3 $(M+H)^+$ at 1.51 min. $^1H$ NMR (500 MHz, DMSO-$d_6$) δ 7.10 (s, 1H), 7.04 (s, 1H), 5.29 (s, 2H), 4.25 (t, J=5.1 Hz, 1H), 3.27-3.22 (m, 2H), 3.13-3.08 (m, 1H), 3.02-2.94 (m, 1H), 2.49-2.46 (m, 1H), 1.87-1.80 (m, 1H), 1.71-1.53 (m, 3H), 1.45-1.39 (m, 2H), 1.34-1.20 (m, 3H), 1.15-1.12 (m, 2H), 1.10-1.03 (m, 1H).

(R)-3-chloro-2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide (4.5 mg, 7.8 μmol, 85% purity) was obtained as a white solid from the product from Step 7 above following the general method outlined in Example 4 Steps 3-5. UPLC-MS (Method 1): m/z 490.0 $(M+H)^+$, 488.2 $(M-H)^-$, at 1.72 min. $^1$H NMR (400 MHz, $CD_3OD$) δ 8.78-8.73 (m, 1H), 8.29-8.23 (m, 1H), 7.58-7.53 (m, 1H), 7.32-7.29 (m, 1H), 7.29-7.24 (m, 1H), 4.36-4.26 (m, 1H), 4.23-4.12 (m, 1H), 3.07-2.99 (m, 1H), 2.74-2.60 (m, 1H), 2.06-1.85 (m, 2H), 1.85-1.74 (m, 2H), 1.71-1.62 (m, 2H), 1.61-1.33 (m, 6H), 1.33-1.18 (m, 1H). Two exchangeable protons not observed.

Example 53: (S)-3-chloro-2-cyano-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

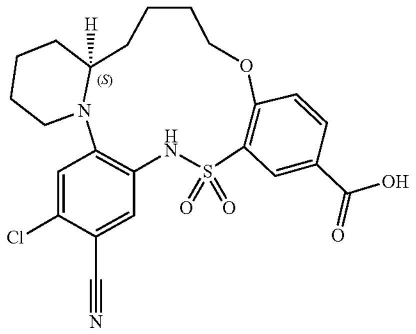

(S)-3-chloro-2-cyano-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide (2.4 mg, 4.8 μmol, 98% purity) was obtained as a white solid from tert-butyl (S)-2-(2-hydroxyethyl)piperidine-1-carboxylate following the general method outlined in Example 52 Steps 1-7 and Example 4 Steps 3-5. UPLC-MS (Method 1): m/z 490.3 $(M+H)^+$, 488.2 $(M-H)^-$, at 1.73 min. 1H NMR (400 MHz, $CD_3OD$) δ 8.78-8.73 (m, 1H), 8.30-8.23 (m, 1H), 7.58-7.54 (m, 1H), 7.32-7.29 (m, 1H), 7.29-7.24 (m, 1H), 4.36-4.27 (m, 1H), 4.23-4.12 (m, 1H), 3.08-2.99 (m, 1H), 2.74-2.61 (m, 1H), 2.06-1.95 (m, 1H), 1.95-1.86 (m, 1H), 1.84-1.74 (m, 2H), 1.71-1.61 (m, 2H), 1.62-1.28 (m, 7H). Two exchangeable protons not observed.

Example 54: 3-chloro-2-(1H-tetrazol-1-yl)-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

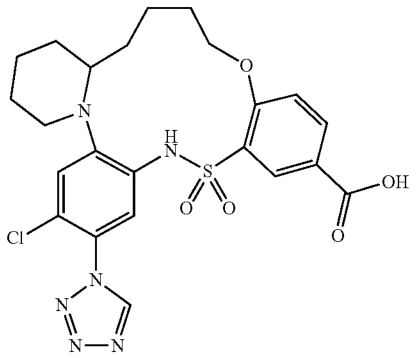 [SMILES: O=C(O)c1ccc2c(c1)S(=O)(=O)Nc1cc(-n3cnnn3)c(Cl)cc1N1CCCCC1CCCCO2]

Step 1: 1-(2-chloro-4-fluoro-5-nitrophenyl)tetrazole: 2-chloro-4-fluoro-5-nitroaniline (2.00 g, 10.5 mmol) and triethyl orthoformate (5.30 mL, 31.8 mmol) in acetic acid (14.5 mL, 253 mmol) was heated to 80° C. and stirred for 1 h. Azidotrimethylsilane (1.40 mL, 10.5 mmol) was added dropwise over 10 min and the mixture was stirred at 80° C. overnight. The reaction was allowed to cool to RT and was concentrated in vacuo. The residue was diluted with EtOAc (50 mL) and sequentially washed with saturated $NaHCO_3$ (aq) (3×30 mL), water (30 mL) and brine (30 mL). The organic layer was dried ($Na_2SO_4$) and concentrated in vacuo. The residue was purified by chromatography on silica gel (40 g cartridge, 0-10% MeOH/DCM) to afford the title compound (996 mg, 3.68 mmol, 35% yield, 90% purity) as a dark brown oil. $^1$H NMR (500 MHz, DMSO-$d_6$) δ 9.93 (s, 1H), 8.84 (d, J=7.4 Hz, 1H), 8.38 (d, J=10.8 Hz, 1H).

Step 2: 3-(1-(5-chloro-2-nitro-4-(tetrazol-1-yl)phenyl)piperidin-2-yl)propan-1-ol: A mixture of the product from Step 1 above (300 mg, 1.11 mmol, 90% purity), 3-(piperidin-2-yl)propan-1-ol hydrochloride (209 mg, 1.16 mmol) and $Et_3N$ (620 μL, 4.45 mmol) in DCM (5 mL) was stirred at 35° C. overnight. The mixture was concentrated onto silica and purified by chromatography on silica gel (12 g cartridge, 0-100% EtOAc/isohexane) to afford the title compound (164 mg, 443 μmol, 40% yield, 99% purity) as a brown solid. UPLC-MS (Method 1): m/z 339.3 $(M+H-N_2)^+$ at 1.30 min. $^1$H NMR (500 MHz, DMSO-$d_6$) δ 9.83 (s, 1H), 8.33 (s, 1H), 7.72 (s, 1H), 4.39 (t, J=5.1 Hz, 1H), 3.76-3.70 (m, 1H), 3.36-3.32 (m, 2H), 3.30-3.20 (m, 1H), 2.87-2.81 (m, 1H), 1.85-1.46 (m, 8H), 1.42-1.24 (m, 2H).

Step 3: 3-(1-(2-amino-5-chloro-4-(tetrazol-1-yl)phenyl)piperidin-2-yl)propan-1-ol: A mixture of the product from Step 2 above (164 mg, 443 μmol, 99% purity), ammonium chloride (142 mg, 2.66 mmol) and zinc (174 mg, 2.66 mmol) in THF (1.8 mL) and water (0.6 mL) was stirred at RT overnight. The mixture was filtered through Celite®, the filter cake was washed with EtOAc, and the filtrate extracted with EtOAc (3×15 mL). The organic extracts were combined, washed with brine (10 mL), dried ($Na_2SO_4$) and the solvent was removed in vacuo to afford the title compound (153 mg, 409 μmol, 92% yield, 90% purity) as a dark brown gum. UPLC-MS (Method 1): m/z 309.3 $(M+H-N_2)^+$ at 1.26 min. $^1$H NMR (500 MHz, DMSO-$d_6$) δ 9.86 (s, 1H), 7.23 (s, 1H), 6.91 (s, 1H), 5.43 (s, 2H), 4.32 (t, J=5.1 Hz, 1H), 3.28-3.22 (m, 2H), 3.06-3.00 (m, 1H), 2.98-2.92 (m, 1H), 2.49-2.44 (m, 1H), 1.88-1.82 (m, 1H), 1.78-1.71 (m, 1H), 1.68-1.57 (m, 2H), 1.47-1.39 (m, 2H), 1.35-1.22 (m, 4H).

3-chloro-2-(tetrazol-1-yl)-6,7,8,9,9a,10,11,12-octahydro-19H-dibenzo[b,f]pyrido[1,2-h][1]oxa[4]thia[5,8]diazacyclododecine-16-carboxylic acid 18,18-dioxide (4.6 mg, 8.4 μmol, 94% purity) was obtained as a tan solid from the product from Step 3 above following the general method outlined in Example 5 Steps 3-5. UPLC-MS (Method 1): m/z 541.2 $(M+Na)^+$, 517.1 $(M-H)^-$, at 1.52 min. $^1$H NMR (500 MHz, DMSO-$d_6$) δ 13.18 (s, 1H), 9.76 (s, 1H), 8.97 (s, 1H), 8.42 (d, J=2.2 Hz, 1H), 8.15 (dd, J=8.7, 2.2 Hz, 1H), 7.86 (s, 1H), 7.38 (s, 1H), 7.21 (d, J=8.8 Hz, 1H), 4.23-4.17 (m, 1H), 4.07-4.01 (m, 1H), 3.46-3.40 (m, 1H), 2.92-2.86 (m, 1H), 2.57-2.52 (m, 1H), 2.01-1.92 (m, 1H), 1.89-1.75 (m, 2H), 1.72-1.56 (m, 5H), 1.51-1.38 (m, 1H), 1.19-1.11 (m, 1H).

Example 55: 2-cyano-3-fluoro-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide Enantiomer 1

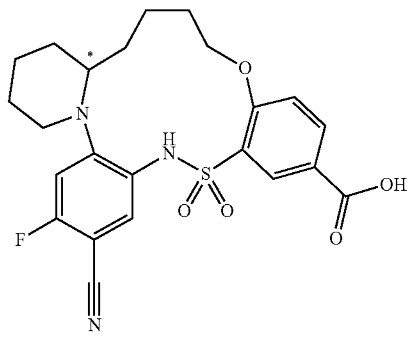 [SMILES: N#Cc1cc2c(cc1F)N1CCCCC1CCCCOc1ccc(C(=O)O)cc1S(=O)(=O)N2]

Example 28 was dissolved in DCM/MeOH (1:1, 1.2 mL) with sonication and then filtered. The sample was separated by chiral SFC (Waters prep 15 with UV detection by DAD at 210-400 nm, 40° C., 120 bar on a ChiralPak IC 10×250 mm, 5 μm column, flow rate 15 mL/min, eluting with 20% (0.07 M $NH_3$/MeOH)/$CO_2$). The clean fractions were pooled, rinsed with MeOH/DCM, and then concentrated in vacuo to afford the title compound (13 mg, 26 μmol, 26% yield, 95% purity) as a white solid. SFC (Waters UPC$^2$, ChiralPak IC, 4.6×250 mm column, flow rate 4 mL/min, eluting with 20% (0.07 M $NH_3$/MeOH)/$CO_2$) $t_R$ 3.56 min. UPLC-MS (Method 2): m/z 474.2 $(M+H)^+$, 472.4 $(M-H)^-$, at 0.77 min. $^1$H NMR (500 MHz, Methanol-$d_4$) δ 8.77 (d, J=2.1 Hz, 1H), 8.25 (dd, J=8.8, 2.1 Hz, 1H), 7.38 (d, J=10.4 Hz, 1H), 7.29 (d, J=6.3 Hz, 1H), 7.22 (d, J=8.8 Hz, 1H), 4.34-4.26 (m, 1H), 4.20-4.13 (m, 1H), 3.39-3.35 (m, 1H), 3.11-3.05 (m, 1H), 2.74-2.66 (m, 1H), 2.03-1.95 (m, 1H), 1.95-1.88 (m, 1H), 1.85-1.78 (m, 2H), 1.71-1.64 (m, 2H), 1.62-1.54 (m, 3H), 1.53-1.46 (m, 2H), 1.44-1.35 (m, 1H). Two exchangeable protons not observed.

Example 56: 2-cyano-3-fluoro-7,8,9,9a,10,11,12,13-octahydro-6H,20H-dibenzo[b,f]pyrido[1,2-h][1]oxa[4]thia[5,8]diazacyclotridecine-17-carboxylic acid 19,19-dioxide Enantiomer 2

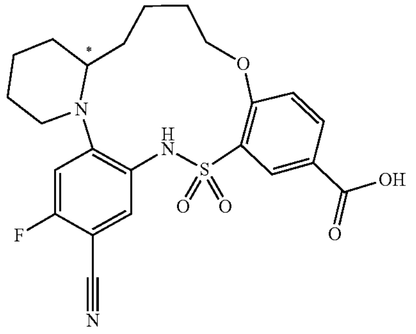 [SMILES: N#Cc1cc2c(cc1F)N1CCCCC1CCCCOc1ccc(C(=O)O)cc1S(=O)(=O)N2]

The title compound (13 mg, 25 μmol, 26% yield, 95% purity) was obtained as a white solid from the chiral separation performed in Example 55. SFC (Waters UPC$^2$, ChiralPak IC, 4.6×250 mm column, flow rate 4 mL/min eluting with 20% (0.07 M $NH_3$/MeOH)/$CO_2$) $t_R$ 4.20 min. Other analytical data consistent with Example 55.

Example 57: (S)-2-cyano-3-fluoro-7,8,9,9a,10,11,12,13-octahydro-6H, 20H-dibenzo[b,f]pyrido[1,2-h][1]oxa[4]thia[5,8]diazacyclotridecine-17-carboxylic acid 19,19-dioxide

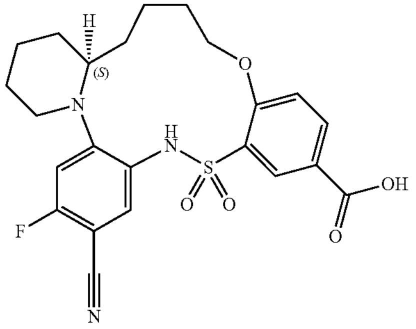

Step 1: tert-butyl (S)-2-(2-oxoethyl)piperidine-1-carboxylate: To a stirred solution of DMSO (4.70 mL, 66.2 mmol) in DCM (135 mL) was added oxalyl chloride (2.80 mL, 33 mmol) at 78° C. and the reaction mixture was stirred at −78° C. for 15 min. tert-butyl (S)-2-(2-hydroxyethyl)piperidine-1-carboxylate (5.00 g, 21.8 mmol) in DCM (45.0 mL) was then added dropwise at −78° C. and the solution was stirred at the same temperature for 1 h. $Et_3N$ (15.0 mL, 108 mmol) was then added and the reaction mixture was allowed to warm to rt. The reaction mixture was diluted with DCM (100 mL) and the organic phase was washed with water (2×200 mL) and brine (200 mL), dried ($Na_2SO_4$), filtered and concentrated in vacuo to afford the title compound (4.96 g) as a yellow oil. The product was used in subsequent reactions without further purification.

Step 2: tert-butyl (S,E)-2-(4-ethoxy-4-oxobut-2-en-1-yl)piperidine-1-carboxylate: To a solution of the product from Step 1 above (4.96 g) in THE (200 mL) at 0° C. was added ethyl (triphenylphosphoranylidene)acetate (10.0 g, 28.7 mmol). The resultant mixture was allowed to warm to RT and stirred overnight. The mixture was loaded onto silica and purified by chromatography on silica gel (120 g cartridge, 0-20 EtOAc/isohexane) to afford the title compound (6.76 g, 20.7 mmol, 95% yield, 91% purity) as a pale yellow oil. $^1$H NMR (500 MHz, DMSO-$d_6$) δ 6.78 (ddd, J=15.4, 8.5, 6.6 Hz, 1H), 5.88 (dt, J=15.4, 1.4 Hz, 1H), 4.32-4.24 (m, 1H), 4.08 (q, J=7.1 Hz, 2H), 3.88-3.77 (m, 1H), 2.84-2.64 (m, 2H), 2.31-2.21 (m, 1H), 1.61-1.49 (m, 5H), 1.35 (s, 9H), 1.29-1.22 (m, 1H), 1.18 (t, J=7.1 Hz, 3H). NMR showed a 94:6 ratio of E:Z.

Step 3: tert-butyl (S)-2-(4-ethoxy-4-oxobutyl)piperidine-1-carboxylate: 5% Pd/C (Type 87L, 60% water) (1.32 g, 621 μmol) was added to a solution of the product from Step 2 above (6.76 g, 20.7 mmol) in EtOH (40 mL). The suspension was hydrogenated at RT at 5 bar for 2 h. The reaction mixture was filtered through a glass microfibre frit, washed with EtOH (10 mL) and then concentrated in vacuo to afford the title compound (6.00 g, 19.6 mmol, 95% yield, 98% purity) as a colourless oil. $^1$H NMR (500 MHz, DMSO-$d_6$) δ 4.09 (s, 1H), 4.04 (q, J=7.1 Hz, 2H), 3.82 (d, J=12.9 Hz, 1H), 2.76-2.61 (m, 1H), 2.39-2.23 (m, 2H), 1.76-1.66 (m, 1H), 1.58-1.51 (m, 1H), 1.51-1.47 (m, 4H), 1.46-1.40 (m, 2H), 1.38 (s, 9H), 1.36-1.28 (m, 1H), 1.27-1.19 (m, 1H), 1.17 (t, J=7.1 Hz, 3H).

Step 4: tert-butyl (S)-2-(4-hydroxybutyl)piperidine-1-carboxylate: $LiAlH_4$ (8.80 mL, 2.4 M in THF, 21.1 mmol) was added to a solution of the product from step 3 above (6.00 g, 19.6 mmol) in dry THF (60 mL) at 0° C. The reaction mixture was stirred at 0° C. for 30 min. The reaction was quenched with $Na_2SO_4$' $10H_2O$ (~6 g) and stirred for 1 h. The reaction mixture was allowed to warm to RT then $Na_2SO_4$ (~6 g) was added. The mixture was filtered, washed with THF (50 mL) and concentrated in vacuo to afford the title compound (5.09 g, 19.4 mmol, 99% yield, 98% purity) as a clear colourless oil. $^1H$ NMR (500 MHz, DMSO-$d_6$) b 4.32 (t, J=5.1 Hz, 1H), 4.12-4.04 (m, 1H), 3.87-3.76 (m, 1H), 3.41-3.34 (m, 2H), 2.70 (t, J=13.5 Hz, 1H), 1.68-1.30 (m, 18H), 1.30-1.12 (m, 3H).

Step 5: (S)-4-(piperidin-2-yl)butan-1-o/hydrochloride: To a solution of the product from Step 4 above (5.09 g, 19.4 mmol) in dioxane (40 mL) was added 4 M HCl in dioxane (24.0 mL, 96.0 mmol) and the mixture was stirred at RT overnight. The solvent was removed in vacuo and the residue was triturated with TBME (15 mL). The solid was collected and dried to afford the title compound (3.73 g, 19.1 mmol, 98% yield, 99% purity) as a white solid. $^1H$ NMR (500 MHz, DMSO-$d_6$) δ 8.75 (s, 2H), 4.42 (s, 1H), 3.44-3.36 (m, 2H), 3.22-3.14 (m, 1H), 2.99-2.90 (m, 1H), 2.80 (td, J=12.7, 3.2 Hz, 1H), 1.88-1.80 (m, 1H), 1.77-1.67 (m, 2H), 1.67-1.53 (m, 2H), 1.53-1.26 (m, 7H).

Step 6: (S)-2-fluoro-4-(2-(4-hydroxybutyl)piperidin-1-yl)-5-nitrobenzonitrile: A mixture of 2,4-difluoro-5-nitrobenzonitrile (500 mg, 2.72 mmol), the product from Step 5 above (550 mg, 2.81 mmol) and $Et_3N$ (1.50 mL, 10.8 mmol) in DCM (10 mL) was stirred at 35° C. for 4 days. The mixture was concentrated onto silica and purified by chromatography on silica gel (24 g cartridge, 0-100% EtOAc/isohexane) to afford the title compound (780 mg, 2.18 mmol, 80% yield, 90% purity) as an orange oil. UPLC-MS (Method 1): m/z 322.4 $(M+H)^+$, no ionisation $(M-H)^-$, at 1.42 min. $^1H$ NMR (500 MHz, DMSO-$d_6$) δ 8.40 (d, J=7.3 Hz, 1H), 7.40 (d, J=13.3 Hz, 1H), 4.30 (t, J=5.1 Hz, 1H), 3.79-3.74 (m, 1H), 3.31-3.27 (m, 2H), 3.21 (td, J=13.0, 2.9 Hz, 1H), 2.84 (d, J=12.4 Hz, 1H), 1.79-1.69 (m, 2H), 1.69-1.59 (m, 3H), 1.57-1.48 (m, 2H), 1.44 (td, J=10.9, 8.7, 5.4 Hz, 1H), 1.41-1.27 (m, 2H), 1.26-1.09 (m, 2H).

Step 7: (S)-2-fluoro-5-nitro-4-(2-(4-((2-(trimethylsilyl)ethoxy)methoxy)butyl)piperidin-1-yl)benzonitrile: To a solution of the product from Step 6 (780 mg, 2.18 mmol) and DIPEA (1.20 mL, 6.89 mmol) in DCM (10 mL) was added SEM-CI (600 μL, 3.39 mmol) drop-wise. The mixture was stirred at RT for 90 min. The reaction was quenched with saturated $NaHCO_3$(aq) (20 mL) and extracted with DCM (2×20 mL). The combined organic extracts were washed with brine (20 mL), dried ($Na_2SO_4$) and the solvent was removed in vacuo. The title compound (1.03 g, 1.82 mmol, 84% yield, 80% purity) was obtained as a yellow oil. UPLC-MS (Method 1): m/z no ionisation at 2.12 min. $^1H$ NMR (500 MHz, DMSO-$d_6$) δ 8.40 (d, J=7.2 Hz, 1H), 7.40 (d, J=13.3 Hz, 1H), 4.51 (s, 2H), 3.80-3.75 (m, 1H), 3.51-3.44 (m, 2H), 3.39-3.32 (m, 2H), 3.21 (td, J=12.9, 2.9 Hz, 1H), 2.87-2.81 (m, 1H), 1.82-1.70 (m, 2H), 1.67-1.58 (m, 3H), 1.58-1.50 (m, 2H), 1.47-1.42 (m, 2H), 1.29-1.21 (m, 2H), 1.21-1.11 (m, 1H), 0.85-0.79 (m, 2H), −0.02 (s, 9H).

Step 8: (S)-5-amino-2-fluoro-4-(2-(4-((2-(trimethylsilyl)ethoxy)methoxy)butyl)piperidin-1-yl)benzonitrile: A mixture of the product from Step 6 (1.03 g, 1.82 mmol), ammonium chloride (586 mg, 10.9 mmol) and zinc (716 mg, 10.9 mmol) in THE (12.0 mL) and water (4.00 mL) was stirred at RT overnight. The mixture was filtered through Celite®, the filter cake was washed with EtOAc and the filtrate was extracted with EtOAc (3×30 mL). The combined organic extracts were washed with brine (30 mL), dried ($Na_2SO_4$) and the solvent was removed in vacuo. The title compound (983 mg, 1.77 mmol, 97% yield, 76% purity) was obtained as a brown oil. UPLC-MS (Method 1): m/z 422.5 $(M+H)^+$, no ionisation $(M-H)^-$, at 2.15 min. $^1H$ NMR (500 MHz, DMSO-$d_6$) δ 6.99 (d, J=11.1 Hz, 1H), 6.93 (d, J=6.7 Hz, 1H), 4.99 (s, 2H), 4.49 (s, 2H), 3.51-3.45 (m, 2H), 3.31-3.28 (m, 2H), 3.20-3.16 (m, 1H), 3.03-2.97 (m, 1H), 2.49-2.46 (m, 1H), 1.87-1.80 (m, 1H), 1.70-1.55 (m, 3H), 1.44-1.28 (m, 5H), 1.23-1.07 (m, 3H), 0.85-0.80 (m, 2H), −0.01 (s, 9H).

Step 9: methyl (S)-3-(N-(5-cyano-4-fluoro-2-(2-(4-((2-(trimethylsilyl)ethoxy)methoxy)butyl)piperidin-1-yl)phenyl)sulfamoyl)-4-hydroxybenzoate: A mixture of the compound from Step 8 above (583 mg, 1.05 mmol), the compound from Example 14, Step 1 (416 mg, 1.58 mmol) and pyridine (250 μL, 3.10 mmol) in DCM (5 mL) was heated to 35° C. and stirred for 2 days. Additional compound from Example 14, Step 1 (416 mg, 1.58 mmol) and pyridine (250 μL, 3.10 mmol) were added and stirring at 35° C. was continued for 2 days. Additional compound from Example 14, Step 1 (416 mg, 1.58 mmol) and pyridine (250 μL, 3.10 mmol) were added and stirring at 35° C. was continued for 3 days. The mixture was concentrated onto silica and purified by chromatography on silica gel (24 g cartridge, 0-50% EtOAc/isohexane) to afford the title compound (426 mg, 489 μmol, 47% yield, 73% purity) as a brown solid. UPLC-MS (Method 1): m/z 636.5 $(M+H)^+$, 634.3 $(M-H)^-$, at 2.03 min.

Step 10: methyl (S)-3-(N-(5-cyano-4-fluoro-2-(2-(4-hydroxybutyl)piperidin-1-yl)phenyl)sulfamoyl)-4-hydroxybenzoate: A solution of the product from Step 9 above (426 mg, 489 μmol, 73%) and TBAF (540 μL, 1 M in THF, 540 μmol) in THF (2 mL) was stirred at RT overnight. Additional TBAF (540 μL, 1 M in THF, 540 μmol) was added and the mixture was warmed to 40° C. and stirred over the weekend. The mixture was diluted with EtOAc (10 mL), sequentially washed with water (5 mL) and brine (5 mL), dried ($Na_2SO_4$), and the solvent was removed in vacuo. The title compound (327 mg) was recovered.

Step 11: methyl (S)-3-(N-(5-cyano-4-fluoro-2-(2-(4-hydroxybutyl)piperidin-1-yl)phenyl)sulfamoyl)-4-hydroxybenzoate: A solution of the product from Step 10 above (327 mg) and TFA (1.50 mL, 19.5 mmol) in DCM (1.5 mL) was stirred at RT for 2 h. The mixture was concentrated, and the residue was dissolved in DCM (1 mL) and 7 M $NH_3$ in MeOH (1 mL) and stirred for 20 min. The mixture was concentrated onto silica in vacuo and purified by chromatography on silica gel (24 g cartridge, 0-10% MeOH/DCM) to afford the title compound (284 mg, 444 μmol, 91% yield, 79% purity) as a sticky brown gum. UPLC-MS (Method 1): m/z 506.3 $(M+H)^+$, 504.2 $(M-H)^-$ at 1.45 min.

Step 12: methyl (S)-2-cyano-3-fluoro-7,8,9,9a,10,11,12,13-octahydro-6H,20H-dibenzo[b,f]pyrido[1,2-h][1]oxa[4]thia[5,8]diazacyclotridecine-17-carboxylate 19,19-dioxide: To a solution of the product from Step 11 above (284 mg, 444 μmol) and triphenylphosphine (349 mg, 1.33 mmol) in DCM (14.0 mL) was added DIAD (260 μL, 1.34 mmol) and the mixture was stirred at RT for 1 h. The mixture was concentrated onto silica and purified by chromatography on silica gel (12 g cartridge, 0-100% EtOAc/isohexane) to afford the title compound (212 mg, 391 μmol, 88% yield, 90% purity) the title compound as a white solid. UPLC-MS (Method 1): m/z 488.4 $(M+H)^+$, 486.2 $(M-H)^-$, at 1.78 min. 58 mg of the title compound were purified by chromatography on silica gel (4 g cartridge, 0-100% EtOAc/isohexane)

to afford the title compound (21.3 mg, 42.8 μmol, 10% yield, 98% purity) as a white solid. UPLC-MS (Method 1): m/z 488.4 $(M+H)^+$, 486.1 $(M-H)^-$, at 1.79 min. $^1H$ NMR (500 MHz, DMSO-$d_6$) δ 8.58 (s, 1H), 8.56 (d, J=2.3 Hz, 1H), 8.20 (dd, J=8.9, 2.3 Hz, 1H), 7.52 (d, J=10.8 Hz, 1H), 7.38 (d, J=8.9 Hz, 1H), 7.25 (d, J=6.5 Hz, 1H), 4.34-4.26 (m, 1H), 4.21-4.15 (m, 1H), 3.89 (s, 3H), 3.42-3.35 (m, 1H), 2.97-2.91 (m, 1H), 2.71-2.64 (m, 1H), 1.86-1.61 (m, 4H), 1.59-1.39 (m, 4H), 1.37-1.15 (m, 4H).

Step 13: (S)-2-cyano-3-fluoro-7,8,9,9a,10, 11, 12, 13-octahydro-6H, 20H-dibenzo[b,f]pyrido[1,2-h][1]oxa[4]thia[5,8]diazacyclotridecine-17-carboxylic acid 19,19-dioxide: A mixture of the product from Step 12 above (154 mg, 284 μmol) and LiOH (27.2 mg, 1.14 mmol) in THF/MeOH/water (4:1:1, 0.9 mL) was stirred at 40° C. overnight. The mixture was diluted with water (5 mL), acidified to ~pH 4 with 1 M HCl(aq) and extracted with EtOAc (3×10 mL). The organic extracts were combined and washed with brine (10 mL), dried ($Na_2SO_4$) and the solvent was removed in vacuo. The residue was loaded onto silica and purified by chromatography on silica gel (4 g cartridge, 0-5% MeOH/DCM) to afford the title compound (51.3 mg, 104 μmol, 37% yield, 96% purity) as a white solid. UPLC-MS (Method 1): m/z 474.5 $(M+H)^+$, 472.2 $(M-H)^-$, at 1.64 min. $^1H$ NMR (500 MHz, DMSO-$d_6$) δ 13.24 (s, 1H), 8.57-8.53 (m, 2H), 8.17 (dd, J=8.8, 2.2 Hz, 1H), 7.52 (d, J=10.8 Hz, 1H), 7.35 (d, J=8.9 Hz, 1H), 7.23 (d, J=6.5 Hz, 1H), 4.33-4.23 (m, 1H), 4.21-4.09 (m, 1H), 3.42-3.34 (m, 1H), 3.00-2.90 (m, 1H), 2.72-2.65 (m, 1H), 1.87-1.40 (m, 6H), 1.39-1.07 (m, 6H).

Example 58: (S,E)-3-chloro-2-cyano-N-(methylsulfonyl)-6,7,8,9,9a,12-hexahydro-19H-dibenzo[b,f]pyrido[1,2-h][1]oxa[4]thia[5,8]diazacyclododecine-16-carboxamide 18,18-dioxide

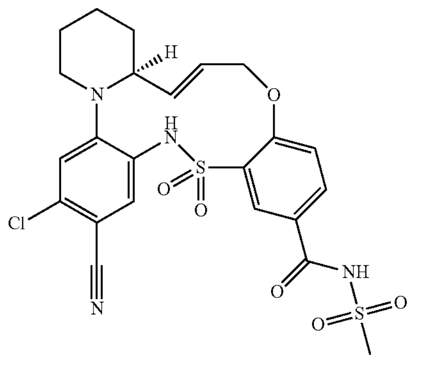 [SMILES: CS(=O)(=O)NC(=O)c1ccc2c(c1)S(=O)(=O)Nc1cc(C#N)c(Cl)cc1N1CCCC[C@H]1/C=C/CO2]

Step 1: (S,E)-3-chloro-2-cyano-N-(methylsulfonyl)-6,7,8,9,9a,12-hexahydro-19H-dibenzo[b,f]pyrido[1,2-h][1]oxa[4]thia[5,8]diazacyclododecine-16-carboxamide 18,18-dioxide: A solution of Example 48 (enantiomer 2, arbitrarily assigned as S) (25.0 mg, 52.8 μmol) in DCM (1 mL) was added to a vial containing methanesulfonamide (7.0 mg, 74 μmol), EDC (24.0 mg, 125 μmol) and DMAP (15.0 mg, 123 μmol). The resultant solution was allowed to stand at RT for 24 h. The mixture was directly purified by chromatography on silica gel (4 g cartridge, 0-10% MeOH/DCM) to afford a white powder (23 mg). To remove residual solvents and methanesulfonamide, the powder was dissolved in 1:1 MeCN/water (2 mL) and then diluted with water (4 mL). The mixture was concentrated in vacuo to remove MeCN and the resultant tan precipitate was collected by filtration, washing with water, and dried in vacuo to afford the title compound (10.0 mg, 34% yield, 98% purity) as a tan solid. UPLC-MS (Method 1): 551.3 $(M+H)^+$, 549.1 $(M-H)^-$, at 1.54 min. $^1H$ NMR (500 MHz, DMSO-$d_6$) δ 12.35 (s, 1H), 9.47 (s, 1H), 8.51 (d, J=2.3 Hz, 1H), 8.13 (dd, J=8.8, 2.4 Hz, 1H), 7.74 (s, 1H), 7.45-7.08 (m, 2H), 5.95 (t, J=10.8 Hz, 1H), 5.72-5.54 (m, 1H), 4.91 (dd, J=15.3, 5.4 Hz, 1H), 4.45 (s, 1H), 4.21-4.06 (m, 1H), 3.37 (s, 3H), 3.12-2.97 (m, 1H), 2.81-2.66 (m, 1H), 1.87-1.73 (m, 1H), 1.72-1.49 (m, 3H), 1.51-1.39 (m, 1H), 1.31-1.11 (m, 1H).

Example 59: (R)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

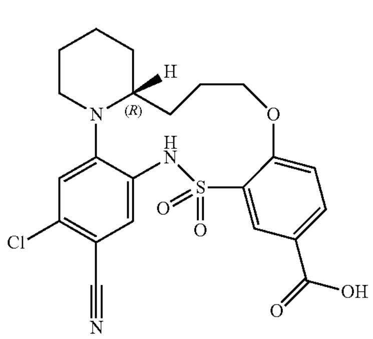

Step 1: tert-butyl (R)-2-formylpiperidine-1-carboxylate: To a stirred solution of dimethyl sulfoxide (4.00 mL, 56.4 mmol) in DCM (120 mL) was added oxalyl chloride (2.40 mL, 28 mmol) at −78° C. and the reaction mixture was stirred at −78° C. for 15 min. tert-butyl (R)-2-(hydroxymethyl)piperidine-1-carboxylate (4.00 g, 18.6 mmol) in DCM (40.0 mL) was then added dropwise at −78° C. and the solution was stirred at the same temperature for 1 h. $Et_3N$ (13.0 mL, 93.3 mmol) was then added and the reaction mixture was allowed to warm to rt. The reaction mixture was diluted with DCM (100 mL) and the organic phase was washed with water (2×200 mL) and brine (200 mL), dried ($Na_2SO_4$), filtered and concentrated in vacuo to afford the title compound (3.96 g) as a yellow oil.

Step 2: tert-butyl (R,E)-2-(3-ethoxy-3-oxoprop-1-en-1-yl)piperidine-1-carboxylate: To a solution of the product from Step 1 (3.96 g) in THE (200 mL) at 0° C. was added ethyl (triphenylphosphoranylidene)acetate (8.40 g, 24.1 mmol). The resultant mixture was allowed to warm to RT and stirred overnight. The mixture was loaded onto silica and purified by chromatography on silica gel (120 g cartridge, 0-20 EtOAc/isohexane) to afford the title compound (5.06 g, 86% yield, 90% purity) as a clear colourless oil. UPLC-MS (Method 1): m/z 184.3 $(M-Boc+H)^+$1.62 min. $^1H$ NMR (500 MHz, DMSO-$d_6$) δ 6.83 (dd, J=15.9, 4.1 Hz, 1H), 5.71 (dd, J=15.9, 2.2 Hz, 1H), 4.87-4.79 (m, 1H), 4.13 (q, J=7.1 Hz, 2H), 3.84 (d, J=13.1 Hz, 1H), 2.80-2.70 (m, 1H), 1.88-1.79 (m, 1H), 1.67-1.52 (m, 3H), 1.39 (s, 9H), 1.34-1.27 (m, 2H), 1.22 (t, J=7.1 Hz, 3H).

Step 3: tert-butyl (R)-2-(3-ethoxy-3-oxopropyl)piperidine-1-carboxylate: 5% Pd/C (Type 87L, 5% Pd, 60% water) (1.07 g, 502 μmol) was added to a solution of the product from Step 2 above (5.27 g, 16.7 mmol) in EtOH (30 mL). The suspension was hydrogenated at RT at 5 bar overnight. The reaction mixture was filtered through a glass microfibre frit, washed with EtOH (10 mL) and then concentrated in vacuo to afford the title compound (4.86 g, 16.7 mmol, 100% yield, 98% purity) as a light grey oil. $^1$H NMR (500 MHz, DMSO-$d_6$) δ 4.16-4.09 (m, 1H), 4.04 (q, J=7.1 Hz, 2H), 3.81 (d, J=13.5 Hz, 1H), 2.75-2.66 (m, 1H), 2.26-2.13 (m, 2H), 2.00-1.89 (m, 1H), 1.67-1.57 (m, 1H), 1.57-1.44 (m, 5H), 1.37 (s, 9H), 1.26-1.20 (m, 1H), 1.17 (t, J=7.1 Hz, 3H).

Step 4: tert-butyl (R)-2-(3-hydroxypropyl)piperidine-1-carboxylate: $LiAlH_4$ (7.50 mL, 2.4 M in THF, 18.0 mmol) was added to a solution of the product from Step 3 above (4.86 g, 16.7 mmol) in dry THF (50 mL) at 0° C. The reaction mixture was stirred at 0° C. for 30 min. The reaction was quenched with sodium sulfate decahydrate (~5 g) and stirred for 1 h. The reaction mixture was allowed to warm to RT then $Na_2SO_4$ (~5 g) was added. The mixture was filtered, washed with THF (50 mL) and concentrated in vacuo to afford the title compound (4.23 g, 16.7 mmol, 100% yield, 96% purity) as a clear colourless oil. $^1$H NMR (500 MHz, DMSO-$d_6$) δ 4.36 (t, J=5.2 Hz, 1H), 4.08 (s, 1H), 3.81 (d, J=13.3 Hz, 1H), 3.42-3.35 (m, 2H), 2.77-2.65 (m, 1H), 1.72-1.61 (m, 1H), 1.58-1.43 (m, 5H), 1.38 (s, 9H), 1.36-1.18 (m, 4H).

Step 5: (R)-3-(piperidin-2-yl)propan-1-o/hydrochloride: To a solution of the product from Step 4 above (4.23 g, 16.7 mmol) in dioxane (30 mL) was added 4 M HCl in dioxane (22.0 mL, 88.0 mmol) and the mixture was stirred at RT overnight. The solid was collected, washed with TBME (20 mL) and dried to afford the title compound (2.98 g, 16.4 mmol, 98% yield, 99% purity) as a white solid. $^1$H NMR (500 MHz, DMSO-$d_6$) δ 8.74 (s, 1H), 8.53 (s, 1H), 4.57 (s, 1H), 3.40 (t, J=5.9 Hz, 2H), 3.33 (s, 1H), 3.19 (d, J=12.6 Hz, 1H), 3.03-2.91 (m, 1H), 2.89-2.73 (m, 1H), 1.85 (d, J=13.7 Hz, 1H), 1.76-1.68 (m, 2H), 1.68-1.55 (m, 1H), 1.55-1.37 (m, 4H), 1.37-1.27 (m, 1H).

Step 6: (R)-2-chloro-4-(2-(3-hydroxypropyl)piperidin-1-yl)-5-nitrobenzonitrile: A mixture of the product of Example 14, Step 1 (1.00 g, 4.39 mmol, 88% purity), the product from Step 5 above (836 mg, 4.61 mmol, 99% purity) and $Et_3N$ (1.82 g, 2.50 mL, 17.9 mmol) in DCM (25 mL) was stirred at RT over the weekend. The mixture was concentrated onto silica and purified by chromatography on silica gel (24 g cartridge, 0-100% EtOAc/isohexane) to afford the title compound (912 mg, 2.42 mmol, 55% yield, 86% purity) as an orange oil. UPLC-MS (Method 1): m/z 324.3 $(M+H)^+$ at 1.42 min. $^1$H NMR (500 MHz, DMSO-$d_6$) δ 8.39 (s, 1H), 7.60 (s, 1H), 4.38 (t, J=5.1 Hz, 1H), 3.86-3.81 (m, 1H), 3.36-3.31 (m, 2H), 3.22 (td, J=12.9, 2.9 Hz, 1H), 2.86-2.80 (m, 1H), 1.81-1.70 (m, 2H), 1.68-1.51 (m, 5H), 1.50-1.41 (m, 1H), 1.39-1.20 (m, 2H).

Step 7: (R)-2-chloro-5-nitro-4-(2-(3-((2-(trimethylsilyl)ethoxy)methoxy)propyl)piperidin-1-yl)benzonitrile: To a solution the product from Step 6 above (912 mg, 2.42 mmol) and DIPEA (1.30 mL, 7.46 mmol) in DCM (10 mL) was added SEM-CI (640 μL, 3.62 mmol) drop-wise. The mixture was stirred at RT for 90 min. The reaction was quenched with saturated $NaHCO_3$(aq) (20 mL) and extracted with DCM (2×20 mL). The combined organic extracts were washed with brine (20 mL), dried ($Na_2SO_4$) and the solvent was removed in vacuo. The residue was loaded onto silica and purified by chromatography on silica gel (24 g cartridge, 0-50% EtOAc/isohexane) to afford the title compound (1.07 g, 2.24 mmol, 92% yield, 95% purity) as a clear orange oil. UPLC-MS (Method 1): m/z 454.2 $(M+H)^+$ at 2.12 min. $^1$H NMR (500 MHz, DMSO-$d_6$) δ 8.39 (s, 1H), 7.60 (s, 1H), 4.52 (s, 2H), 3.93-3.85 (m, 1H), 3.51-3.45 (m, 2H), 3.39 (t, J=6.3 Hz, 2H), 3.26-3.17 (m, 1H), 2.81 (d, J=13.1 Hz, 1H), 1.87-1.73 (m, 2H), 1.69-1.57 (m, 3H), 1.58-1.50 (m, 2H), 1.51-1.40 (m, 2H), 1.43-1.29 (m, 1H), 0.86-0.79 (m, 2H), −0.02 (s, 9H).

Step 8: (R)-5-amino-2-chloro-4-(2-(3-((2-(trimethylsilyl)ethoxy)methoxy)propyl)piperidin-1-yl)benzonitrile: A mixture of the product from Step 7 above (1.07 g, 2.24 mmol), ammonium chloride (719 mg, 13.4 mmol) and zinc (878 mg, 13.4 mmol) in THE (7.5 mL) and water (2.5 mL) was stirred at RT overnight. Additional ammonium chloride (719 mg, 13.4 mmol) and zinc (878 mg, 13.4 mmol) were added and stirring was continued for 4 h. The mixture was filtered through Celite®, the filter cake was washed with EtOAc and the filtrate was extracted with EtOAc (3×20 mL). The combined organic extracts were washed with brine (20 mL), dried ($Na_2SO_4$) and the solvent was removed in vacuo. The title compound (946 mg, 2.19 mmol, 98% yield, 98% purity) was obtained as a red oil. UPLC-MS (Method 1): m/z 424.6 $(M+H)^+$ at 2.15 min. $^1$H NMR (500 MHz, DMSO-$d_6$) δ 7.10 (s, 1H), 7.04 (s, 1H), 5.31 (s, 2H), 4.47 (s, 2H), 3.49-3.42 (m, 2H), 3.31-3.25 (m, 2H), 3.15-3.09 (m, 1H), 2.99-2.93 (m, 1H), 2.50-2.43 (m, 1H), 1.87-1.79 (m, 1H), 1.73-1.53 (m, 3H), 1.45-1.22 (m, 6H), 0.85-0.78 (m, 2H), −0.02 (s, 9H).

Step 9: methyl (R)-4-(allyloxy)-3-(N-(4-chloro-5-cyano-2-(2-(3-((2-(trimethylsilyl)ethoxy)methoxy)propyl)piperidin-1-yl)phenyl)sulfamoyl)benzoate: A mixture of the product from step 8 above (380 mg, 878 μmol), the product from Example 15, Step 3 (383 mg, 1.32 mmol) and pyridine (220 μL, 2.73 mmol) in DOE (4 mL) was heated to 50° C. and stirred for 2 days. The mixture was concentrated onto silica and purified by chromatography on silica gel (24 g cartridge, 0-75% EtOAc/isohexane) to afford the title compound (506 mg, 709 μmol, 81% yield, 95% purity) as a clear brown gum. UPLC-MS (Method 1): m/z 700.5 $(M+Na)^+$, 676.3 $(M-H)^-$, at 2.21 min. $^1$H NMR (500 MHz, DMSO-$d_6$) b 8.99 (s, 1H), 8.35 (d, J=2.2 Hz, 1H), 8.19 (dd, J=8.8, 2.2 Hz, 1H), 7.58 (s, 1H), 7.46 (s, 1H), 7.39 (d, J=8.8 Hz, 1H), 6.01-5.90 (m, 1H), 5.46 (dd, J=17.3, 1.7 Hz, 1H), 5.30 (dd, J=10.7, 1.7 Hz, 1H), 4.86-4.74 (m, 2H), 4.44 (s, 2H), 3.86 (s, 3H), 3.39 (t, J=8.0 Hz, 2H), 3.26-3.18 (m, 3H), 2.80-2.74 (m, 1H), 2.69-2.63 (m, 1H), 1.78-1.72 (m, 1H), 1.69-1.62 (m, 1H), 1.54-1.46 (m, 2H), 1.41-1.30 (m, 2H), 1.29-1.16 (m, 2H), 1.15-1.05 (m, 2H), 0.81-0.74 (m, 2H), −0.05 (s, 9H).

Step 10: methyl (R)-3-(N-(4-chloro-5-cyano-2-(2-(3-((2-(trimethylsilyl) ethoxy)methoxy) propyl) piperidin-1-yl)phenyl) sulfamoyl)-4-hydroxybenzoate To a solution of the product from Step 9 above (506 mg, 709 μmol) in MeOH (8 mL) was added $Pd(PPh_3)_4$ (10.0 mg, 8.65 μmol) and the mixture was stirred for 5 min. $K_2CO_3$ (294 mg, 2.13 mmol) was added and the mixture was stirred at RT overnight. The mixture was concentrated in vacuo and the residue was treated with 1 M HCl(aq) (10 mL) and extracted with DCM (3×20 mL). The combined organic extracts were dried ($Na_2SO_4$), concentrated onto silica in vacuo, and purified by chromatography on silica gel (12 g cartridge, 0-100% EtOAc/isohexane) to afford the title compound (436 mg, 683 μmol, 96% yield) as a clear brown gum. UPLC-MS (Method 1): m/z 638.5 $(M+H)^+$, 636.3 $(M-H)^-$, at 2.04 min.

Step 11: methyl (R)-3-(N-(4-chloro-5-cyano-2-(2-(3-hydroxypropyl)piperidin-1-yl)phenyl)sulfamoyl)-4-hydroxybenzoate: A solution of the product from Step 10 above (609 mg, 945 μmol) and TFA (3.00 mL, 38.9 mmol) in DCM (3 mL) was stirred at RT for 2 h. The mixture was concentrated and the residue was dissolved in DCM (5 mL) and 7 M $NH_3$ in MeOH (5 mL) and stirred for 20 min. The mixture was concentrated onto silica in vacuo and purified by chromatography on silica gel (24 g cartridge, 0-10% MeOH/DCM) to afford the title compound (462 mg, 92% yield, 96% purity) as a sticky brown gum. UPLC-MS (Method 1): m/z 508.3 $(M+H)^+$506.2 $(M-H)^-$, at 1.47 min.

Step 12: methyl (R)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylate 18,18-dioxide: To a solution of the product from Step 11 above (462 mg, 873 μmol) and triphenylphosphine (687 mg, 2.62 mmol) in DCM (20 mL) was added DIAD (500 μL, 2.57 mmol) and the mixture was stirred at RT for 1 h. The mixture was concentrated onto silica and purified by chromatography on silica gel (24 g cartridge, 0-100% EtOAc/isohexane) to afford the title compound (99.1 mg, 22% yield, 94% purity) as a light yellow gum. UPLC-MS (Method 1): m/z 490.4 $(M+H)^+$, 488.2 $(M-H)^-$, at 1.80 min.

Step 13: (R)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide: A mixture of the product from Step 12 above (99.1 mg, 190 μmol) and LiOH (32.0 mg, 763 μmol) in THF/MeOH/water (4:1:1, 1.05 mL) was stirred at 40° C. overnight. The mixture was diluted with water (10 mL), acidified to ~pH 4 with 1 M HCl(aq) and extracted with EtOAc (3×20 mL). The combined organic extracts were washed with brine (20 mL), dried ($Na_2SO_4$) and the solvent was removed in vacuo. The residue was loaded onto silica and purified by chromatography on silica gel (4 g cartridge, 0-100% EtOAc/isohexane) to afford the title compound (29.4 mg, 32% yield, 98% purity) as a white solid after trituration with TBME. UPLC-MS (Method 1): m/z 476.4 $(M+H)^+$, 474.2 $(M-H)^-$ at 1.64 min. $^1$H NMR (500 MHz, DMSO-$d_6$) δ 13.23 (s, 1H), 9.06 (s, 1H), 8.51 (d, J=2.2 Hz, 1H), 8.15 (dd, J=8.7, 2.2 Hz, 1H), 7.64 (s, 1H), 7.45 (s, 1H), 7.22 (d, J=8.7 Hz, 1H), 4.17-4.05 (m, 2H), 3.56-3.48 (m, 1H), 2.93-2.87 (m, 1H), 2.60-2.53 (m, 1H), 1.90-1.75 (m, 2H), 1.74-1.54 (m, 5H), 1.53-1.46 (m, 1H), 1.45-1.36 (m, 1H), 1.33-1.25 (m, 1H).

Example 60: (S)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide

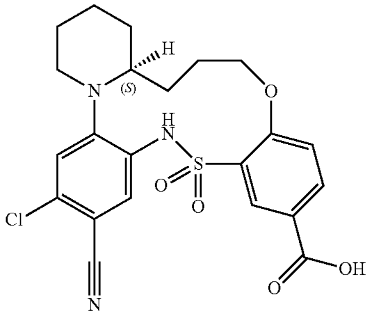

Step 1: tert-butyl (S)-2-formylpiperidine-1-carboxylate: To a stirred solution of dimethyl sulfoxide (4.00 mL, 56.4 mmol) in DCM (120 mL) was added oxalyl chloride (2.4 mL, 27.9 mmol) at −78° C. and the reaction mixture was stirred at −78° C. for 15 min. tert-butyl (S)-2-(hydroxymethyl)piperidine-1-carboxylate (4.00 g, 18.6 mmol) in DCM (40.0 mL) was then added dropwise at −78° C. and the solution was stirred at the same temperature for 1 h. $Et_3N$ (13.0 mL, 93.3 mmol) was added and the reaction mixture was allowed to warm to rt. The reaction mixture was diluted with DCM (100 mL) and the organic phase was washed with water (2×200 mL) and brine (200 mL), dried ($MgSO_4$), filtered and concentrated in vacuo to afford the title compound (3.97 g) as a yellow oil.

Step 2: tert-butyl (S,E)-2-(3-ethoxy-3-oxo prop-1-en-1-yl)piperidine-1-carboxylate: To a solution of the product from Step 1 above (3.97 g) in THF (200 mL) at 0° C. was added ethyl (triphenylphosphoranylidene)acetate (8.40 g, 24.1 mmol). The resultant mixture was allowed to warm to RT and stirred overnight. The crude product was concentrated onto silica and purified by chromatography on silica gel (120 g cartridge, 0-20% EtOAc/isohexane) to afford the title compound (4.71 g, 16 mmol, 86% yield, 95% purity) as a colourless liquid. $^1$H NMR (500 MHz, DMSO-$d_6$) δ 6.83 (dd, J=15.9, 4.1 Hz, 1H), 5.71 (dd, J=15.9, 2.2 Hz, 1H), 4.87-4.78 (m, 1H), 4.13 (q, J=7.1 Hz, 2H), 3.88-3.80 (m, 1H), 2.79-2.69 (m, 1H), 1.88-1.80 (m, 1H), 1.69-1.51 (m, 3H), 1.39 (s, 9H), 1.35-1.24 (m, 2H), 1.22 (t, J=7.1 Hz, 3H).

Step 3: tert-butyl (S)-2-(3-ethoxy-3-oxopropyl)piperidine-1-carboxylate: 5% Pd/C (Type 87L, 5% Pd, 60% water) (1.00 g, 470 μmol) was added to a solution of the product from Step 2 above (4.71 g, 15.8 mmol) in EtOH (30 mL). The suspension was hydrogenated at RT at 5 bar overnight. The reaction mixture was filtered through a glass microfibre frit, washed with EtOH (50 mL) and then concentrated in vacuo to afford (4.08 g, 14 mmol, 86% yield, 95% purity) as a pale grey oil. $^1$H NMR (500 MHz, DMSO-$d_6$) δ 4.15-4.08 (m, 1H), 4.04 (q, J=7.1 Hz, 2H), 3.81 (d, J=13.5 Hz, 1H), 2.70 (t, J=13.2 Hz, 1H), 2.25-2.13 (m, 2H), 2.00-1.88 (m, 1H), 1.66-1.57 (m, 1H), 1.58-1.44 (m, 5H), 1.37 (s, 9H), 1.27-1.20 (m, 1H), 1.17 (t, J=7.1 Hz, 3H).

Step 4: tert-butyl (S)-2-(3-hydroxypropyl)piperidine-1-carboxylate: $LiAlH_4$ (6.00 mL, 2.4 M in THF, 14.4 mmol) was added to a solution of the product from Step 3 above (4.08 g, 13.6 mmol) in dry THF (50 mL) at 0° C. The reaction mixture was stirred at 0° C. for 30 min. The reaction was quenched with sodium sulfate decahydrate (~5 g) and stirred for 1 h. The reaction mixture was allowed to warm to RT then $MgSO_4$ (~5 g) was added. The mixture was filtered, washed with THF (50 mL) and concentrated in vacuo to afford the title compound (3.39 g, 13 mmol, 97% yield, 95% purity) as a colourless liquid. $^1$H NMR (500 MHz, DMSO-$d_6$) δ4.36 (t, J=5.2 Hz, 1H), 4.19-3.99 (m, 1H), 3.81 (d, J=13.5 Hz, 1H), 3.39 (q, J=6.2 Hz, 2H), 2.77-2.62 (m, 1H), 1.72-1.60 (m, 1H), 1.58-1.43 (m, 5H), 1.38 (s, 9H), 1.37-1.18 (m, 4H).

Step 5: (S)-3-(piperidin-2-yl)propan-1-o/hydrochloride: To a solution of the product from Step 4 above (3.39 g, 13.2 mmol) in dioxane (25 mL) was added 4 M HCl in dioxane (17.0 mL, 68.0 mmol) and the mixture was stirred at RT overnight. The reaction mixture was concentrated in vacuo to afford the title compound (2.55 g, 13 mmol, 100% yield, 95% purity) as a white solid. $^1$H NMR (500 MHz, DMSO-$d_6$) δ 8.90-8.81 (m, 1H), 8.74-8.62 (m, 1H), 4.57 (s, 1H), 3.40 (t, J=6.0 Hz, 2H), 3.22-3.14 (m, 1H), 3.03-2.90 (m, 1H), 2.88-2.74 (m, 1H), 1.90-1.79 (m, 1H), 1.79-1.24 (m, 9H)

Step 6: (S)-2-chloro-4-(2-(3-hydroxypropyl)piperidin-1-yl)-5-nitrobenzonitrile: A mixture of Example 14, Step 1 (1.00 g, 4.39 mmol, 88% purity), the product from Step 5 above (870 mg, 4.60 mmol, 95% purity) and $Et_3N$ (2.50 mL, 17.9 mmol) in DCM (25 mL) was stirred at RT overnight. The mixture was concentrated onto silica and purified by chromatography on silica gel (24 g cartridge, 0-100%

EtOAc/isohexane) to afford the title compound (940 mg, 2.5 mmol, 56% yield, 85% purity) as an orange oil. UPLC-MS (Method 1): m/z 324.3 $(M+H)^+$, at 1.42 min. $^1$H NMR (500 MHz, DMSO-$d_6$) δ 8.39 (s, 1H), 7.60 (s, 1H), 4.38 (t, J=5.1 Hz, 1H), 3.89-3.76 (m, 1H), 3.40-3.27 (m, 2H), 3.22 (td, J=12.9, 2.9 Hz, 1H), 2.87-2.77 (m, 1H), 1.81-1.70 (m, 2H), 1.68-1.58 (m, 3H), 1.58-1.51 (m, 2H), 1.50-1.40 (m, 1H), 1.38-1.29 (m, 1H), 1.28-1.21 (m, 1H).

Step 7: (S)-2-chloro-5-nitro-4-(2-(3-((2-(trimethylsilyl) ethoxy)methoxy)propyl)piperidin-1-yl)benzonitrile: To a solution of the product from Step 6 above (940 mg, 2.47 mmol) and DIPEA (1.30 mL, 7.46 mmol) in DCM (10 mL) was added SEM-CI (660 μL, 3.73 mmol) drop-wise. The mixture was stirred at RT for 90 min. The reaction was quenched with saturated $NaHCO_3$(aq) (20 mL) and extracted with DCM (2×20 mL). The combined organic extracts were washed with brine (20 mL), dried ($MgSO_4$) concentrated onto silica. The crude product was purified by chromatography on silica gel (24 g cartridge, 0-50% EtOAc/isohexane) to afford the title compound (970 mg, 2.0 mmol, 80% yield, 92% purity) as an orange oil. UPLC-MS (Method 1): m/z 455.4 $(M+H)^+$, at 2.15 min.

Step 8: (S)-5-amino-2-chloro-4-(2-(3-((2-(trimethylsilyl) ethoxy)methoxy) propyl)piperidin-1-yl)benzonitrile: A mixture of the product from Step 7 above (970 mg, 1.97 mmol), ammonium chloride (630 mg, 11.8 mmol) and zinc (770 mg, 11.8 mmol) in THE (7.5 mL) and water (2.5 mL) was stirred at RT for 3 h. Additional ammonium chloride (630 mg, 11.8 mmol) and zinc (770 mg, 11.8 mmol) were added and stirring was continued overnight. The mixture was filtered through Celite®, the filter cake was washed with EtOAc and the filtrate was washed with brine (2×20 mL), dried ($MgSO_4$) and the solvent was removed in vacuo to afford the title compound (650 mg, 1.5 mmol, 74% yield, 95% purity) as a dark red oil. UPLC-MS (Method 1): m/z 424.8 $(M+H)^+$, at 2.18 min. $^1$H NMR (500 MHz, DMSO-$d_6$) δ 7.10 (s, 1H), 7.04 (s, 1H), 5.31 (s, 2H), 4.48-4.45 (m, 2H), 3.50-3.43 (m, 2H), 3.30-3.25 (m, 2H), 3.16-3.08 (m, 1H), 3.00-2.93 (m, 1H), 2.49-2.44 (m, 1H), 1.87-1.79 (m, 1H), 1.72-1.52 (m, 3H), 1.47-1.22 (m, 6H), 0.85-0.78 (m, 2H), −0.02 (s, 9H).

Step 9: methyl (S)-4-(allyloxy)-3-(N-(4-chloro-5-cyano-2-(2-(3-((2-(trimethylsilyl)ethoxy)methoxy)propyl)piperidin-1-yl)phenyl)sulfamoyl)benzoate: A mixture of the product from Step 8 above (633 mg, 1.42 mmol), Example 15, Step 3 (618 mg, 2.13 mmol) and pyridine (350 μL, 4.35 mmol) in DOE (8 mL) was heated to 50° C. and stirred for 2 days. The mixture was concentrated onto silica and purified by chromatography on silica gel (40 g cartridge, 0-75% EtOAc/isohexane) to afford the title compound (800 mg, 1.16 mmol, 82% yield, 98% purity) as a clear brown gum. UPLC-MS (Method 1): m/z 700.4 $(M+Na)^+$, 676.4 $(M-H)^-$, at 2.21 min. $^1$H NMR (500 MHz, DMSO-$d_6$) δ 8.99 (s, 1H), 8.35 (d, J=2.2 Hz, 1H), 8.19 (dd, J=8.8, 2.2 Hz, 1H), 7.58 (s, 1H), 7.46 (s, 1H), 7.39 (d, J=8.8 Hz, 1H), 6.01-5.90 (m, 1H), 5.46 (dd, J=17.3, 1.7 Hz, 1H), 5.30 (dd, J=10.7, 1.7 Hz, 1H), 4.86-4.74 (m, 2H), 4.44 (s, 2H), 3.86 (s, 3H), 3.39 (t, J=8.0 Hz, 2H), 3.26-3.18 (m, 3H), 2.80-2.74 (m, 1H), 2.69-2.63 (m, 1H), 1.78-1.72 (m, 1H), 1.69-1.62 (m, 1H), 1.54-1.46 (m, 2H), 1.41-1.30 (m, 2H), 1.29-1.16 (m, 2H), 1.15-1.05 (m, 2H), 0.81-0.74 (m, 2H), −0.05 (s, 9H).

Step 10: methyl (S)-3-(N-(4-chloro-5-cyano-2-(2-(3-((2-(trimethylsilyl) ethoxy)methoxy) propyl) piperidin-1-yl) phenyl) sulfamoyl)-4-hydroxybenzoate: To a solution the product from Step 9 above (800 mg, 1.16 mmol, 98%) in MeOH (10 mL) was added $Pd(PPh_3)_4$ (14.0 mg, 12.1 μmol) and the mixture was stirred for 5 min. $K_2CO_3$ (479 mg, 3.47 mmol) was added and the mixture was stirred at RT overnight. The mixture was concentrated in vacuo and the residue was treated with 1 M HCl(aq) (15 mL) and extracted with DCM (3×30 mL). The combined organic extracts were dried ($Na_2SO_4$), concentrated onto silica in vacuo, and purified by chromatography on silica gel (24 g cartridge, 0-100% EtOAc/isohexane,) to afford the title compound (388 mg, 590 μmol, 51% yield, 97% purity) as a clear brown gum. UPLC-MS (Method 1): m/z 638.5 $(M+H)^+$, 636.3 $(M-H)^-$, at 2.04 min.

Step 11: methyl (S)-3-(N-(4-chloro-5-cyano-2-(2-(3-hydroxypropyl)piperidin-1-yl)phenyl)sulfamoyl)-4-hydroxybenzoate: A solution of the product from Step 10 above (388 mg, 590 μmol) and TFA (1.80 mL, 23.4 mmol) in DCM (1.80 mL) was stirred at RT for 2 h. The mixture was concentrated, and the residue was dissolved in DCM (5 mL) and 7 M $NH_3$ in MeOH (5 mL) and stirred for 20 min. The mixture was concentrated onto silica in vacuo and purified by chromatography on silica gel (24 g cartridge, 0-10% MeOH/DCM) to afford the title compound (249 mg, 471 μmol, 80% yield, 96% purity) as a white foam. UPLC-MS (Method 1): m/z 508.3 $(M+H)^+$, 506.1 $(M-H)^-$, at 1.47 min.

Step 12: methyl (S)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylate 18,18-dioxide: To a solution of the product from Step 11 above (249 mg, 471 μmol) and triphenylphosphine (370 mg, 1.41 mmol) in DCM (10 mL) was added DIAD (270 μL, 1.39 mmol) and the mixture was stirred at RT for 1 h. The mixture was concentrated onto silica and purified by chromatography on silica gel (24 g cartridge, 0-100% EtOAc/isohexane) to afford the title compound (52.3 mg, 106 μmol, 23% yield, 99% purity) as a clear colourless glass. UPLC-MS (Method 1): m/z 490.3 $(M+H)^+$, 488.2 $(M-H)^-$, at 1.80 min.

Step 13: (S)-3-chloro-2-cyano-6,7,8,9,9a,10,11,12-octahydro-19H-dibenzo[b,f]pyrido[1,2-h][1]oxa[4]thia[5,8]diazacyclododecine-16-carboxylic acid 18,18-dioxide: A mixture of the product from Step 12 above (52.3 mg, 106 μmol) and LiOH (18.0 mg, 429 μmol) in THE/MeOH/water (4:1:1, 525 μL) was stirred at 40° C. overnight. The mixture was diluted with water (5 mL), acidified to ~pH 4 with 1 M HCl(aq) and extracted with EtOAc (3×10 mL). The combined organic extracts were washed with brine (10 mL), dried ($Na_2SO_4$) and the solvent was removed in vacuo. The residue was loaded onto silica and purified by chromatography on silica gel (4 g cartridge, 0-100% EtOAc/isohexane) to afford the title compound (22.3 mg, 45.9 μmol, 44% yield, 98% purity) as a white solid after trituration with TBME. UPLC-MS (Method 1): m/z 476.3 $(M+H)^+$, 474.2 $(M-H)^-$, at 1.64 min. $^1$H NMR (500 MHz, DMSO-$d_6$) δ 13.23 (s, 1H), 9.06 (s, 1H), 8.51 (d, J=2.2 Hz, 1H), 8.15 (dd, J=8.7, 2.2 Hz, 1H), 7.64 (s, 1H), 7.45 (s, 1H), 7.22 (d, J=8.7 Hz, 1H), 4.17-4.05 (m, 2H), 3.56-3.48 (m, 1H), 2.93-2.87 (m, 1H), 2.60-2.53 (m, 1H), 1.90-1.75 (m, 2H), 1.74-1.54 (m, 5H), 1.53-1.46 (m, 1H), 1.45-1.36 (m, 1H), 1.33-1.25 (m, 1H).

Example 61: (S,E)-3-chloro-2-cyano-7,8,9,9a,10,13-hexahydro-6H, 20H-dibenzo[b,f]pyrido[1,2-h][1]oxa[4]thia[5,8]diazacyclotridecine-17-carboxylic acid 19,19-dioxide

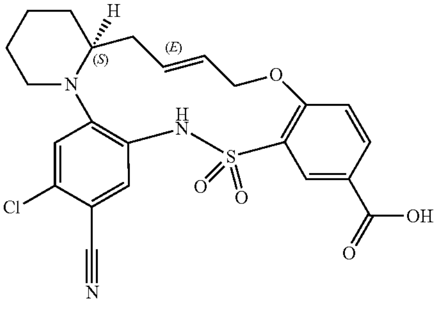

Step 1: (S)-4-(2-ally/piperidin-1-yl)-2-chloro-5-nitrobenzonitrile: A mixture of the product from Example 14, Step 1 (1.20 g, 5.98 mmol), (S)-2-allylpiperidine hydrochloride (1.00 g, 6.19 mmol) and $Et_3N$ (3.30 mL, 23.7 mmol) in DCM (20 mL) was stirred at RT for 4 days. The mixture was sequentially washed with 1 M HCl(aq) (2×10 mL) and brine (10 mL), dried ($MgSO_4$) and concentrated in vacuo to afford the title compound (1.97 g, 5.99 mmol, 100% yield, 93% purity) as an orange oil. UPLC-MS (Method 1): m/z 306.3 $(M+H)^+$ at 1.82 min).

Step 2: (S)-4-(2-allylpiperidin-1-yl)-5-amino-2-chlorobenzonitrile: A mixture of the product from Step 1 above (1.97 g, 5.99 mmol), ammonium chloride (1.92 g, 36.0 mmol) and zinc (2.35 g, 36.0 mmol) in THE (15 mL) and water (5.0 mL) was stirred at RT overnight. Additional ammonium chloride (321 mg, 5.99 mmol) and zinc (392 mg, 5.99 mmol) were added and stirring was continued for 24 h. Additional ammonium chloride (321 mg, 5.99 mmol) and zinc (392 mg, 5.99 mmol) were added and stirring was continued for 24 h. The mixture was diluted with EtOAc (20 mL) and filtered through Celite®. The solid inorganic material was slurried in EtOAc (2×20 mL) and filtered through Celite®. The filtrate was dried over $MgSO_4$, filtered and concentrated in vacuo. The residue was purified by chromatography on silica gel (24 g cartridge, 0-20% EtOAc/isohexane) to afford the title compound (1.60 g, 5.80 mmol, 97% yield) as a red oil. UPLC-MS (Method 1): m/z 276.2 $(M+H)^+$, at 1.85 min).

Step 3: methyl (S)-4-(allyloxy)-3-(N-(2-(2-allylpiperidin-1-yl)-4-chloro-5-cyanophenyl)sulfamoyl)benzoate: A mixture of the product from Step 2 above (1.60 g, 5.80 mmol), the product from Example 15, Step 3 (1.90 g, 6.54 mmol) and pyridine (1.40 mL, 17.4 mmol) in DCM (24 mL) was heated to 35° C. and stirred for 2 days. The mixture was concentrated onto silica and purified by chromatography on silica gel (40 g cartridge, 0-100% EtOAc/isohexane) to afford the title compound (2.38 g, 4.4 mmol, 76% yield, 98% purity) as a pale brown solid. UPLC-MS (Method 1): m/z 530.0 $(M+H)^+$, 528.2 $(M-H)^-$ at 1.99 min. $^1H$ NMR (500 MHz, DMSO-$d_6$) δ 9.00 (s, 1H), 8.35 (d, J=2.2 Hz, 1H), 8.19 (dd, J=8.7, 2.2 Hz, 1H), 7.59 (s, 1H), 7.49 (s, 1H), 7.40 (d, J=8.8 Hz, 1H), 6.01-5.84 (m, 1H), 5.56-5.40 (m, 2H), 5.33-5.26 (m, 1H), 4.89-4.74 (m, 4H), 3.86 (s, 3H), 3.43-3.34 (m, 1H), 2.83-2.74 (m, 1H), 2.71-2.60 (m, 1H), 1.87 (t, J=6.8 Hz, 2H), 1.73-1.60 (m, 2H), 1.54-1.45 (m, 2H), 1.41-1.29 (m, 2H).

Step 4: methyl (S,E)-3-chloro-2-cyano-7,8,9,9a,10,13-hexahydro-6H, 20H-dibenzo[b,f]pyrido[1,2-h][1]oxa[4]thia[5,8]diazacyclotridecine-17-carboxylate 19,19-dioxide: A solution of the product from Step 3 above (2.17 g, 4.01 mmol) and Grubbs-Hoveyda 2nd Gen (52.0 mg, 82.7 μmol) in DCM (200 mL) was stirred at RT overnight. The mixture was loaded onto silica and purified by chromatography on silica gel (80 g cartridge, 0-100% EtOAc/isohexane) to afford the title compound (1.67 g, 3.26 mmol, 81% yield, 98% purity) as a light grey solid after trituration from DCM with hexane. UPLC-MS (Method 1): m/z 502.0 $(M+H)^+$, 500.1 $(M-H)^-$, at 1.80 min. $^1H$ NMR (500 MHz, DMSO-$d_6$) δ 8.55 (d, J=2.2 Hz, 1H), 8.22 (dd, J=8.8, 2.2 Hz, 1H), 8.19 (s, 1H), 7.68 (s, 1H), 7.64 (d, J=8.8 Hz, 1H), 7.19 (s, 1H), 6.01-5.91 (m, 1H), 5.14-5.08 (m, 1H), 5.06-4.98 (m, 1H), 4.74-4.66 (m, 1H), 3.91 (s, 3H), 3.42-3.37 (m, 1H), 2.88-2.82 (m, 1H), 2.44-2.37 (m, 1H), 2.13-1.98 (m, 2H), 1.85-1.74 (m, 3H), 1.66-1.54 (m, 2H), 1.47-1.38 (m, 1H).

Step 5: (S,E)-3-chloro-2-cyano-7,8,9,9a,10,13-hexahydro-6H,20H-dibenzo[b,f]pyrido[1,2-h][1]oxa[4]thia[5,8]diazacyclotridecine-17-carboxylic acid 19,19-dioxide: A mixture of the product from Step 4 above (100 mg, 195 μmol) and LiOH (33.0 mg, 786 μmol) in THE/MeOH/water (4:1:1, 1.05 mL) was stirred at 40° C. overnight. The mixture was diluted with water (10 mL), acidified to ~pH 4 with 1 M HCl(aq) and extracted with EtOAc (3×15 mL). The combined organic extracts were washed with brine (10 mL), dried ($Na_2SO_4$) and the solvent was removed in vacuo. The residue was loaded onto silica and purified by chromatography on silica gel (4 g cartridge, 0-100% EtOAc/isohexane) to afford the title compound (69.3 mg, 136 μmol, 70% yield, 96% purity) as a white solid after trituration from TBME with hexane. UPLC-MS (Method 1): m/z 488.3 $(M+H)^+$, 486.1 $(M-H)^-$, at 1.66 min. $^1H$ NMR (500 MHz, DMSO-$d_6$) δ 13.33 (s, 1H), 8.54 (d, J=2.2 Hz, 1H), 8.22-8.16 (m, 2H), 7.68 (s, 1H), 7.61 (d, J=8.8 Hz, 1H), 7.18 (s, 1H), 6.01-5.91 (m, 1H), 5.15-5.08 (m, 1H), 5.04-4.96 (m, 1H), 4.72-4.64 (m, 1H), 3.43-3.36 (m, 1H), 2.88-2.82 (m, 1H), 2.43-2.38 (m, 1H), 2.13-2.04 (m, 1H), 2.04-1.97 (m, 1H), 1.86-1.74 (m, 3H), 1.66-1.56 (m, 2H), 1.46-1.37 (m, 1H).

Example 62: (S,E)-3-chloro-2-cyano-N-(methylsulfonyl)-7,8,9,9a,10,13-hexahydro-6H, 20H-dibenzo[b,f]pyrido[1,2-h][1]oxa[4]thia[5,8]diazacyclotridecine-17-carboxamide 19,19-dioxide

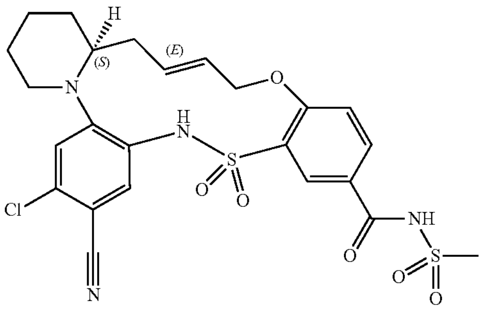

Step 1: (S,E)-3-chloro-2-cyano-N-(methylsulfonyl)-7,8,9,9a,10,13-hexahydro-6H, 20H-dibenzo[b,f]pyrido[1,2-h][1]oxa[4]thia[5,8]diazacyclotridecine-17-carboxamide 19,19-dioxide: The product from Example 46 (16.2 mg, 32.9 μmol) was treated with a solution of methanesulfonamide (4.00 mg, 42.1 μmol) in DCM (0.5 mL), followed by a solution of DMAP (10.0 mg, 81.9 μmol) in DCM (0.5 mL). The resultant solution was added to a vial containing EDC (14.0 mg, 73.0 μmol). The resultant solution was allowed to stand at RT for 24 h. The mixture was diluted with DCM (1 mL), quenched with 0.1 M HCl(aq) (1 mL) and passed through a phase separator, rinsing with DCM (1 mL). The organic phase was dried over $MgSO_4$, filtered, and then purified by chromatography on silica gel (4 g cartridge, 0-10% MeOH/DCM) to afford the title compound (14.0 mg, 23.5 μmol, 75% yield, 95% purity) as a white solid. UPLC-MS (Method 1): m/z 565.3 $(M+H)^+$, 563.2 $(M-H)^-$, at 1.66 min. $^1H$ NMR (500 MHz, Methanol-d4) δ 8.72 (t, J=2.0 Hz, 1H), 8.25-8.21 (m, 1H), 7.56-7.53 (m, 1H), 7.53-7.49 (m, 1H), 7.40-7.36 (m, 1H), 6.07-5.91 (m, 1H), 5.19-5.04 (m, 2H), 4.71 (t, J=10.7 Hz, 1H), 3.45-3.40 (m, 3H), 3.40-3.35 (m, 1H), 3.07-2.98 (m, 1H), 2.53-2.41 (m, 1H), 2.32-2.19 (m, 1H), 2.18-2.06 (m, 1H), 2.00-1.91 (m, 1H), 1.91-1.82 (m, 1H), 1.81-1.63 (m, 2H), 1.56 (d, J=12.4 Hz, 1H), 1.41-1.23 (m, 1H). Two exchangeable protons not observed.

Example 63: (S)-2-cyano-3-fluoro-N-(methylsulfonyl)-7,8,9,9a,10,11,12,13-octahydro-6H, 20H-dibenzo[b,f]pyrido[1,2-h][1]oxa[4]thia[5,8]diazacyclotridecine-17-carboxamide 19,19-dioxide

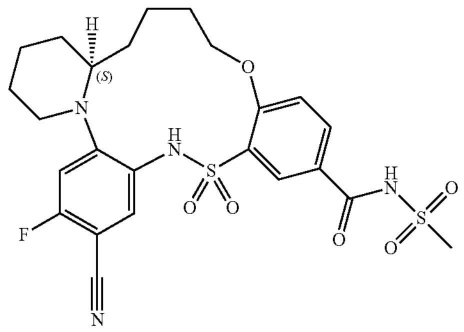

Step 1: (S)-2-cyano-3-fluoro-N-(methylsulfonyl)-7,8,9,9a,10,11,12,13-octahydro-6H,20H-dibenzo[b,f]pyrido[1,2-h][1]oxa[4]thia[5,8]diazacyclotridecine-17-carboxamide 19,19-dioxide: The product from Example 56 (16 mg, 32.4 μmol) was treated with a solution of methanesulfonamide (4.00 mg, 42.1 μmol) in DCM (0.5 mL), followed by a solution of DMAP (10.0 mg, 81.9 μmol) in DCM (0.5 mL). The resultant solution was added to a vial containing EDC (14.0 mg, 73.0 μmol). The resultant solution was allowed to stand at RT for 24 h. The mixture was diluted with DCM (1 mL), quenched with 0.1 M HCl(aq) (1 mL) and passed through a phase separator, rinsing with DCM (1 mL). The organic phase was dried over $MgSO_4$, filtered and then purified by chromatography on silica gel (4 g cartridge, 0-10% MeOH/DCM) to afford the title compound (14.0 mg, 24.2 μmol, 75% yield, 95% purity) as a white solid. UPLC-MS (Method 1): m/z 551.4 $(M+H)^+$, 548.9 $(M-H)^-$ at 1.66 min. $^1H$ NMR (500 MHz, Methanol-d4) δ 8.72 (d, J=2.3 Hz, 1H), 8.21 (dd, J=8.8, 2.4 Hz, 1H), 7.39 (d, J=10.4 Hz, 1H), 7.36 (d, J=6.4 Hz, 1H), 7.31 (d, J=8.9 Hz, 1H), 4.37-4.30 (m, 1H), 4.25-4.18 (m, 1H), 3.41 (s, 3H), 3.14-3.03 (m, 1H), 2.77-2.65 (m, 1H), 2.04-1.95 (m, 1H), 1.95-1.88 (m, 1H), 1.85-1.77 (m, 2H), 1.73-1.33 (m, 8H), 1.34-1.22 (m, 1H). Two exchangeable protons not observed.

Example 64: (S)-3-chloro-2-cyano-N-(methylsulfonyl)-6,7,8,9,9a,10,11,12-octahydro-19H-dibenzo[b,f]pyrido[1,2-h][1]oxa[4]thia[5,8]diazacyclododecine-16-carboxamide 18,18-dioxide

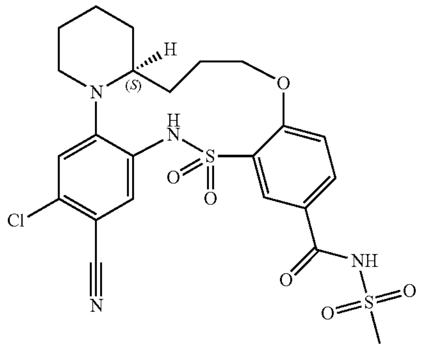

Step 1: (S)-3-chloro-2-cyano-N-(methylsulfonyl)-6,7,8,9,9a,10,11,12-octahydro-19H-dibenzo[b,f]pyrido[1,2-h][1]oxa[4]thia[5,8]diazacyclododecine-16-carboxamide 18,18-dioxide: The product from Example 60, Step 13 (17 mg, 35 μmol) was treated with a solution of methanesulfonamide (4.00 mg, 42.1 μmol) in DCM (0.5 mL), followed by a solution of DMAP (10.0 mg, 81.9 μmol) in DCM (0.5 mL). The resultant solution was added to a vial containing EDC (14.0 mg, 73.0 μmol). The resultant solution was allowed to stand at RT for 24 h. The mixture was diluted with DCM (1 mL), quenched with 0.1 M HCl(aq) (1 mL) and passed through a phase separator, rinsing with DCM (1 mL). The organic phase was dried over $MgSO_4$, filtered and then purified by chromatography on silica gel (4 g cartridge, 0-10% MeOH/DCM) to afford the title compound (15.0 mg, 25.8 μmol, 74% yield, 95% purity) as a white solid. UPLC-MS (Method 1): m/z 552.8 $(M+H)^+$, 550.8 $(M-H)^-$ at 1.62 min. $^1H$ NMR (500 MHz, Methanol-d4) δ 8.67 (d, J=2.3 Hz, 1H), 8.17 (dd, J=8.8, 2.3 Hz, 1H), 7.66 (s, 1H), 7.54 (s, 1H), 7.16 (d, J=8.8 Hz, 1H), 4.24-4.16 (m, 1H), 4.00 (t, J=9.5 Hz, 1H), 3.46-3.38 (m, 4H), 3.05-2.95 (m, 1H), 2.52 (td, J=11.5, 3.0 Hz, 1H), 2.15-2.02 (m, 1H), 2.00-1.87 (m, 2H), 1.86-1.67 (m, 5H), 1.60-1.48 (m, 1H), 1.38-1.23 (m, 1H). Two exchangeable protons not observed.

Example 65: 3-chloro-2-cyano-6,7,8,9,9a,10,12,13-octahydro-20H-dibenzo[e,i]pyrido[1,2-k][1,4]dioxa[7]thia[8,11]diazacyclotridecine-17-carboxylic acid 19,19-dioxide
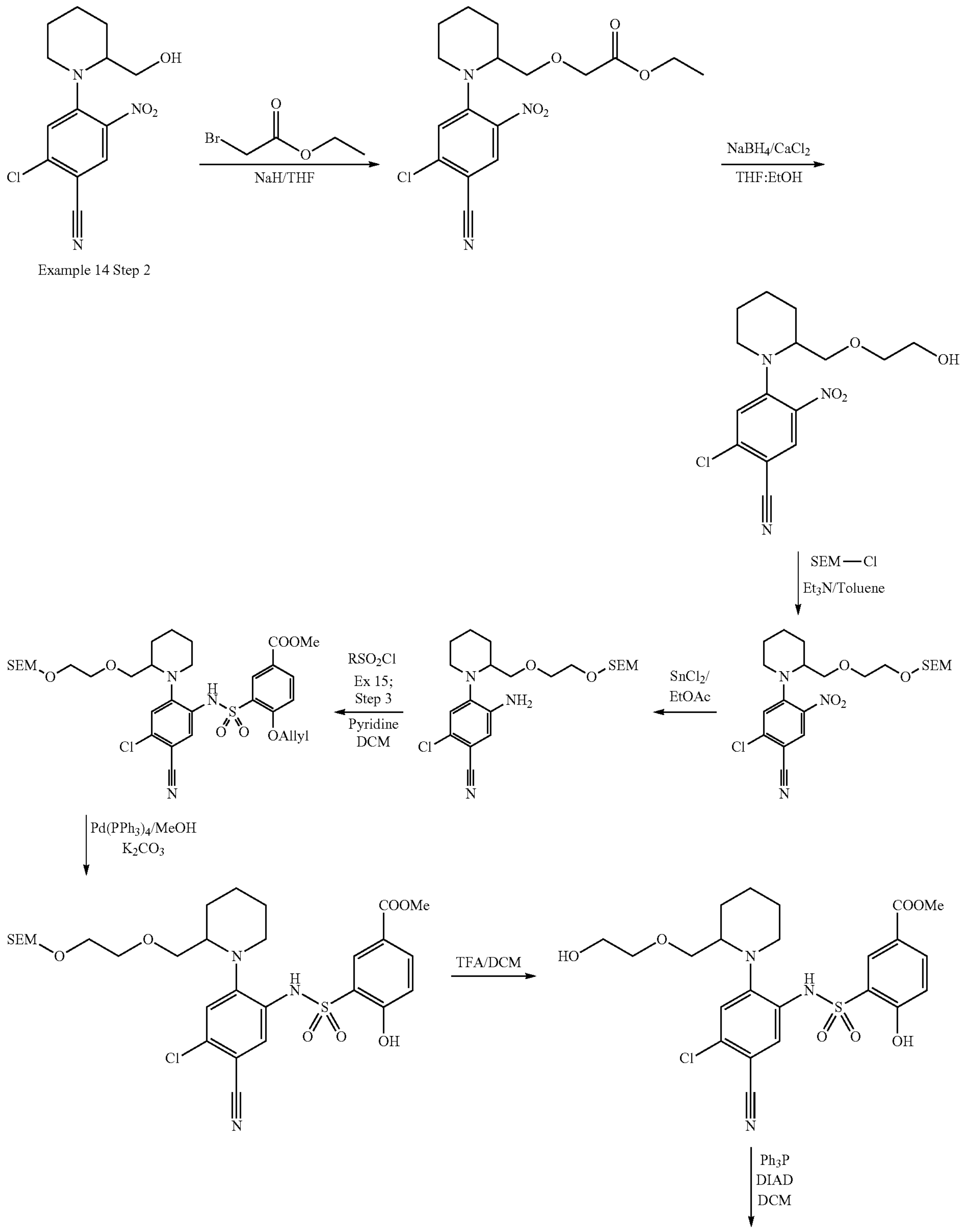

-continued

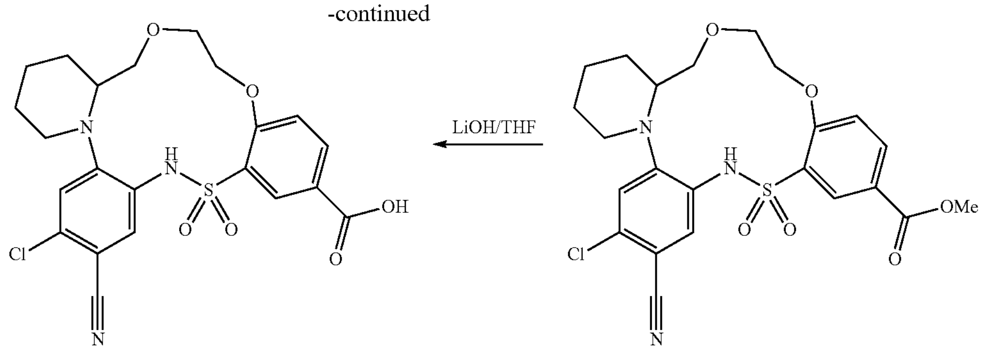

Step-1: Ethyl 2-((1-(5-chloro-4-cyano-2-nitrophenyl)piperidin-2-yl)meth oxy)acetate: Eight reactions were carried out according to the following procedure and combined for work-up and purification. To a stirred solution of the product from Example 14, Step 2 (1.0 g, 3.38 mmol) in THE (10 mL) was added NaH (0.488 g, 20.3 mmol) at rt. The resultant reaction mixture was stirred at RT for 10 min, then ethyl 2-bromoacetate (0.82 g, 5.08 mmol) was added at rt. The resultant reaction mixture was stirred at RT for 30 min. The reaction mixture was diluted with water (100 mL) and extracted with EtOAc (2×200 mL). The combined organic extractions were washed with brine (50 mL), dried over $Na_2SO_4$ and concentrated in vacuo. The resultant crude material was purified by column chromatography (6% EtOAc/hexane) to afford the title compound as light-yellow solid (7.6 g, 73% yield). TLC: Rr 0.4 (50% EtOAc/hexane). $^1H$ NMR (400 MHz, DMSO) δ 8.39 (s, 1H), 7.57 (s, 1H), 4.06 (dd, J=14.4, 7.2 Hz, 2H), 3.99 (s, 2H), 3.85-3.70 (m, 2H), 3.58 (dd, J=9.1, 4.7 Hz, 1H), 3.27 (m, 1H), 2.99 (d, J=12.6 Hz, 1H), 1.62 (s, 3H), 1.53-1.32 (m, 3H), 1.17 (t, J=4.0 Hz, 3H).

Step-2: 2-chloro-4-(2-((2-hydroxyethoxy)methyl)piperidin-1-yl)-5-nitro benzonitrile: Twelve reactions were carried out according to the following procedure and combined for work-up and purification. To a solution of the compound from Step 1 above (0.5 g, 1.30 mmol) in THF/EtOH (1:1, 100 mL) was added $CaCl_2$ (0.23 g, 1.96 mmol) and $NaBH_4$ (0.14 g, 3.92 mmol) at rt. The reaction mixture was stirred at RT for 1 h. The reaction mixture was diluted with water (100 mL) and extracted with EtOAc (2×100 mL). The combined organic extractions were washed with brine (50 mL), dried over anhydrous $Na_2SO_4$ and concentrated in vacuo. The resultant crude material was purified by column chromatography (30% EtOAc/hexane) to afford the title compound as light-yellow semi solid (3.6 g, 67%). TLC: Rr 0.3 (60% EtOAc/hexane). $^1H$ NMR (400 MHz, DMSO) δ 8.39 (s, 1H), 7.57 (s, 1H), 5.23 (s, 1H), 4.50 (br s, 1H), 3.85-3.70 (m, 2H), 3.41 (dd, J=9.7, 5.1 Hz, 1H), 3.26-3.04 (m, 6H), 2.98 (d, J=13.3 Hz, 1H), 1.68 (s, 2H), 1.53 (m, 2H).

Step-3: 2-chloro-4-(2-(2,2-dimethyl-5,7,10-trioxa-2-silaundecan-11-yl) piperidin-1-yl)-5-nitrobenzonitrile: Four reactions were carried out according to the following procedure and combined for work-up and purification. To a stirred solution of the product from Step 2 above (1.0 g, 2.94 mmol) and SEM-Cl (0.74 g, 4.42 mmol) in toluene (10 mL) was added $Et_3N$ (0.89 g, 8.84 mmol) at rt. The resultant reaction mixture was stirred at 80° C. for 2 h. The reaction mixture was diluted with water (100 mL) and extracted with EtOAc (2×100 mL). The combined organic phase was washed with brine (50 mL), dried over anhydrous $Na_2SO_4$ and concentrated in vacuo. The resultant crude material was purified by column chromatography (10% EtOAc/hexane) to afford the title compound as light brown semi-solid (3.5 g, 63%). TLC: $R_f$ 0.4 (20% EtOAc/hexane). $^1H$ NMR (400 MHz, DMSO) δ 8.37 (s, 1H), 7.55 (s, 1H), 4.44 (s, 2H), 3.74 (m, 2H), 3.48-3.30 (m, 5H), 3.20 (m, 1H), 3.04 (m, 1H), 1.66 (m, 4H), 1.52 (m, 4H), 0.83 (t, J=8.4 Hz, 2H), 0.07--0.01 (m, 9H).

Step-4: 5-amino-2-chloro-4-(2-(2,2-dimethyl-5,7,10-trioxa-2-silaundecan-11-yl)piperidin-1-yl)benzonitrile: To a solution of the product from Step 3 above (2.0 g, 4.26 mmol) in EtOAc (50 mL) was added $SnCl_2$ (3.84 g, 17.1 mmol) at 0° C. The resultant reaction mixture was stirred at RT for 1 h. The reaction mixture was poured into water (10 mL) and filtered through Celite®. The filtrate was extracted with EtOAc (3×50 mL). The combined organic extractions were dried over anhydrous $Na_2SO_4$ and concentrated in vacuo. The resultant crude material was purified by column chromatography (5% EtOAc/isohexane) to afford the title compound (1.2 g, 64%) as a light yellow liquid. TLC: $R_f$ 0.3 (20% EtOAc/hexane). $^1H$ NMR (400 MHz, DMSO) δ 7.15 (s, 1H), 7.01 (s, 1H), 5.30 (s, 2H), 4.51 (s, 2H), 3.49 (t, J=8.0 Hz, 2H), 3.41 (m, 2H), 3.30 (m, 2H), 3.03 (m, 1H), 2.65 (m, 1H), 1.84 (m, 1H), 1.61 (m, 4H), 1.50 (m, 2H), 0.82 (t, J=4.8 Hz, 2H), 0.013 (s, 9H). Two exchangeable protons not observed.

Step 5: methyl 4-(allyloxy)-3-(N-(4-chloro-5-cyano-2-(2-(2,2-dimethyl-5,7,10-trioxa-2-silaundecan-11-yl)piperidin-1-yl)phenyl)sulfamoyl)benzoate: A mixture of the product from Step 4 above (550 mg, 1.25 mmol), the product from Example 15, Step 3 (410 mg, 1.41 mmol) and pyridine (300 μL, 3.71 mmol) in DCM (6.0 mL) was stirred at 35° C. for 4 days. The mixture was allowed to cool to RT and diluted with DCM (75 mL) and sequentially washed with saturated $NaHCO_3$(aq) (50 mL) and brine (50 mL), dried over $MgSO_4$, filtered and concentrated onto silica. The crude product was purified by chromatography on silica gel (24 g cartridge, 0-50% EtOAc/isohexane) to afford the title compound (960 mg, 1.1 mmol, 90% yield, 81% purity) as an orange oil. UPLC-MS (Method 2): m/z 696.5 $(M+H)^+$, 694.4 $(M-H)^-$, at 1.92 min. $^1H$ NMR (500 MHz, DMSO-$d_6$) δ 9.10 (s, 1H), 8.33 (d, J=2.3 Hz, 1H), 8.17 (dd, J=8.8, 2.2 Hz, 1H), 7.56 (s, 1H), 7.49 (s, 1H), 7.43-7.35 (m, 1H), 5.97-5.84 (m, 1H), 5.45-5.38 (m, 1H), 5.30-5.23 (m, 1H), 4.83-4.72 (m, 2H), 4.49 (s, 2H), 3.85 (s, 3H), 3.53-3.44 (m, 2H), 3.44-3.23 (m, 6H), 3.14-3.05 (m, 1H), 2.85-2.70 (m, 2H), 1.71-1.49 (m, 3H), 1.42 (d, J=8.4 Hz, 3H), 0.88-0.80 (m, 2H), −0.02 (s, 9H).

Step 6: methyl 3-(N-(4-chloro-5-cyano-2-(2-(2,2-dimethyl-5,7,10-trioxa-2-silaundecan-11-yl)piperidin-1-yl)phenyl)sulfamoyl)-4-hydroxybenzoate: To a solution of the product from Step 5 above (960 mg, 1.12 mmol) in MeOH (10 mL) was added $Pd(PPh_3)_4$ (30 mg, 26 μmol) and the mixture was stirred for 5 min. $K_2CO_3$ (470 mg, 3.40 mmol) was added and the mixture was stirred at RT overnight. The reaction mixture was heated to 50° C. and stirred for 2 h. The solution was allowed to cool to rt, the solvent was evaporated and the residue was treated with 1 M HCl(aq) (15 mL) and extracted with DCM (3×30 mL). The combined organic extracts were dried ($MgSO_4$), concentrated onto silica in vacuo, and purified by chromatography on silica gel (12 g cartridge, 0-100% EtOAc/isohexane) to afford the title compound (480 mg, 0.62 mmol, 56% yield, 85% purity) as a dark yellow oil. UPLC-MS (Method 2): m/z 652.3 $(M-H)^-$, at 1.31 min. $^1H$ NMR (500 MHz, DMSO-$d_6$) δ 12.16 (br s, 1H), 9.08 (br s, 1H), 8.24 (d, J=2.2 Hz, 1H), 8.03 (dd, J=8.6, 2.3 Hz, 1H), 7.62 (s, 1H), 7.57 (s, 1H), 7.10 (d, J=8.7 Hz, 1H), 4.48 (s, 2H), 3.82 (s, 3H), 3.50-3.45 (m, 2H), 3.39-3.33 (m, 3H), 3.30-3.18 (m, 3H), 3.06 (dd, J=10.0, 5.2 Hz, 1H), 2.82-2.66 (m, 2H), 1.80-1.71 (m, 1H), 1.70-1.62 (m, 1H), 1.62-1.38 (m, 4H), 0.86-0.80 (m, 2H), −0.02 (s, 9H).

Step 7: methyl 3-(N-(4-chloro-5-cyano-2-(2-((2-hydroxyethoxy) methyl) piperidin-1-yl)phenyl)sulfamoyl)-4-hydroxybenzoate: A solution of the product of Step 6 above (480 mg, 624 μmol) and TFA (2.00 mL, 26.0 mmol) in DCM (2 mL) was stirred at RT for 2 h. The mixture was concentrated, and the residue was dissolved in DCM (5 mL) and 7 M $NH_3$ in MeOH (5 mL) and stirred for 20 min. The mixture was concentrated onto silica in vacuo and purified by chromatography on silica gel (24 g cartridge, 0-10% MeOH/DCM) to afford the title compound (310 mg, 0.53 mmol, 85% yield, 90% purity) as a white foam. UPLC-MS (Method 2): m/z 524.6 $(M+H)^+$, 522.2 $(M-H)^-$, at 0.91 min. $^1H$ NMR (500 MHz, DMSO-$d_6$) b 8.24 (d, J=2.2 Hz, 1H), 8.03 (dd, J=8.6, 2.3 Hz, 1H), 7.61 (s, 1H), 7.57 (s, 1H), 7.10 (d, J=8.6 Hz, 1H), 3.82 (s, 3H), 3.36-3.30 (m, 5H), 3.29-3.24 (m, 1H), 3.22-3.11 (m, 2H), 3.09-3.03 (m, 1H), 2.83-2.75 (m, 1H), 2.75-2.68 (m, 1H), 1.79-1.70 (m, 1H), 1.70-1.63 (m, 1H), 1.62-1.39 (m, 4H). 1 exchangeable proton not observed.

Step 8: methyl 3-chloro-2-cyano-6,7,8,9,9a,10,12,13-octahydro-20H-dibenzo[e,i]pyrido[1,2-k][1, 4]dioxa[7]thia[8,11]diazacyclotridecine-17-carboxylate 19,19-dioxide: To a solution of the product from Step 7 above (200 mg, 344 μmol) and triphenylphosphine (270 mg, 1.03 mmol) in DCM (7.5 mL) was added DIAD (200 μL, 1.03 mmol) and the mixture was stirred at RT for 1 h. DCM (20 mL) was added and the reaction mixture was washed with water (2×30 mL) and brine (30 mL) the organic phase was dried ($MgSO_4$) and concentrated onto silica. The crude product was purified by chromatography on silica gel (12 g cartridge, 0-100% EtOAc/isohexane) to afford the title compound (140 mg, 0.23 mmol, 67% yield, 84% purity) as a white solid. UPLC-MS (Method 2): m/z 506.3 $(M+H)^+$, 504.3 $(M-H)^-$, at 1.24 min.

Step 9: 3-chloro-2-cyano-6,7,8,9,9a,10,12,13-octahydro-20H-dibenzo[e,i]pyrido[1,2-k][1, 4]dioxa[7]thia[8,11]diazacyclotridecine-17-carboxylic acid 19,19-dioxide: A mixture of the product of Step 8 above (140 mg, 232 μmol) and 1 M LiOH(aq) (1 mL, 1 mmol) in THF (2 mL) was stirred at RT for 3 days. The mixture was concentrated to remove the THF, diluted with EtOAc (10 mL) and washed with water (10 mL). The aqueous phase was acidified to ~pH 4 with 1 M HCl(aq) and extracted with EtOAc (3×10 mL). The combined organic extracts were, dried ($MgSO_4$) and the solvent was removed in vacuo. The residue was purified by chromatography (12 g reverse phase cartridge, 5-40% MeCN/10 mM ammonium bicarbonate) to afford the title compound (46 mg, 91 μmol, 39% yield, 98% purity) as a white solid. UPLC-MS (Method 2): m/z 492.2 $(M+H)^+$, 490.2 $(M-H)^-$, at 0.78 min. $^1H$ NMR (500 MHz, DMSO-$d_6$) δ 13.31 (br s, 1H), 8.65 (br s, 1H), 8.53 (d, J=2.2 Hz, 1H), 8.18 (dd, J=8.8, 2.2 Hz, 1H), 7.83 (s, 1H), 7.47 (d, J=8.8 Hz, 1H), 7.24 (s, 1H), 4.72-4.60 (m, 1H), 4.50-4.35 (m, 1H), 3.64-3.52 (m, 1H), 3.26-3.12 (m, 3H), 3.04-2.93 (m, 1H), 2.87-2.74 (m, 1H), 2.75-2.59 (m, 1H), 1.94-1.76 (m, 2H), 1.76-1.62 (m, 2H), 1.62-1.35 (m, 2H).

Example 66: 3-chloro-2-cyano-7,8,9,9a,10,11,12,13-octahydro-6H, 20H-dibenzo[b,f]pyrido[1,2-h][1]oxa[4]thia[5,8,11]triazacyclotridecine-17-carboxylic acid 19,19-dioxide

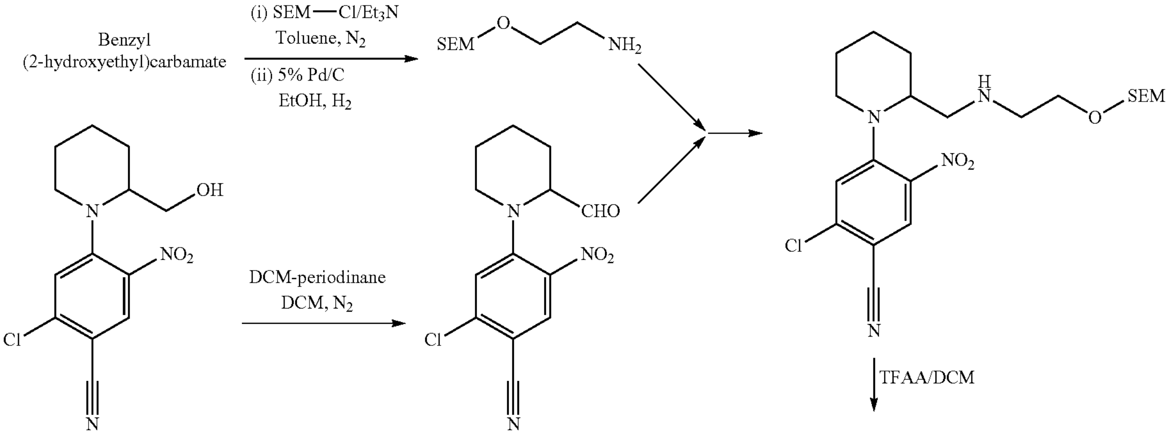

Example 14 Step 2

-continued

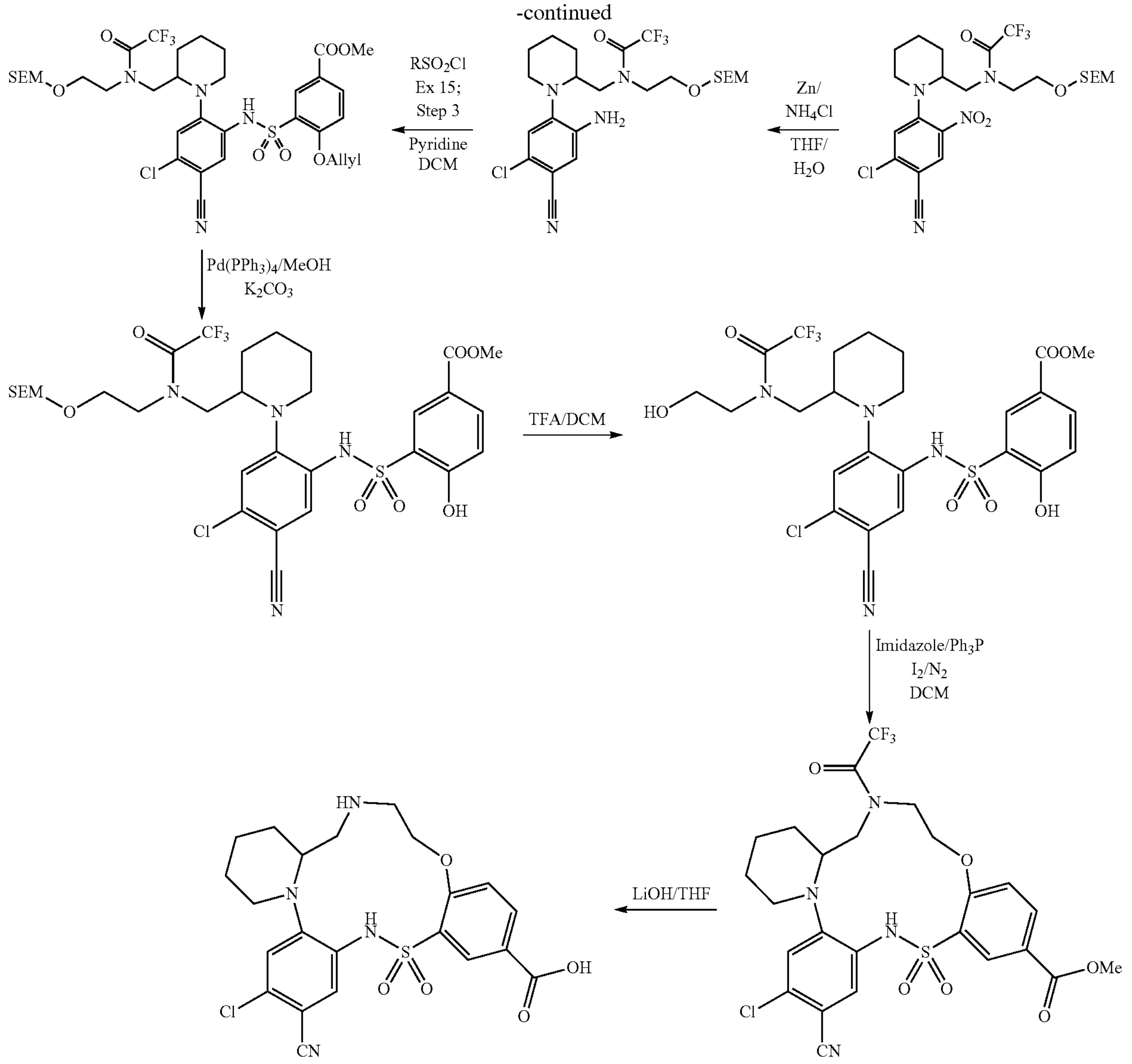

Step 1: benzyl (2-((2-(trimethylsilyl)ethoxy)methoxy)ethyl)carbamate: To a solution of benzyl (2-hydroxyethyl) carbamate (10 g, 51 mmol) in toluene (100 mL), at 0° C. under $N_2$, was added $Et_3N$ (29 mL, 0.21 mol) and SEM-Cl (11 mL, 61 mmol). The resultant reaction mixture was stirred at 0° C. for 15 min then was heated to 85° C. and stirred for 2 h. The reaction mixture was diluted with water (100 mL) and extracted with EtOAc (3×100 mL). The organic phases were combined, dried over $MgSO_4$, filtered, and concentrated onto silica. The crude product was purified by chromatography on silica gel (120 g cartridge, 0-50% EtOAc/isohexane) to afford the title compound (4.14 g, 12 mmol, 23% yield, 94% purity) as a clear colourless liquid. UPLC-MS (Method 2): m/z no ionisation $(M+H)^+$ at 1.75 min. $^1H$ NMR (500 MHz, DMSO-$d_6$) δ 7.60-7.22 (m, 6H), 5.01 (s, 2H), 4.58 (s, 2H), 3.57-3.50 (m, 2H), 3.47 (t, J=6.0 Hz, 2H), 3.17 (q, J=5.9 Hz, 2H), 0.92-0.76 (m, 2H), −0.00 (s, 9H).

Step 2: 2-((2-(trimethylsilyl)ethoxy)methoxy)ethan-1-amine: To a solution of the compound from Step 1 above (4.14 g, 12.0 mmol) in EtOH (80 mL) was added 5% Pd/C (Type 87L, 5% Pd, 60% water) (640 mg, 301 μmol). The reaction mixture was purged three times with $N_2$ followed by $H_2$. The reaction mixture was stirred at RT under $H_2$ (3 bar) for 2 h. The reaction mixture was filtered through a glass microfibre filter, washing with MeOH (200 mL) and concentrated in vacuo to afford the title compound (2.36 g, 11 mmol, 93% yield, 90% purity) as a pale green solid. $^1H$ NMR (500 MHz, DMSO-$d_6$) δ 4.66-4.56 (m, 2H), 3.63 (t, J=6.1 Hz, 1H), 3.60-3.50 (m, 2H), 3.48-3.40 (m, 1H), 3.30 (t, J=6.2 Hz, 1H), 2.94-2.68 (m, 1H), 1.89 (s, 1H), 1.77 (s, 1H), 0.93-0.83 (m, 2H), 0.00 (s, 9H).

Step 3: 2-chloro-4-(2-formylpiperidin-1-yl)-5-nitrobenzonitrile: The product from Example 14, Step 2 (6.66 g, 15.8 mmol) was dissolved in DCM (60 mL), under a $N_2$ atmosphere at 0° C., and treated with a solution of Dess-Martin periodinane (8.00 g, 18.9 mmol) in DCM (60 mL). The resultant solution was allowed to warm to RT and stirred for 30 min at rt. The reaction mixture was diluted with DCM (50 mL) and washed with sat. $NaHCO_3$(aq) (2×100 mL) followed by brine (100 mL). The organic phase was dried over $MgSO_4$ then concentrated onto silica. The crude product was purified by chromatography on silica gel (80 g cartridge, 0-100% EtOAc/isohexane) to afford the title compound (4.73 g, 15 mmol, 97% yield, 95% purity) as a bright orange solid. $^1$H NMR (500 MHz, DMSO-$d_6$) δ 9.57 (s, 1H), 8.49 (s, 1H), 7.58 (s, 1H), 4.46-4.38 (m, 1H), 3.25-3.13 (m, 2H), 2.30-2.15 (m, 1H), 1.87-1.74 (m, 1H), 1.74-1.65 (m, 1H), 1.65-1.48 (m, 2H), 1.34-1.13 (m, 1H).

Step 4: 2-chloro-4-(2-(10,10-dimethyl-5,7-dioxa-2-aza-10-silaundecyl)piperidin-1-yl)-5-nitrobenzonitrile: A solution of the product from Step 3 above (2.15 g, 6.95 mmol) and the product from Step 2 above (1.48 g, 6.95 mmol) in DCM (50 mL) was stirred at RT for 5 min before the addition of sodium triacetoxyborohydride (3.00 g, 14.2 mmol). The resultant mixture was stirred at RT overnight. The mixture was diluted with water (25 mL) and extracted with DCM (2×25 mL). The combined organic extracts were washed with brine (50 mL), dried ($MgSO_4$), concentrated onto silica and purified by chromatography on silica gel (80 g cartridge, 0-100% EtOAc/isohexane followed by 0-10% MeOH/DCM) to afford the title compound (500 mg, 0.65 mmol, 9% yield, 61% purity) as a brown oil. UPLC-MS (Method 1): m/z 469.4 $(M+H)^+$, 467.4 $(M-H)^-$, at 1.30 min.

Step 5: N-((1-(5-chloro-4-cyano-2-nitrophenyl)piperidin-2-yl)methyl)-2,2,2-trifluoro-N-(2-((2-(trimethylsilyl)ethoxy)methoxy)ethyl)acetamide: The product from Step 4 (978 mg, 1.31 mmol) and $Et_3N$ (920 μL, 6.60 mmol) were combined in dry DCM (10 mL) at 0° C., treated with trifluoroacetic anhydride (470 μL, 3.33 mmol), and stirred at RT for 2 h. The reaction mixture was concentrated in vacuo, dissolved in DCM (50 mL) and concentrated onto silica. The crude product was purified by chromatography on silica gel (40 g cartridge, 0-30% EtOAc/isohexane) to afford crude product. The crude product was repurified by chromatography on silica gel (40 g cartridge, 0-100% DCM/isohexane followed by 0-30% EtOAc/isohexane) to afford the title compound (320 mg, 0.44 mmol, 34% yield, 78% purity) as an orange oil. UPLC-MS (Method 2): m/z 564.9 $(M-H)^-$, at 2.16 min. $^1$H NMR (500 MHz, DMSO-$d_6$) δ 8.45 (s, 1H), 7.71 (s, 1H), 4.80-4.70 (m, 1H), 4.48 (s, 2H), 3.76-3.66 (m, 2H), 3.65-3.51 (m, 3H), 3.43-3.37 (m, 2H), 3.38-3.32 (m, 1H), 3.30-3.24 (m, 1H), 3.23-3.13 (m, 1H), 1.81-1.65 (m, 2H), 1.65-1.53 (m, 3H), 1.44-1.30 (m, 1H), 0.82-0.74 (m, 2H), −0.03 (s, 9H).

Step 6: N-((1-(2-amino-5-chloro-4-cyanophenyl)piperidin-2-yl)methyl)-2,2,2-trifluoro-N-(2-((2-(trimethylsilyl)ethoxy)methoxy)ethyl)acetamide: A mixture of the product from Step 5 above (320 mg, 442 μmol), ammonium chloride (140 mg, 2.62 mmol) and zinc (170 mg, 2.60 mmol) in THE (1.8 mL) and water (0.60 mL) was stirred at RT overnight. Additional zinc (170 mg, 2.60 mmol) and ammonium chloride (140 mg, 2.62 mmol) was added and the reaction was stirred at RT overnight. The mixture was filtered through Celite®, the filter cake was washed with EtOAc (100 mL) and concentrated onto silica. The crude product was purified by chromatography on silica gel (12 g cartridge, 0-50% EtOAc/isohexane) to afford the title compound (220 mg, 0.29 mmol, 66% yield, 71% purity) as a red oil. UPLC-MS (Method 2): m/z 535.2 $(M+H)^+$, 533.0 $(M-H)^-$, at 2.06 min.

Step 7: methyl 4-(allyloxy)-3-(N-(4-chloro-5-cyano-2-(2-(10,10-dimethyl-2-(2,2,2-trifluoroacetyl)-5,7-dioxa-2-aza-10-silaundecyl)piperidin-1-yl)phenyl)sulfamoyl)benzoate: A mixture of the product from Step 6 above (220 mg, 292 μmol), the product from Example 15, Step 3 (130 mg, 447 μmol) in pyridine (100 μL, 1.24 mmol) was stirred at 35° C. overnight. Additional pyridine (2 mL) was added, the reaction was heated to 60° C. and stirred for 6 h. The reaction mixture was then cooled to 35° C. before the addition of further product from Example 15, Step 3 (65 mg, 0.22 mmol) and stirred at this temperature overnight. The mixture was allowed to cool to RT and diluted with DCM (20 mL) and sequentially washed with saturated $NaHCO_3$(aq) (20 mL) and brine (20 mL), dried over $MgSO_4$, filtered and concentrated in vacuo, azeotroping with toluene (20 mL). The residue dissolved in DCM and concentrated onto silica. The crude product was purified by chromatography on silica gel (12 g cartridge, 0-30% EtOAc/isohexane) to afford the title compound (127 mg, 0.10 mmol, 34% yield, 62% purity) as a brown oil. The product was analysed by LCMS (Method 7): m/z no ionisation at 2.75 min.

Step 8: methyl 3-(N-(4-chloro-5-cyano-2-(2-(10,10-dimethyl-2-(2,2,2-trifluoroacetyl)-5,7-dioxa-2-aza-10-silaundecyl)piperidin-1-yl)phenyl)sulfamoyl)-4-hydroxybenzoate: To a solution of the product from Step 7 above (127 mg, 99.8 μmol) in MeOH (1.0 mL) was added $Pd(PPh_3)_4$ (10 mg, 8.7 μmol) and the mixture was stirred for 5 min. $K_2CO_3$ (42 mg, 0.30 mmol) was added and the mixture was stirred at RT overnight. The solvent was evaporated and the residue was treated with 1 M HCl(aq) (5 mL) and extracted with DCM (2×5 mL). The combined organic extracts were dried ($MgSO_4$), concentrated onto silica, and purified by chromatography on silica gel (40 g cartridge, 0-100% EtOAc/isohexane) to afford the title compound (84 mg, 62 μmol, 62% yield, 55% purity) as a brown oil. The product was analysed by LCMS (Method 7): m/z no ionisation at 2.54 min Step 9: methyl 3-(N-(4-chloro-5-cyano-2-(2-((2,2,2-trifluoro-N-(2-hydroxyethyl)acetamido)methyl)piperidin-1-yl)phenyl)sulfamoyl)-4-hydroxybenzoate: A solution of the product from Step 8 above (84 mg, 62 μmol) and TFA (200 μL, 2.60 mmol) in DCM (400 μL) was stirred at RT for 2 h. The mixture slowly quenched with saturated $NaHCO_3$(aq) (20 mL). The phases were separated, and the aqueous phase extracted with DCM (2×15 mL). The organic phases were combined, dried over $MgSO_4$, filtered and concentrated on to silica. The crude product was purified by chromatography on silica gel (4 g cartridge, 0-10% MeOH/DCM) to afford the title compound (55 mg, 40 μmol, 65% yield, 45% purity) as a dark yellow solid. The product was analysed by LCMS (Method 7): m/z 619.0 $(M+H)^+$, 617.2 $(M-H)^-$, at 1.97 min.

Step 10: methyl 3-chloro-2-cyano-11-(2,2,2-trifluoroacetyl)-7,8,9,9a,10,11,12,13-octahydro-6H, 20H-dibenzo[b,f]pyrido[1,2-h][1]oxa[4]thia[5,8,11]triazacyclotridecine-17-carboxylate 19,19-dioxide: To a solution of the product from Step 9 above (55 mg, 40 μmol) in DCM (400 μL), under an atmosphere of $N_2$, was added imidazole (20 mg, 0.29 mmol) and triphenylphosphine (70 mg, 0.27 mmol). After 5 min, iodine (70 mg, 0.28 mmol) in DCM (300 μL) was added dropwise to the reaction mixture which was stirred at RT for 1 h. The reaction mixture was diluted with DCM (5 mL) and washed with sat. $NaHCO_3$ (5 mL) followed by brine (5 mL). The organic phase was dried ($MgSO_4$) and concentrated onto silica. The crude product was partially purified by chromatography on silica gel (4 g cartridge, 0-100% EtOAc/isohexane) and then purified by reversed phase preparative HPLC (Waters X-Select CSH 018 ODB prep column, 130 Å, 5 μm, 30×100 mm, 35-65% (0.1% formic acid in water)/MeCN) to afford the title compound (17 mg, 28 μmol, 71% yield) as a clear colourless glass. UPLC-MS (Method 2): m/z 599.1 $(M-H)^-$ at 1.05 min.

Step 11: 3-chloro-2-cyano-7,8,9,9a,10, 11, 12, 13-octahydro-6H, 20H-dibenzo[b,f]pyrido[1,2-h][1]oxa[4]thia[5,8,11]triazacyclotridecine-17-carboxylic acid 19,19-dioxide: A mixture the product from Step 10 above (17 mg, 28 μmol) and 1 M LiOH(aq) (120 μL, 120 μmol) in THF (240 μL) was stirred at RT overnight. Additional 1 M LiOH(aq) (120 μL, 120 μmol) was added and the reaction was stirred at RT for 2 days. MeOH (240 μL) was added, and the reaction mixture was heated to 40° C. and stirred for 2 days. The reaction mixture was concentrated under reduced pressure for the removal of THF and MeOH then acidified to pH 4-6 using 1 M HCl(aq). Water (5 mL) was added, and the product was extracted with EtOAc (3×5 mL) The organic phases were combined, dried ($MgSO_4$), and concentrated in vacuo to afford the title compound (5 mg, 9 μmol, 30% yield, 90% purity) as a white solid. The product was analysed by LCMS (Method 7): m/z 491.0 $(M+H)^+$, 489.0 $(M-H)^-$, at 1.23 min. $^1H$ NMR (500 MHz, DMSO-$d_6$) δ 13.02 (br s, 1H), 11.87 (br s, 1H), 8.49 (br s, 1H), 8.32 (d, J=2.3 Hz, 1H), 8.09-7.97 (m, 1H), 7.66 (s, 1H), 7.12 (s, 1H), 7.00 (s, 1H), 3.76-3.54 (m, 3H), 3.42-3.38 (m, 1H), 3.19 (t, J=5.1 Hz, 2H), 2.92-2.80 (m, 1H), 1.80-1.66 (m, 2H), 1.67-1.58 (m, 1H), 1.45-1.26 (m, 4H), 1.23 (s, 1H).

Example 67: (R)-3-chloro-2-cyano-6,7,8,9,9a,10,12,13-octahydro-20H-dibenzo[e,i]pyrido[1,2-k][1,4]dioxa[7]thia[8,11]diazacyclotridecine-17-carboxylic acid 19,19-dioxide Enantiomer 1

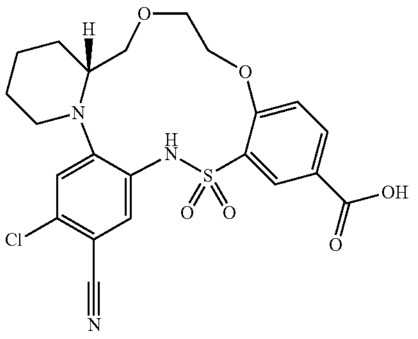 [SMILES: N#Cc1cc2c(cc1Cl)N1CCCC[C@@H]1COCCOc1ccc(C(=O)O)cc1S(=O)(=O)N2]

Example 65 (39 mg, 78 μmol, 98% purity) dissolved at 8 mg/mL in 4:1 MeOH/DCM. The resultant mixture was filtered and then separated by chiral SFC (UV detection by DAD at 210 nm, 40° C., 125 bar on a Lux iC5 21.2×250 mm, 5 μm column, flow rate 50 mL/min, eluting with 25% (0.2% $NH_3$/MeOH)/$CO_2$). The clean fractions were pooled, rinsed with MeOH and DCM, and concentrated in vacuo. Purification by chromatography on silica gel (4 g cartridge, 0-10% MeOH/DCM) afforded the title compound (4.0 mg, 7.3 μmol, 9% yield, 90% purity) as a white solid. SFC (UV detection by DAD at 210-400 nm, 40° C., 125 bar on a Lux iC5, 4.6×250 mm, 5 μm column, flow rate 4 mL/min, eluting with 25% (0.2% $NH_3$/MeOH)/$CO_2$) $t_R$ 7.03 min. Other analytical data consistent with Example 65.

Example 68: (S)-3-chloro-2-cyano-6,7,8,9,9a,10,12,13-octahydro-20H-dibenzo[e,i]pyrido[1,2-k][1,4]dioxa[7]thia[8,11]diazacyclotridecine-17-carboxylic acid 19,19-dioxide Enantiomer 2

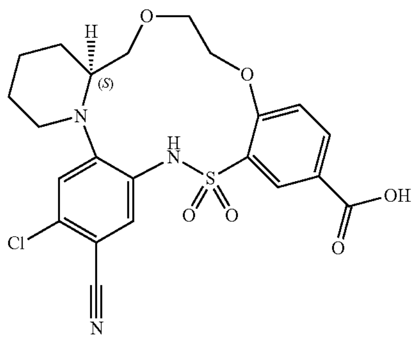

The title compound (7.0 mg, 14 μmol, 17% yield, 95% purity) was obtained as a white solid from the chiral separation performed in Example 67. SFC (UV detection by DAD at 210-400 nm, 40° C., 125 bar on a Lux iC5, 4.6×250 mm, 5 μm column, flow rate 4 mL/min, eluting with 25% (0.2% $NH_3$/MeOH)/$CO_2$) $t_R$ 8.46 min. Other analytical data consistent with Example 65.

Example 69: (S)-3-chloro-2-cyano-6,7,8,9,9a,10,12,13-octahydro-20H-dibenzo[e,i]pyrido[1,2-k][1,4]dioxa[7]thia[8,11]diazacyclotridecine-17-carboxylic acid 19,19-dioxide

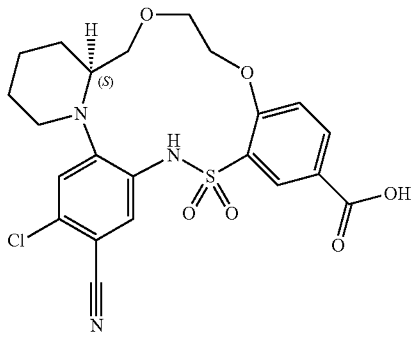

Step 1: (S)-2-chloro-4-(2-(hydroxymethyl) piperidin-1-yl)-5-nitrobenzonitrile: A mixture of the product from Example 14, Step 1 (2.00 g, 9.87 mmol), (S)-piperidin-2-ylmethanol (1.19 g, 10.4 mmol) and $Et_3N$ (1.80 mL, 12.9 mmol) in DCM (25 mL) was stirred at RT for 3 h. The mixture was concentrated onto silica and purified by chromatography on silica gel (40 g cartridge, 0-100% EtOAc/isohexane) to afford the title compound (2.49 g, 8.34 mmol, 84% yield, 99% purity) as an orange solid. UPLC-MS (Method 5): m/z 296.3 $(M+H)^+$, 294.2 $(M-H)^-$, at 1.44 min. $^1H$ NMR (500 MHz, DMSO-$d_6$) δ 8.37 (s, 1H), 7.53 (s, 1H), 4.69 (t, J=5.5 Hz, 1H), 3.72-3.63 (m, 1H), 3.62-3.56 (m, 1H), 3.51-3.43 (m, 1H), 3.27-3.19 (m, 1H), 3.07-3.01 (m, 1H), 1.72-1.64 (m, 3H), 1.58-1.46 (m, 3H).

Step 2: ethyl (S)-2-((1-(5-chloro-4-cyano-2-nitrophenyl)piperidin-2-yl) methoxy)acetate: To a solution of the product from Step 1 (2.39 g, 8.00 mmol) and rhodium(II)acetatedimer (70.0 mg, 158 μmol) in DCM (40 mL) at 0° C. was added ethyl 2-diazoacetate (1.00 mL, 8.27 mmol) dropwise. The mixture was warmed to RT and stirred for 2 h. Additional ethyl 2-diazoacetate (1.00 mL, 8.27 mmol) was added at 0° C. and stirring was continued at RT overnight. Additional ethyl 2-diazoacetate (1.00 mL, 8.27 mmol) was added at 0° C. and stirring was continued at RT for 4 h. Additional ethyl 2-diazoacetate (1.00 mL, 8.27 mmol) was added at 0° C. and stirring was continued at RT overnight. Additional ethyl 2-diazoacetate (1.00 mL, 8.27 mmol) was added at 0° C. and stirring was continued at RT for 4 h. Additional ethyl 2-diazoacetate (1.00 mL, 8.27 mmol) was added at 0° C. and stirring was continued at RT overnight. The mixture was concentrated onto silica in vacuo and purified by chromatography on silica gel (80 g cartridge, 0-50% EtOAc/isohexane) to afford the title compound (1.71 g, 4.03 mmol, 50% yield, 90% purity) as a yellow oil. UPLC-MS (Method 5): m/z 382.3 $(M+H)^+$, at 1.81 min. $^1$H NMR (500 MHz, DMSO-$d_6$) δ 8.39 (s, 1H), 7.58 (s, 1H), 4.07 (q, J=7.1 Hz, 2H), 4.00 (s, 2H), 3.85-3.74 (m, 2H), 3.58 (dd, J=9.4, 5.1 Hz, 1H), 3.29-3.24 (m, 1H), 3.04-2.98 (m, 1H), 1.75-1.65 (m, 3H), 1.60-1.49 (m, 3H), 1.17 (t, J=7.1 Hz, 3H).

Step 3: (S)-2-chloro-4-(2-((2-hydroxyethoxy)methyl)piperidin-1-yl)-5-nitrobenzonitrile: To a mixture of the product from Step 2 above (1.71 g, 4.03 mmol) and calcium chloride (671 mg, 6.05 mmol) in THE (50 mL) and EtOH (50 mL) was added $NaBH_4$ (457 mg, 12.1 mmol) portionwise. The mixture was stirred at RT for 4 h and then carefully quenched with water (100 mL). The mixture was extracted with EtOAc (3×100 mL) and the combined organic extracts were washed with brine (100 mL), dried ($MgSO_4$) and the solvent was removed in vacuo. The residue was loaded onto silica and purified by chromatography on silica gel (40 g cartridge, 0-100% EtOAc/isohexane) to afford the title compound (758 mg, 1.96 mmol, 49% yield, 88% purity) as an orange oil. UPLC-MS (Method 5): m/z 340.2 $(M+H)^+$, at 1.46 min.

Step 4: (S)-2-chloro-4-(2-(2,2-dimethyl-5,7,10-trioxa-2-silaundecan-11-yl)piperidin-1-yl)-5-nitrobenzonitrile: To a solution of the product from Step 3 above (758 mg, 1.96 mmol) and DIPEA (1.00 mL, 5.74 mmol) in DCM (8 mL) was added SEM-CI (520 μL, 2.94 mmol). The reaction was quenched with saturated $NaHCO_3$(aq) (50 mL) and extracted with DCM (2×50 mL). The combined organic extracts were washed with brine (100 mL), dried ($MgSO_4$) concentrated onto silica. The crude product was purified by chromatography on silica gel (24 g cartridge, 0-50% EtOAc/isohexane) to afford the title compound (804 mg, 1.5 mmol, 78% yield, 90% purity) as an orange oil. UPLC-MS (Method 5): m/z no ionisation $(M+H)^+$, at 2.22 min. $^1$H NMR (500 MHz, DMSO-$d_6$) δ 8.37 (s, 1H), 7.55 (s, 1H), 4.50-4.42 (m, 2H), 3.85-3.70 (m, 2H), 3.55-3.44 (m, 3H), 3.44-3.38 (m, 2H), 3.37-3.32 (m, 2H), 3.28-3.20 (m, 1H), 3.08-2.98 (m, 1H), 1.80-1.62 (m, 3H), 1.62-1.44 (m, 3H), 0.88-0.81 (m, 2H), −0.01 (s, 9H).

Step 5: (S)-5-amino-2-chloro-4-(2-(2,2-dimethyl-5,7,10-trioxa-2-silaundecan-11-yl)piperidin-1-yl)benzonitrile: A mixture of the product from Step 4 above (804 mg, 1.54 mmol), ammonium chloride (500 mg, 9.35 mmol) and zinc (600 mg, 9.18 mmol) in THE (6 mL) and water (2 mL) was stirred at RT overnight. Additional ammonium chloride (500 mg, 9.35 mmol) and zinc (600 mg, 9.18 mmol) were added and the reaction was stirred overnight. The mixture was diluted with water (10 mL), filtered through Celite®, the filter cake was washed with EtOAc and the filtrate was extracted with EtOAc (3×10 mL). The combined organic extracts were washed with brine (10 mL), dried ($MgSO_4$) and the solvent was removed in vacuo. The residue was dissolved in DCM (50 mL) and concentrated onto silica. The crude product was purified by chromatography on silica gel (24 g cartridge, 0-100% EtOAc/isohexane) to afford the title compound (624 mg, 1.4 mmol, 88% yield, 96% purity) as a red oil. UPLC-MS (Method 5): m/z no ionisation $(M+H)^+$ at 2.22 min. $^1$H NMR (500 MHz, DMSO) δ 7.16 (s, 1H), 7.03 (s, 1H), 5.29 (s, 2H), 4.52 (s, 2H), 3.54-3.45 (m, 2H), 3.44-3.40 (m, 2H), 3.38-3.32 (m, 4H), 3.31-3.25 (m, 1H), 3.07-3.00 (m, 1H), 2.68-2.60 (m, 1H), 1.89-1.82 (m, 1H), 1.68-1.56 (m, 3H), 1.54-1.43 (m, 2H), 0.88-0.77 (m, 2H), −0.01 (s, 9H).

Step 6: methyl (S)-4-(allyloxy)-3-(N-(4-chloro-5-cyano-2-(2-(2,2-dimethyl-5,7,10-trioxa-2-silaundecan-11-yl)piperidin-1-yl)phenyl)sulfamoyl)benzoate: A mixture of the product from Step 5 (624 mg, 1.36 mmol), the product from Example 15, Step 3 (500 mg, 1.72 mmol) and pyridine (330 μL, 4.08 mmol) in DCM (6.0 mL) was stirred at RT for 4 days. The mixture was allowed to cool to RT and diluted with DCM (75 mL) and sequentially washed with saturated $NaHCO_3$(aq) (50 mL) and brine (50 mL), dried over $MgSO_4$, filtered and concentrated onto silica. The crude product was purified by chromatography on silica gel (24 g cartridge, 0-50% EtOAc/isohexane) to afford the title compound (914 mg, 1.2 mmol, 87% yield, 90% purity) as a red oil. UPLC-MS (Method 7): m/z no ionisation $(M+H)^+$2.35 min. $^1$H NMR (500 MHz, DMSO-$d_6$) δ 9.10 (s, 1H), 8.33 (d, J=2.2 Hz, 1H), 8.17 (dd, J=8.7, 2.3 Hz, 1H), 7.56 (s, 1H), 7.49 (s, 1H), 7.38 (d, J=8.9 Hz, 1H), 5.97-5.86 (m, 1H), 5.45-5.36 (m, 1H), 5.30-5.23 (m, 1H), 4.83-4.72 (m, 2H), 4.49 (s, 2H), 3.85 (s, 3H), 3.51-3.45 (m, 2H), 3.43-3.33 (m, 4H), 3.30-3.23 (m, 2H), 3.08 (dd, J=9.3, 4.5 Hz, 1H), 2.84-2.69 (m, 2H), 1.74-1.48 (m, 3H), 1.47-1.34 (m, 3H), 0.88-0.78 (m, 2H), −0.02 (s, 9H).

Step 7: methyl (S)-3-(N-(4-chloro-5-cyano-2-(2-(2,2-dimethyl-5,7,10-trioxa-2-silaundecan-11-yl)piperidin-1-yl)phenyl)sulfamoyl)-4-hydroxybenzoate: To a solution of the product from Step 6 (914 mg, 1.18 mmol) in MeOH (10 mL) was added $Pd(PPh_3)_4$ (34.0 mg, 29.4 μmol) and the mixture was stirred for 5 min. $K_2CO_3$ (491 mg, 3.55 mmol) was added and the mixture was stirred at RT overnight. The reaction mixture was heated to 50° C. and stirred for 2 h. The solution was allowed to cool to RT, the solvent was evaporated and the residue was treated with 1 M HCl(aq) (15 mL) and extracted with DCM (3×30 mL). The combined organic extracts were dried ($MgSO_4$), concentrated onto silica in vacuo, and purified by chromatography on silica gel (24 g cartridge, 0-100% EtOAc/isohexane) to afford the title compound (586 mg, 878 μmol, 74% yield, 98% purity) as a yellow glass. UPLC-MS (Method 7): m/z no ionisation $(M+H)^+$, 652.3 $(M-H)^-$, at 2.18 min. $^1$H NMR (500 MHz, DMSO) δ 12.17 (s, 1H), 9.04 (s, 1H), 8.24 (d, J=2.2 Hz, 1H), 8.03 (dd, J=8.6, 2.3 Hz, 1H), 7.62 (s, 1H), 7.57 (s, 1H), 7.10 (d, J=8.7 Hz, 1H), 4.48 (s, 2H), 3.82 (s, 3H), 3.51-3.44 (m, 2H), 3.42-3.33 (m, 3H), 3.30-3.19 (m, 3H), 3.06 (dd, J=10.0, 5.2 Hz, 1H), 2.80-2.74 (m, 1H), 2.71 (d, J=6.5 Hz, 1H), 1.74 (d, J=10.9 Hz, 1H), 1.66 (s, 1H), 1.56 (d, J=11.4 Hz, 2H), 1.45 (dd, J=18.7, 10.3 Hz, 2H), 0.87-0.80 (m, 2H), −0.02 (s, 9H).

Step 8: methyl (S)-3-(N-(4-chloro-5-cyano-2-(2-((2-hydroxyethoxy) methyl) piperidin-1-yl)phenyl)sulfamoyl)-4-hydroxybenzoate: A solution of the product from Step 7 (586 mg, 878 μmol) and TFA (3.00 mL, 38.9 mmol) in DCM (3 mL) was stirred at RT for 2 h. The mixture was concentrated and the residue was dissolved in DCM (5 mL) and 7 M $NH_3$ in MeOH (5 mL) and stirred for 20 min. The mixture was concentrated onto silica in vacuo and purified by chromatography on silica gel (12 g cartridge, 0-5% MeOH/DCM) to afford the title compound (213 mg, 382 μmol, 44% yield, 94% purity) as a yellow oil. UPLC-MS (Method 5): m/z 524.3 $(M+H)^+$, 522.6 $(M-H)^-$, at 1.54 min. $^1H$ NMR (500 MHz, DMSO-$d_6$) δ 8.24 (d, J=2.2 Hz, 1H), 8.03 (dd, J=8.6, 2.3 Hz, 1H), 7.61 (s, 1H), 7.57 (s, 1H), 7.10 (d, J=8.6 Hz, 1H), 3.82 (s, 3H), 3.36-3.30 (m, 5H), 3.29-3.24 (m, 1H), 3.22-3.11 (m, 2H), 3.09-3.03 (m, 1H), 2.83-2.75 (m, 1H), 2.75-2.68 (m, 1H), 1.79-1.70 (m, 1H), 1.70-1.63 (m, 1H), 1.62-1.39 (m, 4H). 1 exchangeable proton not observed.

Step 9: methyl (S)-3-chloro-2-cyano-6,7,8,9,9a,10,12,13-octahydro-20H-dibenzo[e,i]pyrido[1,2-k][1,4]dioxa[7]thia[8,11]diazacyclotridecine-17-carboxylate 19,19-dioxide: To a solution of the product from Step 8 above (213 mg, 382 μmol) and triphenylphosphine (301 mg, 1.15 mmol) in DCM (8 mL) was added DIAD (230 μL, 1.18 mmol) and the mixture was stirred at RT overnight. DCM (20 mL) was added and the reaction mixture was washed with water (2×30 mL) and brine (30 mL) the organic phase was dried ($MgSO_4$) and concentrated onto silica. The crude product was purified by chromatography on silica gel (12 g cartridge, 0-100% EtOAc/isohexane) to afford the title compound (350 mg, 318 μmol, 83% yield, 46% purity) as a white solid. UPLC-MS (Method 5): m/z 506.1 $(M+H)^+$, 504.1 $(M-H)^-$, at 1.87 min.

Step 10: (S)-3-chloro-2-cyano-6,7,8,9,9a,10,12,13-octahydro-20H-dibenzo[e,i]pyrido[1,2 k][1, 4]dioxa[7]thia[8,11]diazacyclotridecine-17-carboxylic acid 19,19-dioxide: A mixture of the product from Step 9 above (350 mg, 318 μmol) and LiOH (40 mg, 953 μmol) in THF (2 mL), MeOH (0.5 mL) and water (0.5 mL) was stirred at RT overnight. The mixture was concentrated for the removal of THF, diluted with water (10 mL) and washed with EtOAc (10 mL). The aqueous phase was acidified to ~pH 4 with 1 M HCl(aq) and extracted with EtOAc (3×10 mL). The combined organic extracts were dried ($MgSO_4$) and the solvent was removed in vacuo. The residue was loaded onto silica and purified by chromatography on silica gel (4 g cartridge, 0-100% EtOAc/isohexane) to afford the title compound (42.3 mg, 84.3 μmol, 27% yield, 98% purity) as a white solid. UPLC-MS (Method 5): m/z 492.3 $(M+H)^+$, 490.0 $(M-H)^-$, at 1.71 min. $^1H$ NMR (500 MHz, DMSO) δ 13.31 (s, 1H), 8.66 (s, 1H), 8.53 (d, J=2.2 Hz, 1H), 8.19 (dd, J=8.7, 2.2 Hz, 1H), 7.83 (s, 1H), 7.47 (d, J=8.8 Hz, 1H), 7.25 (s, 1H), 4.66 (d, J=12.8 Hz, 1H), 4.45-4.37 (m, 1H), 3.58 (d, J=11.6 Hz, 1H), 3.25-3.14 (m, 3H), 3.02-2.96 (m, 1H), 2.84-2.78 (m, 1H), 2.69-2.61 (m, 1H), 1.92-1.84 (m, 1H), 1.83-1.77 (m, 1H), 1.73-1.63 (m, 2H), 1.56-1.42 (m, 2H).

Example 70: (S,E)-3-chloro-2-cyano-6,7,8,9,9a,10-hexahydro-12H, 20H-dibenzo[e,i]pyrido[2,1-c][1]oxa[8]thia[4,7]diazacyclotridecine-17-carboxylic acid 19,19-dioxide

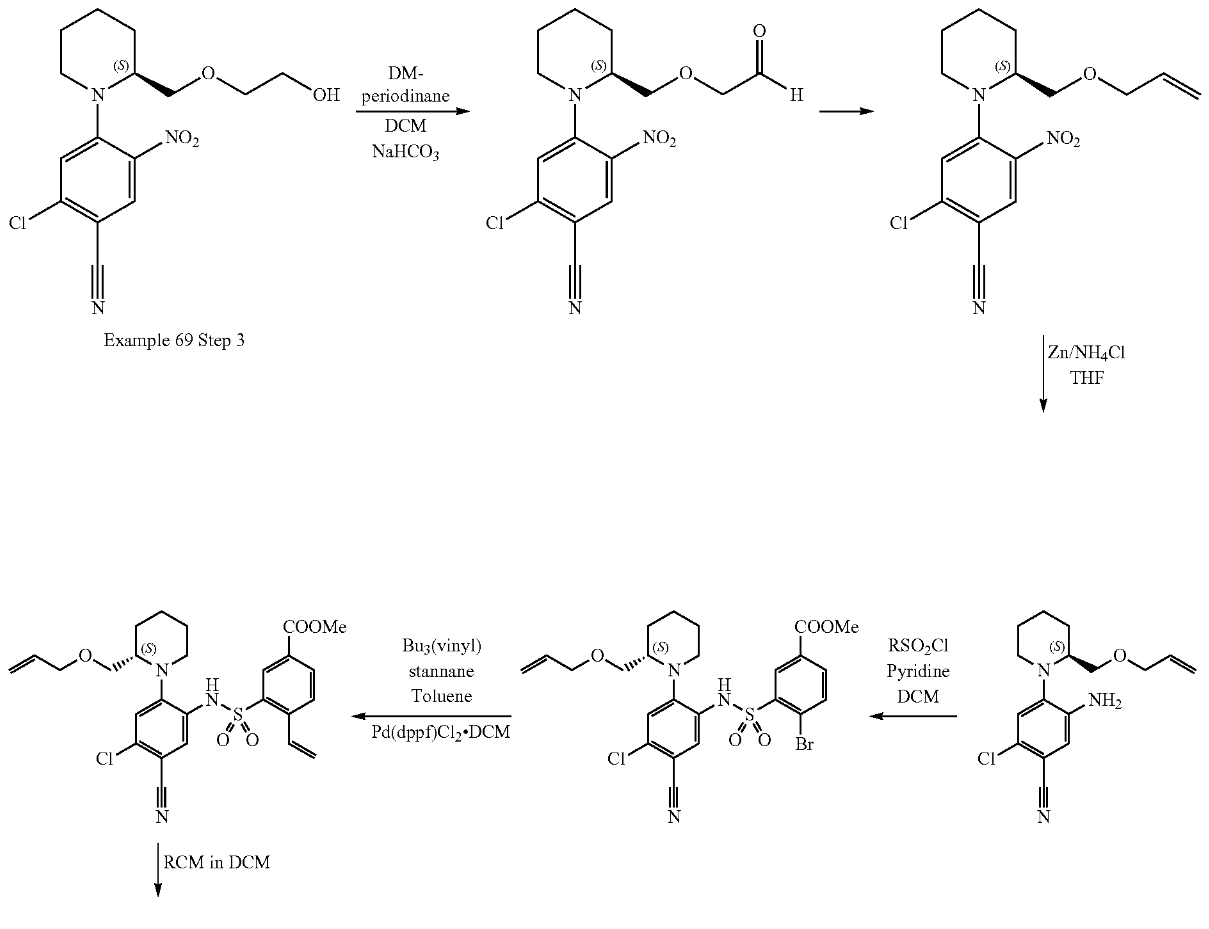

-continued

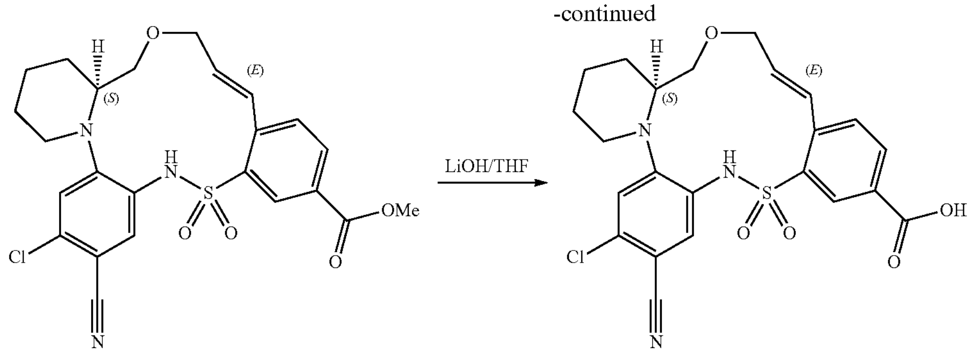

Step 1: (S)-2-chloro-5-nitro-4-(2-((2-oxoethoxy)methyl)piperidin-1-yl)benzonitrile: To a solution of the product from Example 69, Step 3 (3.92 g, 9.58 mmol) in DCM (50 mL) was added DMP (200 mg, 472 μmol). After 5 min sodium bicarbonate (2.41 g, 28.7 mmol) was added followed by DMP (6.80 g, 16.0 mmol) in 2 portions. The mixture was stirred at RT overnight. The mixture was diluted with water (50 mL) and the layers were separated. The organic extract was dried ($MgSO_4$), and the solvent was removed in vacuo. The residue was loaded onto silica and purified by chromatography on silica gel (80 g cartridge, 0-100% EtOAc/isohexane) to afford the title compound (2.23 g, 4.09 mmol, 42% yield, 62% purity) as an orange oil. UPLC-MS (Method 5): m/z 338.3 $(M+H)^+$, 336.3 $(M-H)^-$ at 1.51 min.

Step 2: (S)-4-(2-((allyloxy)methyl)piperidin-1-yl)-2-chloro-5-nitrobenzonitrile: To a suspension of methyltriphenylphosphonium bromide (2.19 g, 6.14 mmol) in THF (20 mL) was added 1 M potassium bis(trimethylsilyl)amide in THF (7.00 mL, 7.00 mmol) dropwise. The mixture was stirred for 30 min at RT and was then cooled to −78° C. The product from step 1 (2.23 g, 4.09 mmol) in THF (12 mL) was added dropwise and the mixture was stirred at −78° C. for 1 h. The mixture was warmed to RT and stirred for 30 min, cooled to 0° C. and quenched with saturated $NH_4Cl$(aq) (100 mL) and extracted with EtOAc (3×150 mL). The combined organic extracts were washed with brine (100 mL), dried ($MgSO_4$) and the solvent was removed in vacuo. The residue was loaded onto silica and purified by chromatography on silica gel (40 g cartridge, 0-50% EtOAc/isohexane) to afford the title compound (1.08 g, 2.96 mmol, 72% yield, 92% purity) as an orange gum. UPLC-MS (Method 5): m/z 336.4 $(M+H)^+$ at 1.92 min. $^1H$ NMR (500 MHz, DMSO-$d_6$) δ 8.39 (s, 1H), 7.57 (s, 1H), 5.69 (ddt, J=17.3, 10.3, 5.0 Hz, 1H), 5.04-4.98 (m, 1H), 4.98-4.90 (m, 1H), 3.82 (dt, J=5.0, 1.7 Hz, 3H), 3.77-3.71 (m, 1H), 3.44 (dd, J=9.7, 4.6 Hz, 1H), 3.31-3.21 (m, 1H), 3.06-3.00 (m, 1H), 1.78-1.64 (m, 3H), 1.61-1.46 (m, 3H).

Step 3: (S)-4-(2-((allyloxy)methyl) piperidin-1-yl)-5-amino-2-chlorobenzonitrile: A mixture of the product from step 2 (1.08 g, 2.96 mmol), $NH_4Cl$ (950 mg, 17.8 mmol) and zinc (1.16 g, 17.8 mmol) in THF (15 mL) and water (5 mL) was stirred at RT overnight. The mixture was filtered through Celite®, the filter cake was washed with EtOAc and the filtrate was extracted with EtOAc (3×20 mL). The combined organic extracts were washed with brine (20 mL), dried ($MgSO_4$) and the solvent was removed in vacuo. The title compound (905 mg, 2.90 mmol, 98% yield, 98% purity) was obtained as a pale red oil. UPLC-MS (Method 5): m/z 306.4 $(M+H)^+$ at 1.97 min. $^1H$ NMR (500 MHz, DMSO-$d_6$) δ 7.16 (s, 1H), 7.03 (s, 1H), 5.72 (ddt, J=17.3, 10.4, 5.2 Hz, 1H), 5.30 (s, 2H), 5.12-5.01 (m, 2H), 3.81-3.71 (m, 2H), 3.42-3.36 (m, 1H), 3.33 (dd, J=9.7, 4.8 Hz, 1H), 3.27 (dd, J=9.7, 6.5 Hz, 1H), 3.07-2.99 (m, 1H), 2.68-2.60 (m, 1H), 1.91-1.82 (m, 1H), 1.69-1.57 (m, 3H), 1.56-1.43 (m, 2H).

Step 4: methyl (S)-3-(N-(2-(2-((allyloxy)methyl)piperidin-1-yl)-4-chloro-5-cyanophenyl)sulfamoyl)-4-bromobenzoate: A mixture of the product from step 3 (905 mg, 2.90 mmol) and methyl 4-bromo-3-(chlorosulfonyl)benzoate (1.38 g, 4.35 mmol) in pyridine (15 mL) was heated to 60° C. and stirred overnight. The mixture was diluted with DCM (80 mL) and washed with 1 M HCl(aq) (80 mL), dried ($MgSO_4$) and the solvent was removed in vacuo. The residue was loaded onto silica and purified by chromatography on silica gel (40 g cartridge, 0-50% EtOAc/isohexane) to afford the title compound (1.19 g, 1.82 mmol, 62% yield, 89% purity) as a yellow glass. UPLC-MS (Method 5): m/z 582.3 $(M+H)^+$, 579.9 $(M-H)^-$ at 2.28 min. $^1H$ NMR (500 MHz, DMSO-$d_6$) δ 9.73 (s, 1H), 8.43-8.39 (m, 1H), 8.08-8.04 (m, 2H), 7.50-7.46 (m, 2H), 5.68 (ddt, J=17.0, 10.7, 5.3 Hz, 1H), 5.06-4.97 (m, 2H), 3.88 (s, 3H), 3.77-3.66 (m, 2H), 3.57-3.50 (m, 1H), 3.35 (dd, J=10.1, 6.2 Hz, 1H), 3.10 (dd, J=10.1, 5.1 Hz, 1H), 2.87-2.77 (m, 2H), 1.69-1.63 (m, 1H), 1.60-1.39 (m, 5H).

Step 5: methyl (S)-3-(N-(2-(2-((allyloxy)methyl)piperidin-1-yl)-4-chloro-5-cyanophenyl)sulfamoyl)-4-vinylbenzoate: To a degassed solution of the product from step 4 (1.19 g, 1.82 mmol) in toluene (25 mL) was added tributyl(vinyl)stannane (590 μL, 2.02 mmol) and Pd(dppf)$Cl_2$·DCM (74.0 mg, 90.6 μmol). The mixture was heated to 115° C. and stirred for 17 h and then left standing at RT for 2 days. Saturated KF(aq) (50 mL) was added and the mixture was stirred at RT for 90 min and then filtered through Celite®. The mixture was diluted with water (50 mL) and extracted with EtOAc (3×100 mL), and the combined organic extracts were washed with brine (100 mL), dried ($MgSO_4$) and the solvent was removed in vacuo. The residue was loaded onto silica and purified by chromatography on silica gel (24 g cartridge, 0-50% EtOAc/isohexane) to afford the title compound (572 mg, 917 μmol, 50% yield, 85% purity) as a light-yellow gum. UPLC-MS (Method 5): m/z 530.1 $(M+H)^+$, 528.3 $(M-H)^-$ at 2.42 min. $^1H$ NMR (500 MHz, DMSO-$d_6$) δ 9.72 (s, 1H), 8.33 (d, J=1.8 Hz, 1H), 8.18-8.12 (m, 1H), 7.97 (d, J=8.2 Hz, 1H), 7.42 (dd, J=17.2, 10.7 Hz, 1H), 7.37-7.33 (m, 2H), 5.96 (d, J=17.0 Hz, 1H), 5.68 (ddt, J=17.2, 10.5, 5.2 Hz, 1H), 5.53 (d, J=11.1 Hz, 1H), 5.05-4.95 (m, 2H), 3.88 (s, 3H), 3.74-3.68 (m, 2H), 3.60-3.53 (m, 1H), 3.40 (dd, J=10.0, 6.9 Hz, 1H), 3.10 (dd, J=10.0, 5.2 Hz, 1H), 2.83-2.76 (m, 2H), 1.70-1.58 (m, 1H), 1.42 (s, 5H).

Step 6: methyl (S,E)-3-chloro-2-cyano-6,7,8,9,9a,10-hexahydro-12H, 20H-dibenzo[e,i]pyrido[2,1-c][1]oxa[8]thia[4,7]diazacyclotridecine-17-carboxylate 19,19-dioxide: To a degassed solution of the product from step 5 (100 mg, 160 μmol) in DCM (8 mL) was added Grubbs-Hoveyda 2nd Gen (10.0 mg, 15.9 μmol) and the mixture was stirred at 40° C. overnight. The mixture was concentrated onto silica in vacuo and purified by chromatography on silica gel (4 g cartridge, 0-50% EtOAc/isohexane) to afford the title compound (38.6 mg, 38% yield, 81% purity) as a sticky brown gum. UPLC-MS (Method 5): m/z 502.4 $(M+H)^+$, 500.3 $(M-H)^-$ at 1.95 min. $^1H$ NMR (500 MHz, DMSO-$d_6$) δ 9.21 (s, 1H), 8.64 (d, J=1.9 Hz, 1H), 8.20 (d, J=8.1 Hz, 1H), 7.95 (d, J=8.3 Hz, 1H), 7.57 (s, 1H), 7.42 (d, J=15.8 Hz, 1H), 7.33 (s, 1H), 6.63 (d, J=15.8 Hz, 1H), 4.20-4.13 (m, 1H), 4.11-4.05 (m, 1H), 3.93 (s, 3H), 3.81-3.73 (m, 1H), 3.64-3.55 (m, 1H), 3.09-3.01 (m, 1H), 2.93-2.86 (m, 1H), 1.83-1.74 (m, 2H), 1.61-1.38 (m, 5H).

Step 7: (S,E)-3-chloro-2-cyano-6,7,8,9,9a,10-hexahydro-12H,20H-dibenzo[e,i]pyrido[2,1-c][1]oxa[8]thia[4,7]diazacyclotridecine-17-carboxylic acid 19,19-dioxide: A mixture of methyl the product from step 6 (38.6 mg, 62.3 μmol) and LiOH·$H_2O$ (10.5 mg, 249 μmol) in THE/MeOH/water (4:1:1, 0.6 mL) was stirred at 40° C. overnight. The mixture was diluted with water (2 mL), acidified to ~pH 4 with 1 M HCl(aq) and extracted with EtOAc (3×5 mL). The combined organic extracts were washed with brine (5 mL), dried ($MgSO_4$) and the solvent was removed in vacuo. The residue was loaded onto silica and partially purified by chromatography on silica gel (4 g cartridge, 0-100% EtOAc/isohexane). The residue was dissolved in DMSO (0.7 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH 018 ODB prep column, 130 Å, 5 μm, 30×100 mm, flow rate 40 mL/min eluting with a 0.1% Formic acid in water-MeCN gradient over 12.5 mins using UV across all wavelengths with PDA as well as a QDA and ELS detector. At-column dilution pump gives 2 mL/min methanol over the entire method, which is included in the following MeCN percentages. Gradient information: 0.0-0.5 min, 40% MeCN; 0.5-10.5 min, ramped from 40% MeCN to 70% MeCN; 10.5-10.6 min, ramped from 70% MeCN to 100% MeCN; 10.6-12.5 min, held at 100% MeCN. The title compound (7.30 mg, 14.2 μmol, 22% yield, 95% purity) was obtained as a white solid. UPLC-MS (Method 5): m/z 488.3 $(M+H)^+$, 486.3 $(M-H)^-$ at 1.95 min. $^1H$ NMR (500 MHz, DMSO-$d_6$) δ 13.51 (s, 1H), 9.18 (s, 1H), 8.64 (s, 1H), 8.18 (d, J=8.1 Hz, 1H), 7.92 (d, J=7.3 Hz, 1H), 7.57 (s, 1H), 7.41 (d, J=15.8 Hz, 1H), 7.32 (s, 1H), 6.60 (d, J=15.8 Hz, 1H), 4.23-4.12 (m, 1H), 4.10-4.03 (m, 1H), 3.80-3.73 (m, 1H), 3.63-3.53 (m, 1H), 3.09-3.02 (m, 1H), 2.94-2.83 (m, 1H), 1.83-1.75 (m, 2H), 1.60-1.44 (m, 5H).

Example 71: (R,E)-3-chloro-2-cyano-6,7,8,9,9a,10,11,12-octahydro-20H-dibenzo[c,l]pyrido[1,2-e][1]thia[2,5]diazacyclotridecine-17-carboxylic acid 19,19-dioxide

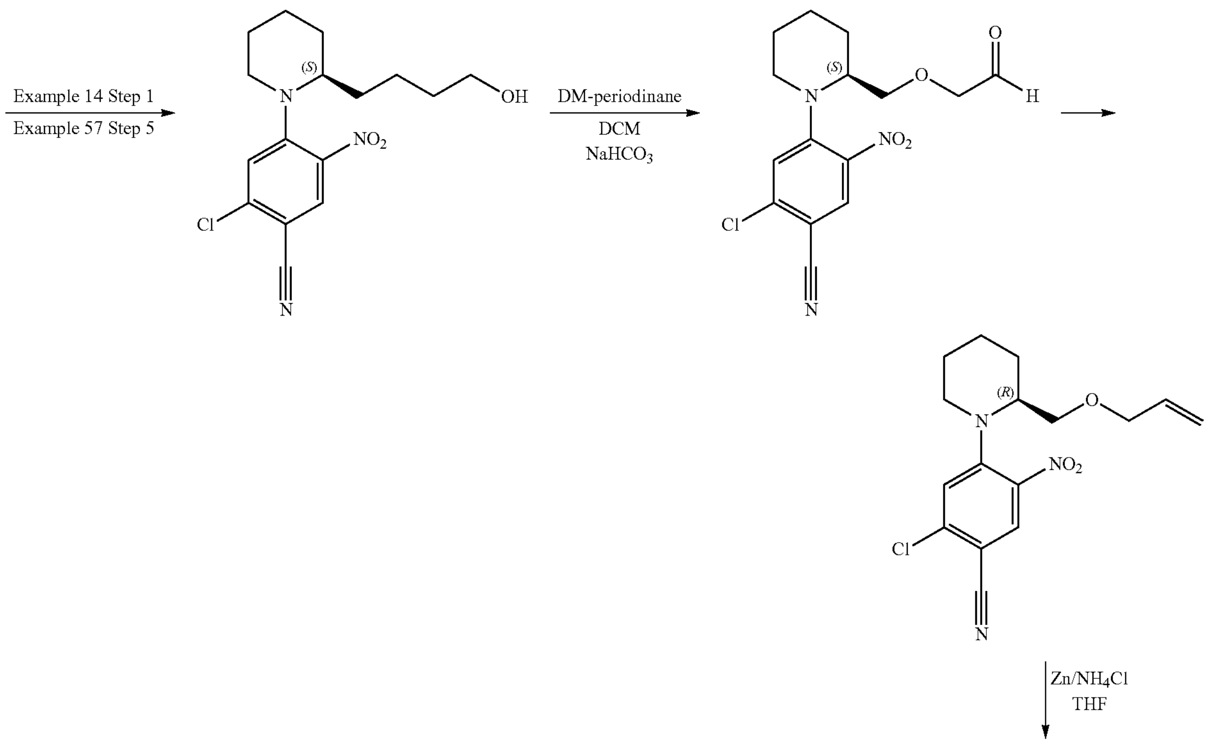

-continued

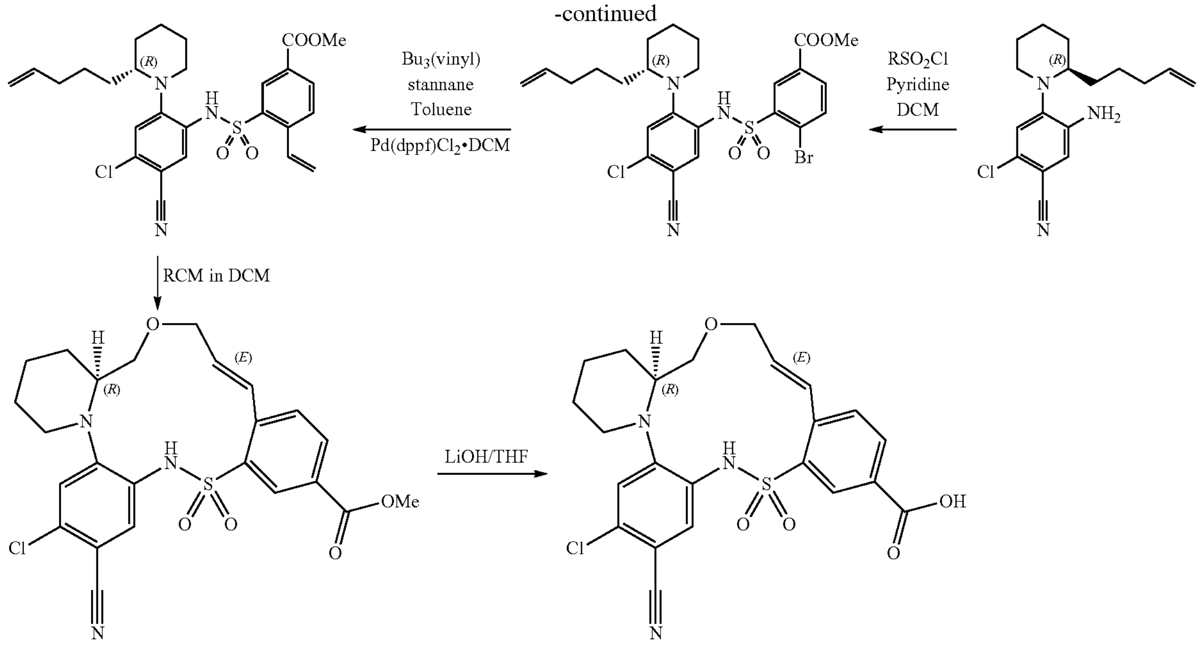

Step 1: (S)-2-chloro-4-(2-(4-hydroxybutyl)piperidin-1-yl)-5-nitrobenzonitrile: A mixture of the product from Example 14, Step 1 (2.50 g, 12.3 mmol), the product from Example 57, Step 5 (2.58 g, 13.2 mmol) and $Et_3N$ (6.00 mL, 43.0 mmol) in DCM (50 mL) was stirred at RT for 4 h. The mixture was concentrated onto silica and purified by chromatography on silica gel (80 g cartridge, 0-75% EtOAc/isohexane) to afford the title compound (4.06 g, 9.98 mmol, 80% yield, 83% purity) as an orange oil. UPLC-MS (Method 5): m/z 338.2 $(M+H)^+$ at 1.72 min. $^1H$ NMR (500 MHz, DMSO-$d_6$) δ 8.38 (s, 1H), 7.59 (s, 1H), 4.30 (t, J=5.1 Hz, 1H), 3.84-3.79 (m, 1H), 3.31-3.26 (m, 2H), 3.22 (td, J=12.9, 2.9 Hz, 1H), 2.86-2.79 (m, 1H), 1.81-1.67 (m, 2H), 1.67-1.58 (m, 3H), 1.57-1.40 (m, 3H), 1.40-1.27 (m, 2H), 1.24-1.11 (m, 2H).

Step 2: (S)-2-chloro-5-nitro-4-(2-(4-oxobutyl)piperidin-1-yl)benzonitrile: To a solution of the product from Step 1 (4.06 g, 9.98 mmol) in DCM (50 mL) was added DMP (6.35 g, 15.0 mmol) and the mixture was stirred at RT for 2 h. The mixture was diluted with DCM (50 mL) and washed with saturated $NaHCO_3$(aq) (100 mL) and the organic extract was dried ($MgSO_4$). The mixture was concentrated onto silica in vacuo and purified by chromatography on silica gel (40 g cartridge, 0-50% EtOAc/isohexane) to afford the title compound (3.64 g, 9.32 mmol, 93% yield, 86% purity) as an orange gum. UPLC-MS (Method 5): m/z 336.4 $(M+H)^+$ at 1.90 min. $^1H$ NMR (500 MHz, DMSO-$d_6$) δ 9.61 (t, J=1.5 Hz, 1H), 8.40 (s, 1H), 7.61 (s, 1H), 3.88-3.83 (m, 1H), 3.22 (td, J=12.8, 2.9 Hz, 1H), 2.84-2.78 (m, 1H), 2.44-2.36 (m, 2H), 1.81-1.69 (m, 2H), 1.68-1.57 (m, 3H), 1.57-1.49 (m, 2H), 1.49-1.29 (m, 3H).

Step 3: (R)-2-chloro-5-nitro-4-(2-(pent-4-en-1-yl)piperidin-1-yl)benzonitrile: To a suspension of methyltriphenylphosphonium bromide (5.00 g, 14.0 mmol) in THF (60 mL) was added 1 M NaHMDS (12.0 mL, 12.0 mmol) dropwise. The mixture was stirred for 30 min at RT and was then cooled to −78° C. A solution of the product from Step 2 (3.64 g, 9.32 mmol) in THF (36 mL) was added dropwise and the mixture was stirred at −78° C. for 1 h. The mixture was warmed to RT and stirred for 30 min, cooled to 0° C. and quenched with saturated $NH_4Cl$(aq) (100 mL) and extracted with EtOAc (3×150 mL). The combined organic extracts were washed with brine (100 mL), dried ($MgSO_4$) and the solvent was removed in vacuo. The residue was loaded onto silica and purified by chromatography on silica gel (40 g cartridge, 0-30% EtOAc/isohexane) to afford the title compound (2.32 g, 6.32 mmol, 67% yield, 91% purity) as an orange gum. UPLC-MS (Method 5): m/z 334.3 $(M+H)^+$ at 2.12 min. $^1H$ NMR (500 MHz, DMSO-$d_6$) δ 8.39 (s, 1H), 7.61 (s, 1H), 5.78-5.66 (m, 1H), 4.97-4.88 (m, 2H), 3.87-3.81 (m, 1H), 3.25-3.16 (m, 1H), 2.86-2.79 (m, 1H), 2.00-1.89 (m, 2H), 1.81-1.70 (m, 2H), 1.67-1.58 (m, 3H), 1.57-1.38 (m, 3H), 1.36-1.24 (m, 1H), 1.24-1.12 (m, 1H).

Step 4: (R)-5-amino-2-chloro-4-(2-(pent-4-en-1-yl)piperidin-1-yl)benzonitrile: A mixture of the product from step 3 (2.32 g, 6.32 mmol), $NH_4Cl$ (2.03 g, 37.9 mmol) and zinc (2.48 g, 37.9 mmol) in THF (50 mL) and water (17 mL) was stirred at RT for 3 days. The mixture was diluted with water (50 mL), filtered through Celite®, the filter cake was washed with EtOAc and the filtrate was extracted with EtOAc (3×100 mL). The combined organic extracts were washed with brine (50 mL), dried ($MgSO_4$) and the solvent was removed in vacuo. The title compound (2.02 g, 6.18 mmol, 97% yield, 93% purity) was obtained as a pale brown gum. UPLC-MS (Method 5): m/z 304.4 $(M+H)^+$ at 2.46 min. $^1H$ NMR (500 MHz, DMSO-$d_6$) δ 7.10 (s, 1H), 7.04 (s, 1H), 5.68-5.58 (m, 1H), 5.33-5.25 (m, 2H), 4.91-4.82 (m, 2H), 3.16-3.10 (m, 1H), 3.00-2.92 (m, 1H), 2.48-2.43 (m, 1H), 1.93-1.76 (m, 3H), 1.72-1.53 (m, 3H), 1.47-1.36 (m, 2H), 1.36-1.26 (m, 1H), 1.22-1.11 (m, 3H).

Step 5: methyl (R)-4-bromo-3-(N-(4-chloro-5-cyano-2-(2-(pent-4-en-1-yl)piperidin-1-yl)phenyl)sulfamoyl)benzoate: A mixture of the product from step 4 (2.02 g, 6.18 mmol) and methyl 4-bromo-3-(chlorosulfonyl)benzoate (2.94 g, 9.27 mmol) in pyridine (30 mL) was heated to 60° C. and stirred overnight. The mixture was diluted with DCM (40 mL) and washed with 1 M HCl(aq) (20 mL), dried ($MgSO_4$) and the solvent was removed in vacuo. The residue was loaded onto silica and purified by chromatography on silica gel (24 g cartridge, 0-30% EtOAc/isohexane) to afford the title compound (2.24 g, 3.43 mmol, 55% yield, 89% purity) as an orange gum. UPLC-MS (Method 5): m/z 580.3 $(M+H)^+$, 578.2 $(M-H)^-$ at 2.31 min. $^1H$ NMR (500 MHz, DMSO-$d_6$) δ 9.69 (s, 1H), 8.44 (d, J=1.7 Hz, 1H), 8.07 (d, J=1.7 Hz, 2H), 7.48 (s, 1H), 7.41 (s, 1H), 5.68-5.56 (m, 1H), 4.90-4.82 (m, 2H), 3.89 (s, 3H), 3.39-3.34 (m, 1H), 2.95-2.87 (m, 1H), 2.76-2.72 (m, 1H), 1.88-1.75 (m, 2H), 1.73-1.67 (m, 1H), 1.65-1.53 (m, 2H), 1.50-1.30 (m, 3H), 1.16-1.06 (m, 4H).

Step 6: methyl (R)-3-(N-(4-chloro-5-cyano-2-(2-(pent-4-en-1-yl)piperidin-1-yl)phenyl)sulfamoyl)-4-vinylbenzoate: To a degassed solution of the product from step 5 (2.24 g, 3.43 mmol) in toluene (50 mL) was added tributyl(vinyl) stannane (1.10 mL, 3.76 mmol) and Pd(dppf)$Cl_2$·DCM (140 mg, 172 μmol). The mixture was heated to 115° C. and stirred overnight. Upon cooling to RT saturated KF(aq) (50 mL) was added and the mixture was stirred at RT for 90 min and then filtered through Celite®. The mixture was diluted with water (50 mL) and extracted with EtOAc (3×100 mL) and the combined organic extracts were washed with brine (100 mL), dried ($MgSO_4$) and the solvent was removed in vacuo. The residue was loaded onto silica and purified by chromatography on silica gel (24 g cartridge, 0-25% EtOAc/isohexane) to afford the title compound (1.55 g, 2.61 mmol, 76% yield, 89% purity) as a light yellow gum. UPLC-MS (Method 5): m/z 528.4 $(M+H)^+$, 526.1 $(M-H)^-$ at 2.33 min.

Step 7: (R,E)-3-chloro-2-cyano-6,7,8,9,9a,10,11,12-octahydro-20H-dibenzo[c,l]pyrido[1,2-e][1]thia[2,5]diazacyclotridecine-17-carboxylate 19,19-dioxide: To a degassed solution of the product from step 6 (1.43 g, 2.41 mmol) in DCM (120 mL) was added Grubbs 2nd-Gen (102 mg, 121 μmol) and the mixture was heated to 40° C. and stirred overnight. Additional Grubbs 2nd-Gen (102 mg, 121 μmol) was added and stirring was continued overnight. Upon cooling to RT the mixture was concentrated onto silica in vacuo and purified by chromatography on silica gel (40 g cartridge, 0-25% EtOAc/isohexane) to afford the title compound (592 mg, 1.07 mmol, 44% yield, 90% purity) as a brown solid. UPLC-MS (Method 5): m/z 501.3 $(M+H)^+$, 499.2 $(M-H)^-$ at 2.15 min.

Step 8: (R,E)-3-chloro-2-cyano-6,7,8,9,9a,10,11,12-octahydro-20H-dibenzo[c,l]pyrido[1,2-e][1]thia[2,5]diazacyclotridecine-17-carboxylic acid 19,19-dioxide: A mixture of the product from step 7 (75.0 mg, 135 μmol) and LiOH·$H_2O$ (22.7 mg, 540 μmol) in THF/MeOH/water (4:1:1, 1.2 mL) was stirred at 40° C. for 3 h. The mixture was diluted with water (2 mL), acidified to ~pH 4 with 1 M HCl(aq) and extracted with EtOAc (3×5 mL). The combined organic extracts were washed with brine (5 mL), dried ($MgSO_4$) and the solvent was removed in vacuo. The residue was dissolved in DMSO (1 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH 018 ODB prep column, 130 Å, 5 μm, 30×100 mm, flow rate 40 mL/min eluting with a 0.1% Formic acid in water-MeCN gradient over 17.5 mins using UV across all wavelengths with PDA as well as a QDA and ELS detector. At-column dilution pump gives 2 mL/min methanol over the entire method, which is included in the following MeCN percentages. Gradient information: 0.0-0.5 min, 50% MeCN; 0.5-15.5 min, ramped from 50% MeCN to 80% MeCN; 15.5-15.6 min, ramped from 80% MeCN to 100% MeCN; 15.6-17.5 min, held at 100% MeCN. The solids were dissolved in EtOAc (10 mL) and combined, and sequentially washed with 1 M HCl(aq) (5 mL) and brine (5 mL). The organic layer was dried ($MgSO_4$) and the solvent was removed in vacuo. The title compound (22.5 mg, 43.5 μmol, 32% yield, 94% purity) was obtained as a white solid. UPLC-MS (Method 5): m/z 486.1 $(M+H)^+$, 484.3 $(M-H)^-$ at 1.99 min. $^1H$ NMR (500 MHz, DMSO-$d_6$) δ 13.50 (s, 1H), 9.87 (s, 1H), 8.65 (d, J=1.8 Hz, 1H), 8.15 (d, J=8.1 Hz, 1H), 7.75 (d, J=8.1 Hz, 1H), 7.22-7.10 (m, 3H), 6.35-6.23 (m, 1H), 4.23-3.98 (m, 1H), 3.17-3.07 (m, 1H), 2.75-2.67 (m, 1H), 2.33-2.27 (m, 1H), 2.21-2.12 (m, 1H), 1.92-1.84 (m, 1H), 1.76-1.66 (m, 2H), 1.66-1.57 (m, 2H), 1.55-1.46 (m, 4H), 1.05-0.93 (m, 1H).

Example 72: (R)-3-chloro-2-cyano-6,7,8,9,9a,10,11,12,13,14-decahydro-20H-dibenzo[c,l]pyrido[1,2-e][1]thia[2,5]diazacyclotridecine-17-carboxylic acid 19,19-dioxide

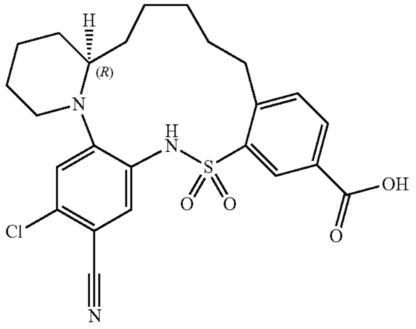

Step 1: methyl (R)-3-chloro-2-cyano-6,7,8,9,9a,10, 11, 12,13, 14-decahydro-20H-dibenzo[c,l]pyrido[1,2-e][1]thia[2,5]diazacyclotridecine-17-carboxylate 19,19-dioxide: A mixture of the product from Example 71, step 7 (403 mg, 725 μmol) and 5% Pd/$Al_2O_3$ (Type 325, 50% water) (309 mg, 72.5 μmol) in MeOH (40 mL) was hydrogenated at 5 bar at RT for 3 h. The catalyst was filtered off and the filtrate was concentrated in vacuo. The residue was loaded onto silica and purified by chromatography on silica gel (24 g cartridge, 0-50% EtOAc/isohexane) to afford the title compound (102 mg, 179 μmol, 24% yield, 88% purity) as a pale yellow gum. UPLC-MS (Method 5): m/z 502.4 $(M+H)^+$, 500.2 $(M-H)^-$, at 2.23 min.

Step 2: (R)-3-chloro-2-cyano-6,7,8,9,9a,10, 11, 12, 13, 14-decahydro-20H-dibenzo[c,l]pyrido[1,2-e][1]thia[2,5]diazacyclotridecine-17-carboxylic acid 19,19-dioxide: A mixture of the product from step 2 (102 mg, 179 μmol) and LiOH·$H_2O$ (30.0 mg, 715 μmol) in THF/MeOH/water (4:1:1, 1.5 mL) was stirred at RT overnight. The mixture was diluted with water (5 mL), acidified to ~pH 4 with 1 M HCl(aq) and extracted with EtOAc (3×20 mL). The combined organic extracts were washed with brine (20 mL), dried ($MgSO_4$) and the solvent was removed in vacuo. The residue was loaded onto silica and partially purified by chromatography on silica gel (12 g cartridge, 0-100% EtOAc/isohexane). The material was dissolved in DMSO (1 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH 018 ODB prep column, 130 Å, 5 μm, 30×100 mm, flow rate 40 mL/min eluting with a 0.1% Formic acid in water-MeCN gradient over 12.5 mins using UV across all wavelengths with PDA as well as a QDA and ELS detector. At-column dilution pump gives 2 mL/min methanol over the entire method, which is included in the following MeCN percentages. Gradient information: 0.0-0.5 min, 55% MeCN; 0.5-10.5 min, ramped from 55% MeCN to 85% MeCN; 10.5-10.6 min, ramped from 85% MeCN to 100% MeCN; 10.6-12.5 min, held at 100% MeCN). The obtained solid was dissolved in EtOAc (10 mL) and sequentially washed with 1 M HCl(aq) (5 mL) and brine (5 mL). The organic extract was dried ($MgSO_4$) and the solvent was removed in vacuo. The title compound (31.1 mg, 60.5 μmol, 33% yield, 95% purity) was obtained as a white solid. UPLC-MS (Method 5): m/z 488.1 $(M+H)^+$, 486.2 $(M-H)^-$ at 2.07 min. $^1H$ NMR (500 MHz, DMSO-$d_6$) δ 13.50 (s, 1H), 9.42 (s, 1H), 8.69 (d, J=1.8 Hz, 1H), 8.16 (dd, J=8.1, 1.8 Hz, 1H), 7.73 (s, 1H), 7.67 (d, J=8.1 Hz, 1H), 7.23 (s, 1H), 3.39-3.33 (m, 1H), 3.25-3.19 (m, 1H), 2.88-2.83 (m, 1H), 2.75-2.65 (m, 1H), 2.49-2.43 (m, 1H), 1.87-1.81 (m, 1H), 1.80-1.74 (m, 1H), 1.70-1.55 (m, 4H), 1.49-1.35 (m, 3H), 1.32-1.21 (m, 2H), 1.04-0.91 (m, 3H).

Example 73: (S)-3-chloro-2-cyano-6,7,8,9,9a,10,13,14-octahydro-12H, 20H-dibenzo[e,i]pyrido[2,1-c][1]oxa[8]thia[4,7]diazacyclotridecine-17-carboxylic acid 19,19-dioxide

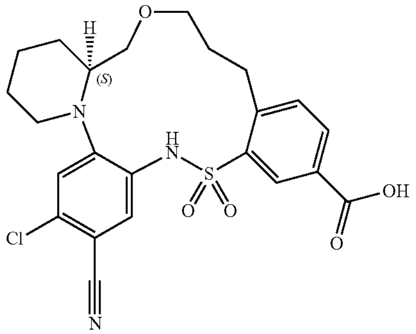

Step 1: methyl (S)-3-chloro-2-cyano-6,7,8,9,9a,10,13,14-octahydro-12H,20H-dibenzo[e,i]pyrido[2,1-c][1]oxa[8]thia[4,7]diazacyclotridecine-17-carboxylate 19,19-dioxide: A mixture of the product from Example 70, step 6 (123 mg, 230 μmol) and 5% Pd/$Al_2O_3$ (Type 325, 50% water) (98.0 mg, 23.0 μmol) in MeOH (10 mL) was hydrogenated at 5 bar at RT for 3 h. The catalyst was filtered off and the filtrate was concentrated in vacuo. The title compound (50.9 mg, 69.7 μmol, 30% yield, 69% purity) was obtained as a pale-yellow solid. UPLC-MS (Method 5): m/z 504.2 $(M+H)^+$, 502.5 $(M-H)^-$ at 2.11 min.

Step 2: (S)-3-chloro-2-cyano-6,7,8,9,9a,10,13,14-octahydro-12H, 20H-dibenzo[e,i]pyrido[2,1-c][1]oxa[8]thia[4,7]diazacyclotridecine-17-carboxylic acid 19,19-dioxide: A mixture of the product from step 1 (50.9 mg, 69.7 μmol) and LiOH·$H_2O$ (12.0 mg, 286 μmol) in THF/MeOH/water (4:1:1, 0.75 mL) was stirred at RT overnight. The mixture was diluted with water (5 mL), acidified to ~pH 4 with 1 M HCl(aq) and extracted with EtOAc (3×20 mL). The combined organic extracts were washed with brine (20 mL), dried ($MgSO_4$) and the solvent was removed in vacuo. The residue was dissolved in DMSO (1 mL), filtered and purified by reversed phase preparative HPLC (Waters 2767 Sample Manager, Waters 2545 Binary Gradient Module, Waters Systems Fluidics Organiser, Waters 515 ACD pump, Waters 515 Makeup pump, Waters 2998 Photodiode Array Detector, Waters QDa) on a Waters X-Select CSH 018 ODB prep column, 130 Å, 5 μm, 30×100 mm, flow rate 40 mL/min eluting with a 0.1% Formic acid in water-MeCN gradient over 12.5 mins using UV across all wavelengths with PDA as well as a QDA and ELS detector. At-column dilution pump gives 2 mL/min methanol over the entire method, which is included in the following MeCN percentages. Gradient information: 0.0-0.5 min, 50% MeCN; 0.5-10.5 min, ramped from 50% MeCN to 80% MeCN; 10.5-10.6 min, ramped from 80% MeCN to 100% MeCN; 10.6-12.5 min, held at 100% MeCN. The obtained material was dissolved in EtOAc (10 mL) and sequentially washed with 1 M HCl(aq) (5 mL) and brine (5 mL). The organic layer was dried ($MgSO_4$) and the solvent was removed in vacuo. The title compound (16.7 mg, 33.4 μmol, 47% yield, 98% purity) was obtained as a white solid. UPLC-MS (Method 5): m/z 490.1 $(M+H)^+$, 488.2 $(M-H)^-$ at 1.94 min. $^1H$ NMR (500 MHz, DMSO-$d_6$) δ 13.50 (s, 1H), 9.04 (s, 1H), 8.66 (d, J=1.7 Hz, 1H), 8.17 (dd, J=8.1, 1.7 Hz, 1H), 7.89 (s, 1H), 7.78 (d, J=8.1 Hz, 1H), 7.42 (s, 1H), 3.53-3.43 (m, 1H), 3.22-3.17 (m, 1H), 3.08-3.02 (m, 2H), 2.89-2.82 (m, 1H), 2.80-2.67 (m, 3H), 2.65-2.57 (m, 1H), 2.06-1.95 (m, 2H), 1.91-1.79 (m, 2H), 1.74-1.63 (m, 2H), 1.62-1.52 (m, 1H), 1.49-1.38 (m, 1H).

Biological Investigations

The following assays can be used to illustrate the commercial utilities of the compounds according to the present invention.

Biological Assay 1: ERAP1 Mediated Hydrolysis of an Amide Substrate Measured in a Biochemical System

Materials and Solutions

- 1× Assay buffer (AB): 25 mM Bis-tris propane, 0.05% w/v Hydroxypropylmethylcellulose pH 7.75 made with Optima grade water
- Decapeptide WRVYEKC(Dnp)ALK-acid (where Dnp is Dinitrophenyl maleimide) (10-mer)
- L-Leucine 7-amido-4-methylcoumarin (L-AMC)
- Purified ERAP1(37-941)-10His (ERAP1)

Assay Procedure:

12.5 μL ERAP1 enzyme in 1×AB was combined with 250 nL test compound in DMSO. 12.5 μL of either 240 μM L-AMC in 1×AB or 100 μM 10-mer in 1×AB was added to the reaction and incubated at 23° C. for 1 h. For detection, plates were read at excitation 365 nm and emission 442 nm (L-AMC) or excitation 279 nm and emission 355 nm (10-mer). Compound $IC_{50}$ was determined using a 4-parameter equation. The results for selected compounds according to the invention are shown in Table 1

OVA Antigen Presentation Assay

The cellular effect of representative compounds according to the invention on antigen presentation can be measured by assessing their effect on the presentation of an ovalbumin-specific peptide (SIINFEKL) to T-cells, as previously described [Reeves et al, (2014) *Proc. Natl. Acad. Sci. USA* 111; 17594-17599]. Briefly, SiHa cells are transiently transfected with plasmids encoding mouse H2Kb and an ER-targeted N-terminally extended precursor peptide derived from ovalbumin (MRYMILGLLALAAVCSAAIVMKSIINFEHL) using Lipofectamine 3000. The cells are harvested 6 h post-transfection and transfected SiHa cells are plated compounds across a 12-point concentration response curve to quantify ERAP1 inhibitor $IC_{50}$. SiHa cells are cultured in the presence of compound for 48 h. Subsequently, B3Z cells [Karttunen et al, (1992) *Proc. Natl. Acad. Sci. USA* 89; 6020-6024] are added to the cell culture for 4 h; the B3Z T-cell hybridoma encodes a TCR recognizing specifically the SIINFEHL/H2Kb complex at the cell surface, which upon activation, triggers a signalling cascade leading to the transcription of the LacZ gene that is under the control of the IL-2 promoter. Intracellular β-galactosidase activity as a readout of T-cell activation is measured by quantifying the conversion of chlorophenored-β-D-galacto-pyranoside (CPRG) to chlorophenol red by measuring absorbance at 570 nm.

Immunopeptidomics

The effect of representative compounds according to the invention on global antigen processing can be determined using an unbiased proteomics pipeline as described by Purcell and colleagues [Purcell et al, (2019) Nat Protoc. 14; 1687-1707]. Briefly, 500 million SiHa cells are treated with compound for 24 h or siRNA for 72 hours and then harvested, lysed and MHC-bound peptides isolated by immunoaffinity capture. The peptides are eluted using 10% (v/v) acetic acid and separated from the MHC-1 and β2-microglobulin proteins by HPLC before analysis by LC-MS/MS.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

| Activity of selected compounds according to the invention | |
|---|---|
| 1 | High |
| 2 | Low |
| 3 | High |
| 4 | High |
| 5 | High |
| 6 | Low |
| 7 | Low |
| 8 | High |
| 9 | High |
| 10 | High |
| 11 | Medium |
| 12 | Medium |
| 13 | High |
| 14 | High |
| 15 | High |
| 16 | Low |
| 17 | High |
| 18 | Medium |
| 19 | High |
| 20 | Low |
| 21 | High |
| 22 | High |
| 23 | Medium |
| 24 | High |
| 25 | High |
| 26 | High |
| 27 | High |
| 28 | High |
| 29 | High |
| 30 | High |
| 31 | High |
| 32 | High |

TABLE 1-continued

| Activity of selected compounds according to the invention | |
|---|---|
| 33 | Low |
| 34 | High |
| 35 | High |
| 36 | High |
| 37 | Low |
| 38 | High |
| 39 | High |
| 40 | Low |
| 41 | High |
| 42 | High |
| 43 | High |
| 44 | Medium |
| 45 | High |
| 46 | High |
| 47 | Medium |
| 48 | High |
| 49 | High |
| 50 | Medium |
| 51 | Medium |
| 52 | High |
| 53 | High |
| 54 | High |
| 55 | High |
| 56 | High |
| 57 | High |
| 58 | Low |
| 59 | High |
| 60 | High |
| 61 | High |
| 62 | Low |
| 63 | Low |
| 64 | Low |
| 65 | High |
| 66 | Low |
| 67 | High |
| 68 | High |
| 69 | High |
| 70 | High |
| 71 | Medium |
| 72 | High |
| 73 | High |

$IC_{50}$ vs Decapeptide WRVYEKC(Dnp)ALK-acid (where Dnp is Dinitrophenyl maleimide) (10-mer); High (<250 nM), Medium (250 nM to1000 nM), Low (>1000 nM).

REFERENCES

1. Serwold et al, (2002), ERAAP customizes peptides for MHC class I molecules in the endoplasmic reticulum; Nature: 419, p 480.
2. Snyder et al, (2014), Genetic Basis for Clinical Response to CTLA-4 Blockade in Melanoma; NEJM: 371, p 2189.
3. Van Allen et al, (2015), Genomic correlates of response to CTLA-4 blockade in metastatic melanoma; Science: 348, p 124.
4. James et al, (2013), Induction of Protective Antitumor Immunity through Attenuation of ERAAP Function; J Immunol: 190, p 5839.
5. Niranjana et al, (2016), ERAAP Shapes the Peptidome Associated with Classical and Nonclassical MHC Class I Molecules; J Immunol: 197, p 1035.
6. Pepelyayeva et al, (2018), ERAP1 deficient mice have reduced Type 1 regulatory T cells and develop skeletal and intestinal features of Ankylosing Spondylitis; Sci. Reports: 8: p 12464.
7. Cifaldi et al, (2015), ERAP1 Regulates Natural Killer Cell Function by Controlling the Engagement of Inhibitory Receptors, Cancer Res.: 75, p 824.
8. Steinbach et al, (2017), ERAP1 overexpression in HPV-induced malignancies: A possible novel immune evasion mechanism, Oncoimmunol: 6, e1336594.

9. Kim et al, (2011), Human cytomegalovirus microRNA miR-US4-1 inhibits CD8+ T cell responses by targeting the aminopeptidase ERAP1, Nat. Immunol.: 12, p 984.
10. Tenzer et al, (2009), Antigen processing influences HIV-specific cytotoxic T lymphocyte immunodominance, Nat. Immunol.: 10, p 636.
11. Reeves et al, (2018), The role of polymorphic ERAP1 in autoinflammatory disease, Biosci. Rep.: 29, p 38.
12. Chen et al, (2014), Silencing or inhibition of endoplasmic reticulum aminopeptidase 1 (ERAP1) suppresses free heavy chain expression and Th17 responses in ankylosing spondylitis, Ann Rheum Dis: 75, p 916.
13. Sheehan, NJ (January 2004). "The ramifications of HLA-B27". *Journal of the Royal Society of Medicine.* 97 (1): 10-4.
14. Smith, JA (January 2015). "Update on ankylosing spondylitis: current concepts in pathogenesis". *Current allergy and asthma reports.* 15 (1): 489.
15. Kuiper J J W, Mutis T, de Jager W, de Groot-Mijnes J D, Rothova A (2011). "Intraocular interleukin-17 and proinflammatory cytokines in HLA-A29-associated birdshot chorioretinopathy". *Am J Ophthalmol.* 152 (2): 177-182
16. Kuiper J J W, Emmelot M E, Rothova A, Mutis T (2013). "Interleukin-17 production and T helper 17 cells in peripheral blood mononuclear cells in response to ocular lysate in patients with birdshot chorioretinopathy". *Mol Vis.* 19: 2606-14
17. Kuiper J J W, van Setten J, Ripke S, Van't Slot R, Mulder F, Missotten T, Baarsma G S, Francioli L C, Pulit S L, de Kovel C G, Ten Dam-van Loon N, den Hollander A I, Huis In Het Veld P, Hoyng C B, Cordero-Coma M, Martin J, Llorenr V, Arya B, Thomas D, Bakker S C, Ophoff R A, Rothova A, de Bakker P I, Mutis T, Koeleman B P (2014). "A genome-wide association study identifies a functional ERAP2 haplotype associated with birdshot chorioretinopathy". *Hum Mol Genet.* 23 (22): 6081-6087
18. Evans et al (2011), Interaction between ERAP1 and HLA-B27 in ankylosing spondylitis implicates peptide handling in the mechanism for HLA-B27 in disease susceptibility. Nat Genet. 10; 43(8):761-7
19. Conde-Jaldon et al (2014), Epistatic interaction of ERAP1 and HLA-B in Behret disease: a replication study in the Spanish population. PLoS One. 14; 9(7)
20. Kuiper et al (2018), Functionally distinct ERAP1 and ERAP2 are a hallmark of HLA-A29-(Birdshot) Uveitis. Hum Mol Genet. doi: 10.1093/hmg/ddy319
21. Strange et al (2010), A genome-wide association study identifies new psoriasis susceptibility loci and an interaction between HLA-C and ERAP1. Nat Genet.; 42(11): 985-90.

The invention claimed is:

1. A compound of formula (I-1), or a pharmaceutically acceptable salt or hydrate thereof, (I-1)

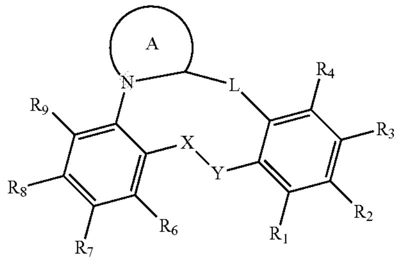

wherein:

ring A is a piperidinyl group;

L is a linker group which is a 2 to 5-membered saturated or unsaturated aliphatic group, wherein one or two carbon atoms in said group, other than the carbon atom directly bonded to ring A, are optionally replaced by a heteroatom-containing group selected from O and NH, and wherein when two carbon atoms are replaced, the heteroatom-containing groups are separated by at least two carbon atoms and the linker group is a 5-membered group;

the group X—Y is —$NR_{23}SO_2$— or —$SO_2NR_{23}$—;

$R_1$ is selected from H, CN and alkyl;

$R_2$ is selected from COOH, tetrazolyl and C(O)$NHSO_2R_{24}$;

$R_3$ is selected from H, halo and alkyl;

$R_4$ is selected from H and halo;

$R_6$ is H;

$R_7$ is selected from H, CN, haloalkyl, halo, $SO_2$-alkyl, $SO_2NR_{18}R_{19}$, $CONR_{20}R_{21}$, heteroaryl and alkyl, wherein said heteroaryl group is optionally substituted by one or more substituents selected from alkyl, halo, alkoxy, CN, haloalkyl and OH;

$R_8$ is selected from H, alkyl, haloalkyl and halo;

$R_9$ is selected from H, alkyl and halo;

$R_{18}$-$R_{21}$ are each independently selected from H and alkyl;

$R_{23}$ is H; and $R_{24}$ is selected from alkyl and cyclopropyl.

2. A compound according to claim 1 wherein L is:

(i) a 3 to 5-membered saturated aliphatic group, wherein one or two carbon atoms in said group, other than the carbon atom directly bonded to ring A, are optionally replaced by a heteroatom-containing group selected from O and NH, and wherein when two carbon atoms are replaced, the heteroatom-containing groups are separated by at least two carbon atoms and the linker group is a 5-membered group; or (ii) a 3 to 5-membered unsaturated aliphatic group, wherein one carbon atom in said group, other than the carbon atom directly bonded to ring A, is optionally replaced by a heteroatom-containing group selected from O and NH.

3. A compound according to claim 1 which is of formula (I), or a pharmaceutically acceptable salt or hydrate thereof, (I)

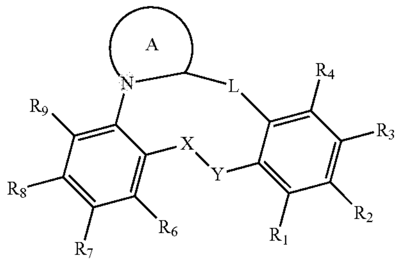

wherein:

ring A is a piperidinyl group;

L is a group selected from:

$-(CR_{10}R_{11})_r-(CR_{12}R_{13})-O-$;

$-(CR_{10}R_{11})_nC(R_{16})=C(R_{17})-(CR_{12}R_{13})_m-O-$;

$-(CR_{14}R_{15})-Q-(CR_{12}R_{13})_s-O-$;

$-(CR_{10}R_{11})_u-(CR_{12}R_{13})-$;

$-(CR_{10}R_{11})_t-C(R_{16})=C(R_{17})-$;

—(CR$_{14}$R$_{15}$)-Q-(CR$_{12}$R$_{13}$)$_m$—C(R$_{16}$)═C(R$_{17}$)—; and —(CR$_{14}$R$_{15}$)-Q-(CR$_{12}$R$_{13}$)$_t$; the group X—Y is —NR$_{23}$SO$_2$— or —SO$_2$NR$_{23}$—;

Q is O or NH;

R$_1$ is selected from H, CN and alkyl;

R$_2$ is selected from COOH, tetrazolyl and C(O)NHSO$_2$R$_{24}$;

R$_3$ is selected from H, halo and alkyl;

R$_4$ is selected from H and halo;

R$_6$ is H;

R$_7$ is selected from H, CN, haloalkyl, halo, SO$_2$-alkyl, SO$_2$NR$_{18}$R$_{19}$, CONR$_{20}$R$_{21}$, heteroaryl and alkyl, wherein said heteroaryl group is optionally substituted by one or more substituents selected from alkyl, halo, alkoxy, CN, haloalkyl and OH;

R$_8$ is selected from H, alkyl, haloalkyl and halo;

R$_9$ is selected from H, alkyl and halo;

each R$_{10}$ is H;

each R$_{11}$ is independently selected from H, F, alkyl and OH;

R$_{12}$-R$_{22}$ are each independently selected from H and alkyl;

R$_{23}$ is H;

R$_{24}$ is selected from alkyl and cyclopropyl;

m is 1;

n is 0 or 1;

r is 0, 1, 2, or 3;

s is 2;

t is 1, 2, or 3; and u is 1, 2, 3, or 4.

4. A compound according to claim 3 wherein L is:

—(CR$_{10}$R$_{11}$)$_r$—(CR$_{12}$R$_{13}$)—O—, wherein r is 0, 1, 2 or 3; or wherein L is selected from:

—CH$_2$—O—;

—CH$_2$—CH$_2$—O—;

—CH$_2$—CH$_2$—CH$_2$—O—;

—CH$_2$—CH$_2$—CH$_2$—CH$_2$—O—;

—CH(OH)—CH(OH)—CH$_2$—O—;

—CH(OH)—CH$_2$—CH$_2$—O—;

—CH$_2$—CH(OH)—CH$_2$—O—;

—CH(F)—CH(F)—CH$_2$—O—;

—CH(F)—CH$_2$—CH$_2$—O—;

—CH$_2$—CH(F)—CH$_2$—O—;

—CH(F)—CH(OH)—CH$_2$—O—;

—CH(OH)—CH(F)—CH$_2$—O—;

—CH$_2$—CH(OH)—CH(OH)—CH$_2$—O—;

—CH$_2$—CH(OH)—CH$_2$—CH$_2$—O—;

—CH$_2$—CH$_2$—CH(OH)—CH$_2$—O—;

—CH$_2$—CH(F)—CH(F)—CH$_2$—O—;

—CH$_2$—CH(F)—CH$_2$—CH$_2$—O—;

—CH$_2$—CH$_2$—CH(F)—CH$_2$—O—;

—CH$_2$—CH(F)—CH(OH)—CH$_2$—O—; and

—CH$_2$—CH(OH)—CH(F)—CH$_2$—O—.

5. A compound according to claim 3 wherein L is:

—(CR$_{10}$R$_{11}$)$_n$C(R$_{16}$)═C(R$_{17}$)—(CR$_{12}$R$_{13}$)$_m$—O— or wherein L is selected from:

—CH$_2$—CH═CH—CH$_2$—O—; and

—CH═CH—CH$_2$—O—.

6. A compound according to claim 3 wherein L is:

—(CR$_{12}$R$_{13}$)-Q-(CR$_{14}$R$_{15}$)$_s$—O— wherein Q is O or NH; or wherein L is selected from:

—CH$_2$—O—CH$_2$—CH$_2$—O—; and

—CH$_2$—NH—CH$_2$—CH$_2$—O—.

7. A compound according to claim 3 wherein L is —(CR$_{10}$R$_{11}$)$_u$—(CR$_{12}$R$_{13}$)— and u is 1, 2, 3 or 4; or wherein L is —CH$_2$—CH$_2$—CH$_2$—CH$_2$—CH$_2$.

8. A compound according to claim 3 wherein L is —(CR$_{10}$R$_{11}$)$_t$—C(R$_{16}$)═C(R$_{17}$)— and t is 1, 2 or 3; or wherein L is —CH$_2$—CH$_2$—CH$_2$—CH═CH—.

9. A compound according to claim 3 wherein L is —(CR$_{14}$R$_{15}$)-Q-(CR$_{12}$R$_{13}$)$_m$—C(R$_{16}$)═C(R$_{17}$)—, and m is 1; or wherein L is —CH$_2$—O—CH$_2$—CH═CH.

10. A compound according to claim 3 wherein L is —(CR$_{14}$R$_{15}$)-Q-(CR$_{12}$R$_{13}$)$_t$— and t is 1, 2 or 3; or wherein L is —CH$_2$—O—CH$_2$—CH$_2$—CH$_2$.

11. A compound according to claim 1, wherein X—Y is NH—SO$_2$ or NMe-SO$_2$.

12. A compound according to claim 1, which is of formula (Ib), or a pharmaceutically acceptable salt or hydrate thereof:

(Ib)

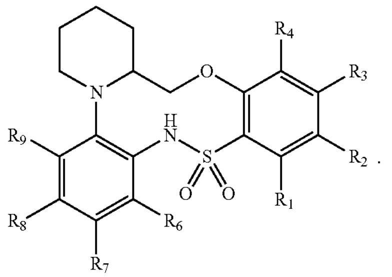

13. A compound according to claim 1—which is of formula (Ic), or a pharmaceutically acceptable salt or hydrate thereof:

(Ic)

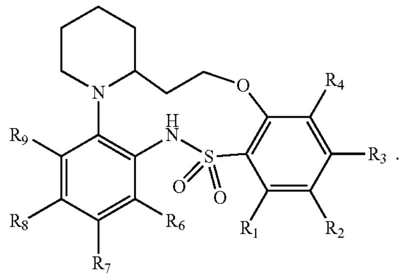

14. A compound according to claim 1 which is of formula (Id), or a pharmaceutically acceptable salt or hydrate thereof:

(Id)

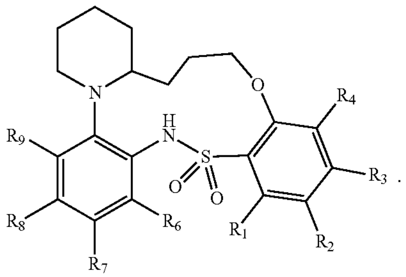

15. A compound according to claim 1 which is of formula (Ie), or a pharmaceutically acceptable salt or hydrate thereof:

(Ie)

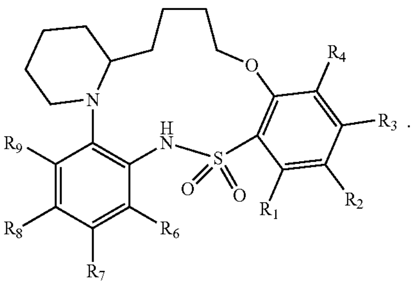

16. A compound according to claim 1 which is of formula (If) or formula (Ij), or a pharmaceutically acceptable salt or hydrate thereof:

(If)

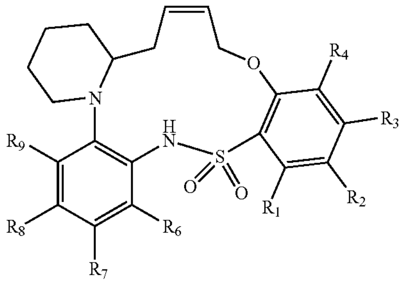

(Ij)

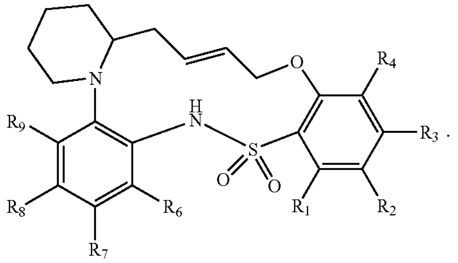

17. A compound according to claim 1 which is of formula (Ig) or formula (m), or a pharmaceutically acceptable salt or hydrate thereof:

(Ig)

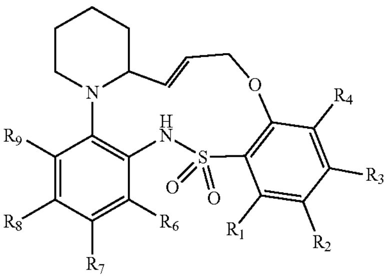

-continued (Im)

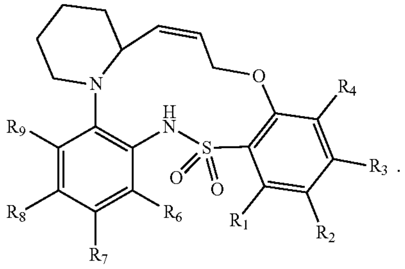

18. A compound according to claim 1 which is of formula (In), or a pharmaceutically acceptable salt or hydrate thereof:

(In)

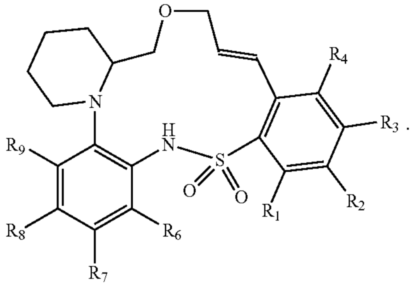

19. A compound according to claim 1 which is of formula (Ip), or a pharmaceutically acceptable salt or hydrate thereof:

(Ip)

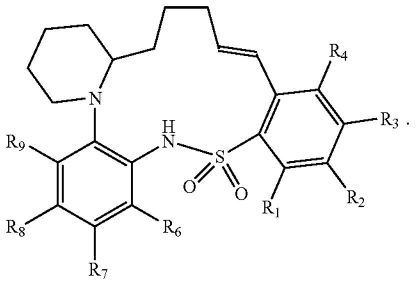

20. A compound according to claim 1 which is of formula (Iq), or a pharmaceutically acceptable salt or hydrate thereof:

(Iq)

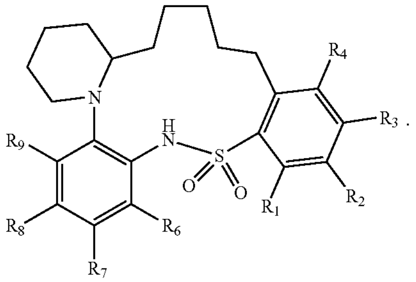

21. A compound according to claim 1 which is of formula (Ir), or a pharmaceutically acceptable salt or hydrate thereof:

(Ir)

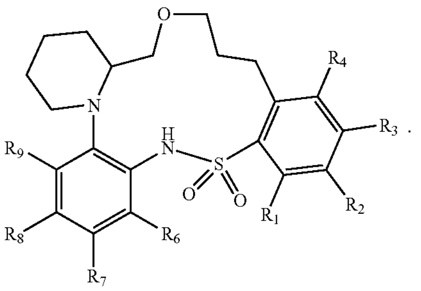

22. A compound according to claim 1, wherein $R_2$ is COOH or $CONHSO_2Me$.

23. A compound according to claim 1, wherein $R_7$ is selected from CN, haloalkyl, $SO_2$-alkyl, $SO_2NR_{18}R_{19}$ and tetrazolyl, or wherein $R_7$ is selected from $CF_3$, CN and $SO_2Me$.

24. A compound according to claim 1, wherein $R_8$ is selected from H, Cl, F and Me.

25. A compound according to claim 1, wherein $R_1$, $R_3$, $R_4$ and Ry are all H.

26. A compound which is selected from the following:

(1)

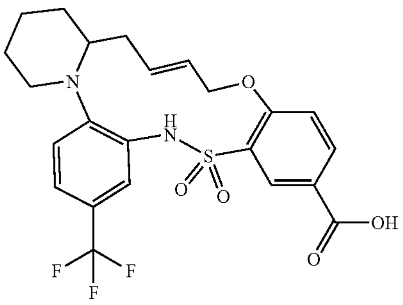

(2)

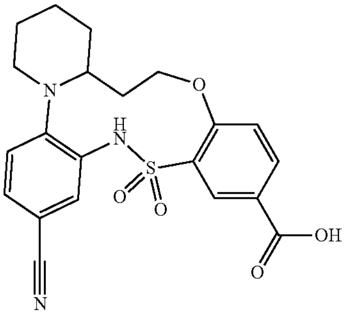

-continued (6) E1

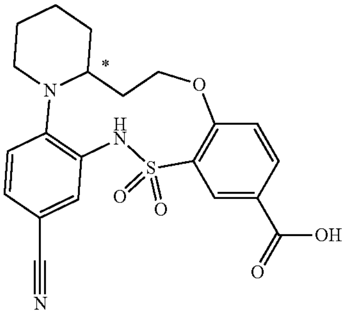

(7) E2

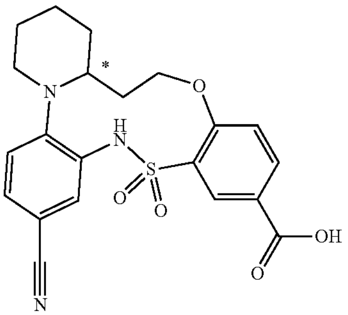

(3)

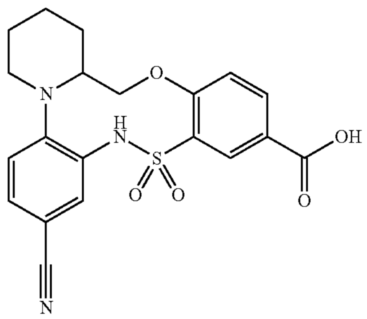

(10) E1

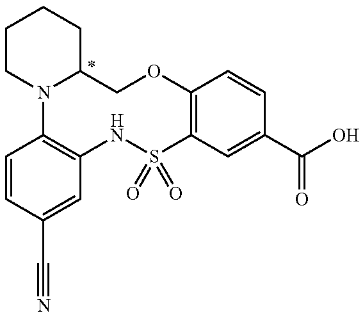

(11) E2

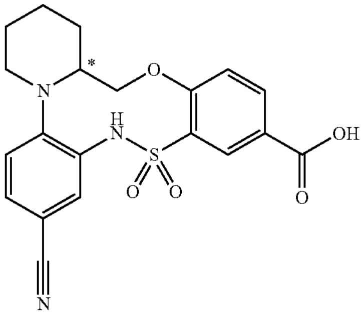

-continued
(4)
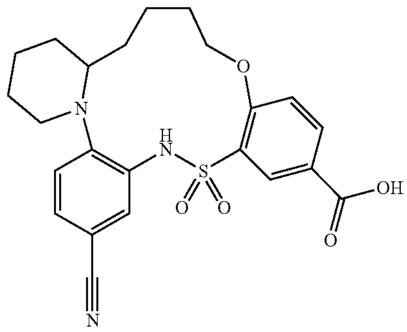
(12) E1
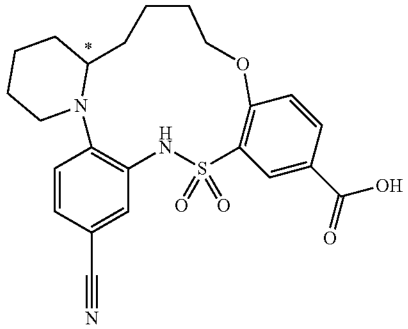
(13) E2
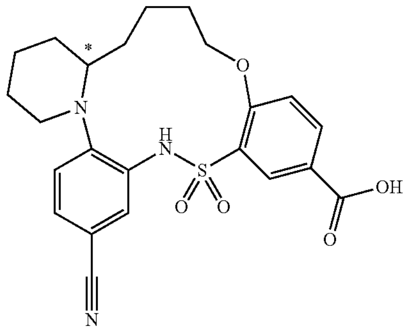
(5)
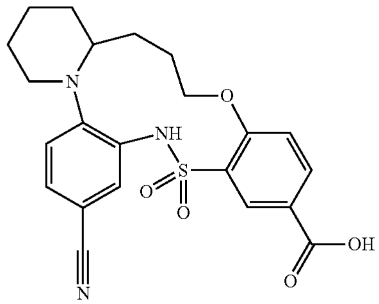
(8) E1
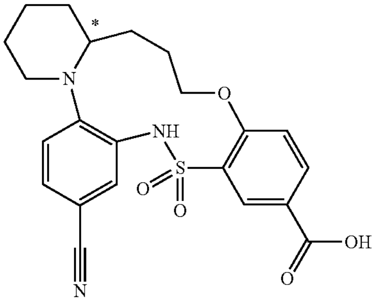
-continued
(9) E2
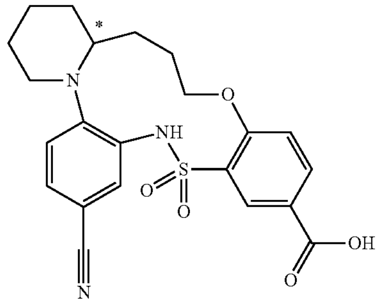
(14)
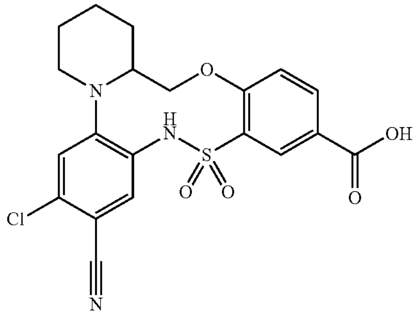
(16) E1
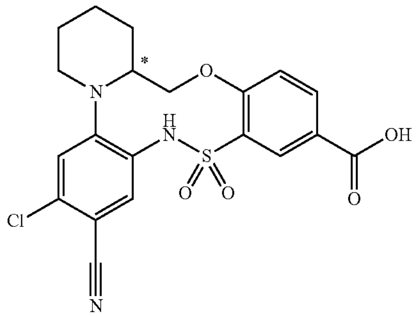
(17) E2
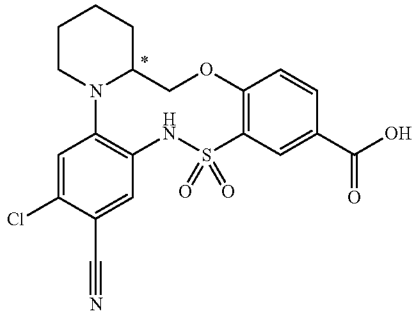
(15)
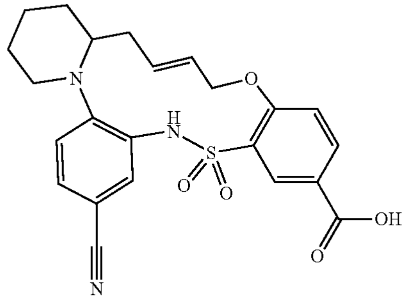

-continued
(32) E1
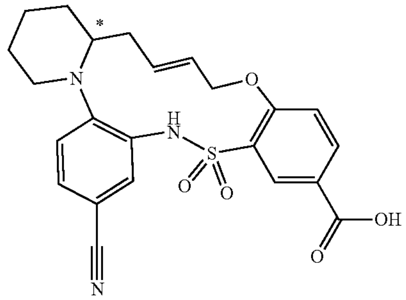
(33) E2
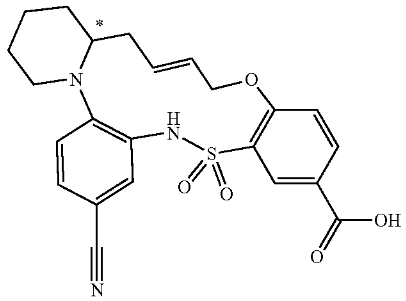
(18)
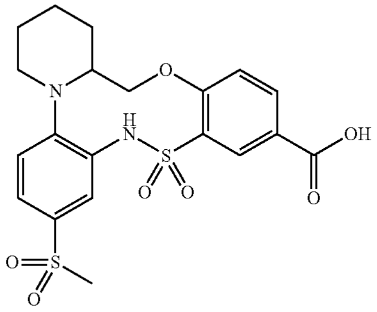
(19) E1
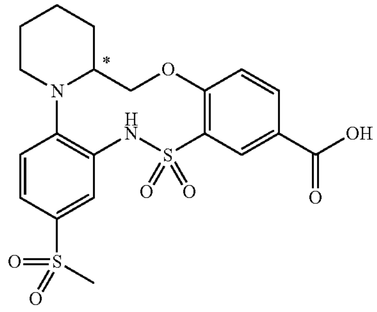
(20) E2
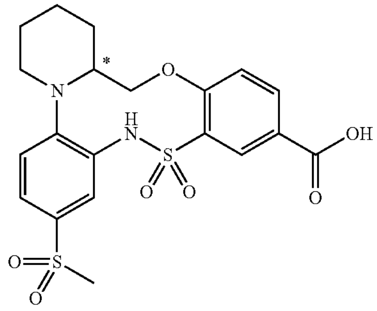
-continued
(21)
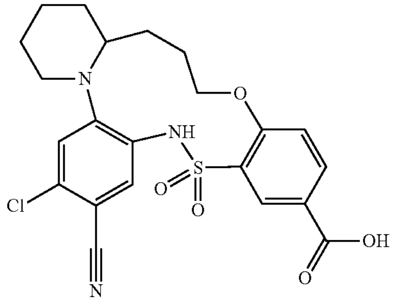
(22)
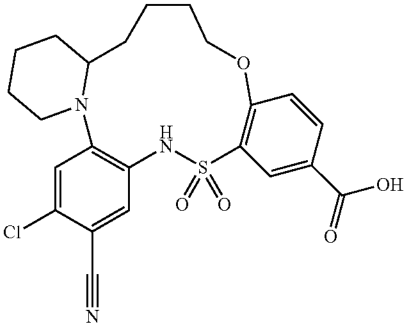
(26) E1
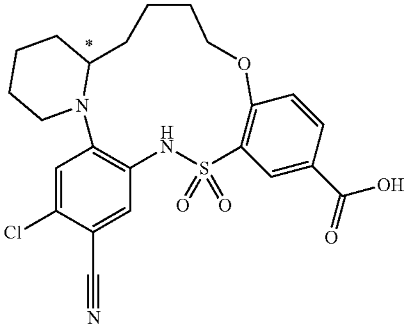
(27) E2
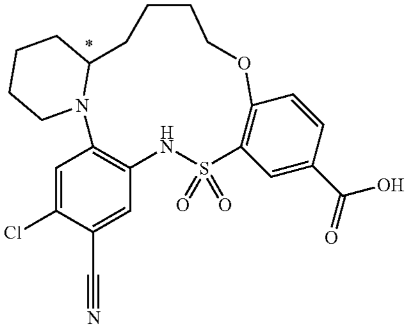
(52) or (26R)
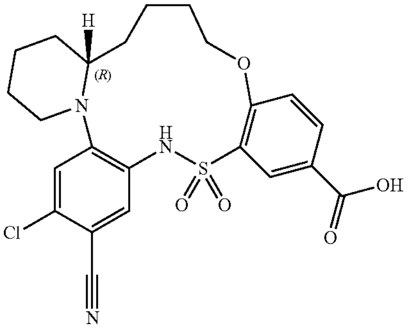

-continued
(53) or (27S)
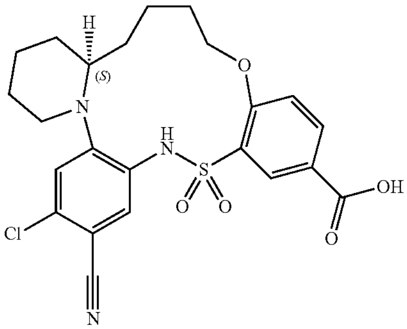
(23)
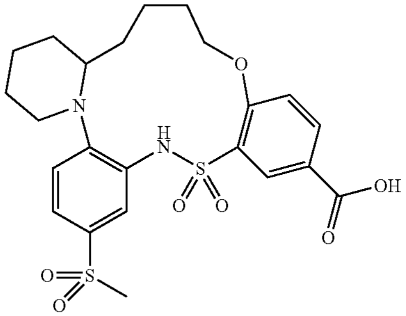
(24)
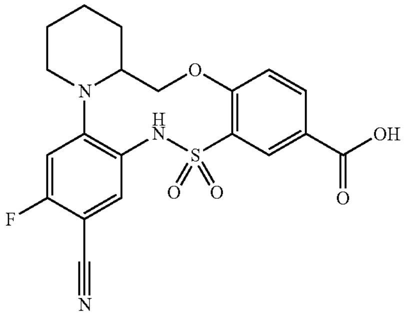
(37) E1
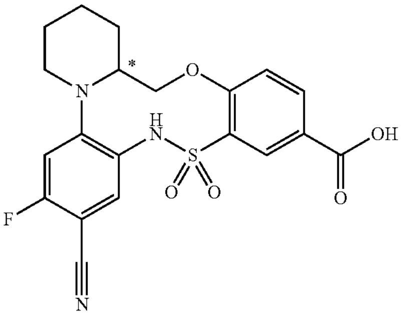
(38) E2
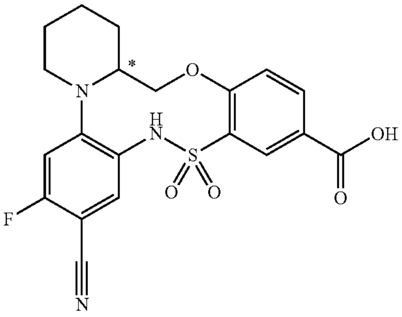
-continued
(25)
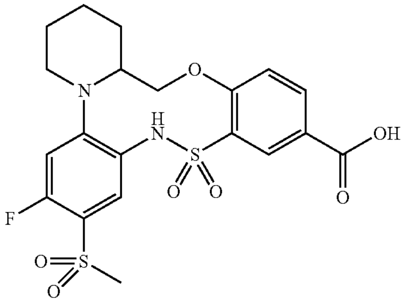
(39) E1
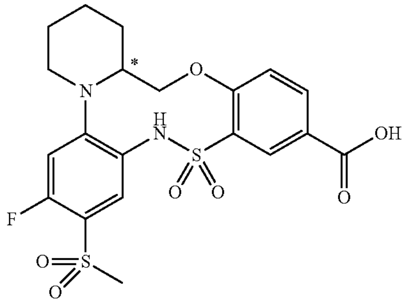
(40) E2
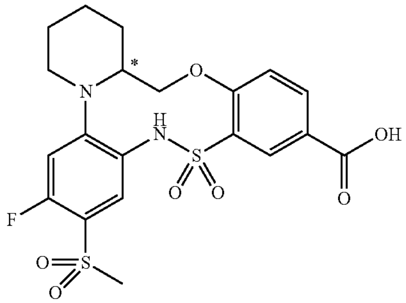
(28)
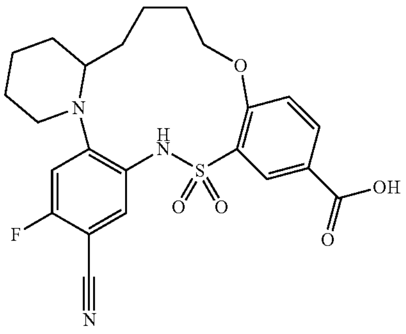
(55) E1
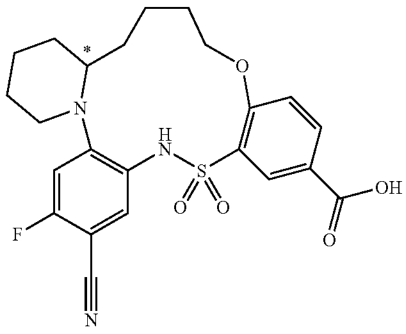

-continued
(56) E2
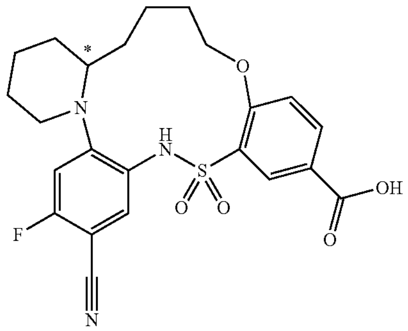
(29)
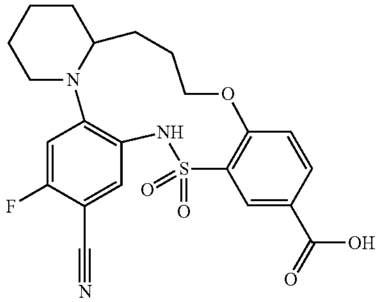
(41) E1
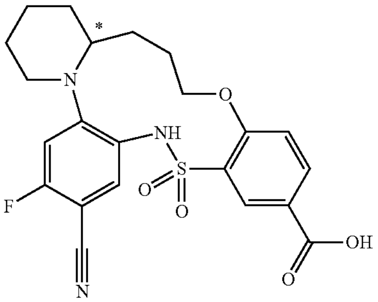
(42) E2
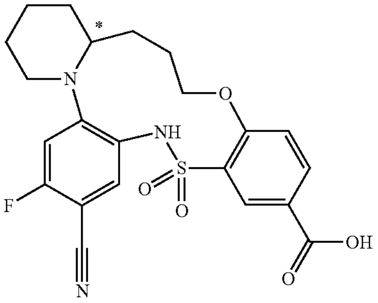
(30)
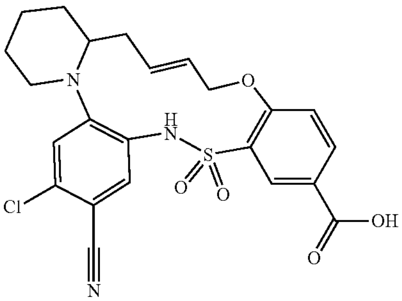
-continued
(45) E1
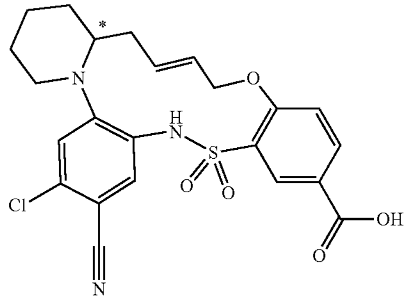
(46) E2
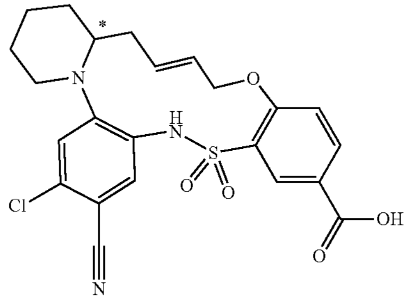
(31)
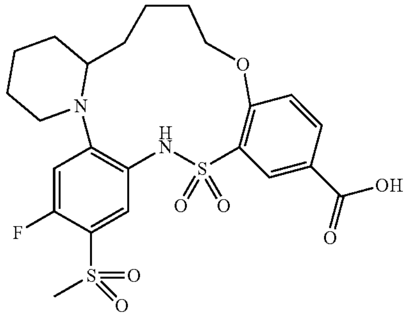
(43) E1
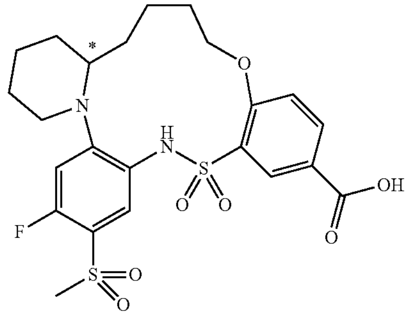
(44) E2
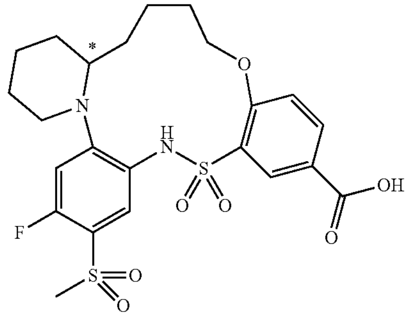

-continued
(34)
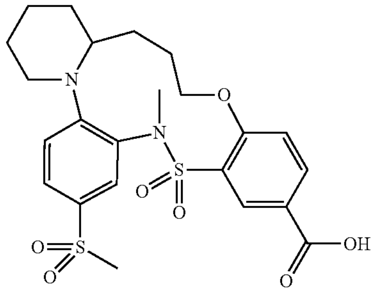
(35)
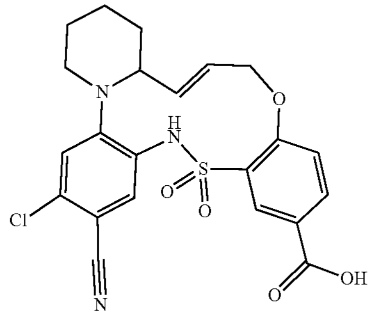
(47) E1
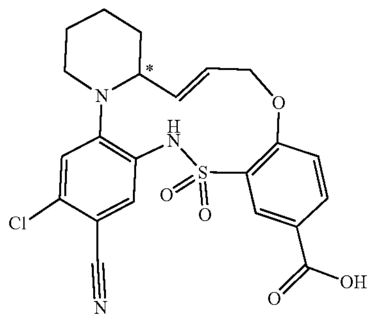
(48) E2
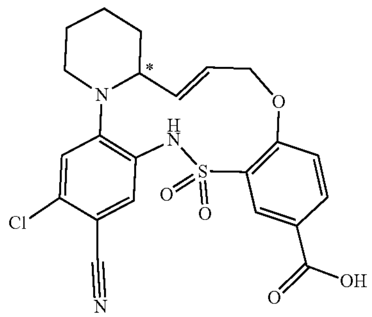
(36)
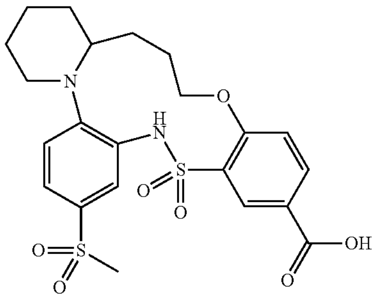
-continued
(49) E1
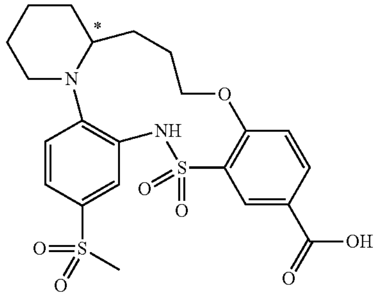
(50) E2
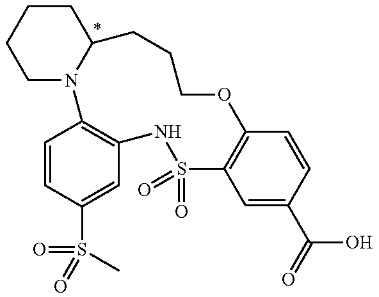
(51)
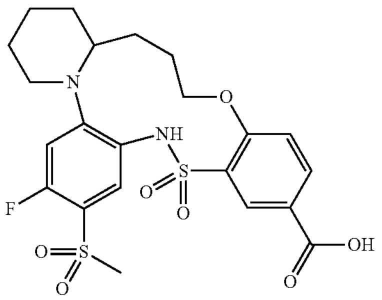
(54)
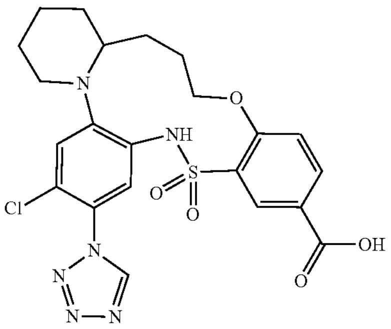
(57)
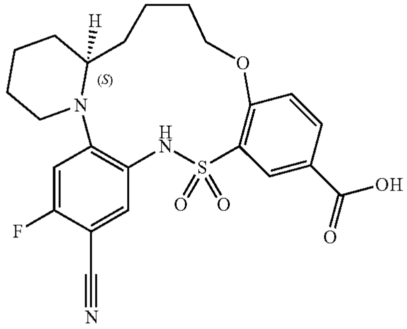

-continued
(58) from (48) E2
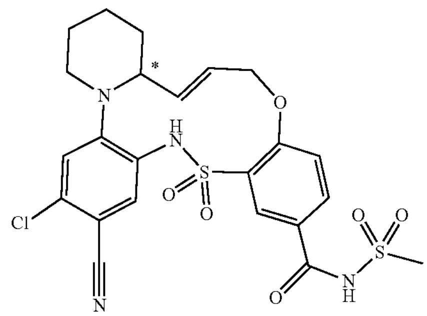
(59)
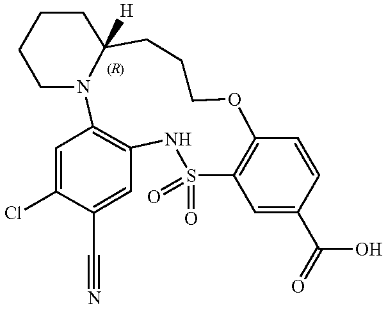
(60)
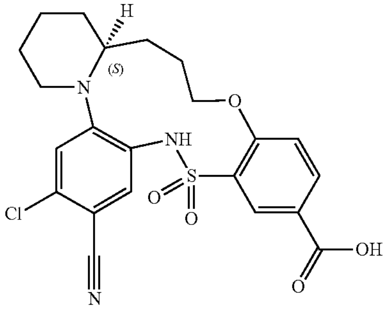
(61)
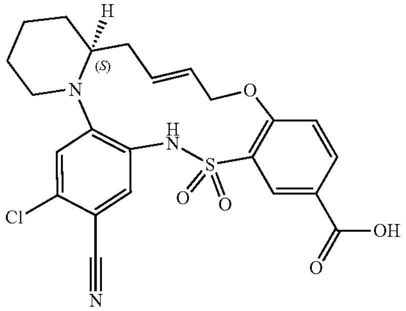
(62)
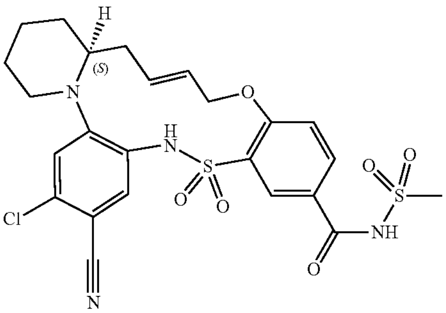
-continued
(63)
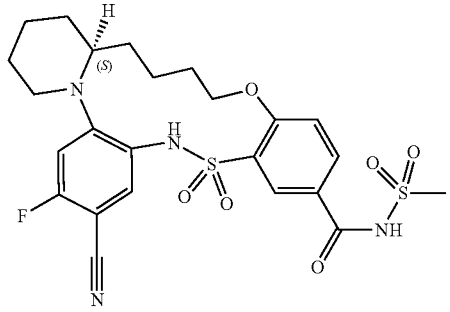
(64)
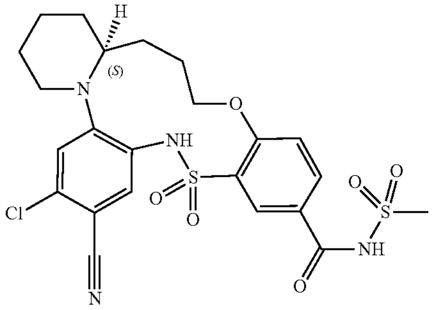
(65)
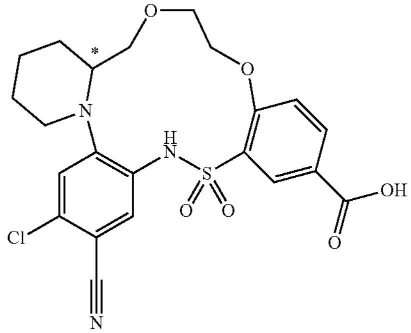
(67) E1
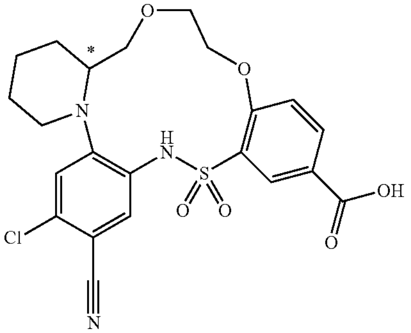
(68) E2
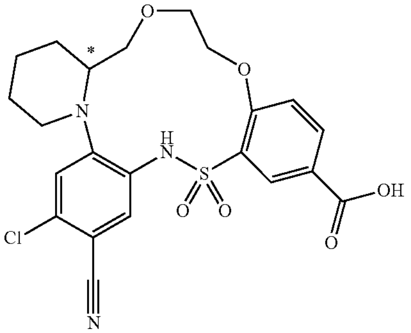

-continued (69)

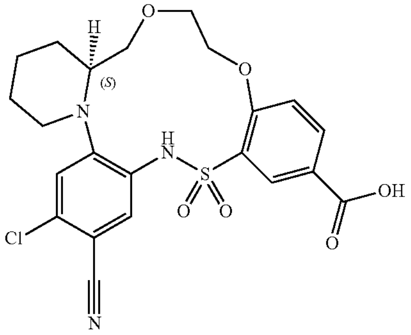

(66)

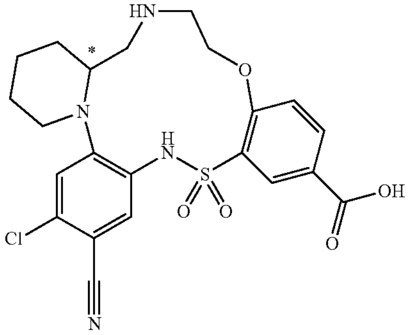

(70)

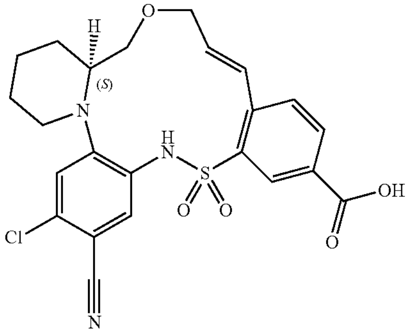

(71)

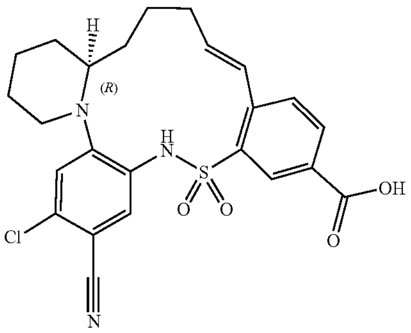

-continued (72)

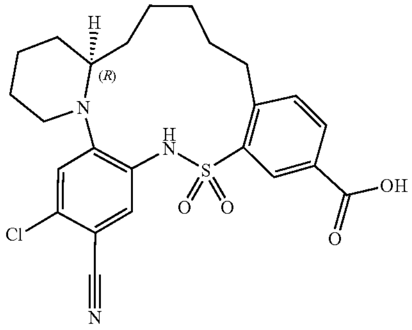

(73)

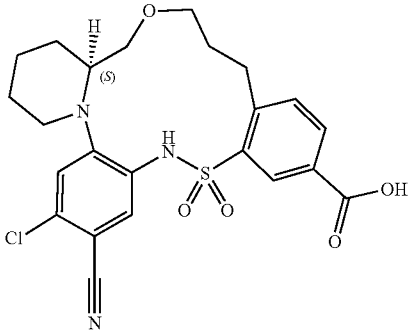

and pharmaceutically acceptable salts and hydrates thereof.

27. A pharmaceutical composition comprising a compound as defined in claim 1 admixed with a pharmaceutically acceptable excipient, diluent or carrier, and optionally one or more additional active agents.

28. An in vitro or in vivo method for producing an antigen-presenting cell which presents a neo-antigen, comprising contacting said antigen-presenting cell with a compound as defined in claim 1 to induce a neo-antigen in said antigen-presenting cell, optionally wherein the antigen-presenting cell is a dendritic cell.

29. An immunogenic composition comprising an antigen-presenting cell obtained or obtainable by the method according to claim 28.

30. A combination comprising a compound according to claim 1 and a further active agent.

31. A process for preparing a compound of formula (Ih) or (Ik), (Ih)

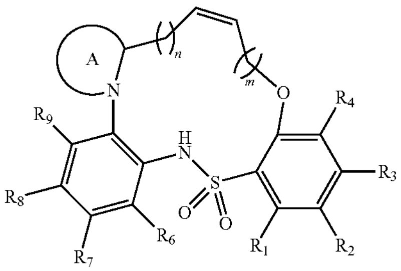

-continued (Ik)

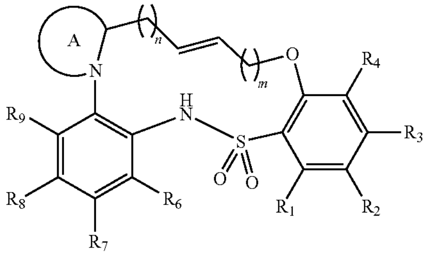

wherein:

A, m, n, $R_1$, $R_3$, $R_4$ and $R_6$-$R_9$ are as defined in claim 3;

$R_2$ is COOH;

said process comprising the steps of:

(i) subjecting a compound of formula (IIh), where $R_{2'}$ is $CO_2$-alkyl, to ring closing metathesis; and (ii) hydrolysing the product formed in step (i) to convert the $R_{2'}$ group to COOH:

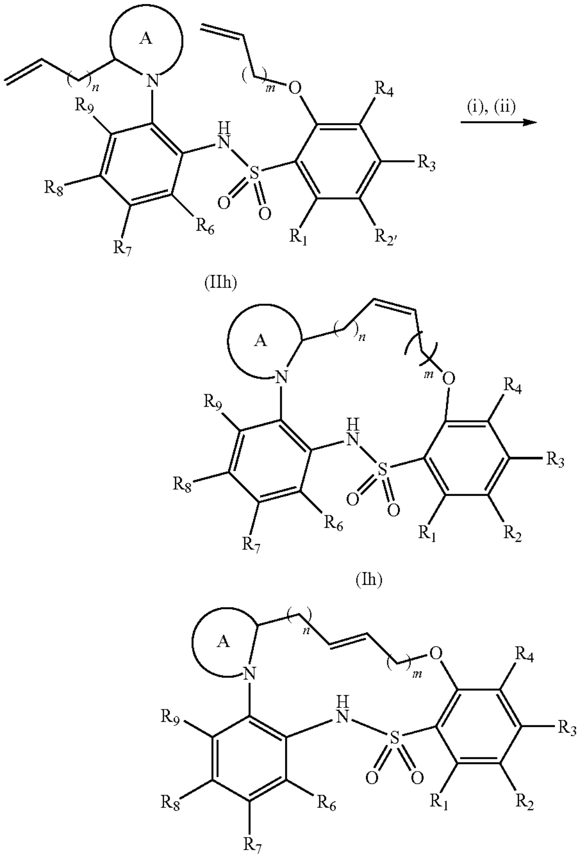

(IIh)

(Ih)

(Ik)

wherein the process comprises preparing said compound of formula (IIh) from a compound of formula (IIIh) and a compound of formula (IVh):

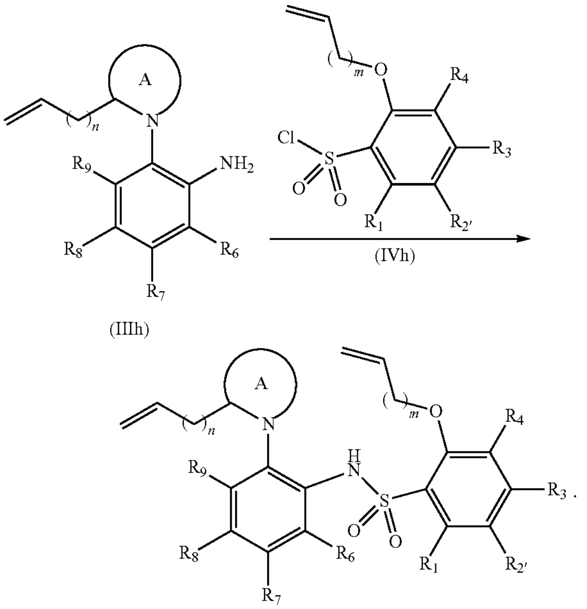

(IIIh)

(IVh)

(IIh)

32. A process for preparing a compound of formula (Ii):

(Ii)

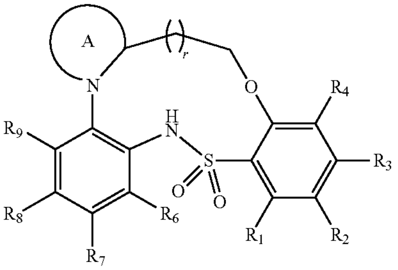

wherein:

A, r, $R_1$, $R_3$, $R_4$ and $R_6$-$R_9$ are as defined in claim 3;

$R_2$ is $CO_2H$;

said process comprising the steps of:

(i) subjecting a compound of formula (IIi), where $R_{2'}$ is $CO_2$-alkyl, to Mitsunobu ring closure; and (ii) hydrolysing the product formed in step (i) to convert the $R_{2'}$ group to COOH:

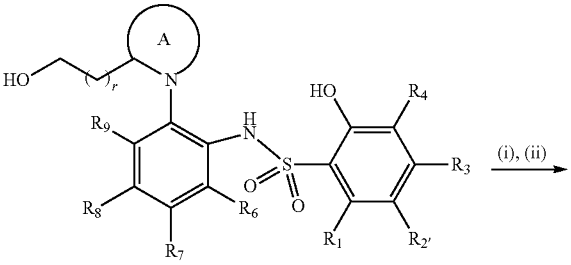

(IIi)

-continued

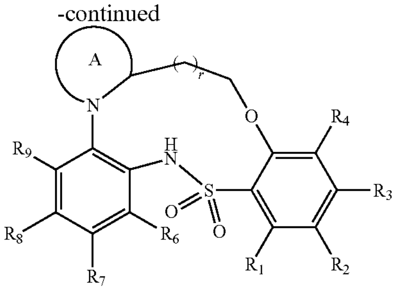

(Ii)

wherein the process comprises preparing said compound of formula (IIj) from a compound of formula (IIIi) and a compound of formula (IVi):

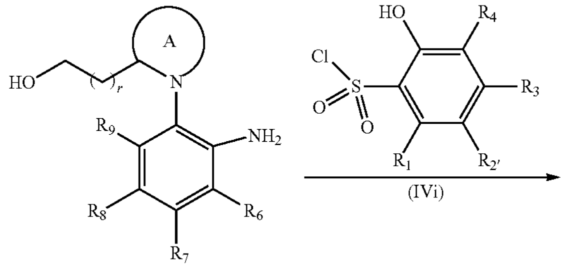

(IVi)

(IIIi)

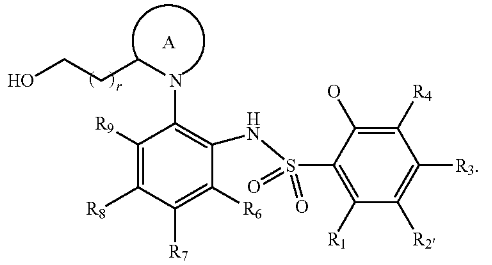

(IIi)

33. A process for preparing a compound of formula (Iv), (Iv)

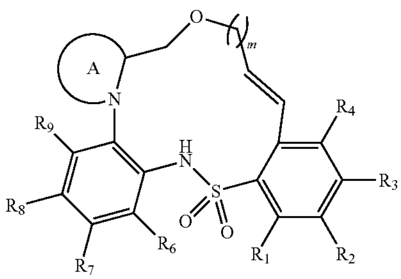

wherein:

A, m, $R_1$, $R_3$, $R_4$ and $R_6$-$R_9$ are as defined in claim 3;

$R_2$ is COOH;

said process comprising the steps of:

(i) subjecting a compound of formula (Iv.1), where $R_{2'}$ is $CO_2$-alkyl, to ring closing metathesis; and (ii) hydrolysing the product formed in step (i) to convert the $R_{2'}$ group to COOH:

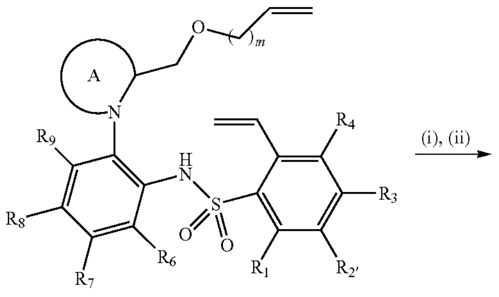

(Iv.1)

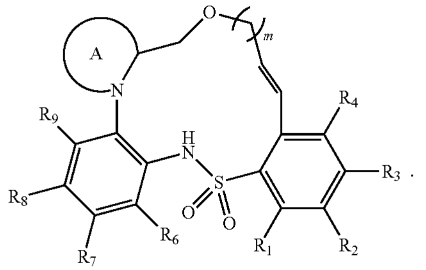

(Iv)

34. A process for preparing a compound of formula (Iw), (Iw)

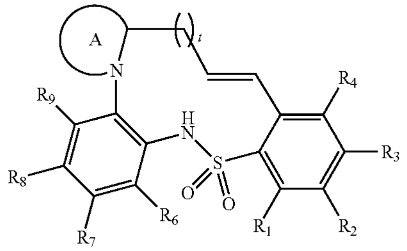

wherein:

A, t, $R_1$, $R_3$, $R_4$ and $R_6$-$R_9$ are as defined in claim 3;

$R_2$ is COOH;

said process comprising the steps of:

(i) subjecting a compound of formula (Iw.1), where $R_{2'}$ is $CO_2$-alkyl, to ring closing metathesis; and (ii) hydrolysing the product formed in step (i) to convert the $R_{2'}$ group to COOH:

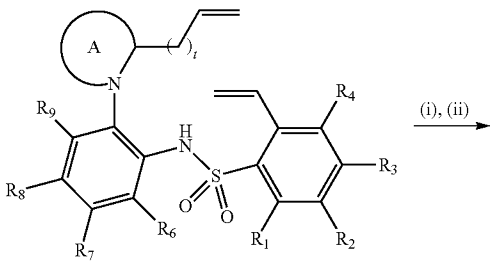

(Iw.1)

-continued
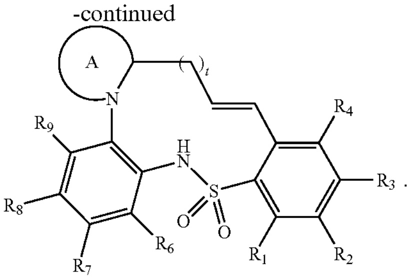
(Iw)
* * * * *